United States Patent [19]

Bukh et al.

[11] Patent Number: 5,514,539
[45] Date of Patent: May 7, 1996

[54] NUCLEOTIDE AND DEDUCED AMINO ACID SEQUENCES OF THE ENVELOPE 1 GENE OF 51 ISOLATES OF HEPATITIS C VIRUS AND THE USE OF REAGENTS DERIVED FROM THESE SEQUENCES IN DIAGNOSTIC METHODS AND VACCINES

[75] Inventors: Jens Bukh, Bethesda; Roger H. Miller, Rockville; Robert H. Purcell, Boyds, all of Md.

[73] Assignee: The United States of America as represented by the Department of Health and Human Services, Washington, D.C.

[21] Appl. No.: 86,428

[22] Filed: Jun. 29, 1993

[51] Int. Cl.[6] .............................. C12Q 1/70; C12Q 1/68; C12P 19/34; C07H 21/04

[52] U.S. Cl. ................... 435/5; 435/6; 435/91.2; 435/810; 536/23.1; 536/23.72; 536/24.32; 536/24.33; 935/76; 935/77; 935/1; 935/2; 935/3; 935/5

[58] Field of Search .................... 435/5, 6, 91.1, 435/91.2, 810, 183; 536/23.1, 23.72, 24.32, 24.33, 25.3; 935/77, 78, 1–5

[56] References Cited

U.S. PATENT DOCUMENTS

| | | | |
|---|---|---|---|
| 4,358,535 | 11/1982 | Falkow et al. | 435/5 |
| 4,683,195 | 7/1987 | Mullis et al. | 435/6 |
| 5,350,671 | 9/1994 | Houghton et al. | 435/5 |

FOREIGN PATENT DOCUMENTS

| | | |
|---|---|---|
| 532167 | 5/1992 | European Pat. Off. |
| 485209 | 5/1992 | European Pat. Off. |
| 468527 | 1/1993 | European Pat. Off. |
| 510952 | 3/1993 | European Pat. Off. |
| 585549 | 3/1994 | European Pat. Off. |
| 2212511 | 1/1992 | United Kingdom |
| WO9208734 | 5/1992 | WIPO |
| WO/9211370 | 7/1992 | WIPO |
| WO9219743 | 11/1992 | WIPO |
| WO9302103 | 2/1993 | WIPO |
| WO9306126 | 4/1993 | WIPO |
| WO9315193 | 8/1993 | WIPO |
| WO9425601 | 11/1994 | WIPO |
| WO9221759 | 12/1994 | WIPO |

OTHER PUBLICATIONS

Choo, A. L. et al. (1989) Science 244:359–362.
Weiner, A. J. et al. (1990) Lancet 335:1–3.
Kuo, G. et al. (1992) Science 244:362–364.
Okamoto, H. et al. (1992) J. Gen. Virol; 73:673–679.
Bukh, J. et al. (1992) Proc. Natl. Acad. Sci. 89:187–191.
Bukh, J. et al. (1992) Proc. Natl. Acad. Sci. U.S.A. 89:4942–4946.
Cha, T. et al. (1992) Proc. Natl. Acad. Sci. U.S.A. 89:7144–148.
Chan, S–W. et al. (1992) J. Gen. Virol., 73:1131–1141.
Lee, C–H. et al. (1992) J. Clin. Microbio. 30:1602–1604.
Choo, et al. (1991) Proc. Natl. Acad. Sci. U.S.A. 88:2451–2455.
Okamoto, et al. (1992) Virology 188:331–341.
Inchauspe, et al. (1991) Proc. Natl. Acad. Sci. USA 88:10292–10296.
Takamizawa, et al. (1991) J. Virol. 65:1105–1113.
Kato, et al. (1990) Proc. Natl. Acad. Sci. U.S.A. 87:9524–9528.
Okamoto, et al. (1992) Virology 190:894–899.
Ogata, et al. (1991) Proc. Natl. Acad. Sci. USA 88:3392–3396.

(List continued on next page.)

Primary Examiner—W. Gary Jones
Assistant Examiner—Bradley L. Sisson
Attorney, Agent, or Firm—Morgan & Finnegan

[57] ABSTRACT

The nucleotide and deduced amino acid sequences of 51 cDNAs are disclosed where each cDNA encodes the envelope 1 gene of an isolate of hepatitis C virus (HCV). The invention relates to the oligonucleotides, peptides and recombinant envelope 1 proteins derived from these sequences and their use in diagnostic methods and vaccines.

10 Claims, 71 Drawing Sheets

OTHER PUBLICATIONS

Mori, et al. (1992) Biochem. Biophys. Res. Comm. 183:334–342.
Weiner, et al. (1991) Virology 180:842–848.
Hijikata, et al. (1991) Biochem. Biophys. Res. Comm. 175:220–228.
Okamoto, et al. (1990) Japan. J. Exp. Med. 60:167–177.
Takeuchi, et al. (1990) J. Gen. Virol. 71:3027–3033.
Chen et al. (1992) Virology 188:102–113.
Liu,. et al. (1992) Gene 114:245–250.
Tanaka, et al. (1992) Virus Research 23:39–53.
Abe, et al. (1992) J. Gen. Virol. 73, 2725–2729.
Honda, et al. (1993) Arch. Virol. 128, 163–169.
Stuyver, L. et al. (1993) Biochem. Biophys. Res. Comm. 192:635–641.
M. Kohara et al., 'Expression and characterisation of glycoprotein gp35 of hepatitis if C virus using recombinant vaccina virus' J. Gen. Virol., vol. 73, 1992, pp. 2313–2318.
Y. Matsura et al. 'Expression of processed envelope protein of hepatitis C virus in mammalian and insect cells' J. Virol., vol. 66, 1992, pp. 1425–1431.
H. Hsu et al., 'Characterisation of HCV structural proteins with a recombinant baculovirus expression system', Hepatology, vol. 17, No. 5, 1993, pp. 763–771.
C. Ishida et al., 'Detection of antibodies to hepatitis C virus structural proteins', J. Clin. Micro., vol. 31, No. 4, 1993 pp. 936–940.
H. Hada et al. 'Sequence variation in the envelope protein of hepatitis C virus', Acta Med Okayama, vol. 45, No. 5, 1991, pp. 347–355.
H. Okamoto et al., 'Nucleotide sequence of the genomic RNA of hepatitis C virus isolated from a human carrier', J. Gen. Virol., vol. 72, 1991, pp. 2697–2704.
M. Houghton et al. & Abstracts of 3rd Intl. Conf. Current trends in chronically evolving viral hepatitis Oct. 4–7, 1992, Pisa, Italy Abstract, J. Hepatol., vol. 17, suppl. 1 1992, p. S10.
M. Sallberg et al., Antigenic regions within the hepatitis C virus envelope and nonstructural proteins, vol. 91, No. 3, 1993, pp. 489–494.

FIGURE 1A-1

| SEQ ID NO: | Isolate | | |
|---|---|---|---|
| 5 | S14 | 1 | TACCAAGTGCGCAACTCCACGGGGCTTTACCATGTtACCAATGATTGCCCTAACTCGAGTA |
| 1 | DK7 | 1 | TACCAAGTGCGCAACTCCACGGGGCTTTACCATGTCACCAATGATTGCCCTAACTCGAGTA |
| 8 | US11 | 1 | TACCAAGTaCGCAACTCCACGGGGCTTTACCATGTCACCAATGATTGCCCTAACTCGAGTA |
| 4 | DR4 | 1 | CACCAAGTGCGCAACTCTACAGGGCTTTACCATGTCACCAATGATTGCCCTAATTCGAGTA |
| 3 | DR1 | 1 | CACCAAGTGCGCAACTCTACAGGGCTTTACCATGTCACCAATGATTGCCCTAATTCGAGTA |
| 2 | DK9 | 1 | TACCAAGTACGCAACTCCTCGGGCCTcTACCATGTCACCAATGATTGCCCTAACTCGAGTA |
| 6 | S18 | 1 | TACCAAGTACGCAACTCCaCGGGCCTTTACCATGTCACCAATGAcTGCCCTAACTCGAGCA |
| 7 | SW1 | 1 | TACCAAGTACGCAACTCCtCGGGCCTTTACCATGTCACCAATGAtTGCCCTAACTCGAGTA |
| 1-8 | consensus | | tACCAAGT-CGCAACTCcaCgGGgCTtTACCATGTcACCAATGAtTGCCCTAAcTCGAGtA |

FIGURE 1A-2

| SEQ ID NO: | Isolate | | |
|---|---|---|---|
| 5 | S14 | 62 | TtGTGTACGAGaCaGCtGATGCtATCCTaCACgCTCCGGGaTGTGTCCCTTGCGTTCGtGA |
| 1 | DK7 | 62 | TcGTGTACGAGGCGGCCGATGCCATCCTGCACACTCCGGGGTGTGTCCCTTGCGTTCGCGA |
| 8 | US11 | 62 | TTGTGTACGAGGCGGCCGATGCCATCCTGCACACTCCGGGGTGTGTtCCTTGCGTTCGCGA |
| 4 | DR4 | 62 | TTGTGTACGAGGCGGCCGATGCCATCCTGCACACGCCGGGGTGTGTCCCTTGCGTTCGCGA |
| 3 | DR1 | 62 | TTGTGTACGAGGCGGCCGATGCCATCCTGCACgCCGCCGGGGTGTGTCCCTTGCGTTCGCGA |
| 2 | DK9 | 62 | TTGTGTACGAGGCGGCCGATGCCATCCTGCAtTCTCCaGGGTGTGTCCCTTGCGTTCGCGA |
| 6 | S18 | 62 | TTGTGTACGAGACGGCCGATaCCATCCTACACTCTCCgGGGTGTGTCCCTTGCGTTCGCGA |
| 7 | SW1 | 62 | TTGTGTACGAGACGGCCGATgCCATtCTACACTCTCCaGGGTGTGTCCCTTGCGTTCGCGA |
| 1-8 | consensus | | TtGTGTACGAGgCgGCCGATgCCATcCTgCAc-CtCCgGGgTGTGTcCCTTGCGTTCGCGA |

FIGURE 1A-3

| SEQ ID NO: | Isolate | | |
|---|---|---|---|
| 5 | S14 | 123 | GGGTAACAcCTCGAGGTGTTGGGTGGCGATGACCCCACGGTGCCACCAGGACGGCAAA |
| 1 | DK7 | 123 | GGGTAACGtCTCGAGGTGTTGGGTGGCGATGACCCCACGGTGCCACCAGGAtGGCAAA |
| 8 | US11 | 123 | GGGTAACGCtTCGAGGTGTTGGGTGGCGATGACCCCACGGTGCCACCAGGACGGCAAA |
| 4 | DR4 | 123 | GGGTAACaCCTCGAGGTGTTGGGTGGCGGTGACCCCACGGTGCCACCAGGACGGCAAA |
| 3 | DR1 | 123 | GGGTAACGCCTCGAGGTGTTGGGTGGCGGTGACCCCACGGTGCCACCAGGACGGCAAA |
| 2 | DK9 | 123 | GGGTAACGCCTCGAaAATGTTGGGTGGCGGTGACCCCACGGTGCCACCAGGACGGCAAg |
| 6 | S18 | 123 | GGGTAACGCCTCGAgATGTTGGGTGcCGGTGGCCCCACAGTtGCCACCAGGACGGCAAA |
| 7 | SW1 | 123 | GGaTggCGCCcCGAagTGTTGGGTGgCGGTGGCCCCACAGTcGCCActAGGGACGGCAAA |
| 1-8 | consensus | | GGgTaaCgcctCGAggTGTTGGGTGgCGgTGaCCCCACGgTGCCAcCAGGGAcGGCAAa |

FIGURE 1A-4

| SEQ ID NO: | Isolate | | |
|---|---|---|---|
| 5 | S14 | 184 | CTCCCCgCAaCGCAGCTTCGACGTtACATCGATCTGCTtGTCGGGAGcGCCACCCTCTGTT |
| 1 | DK7 | 184 | CTCCCCACAgCGCAGCTTCGACGTCACATCGATCTGCTcGTCGGAGtGCCACCCTCTGTT |
| 8 | US11 | 184 | CTCCCACAACGCAaCTTCGACGTCACATCGATCTGCTTGTCGGGAGCGCCACCCTCTGTT |
| 4 | DR4 | 184 | CTCCCCACAACGCAGCTcCGACGTCACATCGATCTGCTTGTCGGGAGCGCCACCCTCTGCT |
| 3 | DR1 | 184 | CTCCCCACAACGCAGCTTCGACGTCACATCGATCTGCTTGTCGGGAGCGCCACCCTCTGCT |
| 2 | DK9 | 184 | CTCCCCGCAAACGCAGCTTCGACGTCACATCGATCTGCTTGTCGGGAGCGCCACCCTCTGCT |
| 6 | S18 | 184 | CTCCCCGCAAACGCAGCTTCGACGTCACATCGATCTGCTTGTtGGGAGCGCCACCCTCTGCT |
| 7 | SW1 | 184 | CTCCCtGCAAACGCAGCTTCGACGTCACATCGATCTGCTTGTcGGaAGCGCCACCCTCTGCT |
| 1-8 | consensus | | CTCCCc-CAaCGCAgCTtCGACGTcACATCGAtCTGCTtGTcGGgAGcGCCACCCTCTGcT |

FIGURE 1A-5

| SEQ ID NO: | Isolate | | |
|---|---|---|---|
| 5 | S14 | 245 | CGGCCCCTCTACGTGGGGGACtTGTGCGGGTCTGTCTTTCTTGTCGGTCAgCTGTTTACCTT |
| 1 | DK7 | 245 | CGGCCCCTCTACGTGGGGGACCTGTGCGGGTCTGTCTTTCTTGTCGGTCAAACTGTTTACCTT |
| 8 | S11 | 245 | CGGCCCCTCTACGTGGGGGACCTGTGCGGGTCTGTCTTTCTTGTCGGTCAAACTGTTTACCTT |
| 4 | DR4 | 245 | CGGCCCCTCTACGTGGGGGACtTGTGCGGGTCTGTCTTCCTTGTCGGTCAAACTGTTCACCTT |
| 3 | DR1 | 245 | CGGCCCCTCTACGTGGGGGACcTGTGCGGGTCTGTCTTCCTTGTCGGTCAAACTGTTCACCTT |
| 2 | DK9 | 245 | CGGCCCCTCTATGTGGGGGACtTGTGCGGGTCTGTCTTCCTTGTCGGCCAAACTGTTCACCTT |
| 6 | S18 | 245 | CGGCCCCTCTATGTGGGGGACCTGTGCGGGTCTGTCTTTCTTGTCAGCCAgCTGTTCACtaT |
| 7 | SW1 | 245 | CGGCCCCTCTAcGTGGGGGACtTGTGCGGGTCTGTCTTTCTCGTCAGtCAaCTGTTCACgtT |
| 1-8 | consensus | | CGGCCCCTCTAcGTGGGGGAC-TGTGCGGGTCTGTCTTtCTtGTCgtCaaCTGTTcACCtT |

FIGURE 1A-6

| SEQ ID NO: | Isolate | | |
|---|---|---|---|
| 5 | S14 | 306 | CTCTCCCCAGGCGCGCCtCTGGACGACGCAAGaCTGCAATTGTTCTATCTATCCGGCCATATA |
| 1 | DK7 | 306 | CTCTCCCCAGGCGCCACTGGACGACGCAAGGCTGCAATTGTTCTATCTATCCtGGCCATATA |
| 8 | S11 | 306 | CTCTCCCCAGaCGCCACTGGACGACGCAAGaCGCAGGGCTGCAATTGTTCTATCTATCCGGCCATATA |
| 4 | DR4 | 306 | CTCTCCCCAGaCGCCACTGGACGCAAGGCAAGACTGCAATTGTTCTATCTATCCGGCCATATA |
| 3 | DR1 | 306 | CTCTCCCCAGGCGCCACTGGACAACGCAAGACTGCAATTGTTCCATCTATCCGGCCATATA |
| 2 | DK9 | 306 | tCTCTCCCCAGGCGCCACTGGACAACGCAAGACTGCAACTGTTCTATCTATCCGGCCATATA |
| 6 | S18 | 306 | CTCCCCCAGGCGCCACTGGACAACGCAAGACTGCAACTGTTCTATCTACCCGGCCATATt |
| 7 | SW1 | 306 | CTCCCCCAGGGCGCCACTGGACAACGCAAGACTGtAACTGTTCTATCTATCCCGGCCATA |
| 1-8 | consensus | | cTCtCCCCAGgCgCCaCTGGACaACGCAaGaCTGCAATTGTTCtATCTATCCcGGCCAcATa |

FIGURE 1A-7

| SEQ ID NO: | Isolate | | |
|---|---|---|---|
| 5 | S14 | 367 | ACGGGTCAtCGCATGGCaTGGGATATGATGATGAACTGGTCCCCTACgACGGCacTGGTAG |
| 1 | DK7 | 367 | ACGGGTCACCGCATGGCgTGGGATATGATGATGAACTGGTCCCCTACCACGGCGTTGGTAG |
| 8 | S11 | 367 | ACGGGTCACCGCATGGCaTGGGATATGATGATGAACTGGTCCCCTACGgCGGGCGTTGGTgG |
| 4 | DR4 | 367 | ACGGGcCACCGCATGGCgTGGGATATGATGATGAACTGGTCCCCTACGACAGCGCTGGTAG |
| 3 | DR1 | 367 | ACGGGaCACCGCGTATGGCATGGGATATGATGATGAACTGGTCCCCTACGACAGCGCTGGTAA |
| 2 | DK9 | 367 | ACGGGTCAtCGCATGGCgTGGGATATGATGATGAACTGGTCCCCTACAgCAGCGCTGGTAA |
| 6 | S18 | 367 | ACGGGTCACCGCtATGGCATGGGATATGATGATGAACTGGTCCCCTACAACgGCGCTGGTAA |
| 7 | SW1 | 367 | ACGGGTCACCGCATGGCATGGGATATGATGATGAACTGGTCCCCCACACaGCGCcTGGTAg |
| 1-8 | consensus | | ACGGGTcACcCGcATGGCATGGGATATGATGATGAACTGGTCCCCtACgaC-GCgcTGGTag |

FIGURE 1A-8

| SEQ ID NO: | Isolate | | |
|---|---|---|---|
| 5 | S14 | 428 | TAGCTCAGCTGCTCCGGATCCCaCAAGCCATCTTGGAtATGATCGCTGGTGCTCACTGGGG |
| 1 | DK7 | 428 | TAGCTCAGCTGCTCCGGATCCCgCAAGCCATCTTGGACATGATCGCTGGTGCTCACTGGGG |
| 8 | S11 | 428 | TAGCTCAGCTGCTCCGGATCCCACAAGCCATCTTGGACATGATCGCTGGTGCTCACTGGGG |
| 4 | DR4 | 428 | TAGCTCAGCTGCTCCGGATCCCACAAGCCATCTTGGACATGATCGCTGGTGCCCACTGGGG |
| 3 | DR1 | 428 | TGGCTCAGCTGCTCCGGATCCCACAAGCCATCTTGGACATGATCGCTGGTGCCCACTGGGG |
| 2 | DK9 | 428 | TGGGCgCAGCTGCTCAGGATCCCGCAAGCCATCTTGGACATGATCGCTGGaGCCCACTGGGG |
| 6 | S18 | 428 | TAGCTCAGCTGCTCAGGgTCCCGCAAGCCGTCTCTTGGACATGATCGCTGGTGCCCACTGGGG |
| 7 | SW1 | 428 | TAGCTCAGCTGCTCAGGaTCCCGCAAGCCGTCTTGGACATGATCGCTGGTGCCCACTGGGG |
| 1-8 | consensus | | TaGCtCAGCTGCTCCgGaTCCC-CAaGCCaTCTCTTGGACATGATCGCTGGtGCCCACTGGGG |

FIGURE 1A-9

| SEQ ID NO: | Isolate | | |
|---|---|---|---|
| 5 | S14 | 489 | AGTCCTaGCGGGCATAGCGTATTTCtCCATGGTGGGaAACTGGGCGAAGGTCCTaGTgGTG |
| 1 | DK7 | 489 | AGTCCTgGCGGGCATAGCGTATTTtCCATGGTGGGGAACTGGGCGAAGGTCCTGGTAGTG |
| 8 | S11 | 489 | AGTCCTAGCGGGCATAGCGTATTTCTCCATGGTGGGGAACTGGGCGAAGGTCCTGGTAGTG |
| 4 | DR4 | 489 | AGTCCTAGCGGGCATAGCGTATTTCTCCATGGTGGGGAACTGGGCGAAGGTCCTGGTAGTG |
| 3 | DR1 | 489 | AGTCCTAGCGGGCATAGCGTATTTCTCCATGGTGGGGAACTGGGCGAAGGTCGTGGTAGTG |
| 2 | DK9 | 489 | AGTCCTAGCGGGCATAGCGTATTTCTCCATGGTGGGGAACTGGGCGAAGGTCGTGgTGgTa |
| 6 | S18 | 489 | AGTCCTAGCGGGCATAGCGTATTTCTCCATGGCGGGGAACTGGGCGAAGGTCCTGcTAGTG |
| 7 | SW1 | 489 | AGTCCTAGCGGGCATAGCGTATTTCTCCATGGTgGGGGAACTGGGCGAAGGTCCTGaTAGTG |
| 1-8 | consensus | | AGTCCTaGCGGGCATAGCGTATTTCTCCATGGtGGGgAACTGGGCGAAGGTCCTggTaGTg |

FIGURE A1-10

| SEQ ID NO: | Isolate | | |
|---|---|---|---|
| 5 | S14 | 550 | CTGCTGCTATTcGCCGGCGTtGACGCG |
| 1 | DK7 | 550 | CTGCTGCTATTTGCCGGCGTCGACGCG |
| 8 | US11 | 550 | CTGCTGCTATTTGCCGGCGTCGACGCG |
| 4 | DR4 | 550 | CTGCTGCTGTTTGCCGGCGTTGATGCG |
| 3 | DR1 | 550 | CTGTTGCTGTTTGCCGGCGTTGATGCG |
| 2 | DK9 | 550 | CTGTTGCTGTTTaCCGGCGTCGATGCG |
| 6 | S18 | 550 | CTGTTGCTGTTTTGCCGGCGTCGATGCG |
| 7 | SW1 | 550 | CTGTTGCTGTTTtCCGGCGTCGATGCG |
| 1-8 | consensus | | CTGtTGCTgTTTtgCCGGGGTCGAtGCG |

FIGURE 1B-1

| SEQ ID NO: | Isolate | | |
|---|---|---|---|
| 11 | DK1 | 1 | TATGAAGTGCGCAACGTGTCCGGGgtGTGTACCACGTCACaAACGACTGCTCCAACTCAAGCA |
| 24 | T10 | 1 | TATGAAGTGCGCAACGTGTCCGGGaTGTGTACCATgTCACgAACGACTGCTCCAACTCAAGCA |
| 10 | D3 | 1 | TATGAAGTGCGCAACGTGTCCGGGGTGTACCAAgTCACCAAtGACTGTTCCAACTCGAGCA |
| 9 | D1 | 1 | TATGAAGTGCGCAACGTGTCCGGGGTGTACCATGTCACGAACGACTGTTCCAACTCGAGCA |
| 14 | HK5 | 1 | TATGAAGTGCGCAACGTGTCCGGGTATACCATGTCACGAACGACTGCTCCAACTtAAGCA |
| 15 | HK8 | 1 | TATGAAGTGCGCAACGTGTCCGGGATATACCATGTCACGAACGACTGCTCCAACTCAAGCA |
| 12 | HK3 | 1 | TATGAAGTGCGCAACGTGTCCGGGATATACCATGTCACGAACGACTGCTCCAACTCAAGCg |
| 23 | T3 | 1 | TAcGAAGTGCGCAACGTGTCCGGGTGTACtATGTCACGAACGACTGCTCCAACTCAAGCA |
| 22 | SW2 | 1 | TATGAAGTGCGCAACGTGTCCGGGTGTAtCATGTCACGAACGACTGCTCCAACTCAAGCA |
| 17 | IND8 | 1 | TATGAgGTGCGCAACGTGTCCGGGGTGTACCATGTCACGAACGACTGCTCCAACTCAAGTA |
| 16 | IND5 | 1 | TATGAAGTGCGCAACGTGTCCGGGGTGTACCATGTCACGAACGACTGCTCCAACTCAAGCA |
| 21 | SA10 | 1 | TATGAAGTGCGCAACGTGTCCGGGaTGTACCATGTCACGAACGACTGCTCCAACTCAAGCA |
| 20 | S45 | 1 | TATGAAGTGCGCAACGTGTCCGGGgcGTACCATGTCACGAACGACTGCTCCAACTCAAGCA |
| 25 | US6 | 1 | TATGAAGTGCGCAACGTGTCCGGGATGTACCATGTCACGAACGACTGCTCCAACTCAAGCA |
| 13 | HK4 | 1 | cATGAAGTGCaCAACGTaTCCGGGATcTACCATGTCACGAACGACTGCTCCAACTCAAGCA |
| 18 | P10 | 1 | TATGAAGTGCGCAACGTgTCCGGGGTGTACCATGTCACGAACGACTGCTCCAACTCAAGTA |
| 19 | S9 | 1 | TATGAAGTGCGCAACGTaTCCGGGcGTACCATGTCACGAACGACTGCTCCAACTCAAGTA |
| 9-25 | consensus | | tAtGAaGTGCgCAACGTgTCCGGGgtgTAccAtgTCACgAAcGACTgCTCCAACTcaAGca |

FIGURE 1B-2

| SEQ ID NO: | Isolate | | |
|---|---|---|---|
| 11 | DK1 | TcGTGTaTGAGGCAGtGGACgTGATCATGCAtACCCCaGGGTGCGTGCCCTGCGTTCGGGA | 62 |
| 24 | T10 | TtGTGTtTGAGGCAGGCGGACtTGATCATGCACACCCCGGGGTGCGTGCCCTGCGTTCGGGA | 62 |
| 10 | D3 | TcGTGTATGAGACAGCGGACATGATCATGCACACCCCGGGGTGCGTGCCCTGCGTTCGGGA | 62 |
| 9 | D1 | TtGTGTATGAGACAGCGGACATGATCATGCACACCCCGGGGTGCGTGCCCTGCGTTCGGGA | 62 |
| 14 | HK5 | TCGTGTACGAGACAaCGGACATGATCATGCACACCCCTGGGTGCGTGCCCTGCGTTCGGGA | 62 |
| 15 | HK8 | TCGTGTATGAaACAGCGGACATGATtATGCATACCCCTGGATGCatGCCCTGCGTTCGGGA | 62 |
| 12 | HK3 | TCGTGTATGAGACAGCaGACATGATCATGCACACCCCTGGATGCGTGCCCTGCGTaCGGGA | 62 |
| 23 | T3 | TCGTGTATGAGACAGCGGACATGATCATGCACACCCCTGGGTGCGTGCCCTGCGTTCGGGA | 62 |
| 22 | SW2 | TTGTGTATGAGGCAGCGGACATGATCATGCACACCCCGGGGTGCGTGCCCTGCGTTCGGGA | 62 |
| 17 | IND8 | TTGTGTATGAGGCAGCGGACATGATCATGCACACCCCGGGGTGCGTGCCCTGCGTTCGGGA | 62 |
| 16 | IND5 | TTGTGTATGAGGCAGCGGACATGATCATGCACACtCCCGGGGTGCGTGCCCTGCGTTCGGGA | 62 |
| 21 | SA10 | TTGTGTATGAGGCAGCGGACATGATCATGCAtACCCCGGGGTGCGTGCCCTGCGTTCGGGA | 62 |
| 20 | S45 | TTGTGTATGAGGCAGtGGACgTGATCCTGCACACCCCtGGGTGCGTGCCCTGCGTTCGGGA | 62 |
| 25 | US6 | TTGTGTATGAGGCAGCGGACATGATCATGCACACtCCCGGGGTGCGTGCCCTGtGTTCGGGA | 62 |
| 13 | HK4 | TTGTGTATGAGGCAGCGGACATGATCATGCAtACCCCGGGGTGCGTGCCCTGcGTcCGGGA | 62 |
| 18 | P10 | TTGTGTATGAGGCAGCGGACATGATGATaATGCACACCCCGGGGTGCGTGCCCTGtGTTCGGGA | 62 |
| 19 | S9 | TTGTGTACGAGGCAGCGGACGTGATCATGCAtACCCCGGGGTGtGTaCCCTGCGTTCaGGA | 62 |
| 9-25 | consensus | TtGTGTatGAggCAgcggACaTGATcaTGCAcACCCCggGgTGcgTgCCCTGcgTcGgGA | |

FIGURE 1B-3

| SEQ ID NO: | Isolate | | |
|---|---|---|---|
| 11 | DK1 | 123 | GaaCAACcaCTCCCGtTGCTGGGTAGCGCTCACcCCCACGCTCGCGGCCAGGAACgCCAGC |
| 24 | T10 | 123 | GGgCAACTCCTCCCGCTGCTGGGTAGCGCTCACtCCCACGCTCGCGGCCAGGAACACCAGC |
| 10 | D3 | 123 | GGACAACTCCTCTCGCTGCTGGGTAGCGCTCACCCCCACGCTCGCGGCTAGGAATAGCAGC |
| 9 | D1 | 123 | GGACAACTCCTCTCGCTGCTGGGTAGCGCTCACCCCCACGCTCGCGGCTAGGAATGGCAaC |
| 14 | HK5 | 123 | aAACAACTCCTCCCGTTGtTGGGTAGCGCTCgCCCCCACGCTCGCGGCCAGGAACGcCAGC |
| 15 | HK8 | 123 | GAACAACTCCTCCCGTTGcTGGGTgCGCTCACTCCCACGCTCGCGGCtAGGAAtGTCAGC |
| 12 | HK3 | 123 | GAACAACTCCTCCCGCTGtTGGGTAGCGCTCACTCCCACGCTCGCGGCCAGGAACGTCAGC |
| 23 | T3 | 123 | GAgCAAtTCCTCCCGCTGCTGGGTAGCGCTCACTtACTCCCACGCTCGCGGCCAGGAACGCCAGC |
| 22 | SW2 | 123 | GGcCAACTCCTCCCGCTGCTGGGTAGCGCTCACTCCCACGCTaGCAGCCAGGAACaCCAGC |
| 17 | IND8 | 123 | GGGCAACTtCTCTaGtTGCTGGGTAGCGCTCACTCTCGCGGCtAGGAACGCCAGC |
| 16 | IND5 | 123 | GGGCAACTCCTCTCGCTGCTGGGTAGCGCTCACTCTCGCGGCCAGGAACGCCAGC |
| 21 | SA10 | 123 | GAACAACTCCTCCCGCTGCTGGGTAGCGCTCACTCCCACGCTCGCGGCCAGGAACTCCAGC |
| 20 | S45 | 123 | GAACAACTCCTCCCGCTGCTGGGTAGCGCTCACTCCCACGCTCGCGGCCAGGAACTCCAGC |
| 25 | US6 | 123 | GAACAAtTCCTCCCGCTGCTGGGTAGCGCTCACTCCCACGCTCGCGGCCAGGAACGCtAGC |
| 13 | HK4 | 123 | GAACAACTCCTCCCGtTGCTGCTGGGTAGCGCTCACTCCCACGCTCGCGGCCAGGAACGCCAGC |
| 18 | P10 | 123 | GAACAACTCCTCCCGCTGCTGGGTAGCGCTCACTCCCACaCTCGCGGCtAGGAAttCCAGC |
| 19 | S9 | 123 | GggtAACTCCTCCCaaTGCTGGGTggCGCTCACcCCCACgCTCGCGGCCAGGAAcgCtAcC |
| 9-25 | consensus | | gaacAActcCTCccgcTgcTGGGTagCGCTcactCCCACgCTcGCgGCcAGGAAcgccAgC |

FIGURE 1B-4

| SEQ ID NO: | Isolate | | |
|---|---|---|---|
| 11 | DK1 | 184 | aTCCCCACTACGACaATATCGACACaATACGAGCGCCATGTCGATTTGCTCGTTGGGGCGGCTGCTTTCTGCT |
| 24 | T10 | 184 | GTCCCCACTACGACgATACGACGCCATGTCGATTTGCTCGTTGGGGCGGCTGCTTTCTGCT |
| 10 | D3 | 184 | GTCCCCACTACGACaATACGAGCGCCACGTCGATTTGCTCGTTGGGGCGGCTGCTTTCTGCT |
| 9 | D1 | 184 | GTCCCCACTACGGCgATACGACGCCACGTCGATTTGCTCGTTGGGGCGGCTGCTTTCTGCT |
| 14 | HK5 | 184 | GTCCCCACCACGGCAATACGACGCCACGTCGACTTGCTCGTTGGGGCGGCTGCTTTCTGCT |
| 15 | HK8 | 184 | GTCCCCACtACGACAATACGACGCCACGTCGACTTGCTCGTTGGGGCGGCTGCTTTCTGCT |
| 12 | HK3 | 184 | GTCCCCACCACGACAATACGACGTCACGTCGACTTGCTCGTTGGGGCGGCTGCCTTCTGCT |
| 23 | T3 | 184 | GTCCCCACTACTAaGACAATACGACGTCACGTCGACTTGCTCGTTGGGGCGGCTGCTTTCTGtT |
| 22 | SW2 | 184 | GTCCCCACTACGACAATACGACGTCACGTCGACTTGCTCGTTGGGGCGGCTGCTTTCTGCT |
| 17 | IND8 | 184 | GTCCCCACCACCACAATACGACGTCACGTCGATTTGCTCGTTGGGGCGGCTGCTTTCTGTT |
| 16 | IND5 | 184 | GTCtCCACTACGACaATACGACACaCCACGTCGATTTGCTCGTTGGGGCGGCTGCTTTCTGTT |
| 21 | SA10 | 184 | GTCCCCACGACGACAATACGAGCGCCACGTCGATTTGCTCGTTGGGGCGGCTGCTTTCTGCT |
| 20 | S45 | 184 | GTCCCCACTACGACAATACGACGCCACGTCGATTTGCTCGTTGGGGCGGCTGCTTTCTGCT |
| 25 | US6 | 184 | GTCCCCACTACGACAATACGACGCCACGTCGATTTGCTCGTTGGGGCGGCTaCTTTCTGCT |
| 13 | HK4 | 184 | aTCCCCACTACGACAATACGTCGACTTGCTCGTCGTCGTTGGGGCGGCTGCTTTCTGCT |
| 18 | P10 | 184 | GTCCCaACTACGgCAATACGACGCCACGTCGATTTGCTCGTTGGGGCGGCTGCTTTCTGCT |
| 19 | S9 | 184 | GTCCCcACcACGaCAATACGACGtCATGTCGATTTGCTCGTTGGGGCGGCTGtTTTCTGCT |

9-25 consensus gTCcCActAcGaCaATATCGAtTGCTCGTTGGGGCGGCTgctTTCTGcT

FIGURE 1B-5

| SEQ ID NO: | Isolate | | |
|---|---|---|---|
| 11 | DK1 | 245 | CCGCTATGTAcGTGGGgGACCTCTGCGGATCCgTTTTCCTCGTCTCTCAGCTGTTCACCTT |
| 24 | T10 | 245 | CCGCTATGTAtGTGGaGACCTCTGCGGATCTGTTTCCTCGTCTCTCCAGCTGTTCACCTT |
| 10 | D3 | 245 | CCGCCATGTACGTGGGGGATCTtTGCGGATCTGTTTTCCTCGTCTCTCCAGCTGTTCACCTT |
| 9 | D1 | 245 | CCGCCATGTACGTGGGGGATCTcTGCGGATCTGTTTTCCTCaTCTCTCCAGCTGTTCACCcT |
| 14 | HK5 | 245 | CCGCTATGTACGTGGGGGATCTtTGCGGATCTGTTTCCTCGTCTCTCCAGCTGTTCACCTT |
| 15 | HK8 | 245 | CCGCTATGTACGTGGGGGATCTCTGCGGATCTGTTTCCTCGTCTCTCCAGCTGTTCACCTT |
| 12 | HK3 | 245 | CCGCTATGTACGTGGGGGATCTCTGCGGATCTGTTTCCTtGTCTCTCCAGCTGTTCACCTT |
| 23 | T3 | 245 | CCGCTATGTACGTGGGGGATCTCTGCGGATCTGTTTTCCTCGTCTCTCCAGCTGTTCACCTT |
| 22 | SW2 | 245 | CCGtTATGTACGTGGGGGATCTCTGCGGATCTGTTTTCCTCGTCTCTCCAGCTGTTCACTTT |
| 17 | IND8 | 245 | CCGCTATGTACGTGGGGGACCTCTGCGGATCTGTTTTCCTCGTCTCTCCAGCTGTTCACCTT |
| 16 | IND5 | 245 | CCGCTATGTACGTGGGGGATcTCTGCGGATCTGTTTTCCTTGTtCTCCAGCTGTTCACCTT |
| 21 | SA10 | 245 | CCGCTATGTACGTGGGGGATcTCTGCGCGTCCgTTTTCCTCGTCTCTCCAGCTGTTCACCTT |
| 20 | S45 | 245 | CCGCCATGTACGTGGGGGATCTGTTTTCCTCaTCTCCAGCTGTTCACCTT |
| 25 | US6 | 245 | CCGCTATGTACGTGGaGAGATCTCTGCGGATCTGTcTCCTCCCTCGTCTCTCCAGtTGTTCACCTT |
| 13 | HK4 | 245 | CCGCCATGTACGTGGGGGATCTCTGCGGATCTGTTcGTTCTCCTCGTCTCTCCAGCTGTTCACCTT |
| 18 | P10 | 245 | CCGCTATGTACGTGGGGGAcCTgTGCGGATCTGTTtCCTCaTCTCCAGCTGTTCACCaT |
| 19 | S9 | 245 | CCGCTATGTACGTGGGGGAcCTgTGCGGATCTGTTtCCTCaTCTCCAGCTGTTCACCaT |

9-25 consensus  CCGctATGTAcGTGGGgGAtCTcTGCGGaTCtGTtttCCTcgTcTCCcAGcTGTTCAcctT

FIGURE 1B-6

| SEQ ID NO: | Isolate | | |
|---|---|---|---|
| 11 | DK1 | 306 | tTCaCCTCGCCGGCATGAGACagcaCAGGACTGCAACTGCTCAATCTATCCGGCCAcgTt |
| 24 | T10 | 306 | CTCGCCTCGCCGGCATGAGACActtTgCAGGACTGCAACTGCTCAATCTATCCGGCCAtcTG |
| 10 | D3 | 306 | CTCGCCTCGCCGGCATGAGACAGTACAGGACagTACAGGAaTGTAACTGCTCAATCTATCCGGCCACGTG |
| 9 | D1 | 306 | CTCGCCTCGCCGGCATGAGACAGTACAGGAGTACAGGAgTGTAAtTGCTCAATCTATCCGGCCACGTG |
| 14 | HK5 | 306 | CTCGCCTCGCCGACACGAGACAGTACAGGACTGCAACTGCTCAATCTATCCGGCCACGTA |
| 15 | HK8 | 306 | CTCGCCTCGCCGACACGAGACAGTACAGGACTGCAACTGCTCAATCTATCCGGCCACGTA |
| 12 | HK3 | 306 | tTCGCCTCGCCGCCGACACGAGACAGTACAGGACTGCAACTGCTCAcTCTATCCGGCCACGTA |
| 23 | T3 | 306 | CTCGCCTCGCCGCCGACAtGAGACAGTACAGGACTGCAACTGCTCAATCTATCCGGCCACGTA |
| 22 | SW2 | 306 | CTCGCCTCGCCGCACGAGACAGTACAGGACTGCAACTGtTCCATCTATCCGGCCACGTA |
| 17 | IND8 | 306 | tTCACCTCGCCGCCGACGAGACAGTACAGGACTGCAATTGCTCAATCTATCCGGCCACGTA |
| 16 | IND5 | 306 | CTCACCGCGCCGCCGACGAGACAGTACAGGACTGCAATTGCTCAATCTATCCGGCCACGTA |
| 21 | SA10 | 306 | CTCGCCTCGCCGGtATGAGACAGTACAGGACTGCAATTGCTCAATCTATCCGGCCgCGTA |
| 20 | S45 | 306 | CTCGCCTCGCCGCCGACGAGACAGTACAGGACTGCAAcTGtTCAATCTATCCGGCCACGTA |
| 25 | US6 | 306 | CTCGCCTCGTCaGCAGACAGACAGAGACAGTACAGGACTGCAATTGtTCAATCTATCCGGCCACGTA |
| 13 | HK4 | 306 | CTCGCCTCGCCGCCGACGAGACggTACAGGACTGCAATTGtTCAATCTATCCGGCCACGTA |
| 18 | P10 | 306 | CTCaCCTCGCCGCCGGCATTgGACAGTACAGGACTGCAATTGtTCAATCTATCCtGGCCACGTA |
| 19 | S9 | 306 | CTCGCCCCGtCGGCATgaGACAGTACAGaACTGCAATTGCTCAATCTATCCgGacACGTg |
| 9-25 | consensus | | cTCgCCTcGccggcAtgaGACagtaCAGgACTGCAAcTGcTCaaTCTATCCgGcCacgTa |

| SEQ ID NO: | Isolate | | |
|---|---|---|---|
| 11 | DK1 | 428 | TaTCGCAGTTACTCCGaATCCCACAAGCTGTCgTGGACATGGTGgCgGGGGCCCACTGGGG |
| 24 | T10 | 428 | TgTCGCAGTTACTCCGGATCCCACAAGCTGTCaTGGACATGGTGaCaGGGGCCCACTGGGG |
| 10 | D3 | 428 | TATCGCAGTTACTCCGGATCCCACAAGCTGTCgTGGACATGGTGGCGGGGCCCACTGGGG |
| 9 | D1 | 428 | TATCGCAGTTACTCCGGATCCCACAAGCTGTCaTGGACATGGTGGCGGGGCCCACTGGGG |
| 14 | HK5 | 428 | TGTCGCAGTTACTCCGCAAGCCCGCAAGCTGTCGTGGACATGGTaGCGGGGCCCACTGGGG |
| 15 | HK8 | 428 | TGTCGCAGTTACTCCGGATCCCGCAAGCTaTCGTGGACATGGTGGCGGGGCCCACTGGGG |
| 12 | HK3 | 428 | TGTCGCAaTTACTCCGGATCCCACAAGCTGTCGTGGACATGGTGGCGGGGCCCACTGGGG |
| 23 | T3 | 428 | TGTCGCAGTTgCTCCGGATCCCACAAGCTGTCGTGGACATGGTGGCGGGGCCCACTGGGG |
| 22 | SW2 | 428 | TGTCGCAGTTaCTCCGGATCCCACAAGCTGTCGTGGACATGGTaGCGGGGCCCACTGGGG |
| 17 | IND8 | 428 | TATCGCAGTTGCTCCGGATCCCACAAGCTGTCGTGGATATGGTGGCGGGGCCCACTGGGG |
| 16 | IND5 | 428 | TATCGCAGTTGCTCCGGATCCCACAAGCTGTCGTGGATATGGTGGCGGGGCCCACTGGGG |
| 21 | SA10 | 428 | TATCGCAGTTACTCCGGATCCCACAAGCTaTCGTGGACATGGTGGCGGGGCCCACTGGGG |
| 20 | S45 | 428 | TATCGCAGTTACTCCGGATCCCACAAGCTGTCGTGGACATGGTGGCGGGGCCCACTGGGG |
| 25 | US6 | 428 | TATCGCAGTTACTCCGGacTCCCACAAGCTGTCATGGACATGGTGGCGGGGCCCACTGGGG |
| 13 | HK4 | 428 | TATCGCAGTTACTCCGGATCCCACAAGCTGTCATGGACATGGTGGCGGaGCCCACTGGGG |
| 18 | P10 | 428 | TgTCGCAGCTACTCCGGATCCCACAAGCTaTCtTGGATgTGGTGGCGGGGCCCACTGGGG |
| 19 | S9 | 428 | TaTCGCAGCTACTCCGGATCCCACAAGCTgTCaTGGATaTGGTGGCGGGGCCCACTGGGG |
| 9-25 | consensus | | TaTCGCAgtTaCTCCggaTCCCaCAAGCTgTCgTGGAcaTGGTggCgGgGGCCCACTGGGG |

FIGURE 1B-9

| SEQ ID NO: | Isolate | | |
|---|---|---|---|
| 11 | DK1 | 489 | AGTCCTGGCGGGGCCCTcGCCTACTAcTCCATGGCCGGGAACTGGGCcAAGGTTTTAATTGTG |
| 24 | T10 | 489 | AGTCCTGGCGGGGCCCTtGCCTACTATTCCATGGCCGGGAACTGGGCTAAGGTTTTAATTGTG |
| 10 | D3 | 489 | GGTCCTGGCGGGGCCCTCGCCTACTATTCCATGGCCGGGAACTGGGCTAAGGTTTTGATTGTG |
| 9 | D1 | 489 | GGTCCTGGCGGGGCCCTCGCCTACTATTCCATGGTCGGGAACTGGGCTAAGGTTTTGATTGTG |
| 14 | HK5 | 489 | GGTCCTGGCGGGGCCCTTGCCTACTATTCCATGGTGGGaAACTGGGCTAAGGTTTTGATTGTG |
| 15 | HK8 | 489 | GGTCCTGGCGGGGCCCTTGCCTACTATTCCATGGTGGGcAACTGGGCTAAGGTTTTGATTGTG |
| 12 | HK3 | 489 | AGTCCTAGCGCGGCCCTTGCCTACTATTCCATGGTGGGaAACTGGGCTAAGGTTTTGATTGTG |
| 23 | T3 | 489 | AGTCCTAGCGCGGCCCTTGCCTACaTACTATTCCATGGTGGGAACTGGGCTAAGGTTTTGATTGTG |
| 22 | SW2 | 489 | AGTCCTGGCGCGGCCCTTGCCTACTATTCCATGGTGGGAACTGGGCTAAGGTTTTGATTGTG |
| 17 | IND8 | 489 | AATCCTGGCGCGGCCCTTGCCTACTATTCCATGGTAGGGAACTGGGCTAAGGTTTTGATTGTG |
| 16 | IND5 | 489 | AATCCTGGCGCGGCCCTTGCCTACTATTCCATGGTAGGGAACTGGGCTAAGGTTTTGATTGTG |
| 21 | SA10 | 489 | AGTCCTAgCGCGGCCCTTGCCTACTATTCCATGGTGGGAACTGGGCTAAGGTTTTGATTGTt |
| 20 | S45 | 489 | AGTCCTGGCGCGGCCCTTGCCTACTATTCCATGGTGGGAACTGGGCTAAGGTTCTGATTGTG |
| 25 | US6 | 489 | AGTCCTGGCGCGGCCCTTGCCTACTATTCCATGGTGGGAACTGGGCTAAGGTTTTGATTGTG |
| 13 | HK4 | 489 | AGTCCTaGCGCGGCCCTTGCCTGCtTACTATTCCATGGTGGGAACTGGGCCAAGGTTTTGATTGTG |
| 18 | P10 | 489 | AGTCCTGGCGCGGCCCTTGCCTACTATTCCATGGTGGGAACTGGGCTAAGGTCTTGATTGTG |
| 19 | S9 | 489 | AGTCCTGGCGCGGCCCTTGCCTACTATTCCATGGTGGGAACTGGGCTAAGGTtTTGATTGTG |
| 9-25 | consensus | | agTCCTgGCGgGGCCCTtGCCTACTAtTCCATGtGGGgAACTGGGCtAAGGTttTgATTGTg |

FIGURE 1B-10

| SEQ ID NO: | Isolate | | |
|---|---|---|---|
| 11 | DK1 | 550 | tTGCTACTCTCTTTGCCGGCGTTGATGGG |
| 24 | T10 | 550 | ATGCTACTCTCTTTGCCGGCGTTGATGGG |
| 10 | D3 | 550 | ATGCTACTCTTTGCTGGCGTcGACGGC |
| 9 | D1 | 550 | ATGCTACTCTTTGCTGGCGTTGACGGC |
| 14 | HK5 | 550 | ATGCTACTtTTTGCCGGCGTTGATGGG |
| 15 | HK8 | 550 | ATGCTACTgTTTGCCGGCGTTGATGGG |
| 12 | HK3 | 550 | ATGCTACTtTTTGCCGGCGTTGATGGG |
| 23 | T3 | 550 | ATGCTACTCTCTTTGCCGGCGTTGATGGG |
| 22 | SW2 | 550 | cTGCTACTCTCTTTGCtGGCGTTGACGGG |
| 17 | IND8 | 550 | ATGCTACTCTCTTTGCCGGCGTTGACGGG |
| 16 | IND5 | 550 | ATGCTACTCTCTTTGCCGGCGTTGACGGG |
| 21 | SA10 | 550 | ATGCTACTCTCTTTGCCGGCGTTGACGGG |
| 20 | S45 | 550 | ATGCTACTCTCTTTGCCGGCGTTGACGGG |
| 25 | US6 | 550 | tTGCTACTCTCTTTGCCGGCGTTGACGGG |
| 13 | HK4 | 550 | ATGCTACTCTCTTTGCCGGCGTTGACGGG |
| 18 | P10 | 550 | ATGCTACTCTCTTTGCCGGCGTTGACGGa |
| 19 | S9 | 550 | ATGCTACTtTTTGCtGGtGTTGACGGg |
| 9-25 | consensus | | aTGCTACTcTTTGCcGGcGTtGAcGGg |

FIGURE 1C-1

| SEQ ID NO: | Isolate | | |
|---|---|---|---|
| 26 | T2 | 1 | GCcCAAGTGAgGAACACCAgccgCggTtTACACATGGTGACtAACGACTGTTCCAATGAGAGCA |
| 27 | T4 | 1 | GCaCAAGTGAAGAACACCActAaCAGCTACACAGTGGTGACcAACGACTGTTCtAATGACAGCA |
| 28 | T9 | 1 | GCCgAAGTGAAGAACACCAGCCAGTACCAGTGGTGACaAATGACTGTTCCAACGACAGCA |
| 29 | US10 | 1 | GtCcAAGTGAAaAACACCAGTACCAGCTATATGGTGACcAATGACTGCTCCAACGACAGCA |
| 26-29 | consensus | | GcccAAGTGAagAACACCAGtacCaGCTACATGGTGACcAA-GACTGtTCcAA-GACAGCA |

| SEQ ID NO: | Isolate | | |
|---|---|---|---|
| 26 | T2 | 62 | TCACcTGGCAGCTCCAaGCCGGCGGTtCTCCACGTCCCCGGGTGTaTCCCGTGtGAGAggct |
| 27 | T4 | 62 | TCACtTGGCAGCTCCAGCCGGCCGGTCCTCCACGTCCCCGGGTGTGTCCCGTGCGAGAAAac |
| 28 | T9 | 62 | TCACcTGGCAACTCCAGGCCGGCCGGTCCTCCACGTCCCCGGGTGCGTCCCGTGCGAGAGAGT |
| 29 | US10 | 62 | TCACtTGGCAACTtgAGGCtGCGGTCCTCCACGTtCCCGGGTGtGTCCCGTGCGAGAaAGT |
| 26-29 | consensus | | TCAC-TGGCA-CTccAgGCcGCGGTcCTCCACGTcCCCGGGTGtgTCCCGTGcGAGA-agt |

FIGURE 1C-2

| SEQ ID NO: | Isolate | | |
|---|---|---|---|
| 26 | T2 | 123 | GGGAAATACATCcCGaTGCTGGATACCGGTcaCACCAAACGTGGCCGTGCGGCAGCCCGGC |
| 27 | T4 | 123 | GGGAAATACATCtCGGTGCTGGATACCGGTtTCACCAAACGTGGCCGTGCGGCAGCCCGGC |
| 28 | T9 | 123 | tGGAAAAcgCgTCgGGTGCTGGATACCGGTCTCgCCAAACGTaGCtGTGCAGCGGCCTGGC |
| 29 | US10 | 123 | gGGAAAtaCaTCtCGGTGCTGGATACCGGTCTCaCCAAAtGTGGCcGTGCAGCGGCCTGGC |
| 26-29 | consensus | | gGGAAAtaCaTCtCGgTGCTGGATACCGGTctCaCCAAACGTGgCcGTGC-GC-GCC-GGC |

| SEQ ID NO: | Isolate | | |
|---|---|---|---|
| 26 | T2 | 184 | GCtCTtACGCAGGGCTTGCGGACGCACATGGACATCGACATGGTTGTGATGTCCGCCACGCTCTGCT |
| 27 | T4 | 184 | GCCCTCACGCAGGGCTTGCGGACGCACATtGACATGGTTGTGATGTCCGCCACGCTCTGCT |
| 28 | T9 | 184 | GCCCTCACGCAGGGCTTGCGGACGCACATGGACATGGTTGTGATGTCCGCCACGCTCTGCT |
| 29 | US10 | 184 | GCCCTCACGCAGGGCTTGCGGACtCACATGGACATGGTcGTGATGTCCGCCACGCTCTGCT |
| 26-29 | consensus | | GCcCTcACGCAGGGCTTGCGGACgCACATcGACATGGTtGTGATGTCCGCCACGCTCTGCT |

FIGURE 1C-3

| SEQ ID NO: | Isolate | | |
|---|---|---|---|
| 26 | T2 | 245 | CTGCcCTcTACGTGGGGACCTCTGCGGGGTGATGCTCGCAGCCCAGATGTTCATtGT |
| 27 | T4 | 245 | CTGCTCTtTACGTGGGGACCTCTGCGGGGTGATGCTCGCAGCCCAGATGTTCATcGT |
| 28 | T9 | 245 | CCGCTCTcTACGTGGGGGAtCTCTGCGGGGTaAATGCTCGCcGCtCAGATGTTCATTaT |
| 29 | US10 | 245 | CCGCTCTtTACGTGGGGGActTCTGCGGtGGGaTgATGCTCGCaGCCCAaATGTTCATTgT |
| 26-29 | consensus | | C-GCtCT-TACGTGGGGAccTCTGCGGcGGGgTgATGCTCGcagCCCAgATGTTCATtgT |

| SEQ ID NO: | Isolate | | |
|---|---|---|---|
| 26 | T2 | 306 | CTCGCCCGgACgcCACTGGTTTGTGCAAGAaTGCAATTGCTCCATCTACCCcGGtACCATC |
| 27 | T4 | 306 | CTCGCCGCAACAtCACTGGTTTGTGCAAGACTGCAATTGCTaTCTACCCTGGcACCATC |
| 28 | T9 | 306 | CTCGCCGCAgCACCACTGGTTTGTGCAGGAATGCAACTGCTCCATtTACCCTGGTACCATC |
| 29 | US10 | 306 | CTCGCCCGcgCCACCACTGgTTTGTGCAGGAATGCAACTGCTCCATcTACCCcGGTACCATC |
| 26-29 | consensus | | CTCGCCCGC-aCacCACTGgTTTGTGCA-GAaTGCAA-TGCTCCATcTACCC-GGtACCATC |

FIGURE 1C-4

| SEQ ID NO: | Isolate | | |
|---|---|---|---|
| 26 | T2 | 367 | ACTGGACACCGTATGGCATGGGACATGATGATGAACTGGTCGCCCACAGCCACCATGATCC |
| 27 | T4 | 367 | ACTGGACACCGTATGGCATGGGAtATGATGATGAACTGGTCGCCCACgGCCACCATGATCC |
| 28 | T9 | 367 | ACTGGACACCGTATGGCATGGGACATGATGATGAACTGGTCGCCCACaaCCACCATGATCt |
| 29 | US10 | 367 | ACcGGgCACCGTATGGCATGGGACATGATGATGAACTGGTCGCCCACggCCACttTGATCc |
| 26-29 | consensus | | ACtGGaCACCGTATGGCATGGGACATGATGATGAACTGGTCGCCCAC-gCCACcatGATCc |

| SEQ ID NO: | Isolate | | |
|---|---|---|---|
| 26 | T2 | 428 | TGGCGTACGCGATGCGCGTTCCCGAGGTCATCaTAGACATCaTcgGCGGGGGCtCACTGGGG |
| 27 | T4 | 428 | TGGCGTACGCGATGCGCGTTCCCGAGGTCATCaTCtTAGACATCgTtAGCGGGGCaCACTGGGG |
| 28 | T9 | 428 | TGGCGTACGCGATGCGCGTTCCCGAGGTCATCATCATAGACATCATcAGCGGaGCtCACTGGGG |
| 29 | US10 | 428 | TGGCGTACGtGATGCGCGTTCCCGAGGTCATCATCATAGACATCATtAGCGGGGCgCAtTGGGG |
| 26-29 | consensus | | TGGCGTACGcGATGCGCGTTCCCGAGGTCATCaTAGACATCaT-aGCGGgGCtCACTGGGG |

FIGURE 1C-5

| SEQ ID NO: | Isolate | | |
|---|---|---|---|
| 26 | T2 | 489 | CGTCATGTTtGGCTTGGCCTACTTCTCTATGCAGGGAGCGTGGGCGAAgGTCaTTGTCATC |
| 27 | T4 | 489 | CGTCATGTTcGGCTTGGCCTACTTCTCTATGCAGGGAGCGTGGGCGAAaGTCGTTGTCATC |
| 28 | T9 | 489 | CGTCATGTTcGGCCTAGCCTACTTCTCTATGCAGGGAGCGTGGGCGAAgGTCGTTGTCATC |
| 29 | US10 | 489 | CGTCtTGTTCGGCtTAGCCTACTTCTCTATGCAGGGAGCGTGGGCGAAaGTCGTTGTCATC |
| 26-29 | consensus | | CGTCaTGTTcGGCtT-GCCTACTTCTCTATGCAGGGAGCGTGGGCGAA-GTCgTTGTCATC |

| SEQ ID NO: | Isolate | | |
|---|---|---|---|
| 26 | T2 | 550 | CTctTGCTGGCtGCTGGGGTGGACGCG |
| 27 | T4 | 550 | CTcTGCTGGCCCGCTGGGGTGGACGCG |
| 28 | T9 | 550 | CTgtTGCTcaCCGCTGGCgTGGACGCG |
| 29 | US10 | 550 | CTtcTGCTagCCGCTGGGgGTGGACGCG |
| 26-29 | consensus | | CTt-TGCTggCcGCTGGgGTGGACGCG |

FIGURE 1D-1

| SEQ ID NO: | Isolate | | |
|---|---|---|---|
| 33 | T8 | 1 | GTGGAAGTtAGaAACAcCAGTTtAGCTACTACGCCACCAATGATTGCTCgAACAACAGCA |
| 30 | DK8 | 1 | GTGGAAGTCAGGAACATCAGTTCcAGCTACTACGCCACCAATGATTGCTCAAACAACAGCA |
| 32 | SW3 | 1 | GTGGAAGTCAGGAACATCAGTTCTAGCTACTACTAtGCCACCAATGATTGCTCAAACAgCAGCA |
| 31 | DK11 | 1 | GTGGAAGTCAGGAACACCAGTTCTAGtTACTACGCCACCAATGATTGCTCAAACAaCAGCA |
| 30-33 | consensus | | GTGGAAGTcAGgAACA-CAGTTctAGCTACTACGCCACCAATGATTGCTCaAACAaCAGCA |

| SEQ ID NO: | Isolate | | |
|---|---|---|---|
| 33 | T8 | 62 | TCACCTGGCAgCTTCACCaACGCAGTTCTCCACCTTCCCGGATGCGTCCCATGTGAGAATGA |
| 30 | DK8 | 62 | TCACCTGGCAACTCACCgACGCAGTTCTCCACCTTCCCGGATGCGTCCCATGTGAGAATGA |
| 32 | SW3 | 62 | TCACCTGGCAACTCACCAACGCAGTcCTCCACCTTCCCGGATGCGTCCCgTGTGAGAATGA |
| 31 | DK11 | 62 | TCACCTGGCAACTCACCAACGCAGTtCTCCACCTTCCCGGATGCGTCCCAtGTGAGAATGA |
| 30-33 | consensus | | TCACCTGGCAaCTCACCaACGCAGTtCTCCACCTTCCCGGATGCGTCCCATGTGAGAATGA |

FIGURE 1D-2

| SEQ ID NO: | Isolate | | |
|---|---|---|---|
| 33 | T8 | 123 | CAATGGCACCTtGCGCTGCTGGATACAAGTaACACCTAAATGTGGCTGTGAAACACCGtGGC |
| 30 | DK8 | 123 | CAATGGCACCCTGCGCTGCTGGATACAAGTGACACCTAAATGTGGCTGTGAAACACCGCGGC |
| 32 | SW3 | 123 | CAATGGCACCCTGCACTGCTGGATACAAGTGACACCTAAATGTGGCTGTGAAACACCGCGGC |
| 31 | DK11 | 123 | tAATGGCACCCTGCACTGCTGGATACAAGTGACACCTAAATGTGGCTGTGAAACACCGCGGC |
| | | 123 | cAATGGCACCCTGCACCCTGCTGGATACAAGTGACACCTAAATGTGGCTGTGAAACACCGCGGC |
| 30-33 | consensus | | cAATGGCACCcTGC-CTGCTGGATACAAGTgACACCTAAATGTGGCTGTGAAACACCGcGGC |

| SEQ ID NO: | Isolate | | |
|---|---|---|---|
| 33 | T8 | 184 | GCACTCaCTTCaCAACCTGGCGAACgCAtGTCGACGTGATCGTAATGGCAGCTACGGTCTGCT |
| 30 | DK8 | 184 | GCACTtACTTCAtAACCTGCGAACACACGTCGACGTGATCGTAATGGCAGCTACGGTCTGCT |
| 32 | SW3 | 184 | GCgCTCACTTCACAACCTGCGAGCACACGTCGATATGATCGTAATGGCAGCTACGGTCTGCT |
| 31 | DK11 | 184 | GCaCTTCACTTCACAACCTGCGAGCACACAtaTaGATATGATtGTAATGGCAGCTACGGTCTGCT |
| 30-33 | consensus | | GCaCTCaCTTCaCAACCTGCCGA-CaCA-gTcGA--TGATCGTAATGGCAGCTACGGTCTGCT |

FIGURE 1D-3

| SEQ ID NO: | Isolate | | |
|---|---|---|---|
| 33 | T8 | 245 | CGGCCCTTGTATGTGGGgGACGTgTGCGGGGCCGTGATGATaGcGTCGCAGGCTtTCATAAT |
| 30 | DK8 | 245 | CGGCCCTTGTATGTGGGGAGACGTaTGCGGGGCCGTGATGATCGTGTCGCAGGCTcTCATAAT |
| 32 | SW3 | 245 | CGGCCCTTGTATGTGGGAGACaTGTGCGGGGCCGTGATGATCGTGTCGCAGGCTTTCATAAT |
| 31 | DK11 | 245 | CGGCCCTTGTATGTGGGAGACgTGTGCGGGGCCGTGATGATCGTGTCGCAGGCTTTCATAgT |
| 30-33 | consensus | | CGGCCCTTGTATGTGGGaGACgTgTGCGGGGCCGTGATGATcGtGTCGCAGGCTtTCATAaT |

| SEQ ID NO: | Isolate | | |
|---|---|---|---|
| 33 | T8 | 306 | ATCGCCaGAAACGCCACAACTTcACCCCAGGAGTGCAACTGTTCCATCTACCAAGGTCATATC |
| 30 | DK8 | 306 | ATCGCCTgAACGCCACAACTTtACCCAGGAGTGCAACTGTTCCATCTACCAAGGTCATATC |
| 32 | SW3 | 306 | ATCGCCAGAACGCCACAACTTtACCCAAGAGTGCAACTGTTCCATCTACCAAGGTCgTATC |
| 31 | DK11 | 306 | ATCGCCAGAACaCCACCACTTtACCCAGGAGTGCAACTGTTCCATCTACCAAGGTCacATC |
| 30-33 | consensus | | ATCGCCaGAAACgCCACaACTTtACCCA-GAGTGCAACTGTTCCATCTACCAAGGTCataTC |

FIGURE 1D-4

```
SEQ ID NO:    Isolate
    33          T8      367  ACCGGCCACCGCATGGCATGGGACATGATGCTgAAACTGGTCACCAACTCTcACCATGATCC
    30          DK8     367  ACCGGCCACCGCATGGCATGGGACATGATGCTAAACTGGTCACCAACTCTTACCATGATCC
    32          SW3     367  ACCGGCCACCGCATGGCATGGGACATGATGCTAAACTGGTCACCAACTCTTACCATGATCC
    31          DK11    367  ACCGGCCACCGCATGGCaTGGGACATGATGCTtAACTGGTCACCAACTCTcACCATGATCC
  30-33       consensus      ACCGGCCACCGCATGGCATGGGACATGATGCTaAACTGGTCACCAACTCT-ACCATGATCC SEQ ID NO:    Isolate
    33          T8      428  TCGCCTAcGCTCGTGTgCCTGAaCTAGtCCTtgAaGTTGTCTTCGGCGGCCATTGGGG
    30          DK8     428  TCGCCTATGCCGTCGTGTTCCTGAGCTAGcCCTccAgGTTGTCTTCGGCGGCCATTGGGG
    32          SW3     428  TtGCCTATGCCGTCGTGTTCCTGAGCTAGTCCTTGAAGTTGTCTTCGGCGGCCATTGGGG
    31          DK11    428  TcGCCTATGCCGcCGTGTTCCTGAGCTAGTCCTTGAAGTGTCTTCGGtGGtCATTGGGG
  30-33       consensus      TcGCCTATGCCGTCGTGTtCCTGAgCTAGtCCTtgAaGTTGTCTTCGGCGGCCATTGGGG
```

FIGURE 1D-5

| SEQ ID NO: | Isolate | | |
|---|---|---|---|
| 33 | T8 | 489 | CGTGGTGTTTGGCTTGGCCTATTTCTCCATGCAAgGAGCGTGGGCCAAAGTCATCGCCATC |
| 30 | DK8 | 489 | CGTGGTGTTTGGCTTGGCCTATTTCTCCATGCAgGGAGCGTGGGCCAAAGTCATTGCCATC |
| 32 | SW3 | 489 | CGTGGTGTTTGGCTTGGCCTATTTCTCCATGCAAgGAGCGTGGGCCAAGGTCATTGCCATC |
| 31 | DK11 | 489 | tGTGGTGTTTGGCTTGGCCTATTTCTCCATGCAgGGAGCGTGGGCCAAGGTCATTGCCATC |
| 30-33 | consensus | | cGTGGTGTTTGGCTTGGCCTATTTCTCCATGCA-GGAGCGTGGGCCAA-GTCATtGCCATC |

| SEQ ID NO: | Isolate | | |
|---|---|---|---|
| 33 | T8 | 550 | CTCCTcCTTGTCGCAGGAGTGGAcGCA |
| 30 | DK8 | 550 | CTCCTtCTTGTCGCAGGAGTGGATGCA |
| 32 | SW3 | 550 | CTCCTgCTTGTCGCAGGAGTGGATGCA |
| 31 | DK11 | 550 | CTCCTtCTTGTaGCAGGAGTGGATGCA |
| 30-33 | consensus | | CTCCTtCTTGTcGCAGGAGTGGAtGCA |

FIGURE 1E-1

| SEQ ID NO: | Isolate | | |
|---|---|---|---|
| 35 | DK12 | 1 | cTAGAGTGTGGCGGAATGTGTCcGGCCTCTAcGTCCTTACCAACGACTGTtCCAATAGCAGTA |
| 36 | HK10 | 1 | CTAGAGTGTGGCGGAATGTGTCTGGCCTCTATGTCCTTACCAACGACTGTcCCAATAGCAGTA |
| 37 | S2 | 1 | CTAGAGTGTGGCGGAATACGTCTGGCCCTCTATGTCCTcACCAACGACTGTTCCAATAGCAGTA |
| 39 | S54 | 1 | CTAGAGTGTGGCGGAATACGTCTGGCCCTCTATaTCCTTACCAACGACTGTTCCAATAGCAGTA |
| 38 | S52 | 1 | CTAGAGTGTGGCGGAATACGTCTGGCCCTCTATgTCCTTACCAACGACTGTTCCAATAGCAGTA |
| 35-39 | consensus | | CTAGAGTGTGGCGGAATAcGTCTgGCCCTCTATgTCCTtACCAACGACTGTtCCAATAGCAGTA |

| SEQ ID NO: | Isolate | | |
|---|---|---|---|
| 35 | DK12 | 62 | TcGTGTATGAGGCCGATGACGTCATTCTGCACACACCTGGCTGTGTACCTTGTGTTCAGGA |
| 36 | HK10 | 62 | TTGTGTATGAGGCCGATGACGTCATTCTGCACACACCTGGCTGTGTACCTTGTGTTCAGGA |
| 37 | S2 | 62 | TTGTGTATGAGGCCGATGACGTtATTCTGCACACACCTGGCTGTGTACCTTGTGTTCAGGA |
| 39 | S54 | 62 | TTGTGTATGAGGCCGATGACGTCATTCTGCACACACCCGGCTGTGTACCTTGTGTTCAGGA |
| 38 | S52 | 62 | TTGTGTATGAGGCCGATGACGTCATTCTGCACACACCCGGCTGTGTACCTTGTGTTCAGGA |
| 35-39 | consensus | | TtGTGTATGAGGCCGATGACGTCATTCTGCACACAcCtGGCTGTGTACCTTGTGTTCAGGA |

FIGURE 1E-2

| SEQ ID NO: | Isolate |     |                                                                |
|------------|---------|-----|----------------------------------------------------------------|
| 35         | DK12    | 123 | CGGCAATACACATCtACGTGCTGGACCTCaGTGACGCCCTACAGTGGCAGTCAGGTACGTCGGA |
| 36         | HK10    | 123 | CGCAATACATCCACGTGCTGGACCTCGGTGACACCTACAGTGGCAGTCAGGTACGTCGGA    |
| 37         | S2      | 123 | CGGtAATACATCCACGTGCTGGACCCCAGTGACACCTACAGTGGCAGTCAGGTAtGTCGGA   |
| 39         | S54     | 123 | CGGCAATACATCCACGTGCTGGACCCCAGTGACACCTACAGTGGCAGTCAGGTACGTCGGA   |
| 38         | S52     | 123 | CGGCAATACATCCAtGTGCTGGACCCCAGTGACACCTACGGTGGCAGTCAGGTACGTCGGA   |
| 35-39      | consensus |   | CGGcAATACATCcACGTGCTGGACCcCaGTGACaCCTACaGTGGCAGTCAGGTAcGTCGGA   |

| SEQ ID NO: | Isolate |     |                                                                |
|------------|---------|-----|----------------------------------------------------------------|
| 35         | DK12    | 184 | GCAACCACCGCTTCGATACGCAGTCATGTGGACCTGCtAGTGGGCGGCCACGATGTGCT     |
| 36         | HK10    | 184 | GCAACCACCGCcTCGATACGCAGTCATGTGGACCTGTTAGTGGGCGGCCACGATGTGCT    |
| 37         | S2      | 184 | GCAACCACCGCTTCGATACGCAGTCATGTGGACCTATTgTTGGGCGGCCACtATGTGCT    |
| 39         | S54     | 184 | GCAACCACCGCTTCGATACGCAGTCATGTGGACCTATTAGTGGGCGGCCACGCTGTGCT    |
| 38         | S52     | 184 | GCAACCACCGCTTCGATACGCAGTCATGTGGACCTATTAGTGGGCGGCCACGCTGTGCT    |
| 35-39      | consensus |   | GCAACCACCGCTTCGATACGCAGTCATGTGGACCTatTagTGGGCGGCCACgaTGTGCT   |

FIGURE 1E-3

| SEQ ID NO: | Isolate | | |
|---|---|---|---|
| 35 | DK12 | 245 | CTGCGCTCTACGTGGGtGATgTGTGTGTGGGGCCGTCTTCCTgGTGGGACAAGCCTTCACGTT |
| 36 | HK10 | 245 | CTGCGCTCTACGTGGGcGATATGTGTGGGGCCCGTCTTCCTCGTGGGACAAGCCTTCACGTT |
| 37 | S2 | 245 | CTGCGCTCTACGTGGGTGATATGTGTGGGGCCCGTCTCTTCGTGGGACAAGCCTTCACGTT |
| 39 | S54 | 245 | CTGCGCTCTATGTGGGTGATATGTGTGGGGCCCGTCTCTTCGTGGGACAAGCCTTCACGTT |
| 38 | S52 | 245 | CTGCGCTCTATGTGGGTGATATGTGTGGGGCCCGTCTTTCTCGTGGGACAAGCCTTCACGTT |
| 35-39 | consensus | | CTGCGCTCTAcGTGGGtGATaTGTGTGGGGCCGTCTTtCTcGTGGGACAAGCCTTCACGTT |

| SEQ ID NO: | Isolate | | |
|---|---|---|---|
| 35 | DK12 | 306 | CAGACCTcGTCGCCATCAAACaGTCCAGACCTGTAACTGCTCGCTGTACCCAGGCCAtCTT |
| 36 | HK10 | 306 | CAGACCgCGTCGCCATCAAACGGTCCAGACCTGTAACTGCTCGCTGTACCCAGGCCAcCTT |
| 37 | S2 | 306 | CAGACCTCGTCGCCATCAAACGGTCCAGACCTGTAACTGCTCGCTGTACCCAGGCCATCTT |
| 39 | S54 | 306 | CAGACCTCGTCGCCATCAAACGGTCCAGACCTGTAACTGCTCGCTGTACCCAGGCCATCTT |
| 38 | S52 | 306 | CAGACCTCGTCGCCATCAAACGGTCCAGACCTGTAACTGCTCGCTGTACCCAGGCCATgTT |
| 35-39 | consensus | | CAGACCtCGTCGCCATCAAACgGTCCAGACCTGTAACTGCTCGCTGTACCCAGGCCAtcTT |

FIGURE 1E-4

| SEQ ID NO: | Isolate | | |
|---|---|---|---|
| 35 | DK12 | 367 | TCAGGACATCGAATGGCTTGGGATATGATGATGAATTGGTCCCCGCtGTGGGTATGGTGG |
| 36 | HK10 | 367 | TCAGGACATCGAATGGCTTGGGATATGATGATGAATTGGTCCCCGCcGTGGGTATGGTGG |
| 37 | S2 | 367 | TCAGGACATCGcATGGCTTGGGATATGATGATGAATTGGTCCCCGCTGTGGGTATGGTGG |
| 39 | S54 | 367 | TCAGGACATCGAATGGCTTGGGATATGATGATGAATTGGTCCCCGCTGTGGGTATGGTGG |
| 38 | S52 | 367 | TCAGGACATCGAATGGCTTGGGATATGATGATGAATTGGTCCCCGCTGTGGGTATGGTGG |
| 35-39 | consensus | | TCAGGACATCGaATGGCTTGGGATATGATGATGAATTGGTCCCCGCtGTGGGTATGGTGG |

| SEQ ID NO: | Isolate | | |
|---|---|---|---|
| 35 | DK12 | 428 | TaGCGCACGTCCTGCGtcTGCCCCAGACCTTGTGTTCGACATAATAGCtGGGGCCCATTGGGG |
| 36 | HK10 | 428 | TGGCGCACGTCCTGCGgTGCCCCAGACCTTGTGTTCGACATAATAGCCGGGGCCCATTGGGG |
| 37 | S2 | 428 | TGGCGCACGTtCTGCGtTGCCCCAGACCgTGTTCGACATAATAGCCGGGGCCCATTGGGG |
| 39 | S54 | 428 | TGGCGCACATCCTGCGATTGCCCCAGACCTTGTTTGACATACTGGCCGGGGCCCATTGGGG |
| 38 | S52 | 428 | TGGCGCACATCCTGCGATTGCCCCAGACCTTGTTTGACATACTGGCCGGGGCCCATTGGGG |
| 35-39 | consensus | | TgGCGCACgTcCTGCG-tTGCCCCAGACCTTGTTcGACATAaTaGCCGGGGCCCATTGGGG |

FIGURE 1E-5

| SEQ ID NO: | Isolate | | |
|---|---|---|---|
| 35 | DK12 | 489 | CATCaTGGCgggCCTAGCCCTATTACTCCATGCAGGGCAACTGGGCCAAGGTCGCTATCATC |
| 36 | HK10 | 489 | CATCTTGGCaGGCCTAGCCCTATTACTCCATGCAGGGCAACTGGGCCAAGGTCGCTATCATC |
| 37 | S2 | 489 | CATCTTGGCGGGCCTAGCCCTATTACTCCATGCAaGGCAACTGGGCCAAGGTCGCTATCATC |
| 39 | S54 | 489 | CATCTTGGCGCGGCCTAGCCCTATTATTCTATGCAGGGCAACTGGGCCAAGGTCGCTATCATC |
| 38 | S52 | 489 | CATCTTGGCGCGGCCCTAGCCCTATTATTCTATGCAGGGCAACTGGGCCAAGGTCGCTATtgTC |
| 35 - 39 | consensus | | CATCtTGGCgGGCCTAGCCCTATTACTcCATGCAgGGCAACTGGGCCAAGGTCGCTATcaTC |

| SEQ ID NO: | Isolate | | |
|---|---|---|---|
| 35 | DK12 | 550 | ATGGTTATGTTTTCAGGaGTCGATGCC |
| 36 | HK10 | 550 | ATGGTTATGTTTTTCAGGGGTCGATGCC |
| 37 | S2 | 550 | ATGGTTATGTTTTTCAGGGGTCGAcGCC |
| 39 | S54 | 550 | ATGATTATGTTTTCAGGGGTCGATGCC |
| 38 | S52 | 550 | ATGATTATGTTTTTCAGGGGTCGATGCC |
| 35 - 39 | consensus | | ATGgTTATGTTTTCAGGgGTCGAtGCC |

FIGURE 1F-1

| SEQ ID NO: | Isolate | |
|---|---|---|
| 43 | Z7 | 1 GTcAACTATCaCAATGCCTCGGGCGTCTATCACATCACCAACGACTGCCCGAACTCGAGCA |
| 42 | Z6 | 1 GTtAACTATCgCAATGCCTCGGGCGTCTATCACGTCACCAACGACTGCCCGAACTCGAGCA |
| 42-43 consensus (Z6) | | GTtAACTATCgCAATGCCTCGGGCGTCTATCACgTCACCAACGACTGCCCGAACTCGAGCA |

| SEQ ID NO: | Isolate | |
|---|---|---|
| 43 | Z7 | 62 TAaTGTATGAGGCCCGAACACCACATCCTACACCTCCCAGGGTGCGTACCCTGTGTGAGGGa |
| 42 | Z6 | 62 TAGTGTATGAGGCCCGAACACCAGATCTTACACCTCCCAGGGTGCtTGcCCCTGTGTGAGGGt |
| 42-43 consensus (Z6) | | TAgTGTATGAGGCCCGAACACCAgATCtTACACCTCCCAGGGTGCtTgCCCTGTGTGAGGGt |

| SEQ ID NO: | Isolate | |
|---|---|---|
| 43 | Z7 | 123 gGGGAACCAGTCACGCTGCTGGGTGGCCCTTACTCCCACCGTGGCGCCTTATATCGGT |
| 42 | Z6 | 123 tGGGAAtCAGTCACGCTGCTGGGTGCCCTTACTCCCACCGTGGCGGtCTTATATCGGT |
| 42-43 consensus (Z6) | | tGGGAAtCAGTCACGCTGCTGGGTGGCCCTTACTCCCACCGTGGCGtCTTATATCGGT |

| SEQ ID NO: | Isolate | |
|---|---|---|
| 43 | Z7 | 184 GCaCCGCTTGAaTCCaTCCGGAGACATGTGGACCTGATGGTAGGCGCtGCTACaGTGTGCT |
| 42 | Z6 | 184 GCTCCGCTTGAcTCCcTCCGGAGACATGTGGACCTGATGGTGGGCGCCTACTGTaTGCT |
| 42-43 consensus (Z6) | | GCtCCGCTTGAcTCCcTCCGGAGACATGTGGACCTGATGGTgGGCGCtACtGTaTGCT |

FIGURE 1F-2

```
SEQ ID NO:   Isolate
    43          Z7    245 CcGCtCTCTACaCATTGGGGACCTGTGCGGTGGCGtATTtTTGGTTGGtCAGAGATGTTtTCTTT
                          ||| ||||||||| |||||||||||||||||| |||| ||||||| ||||||||| ||| |||
    42          Z6    245 CtGCCCTCTACgTTGGAGAtCTGTGCGGTGGTGCATTCTTGGTTGGcCAGATGTTCTCCTT 42-43 consensus (Z6)     CtGCCCTCTACgTTGGAGAtCTGTGCGGTGGTGCATTCTTGGTTGGcCAGATGTTcTCcTT SEQ ID NO:   Isolate
    43          Z7    306 CCAGCCGCGACGCCACTGGACTACGCAGGACTGCAATTGTTCCATCTATGCgGGGCAcgTt
                          ||||||||||||||||||||||||||||||||||||||||||||| ||| |||||||  |
    42          Z6    306 CCAGCCGCGACGCCACTGGACTACGCAGGACTGCAATTGTTCtATCTACGCAGGGCATATC 42-43 consensus (Z6)     CCAGCCGCGACGCCACTGGACTACGCAGGACTGCAATTGTTCtATCTACgCaGGGCAtaTc SEQ ID NO:   Isolate
    43          Z7    367 ACaGGCCACAGaATGGCATGGGACATGATGATGAACTGGAGTCCCACAACCACCtTGgTCC
                          || ||||||||| ||||||||| ||||||||||||||||||||||||||||||||| |||
    42          Z6    367 ACgGGCCACAGgATGGCATGGGACATGATGATGAACTGGAGTCCCACAACCACCCCTGcTtC 42-43 consensus (Z6)     ACgGGCCACAGgATGGCATGGGACATGATGATGAACTGGAGTCCCACAACCACCCTGcTtc SEQ ID NO:   Isolate
    43          Z7    428 TCGCCCAGGTtATGAGGATCCCTAGCACTCaCTGGACCTACTCTCGGTgACCTACTCTCGGTgACCTACTCaCTGGAGGGCACTGGGG
                          ||||||||| ||||||||||||||||| ||||| ||||||||| || ||||||||| ||||||||||||
    42          Z6    428 TCGCCCAGGTcATGAGGATCCCTAGCACTCTGGTaGAtCTACTCGCTGGAGGGCACTGGGG 42-43 consensus (Z6)     TCGCCCAGGTcATGAGGATCCCTAGCACTCTGGTaGAtCTACTCgCTGGAGGGCACTGGGG
```

FIGURE 1F-3

| SEQ ID NO: | Isolate | | |
|---|---|---|---|
| 43 | Z7 | 489 | taTCCTTaTcGGGgTGGCaTACTTCtgCATGCAAGCTAATTGGGCCAAGGTCATtCTGGTC |
| 42 | Z6 | 489 | CgTCCTTGTTGGGtTGGCGTACTTCAGtATGCAAGCTAATTGGGCCAAaGTCATCCTGGTC |
| 42-43 consensus (Z6) | | | cgTCCTTgTtGGGtTGGCgTACTTCaGtATGCAAGCTAATTGGGCCAAaGTCATcCTGGTC |

| SEQ ID NO: | Isolate | | |
|---|---|---|---|
| 43 | Z7 | 550 | CTTTTCCTCTaCGCTGGAGTTGATGCC |
| 42 | Z6 | 550 | CTTTTCCTCTTCGCTGGAGTTGATGCC |
| 42-43 consensus (Z6) | | | CTTTTCCTCTtCGCTGGAGTTGATGCC |

FIGURE 1G-1

| SEQ ID NO: | Isolate | | |
|---|---|---|---|
| 45 | SA1 | 1 | GTtCCCCTACCGgAATGCCTCTGGGGTTTAcCATGTCACCAATGAcTGCCCAAACTCCTCCA |
| 47 | SA5 | 1 | GTCCCCCTACCGgAAATGCCCTCTGGGGTTTATCATGTCACCAATGATTGCCCAAACTCTTCCA |
| 49 | SA7 | 1 | GTCCCCCTACCGgAAATGCCCTCCgGGGTTTATCATGTCACCAATGATTGCCgAACTCTTCCA |
| 46 | SA4 | 1 | GTtCCCCTACCGgAAAACGCCCTCTGGGGTTTATCATGTCACCAATGATTGCCCAAACTCTTCCA |
| 50 | SA13 | 1 | GTTCCCCTACCGgAAAATGCCCTCTGGGGTTTATCATGTCACCAATGATTGCCCAAACTCTTCCA |
| 48 | SA6 | 1 | GTtCCtTACCGgAATGCCCTCTGGGGTgTATCATGTtACCAATGATTGCCCAAACTCTTCCA |
| 45-50 | consensus | | GTtCCcTACCGaAAtGCCTCtGGGGTTtATcATGTCACCAATGATTGCCaAACTCtTCCA |

| SEQ ID NO: | Isolate | | |
|---|---|---|---|
| 45 | SA1 | 62 | TAGTCTACGAGGCTGATAgCCTGATCtTGCACGCACCTGGCTGCGTGCCCTGTGTCAggCA |
| 47 | SA5 | 62 | TAGTCTACGAGGCTGATAACCTGATtCTGCACGCACCTGGTTGCGTGCCCTGTGTCAaGgA |
| 49 | SA7 | 62 | TAGTCTATGAGGCTGAcAACCTGATCCTGCACGCACCTGGTTGCGTGCCCTGTGTCAGaCA |
| 46 | SA4 | 62 | TAGTCTACGAGGCTGATGACCTGATCTTGCAtGCACCTGGTTGCGTGCCCTGTGTCAGGCA |
| 50 | SA13 | 62 | TAGTTtACGAGGCTGATGACCTGATCTTGCAtGCACCTGGTTGCGTGCCCtTGTGTCAGGCA |
| 48 | SA6 | 62 | TcGTCTACGAGGCTGATGACCTGATCTTACACGCACCTGGTTGCGTGCCCTGTGTtAGGCA |
| | | 62 | TaGTCTATgAGGCTGATGACCTGATCCTACACGCACCTGGCTGCGTGCCCTGTGTccGGaA |
| 45-50 | consensus | | TaGTCTAcGAGGCTGAtaaCCTGATc-TgCAcGCACCTGGtTGCGTGCCcTGTGTcaggcA |

FIGURE 1G-2

| SEQ ID NO: | Isolate | | |
|---|---|---|---|
| 45 | SA1 | 123 | AGaTAATGTCAGTAGGTGCTGGGTCCAAATCACCCCCACAcTGTCAGCCCCGAcCtTCGGA |
| 47 | SA5 | 123 | AGgTAATGTCAGTAGGTGCTGGGTCCAAATCACCCCCACATTGTCAGCCCCGAACCTCGGA |
| 49 | SA7 | 123 | AaATAATGTCAGTAGGTGCTGGGTCCAAATCACCCCCACATTGTCAGCCCCGAACCTCGGA |
| 46 | SA4 | 123 | AGATAATGTCAGTAaGTGCTGGGTCCAAATCACCCCCACGtTGTCAGCCCCGAAtCTCGGA |
| 50 | SA13 | 123 | GGgTAATGTCAGTAGGTGCTGGGTCCAgATCACCCCCACACTGTCAGCCCGAGCCTCGGA |
| 48 | SA6 | 123 | GGaTAATGTCAGTAGaTGCTGGGTtCAtATCACCCCCACACTaTCAGCCCGAGCCTCGGA |
| 45-50 | consensus | | agaTAATGTCAGTAggTGCTGGGTcCAaATCACCCCCACa-TgTCAGCCCCGAacTCGGA |

| SEQ ID NO: | Isolate | | |
|---|---|---|---|
| 45 | SA1 | 184 | GCGGTCACGGCTCCTCTCTTCGGAGGGcCGTTGACTACTTAGCGGGAGCTGCTCTCTGCT |
| 47 | SA5 | 184 | GCGGTCACGGCTCCTCTCTTCGGAGGGtCGTTGACTACTTAGCGGGAGGGCTGCCCTCTGCT |
| 49 | SA7 | 184 | GCGGTCACGGCTCCTCTCTTCGGAGGGCCGTTGACTACCTAGCGGGAGGGCTGCCCTCTGCT |
| 46 | SA4 | 184 | GCGGTCACGGCTCCTCTCTTCGGAGGGCCGTTGACTACTTAGCGGGAGGGCTGCCCTCTGCT |
| 50 | SA13 | 184 | GCGGTCACGGCTCCTCTCTTCGGAGGGCCGTTGACTACTTAGCGGGgGGGGCTGCCCTtTGCT |
| 48 | SA6 | 184 | GCGGTCACGGCTCCTCTCTTCGGAGGGCCGTTGAtTACTTgGCGGGaGGGCCGCCCCTgTGCT |
| 45-50 | consensus | | GCGGTCACGGCTCCTCTCTTCGGAGGGCCGTTGACTACTtAgCGGGaGGGCTGCCCTCTGCT |

FIGURE 1G-3

| SEQ ID NO: | Isolate | | |
|---|---|---|---|
| 45 | SA1 | 245 | CCGCACTATACGTCGGcGACGCGTGCGGGGCAGTGTTtcTGGTAGGCCAAATGTTCACCTA |
| 47 | SA5 | 245 | CCGCACTATACGTCGGGGACGCGTGCGGGGCAGTGTTcTTGGTAGGCCAAATGTTCACCTA |
| 49 | SA7 | 245 | CCGCgCTATACGTCGGGGACGCGTGCGGGGCAGTGTTTTTGGTAGGCCAgATGTTCAgCTA |
| 46 | SA4 | 245 | CCGCaCTATACGTCGGGGACGCGTGCGGGGCAGTGTTTTTTGGTAGGCCAAATGTTCACCTA |
| 50 | SA13 | 245 | CCGCGTTATACGTCGGAGACGCGTGCGGGGCAGTGTTTTTGGTAGGtCAAATGTTCACCTA |
| 48 | SA6 | 245 | CCGCGTTATACGTCGGAGACGtGTGCGGGGCAtTGTTTTTTGGTAGGCCAAATGTTCACCTA |
| 45-50 | consensus | | CCGC-cTATACGTCGGgGACGCGTGCGGGGCAgTGTTtTGGTAGGCCAaATGTTCAcCTA |

| SEQ ID NO: | Isolate | | |
|---|---|---|---|
| 45 | SA1 | 306 | TAGGCCCTCGCCAGCATACcACAGTGCAACTGTTCCATTTACAGtGGCCATATC |
| 47 | SA5 | 306 | TAGGCCCTCGCCAGCATACTACGTGCAGGACTGCAACTGTTCCATTTACAGCGGCCATATC |
| 49 | SA7 | 306 | TAGGCCCTCGCCAGCACACTACGGTGCAGGACTGCAACTGTTCCATTTACAGTGGCCATATC |
| 46 | SA4 | 306 | TAGGCCCTCGCCAGCACACTACGGTGCAaGACTGCAAtTGCTtATTTACAGTGGCCATATC |
| 50 | SA13 | 306 | TAGcCCCTCGCCgCgGCATAaTgttGTGCAGGACTGtTCAGGACTGCAACTGCTCCATTTACAGTGGCCAcATC |
| 48 | SA6 | 306 | TAGgCCCTCGCCAGCATgcTacgGTaCAGGACTGCAACTGCTCCATTTACAGTGGCCATATC |
| 45-50 | consensus | | TAGgCCCTCGCCAGCAtactacgGTgCAgGACTGCAACTGtTCCATTTACAGtGGCCAtATC |

FIGURE 1G-4

| SEQ ID NO: | Isolate | | |
|---|---|---|---|
| 45 | SA1 | 367 | ACCGGCCACCGgATGGCtTGGGACATGATGATGAATTGGTCACCTACGACAGCCTTGCTGA |
| 47 | SA5 | 367 | ACCGGCCACCGgAATGGCATGGACATGATGATGAATTGGTCACCTACGACAGCCTTGGTGA |
| 49 | SA7 | 367 | ACCGGCCACCGgAATGGCATGGACATGATGATGAATTGGTCACCTACGACAGCCTTGGTGA |
| 46 | SA4 | 367 | ACCGGCCACCGGATGGCATGGACATGATGATGAATTGGTCACCTACGACAGCCTTGCTGA |
| 50 | SA13 | 367 | ACCGGCCACCGGATGGCATGGACATGATGATGAATTGGTCACCTACAACAGCtTTGGTGA |
| 48 | SA6 | 367 | ActGGCCACCGGATGGCATGGACATGATGATGAATTGGTCACCCgCgACAGCcTTGGTGA |
| 45-50 | consensus | | ACcGGCCACCGgATGGCaTGGGACATGATGATGAATTGGTCACCtaCgACaGCCTTGgTGA |

| SEQ ID NO: | Isolate | | |
|---|---|---|---|
| 45 | SA1 | 428 | TGGCCCAGaTGCTACGGATcCCCCAgtGTGGTCATAgACATCATAGCCGGGGCCACTGGGG |
| 47 | SA5 | 428 | TGGCCCAGgTGCTACGGATTCCCCAaGTGGTCATtGACATCATTGCCGGGGCCACTGGGG |
| 49 | SA7 | 428 | TGGCCCAGTGCTACGGATTCCCCAGGTGGTCATCGACATCATTGCCGGGGCCACTGGGG |
| 46 | SA4 | 428 | TGGCCCAGTGCTACGGATTCCCCAGGTGGTCATCGACATCATTGCCGGGGCCACTGGGG |
| 50 | SA13 | 428 | TGGCCCAGTGtTACGGATTCCCCAGGTGGTCATTGACATCATTGCCGGGGcCCACTGGGG |
| 48 | SA6 | 428 | TGGCCCAaaTGcTACGGATTCCCCAGGTGGTCATTGACATCATTGCCGGGgCCACTGGGG |
| 45-50 | consensus | | TGGCCCAgtTGcTACGGATTCCCCAgtGTGGTCATtGACATCATTGCCGGGGcCACTGGGG |

FIGURE 1G-5

| SEQ ID NO: | Isolate | | |
|---|---|---|---|
| 45 | SA1 | 489 | GGTCTTGTTGCCGcCGCATACTTtGCGTCggCcGCcAACTGGGCTAAGGTaGTGCTGGTt |
| 47 | SA5 | 489 | GGTCTTGTTCGCCGtCGCATACTTCGCGTCGCCGTCAGCGGCTAACTGGGCTAAGGTTGTGCTGGTC |
| 49 | SA7 | 489 | GGTCTTGTTCGCCGCCGCATATTTCGCGTCGCCGTCAGCGGCTAACTGGGCTAAGGTTGTGCTGGTC |
| 46 | SA4 | 489 | GGTCTTGTTtGCCGCCGCATATTTCGCGTCGCCGTCAGCGGCTAACTGGGCTAAGGTTGTGCTGGTC |
| 50 | SA13 | 489 | GGTCTTGTTCGCCGCCGCATACTaCGCGTCGGCGTCGGCGGCTAACTGGGCCAAGGTTGTGCTGGTC |
| 48 | SA6 | 489 | GGTCTTGTTCGCCGtGCATACTtCGCGTCGGCGGCTAACTGGGCtAAGGTTGTGCTGGTC |
| 45-50 | consensus | | GGTCTTGTTcGCCGccGCATAcTtcGCGTC-GCggCtAACTGGGCtAAGGTtgTgCTGGTc |

| SEQ ID NO: | Isolate | | |
|---|---|---|---|
| 45 | SA1 | 550 | CTGTTcCTGTTTGCGGGGGTCGATGGC |
| 47 | SA5 | 550 | CTGTTTCTGTTTGCGGGGGTCGATGGC |
| 49 | SA7 | 550 | TTGTTTCTGTTTGCGGGGGTCGATGCC |
| 46 | SA4 | 550 | TTGTTTCTGTTTGCGGGGGTCGATGCC |
| 50 | SA13 | 550 | cTGTTTCTGTTTGCGGGGGTCGATGCC |
| 48 | SA6 | 550 | tTGTTTCTGTTTGCGGGGGTtGATGCC |
| 45-50 | consensus | | -TGTTtCTGTTTGCGGGGGTCGATGcC |

| SEQ ID NO: | Genotype | | |
|---|---|---|---|
| 30-33 | (IV/2b) | 123 | cAATGCCACCctGCgCTGCTGATACAAGTgACACCTAATGTGGCTGTGAAACACCGCGGC |
| 34 | (2c) | 123 | CGCCAACGTCTCTCGATGTTGGGTGCCGGTTGCCCCAATCTCGCCATAAGTCAACCTGCC |
| 26-29 | (III/2a) | 123 | gGGAAAtaCaTtCGgTGCTGGATACCGGTctCaCCAAAcGTgCCGTGCaGcAGCCCcGGC |
| 35-39 | (V/3a) | 123 | CGGCAATACATCcAcGTGCTGGACCCCaGTGACaCCTACaGTGGCAGTCAGTAGTCGGA |
| 9-25 | (II/1b) | 123 | gaacAActcCTCccgcTCgGCTCcactCTCCCACgCTCgCgCCAGGAAcgccAgC |
| 1-8 | (I/1a) | 123 | GGgTaaCgcctCGaGgTGTTGGGTGgCGgTGaCCCCACgCTGgCCACcAGGGAcGGCAAa |
| 40 | (4a) | 123 | TGGGAACACATCGCGTTGCTGGAcGCCGGTGACGCCTACAGTGGCTGTCGCACACCCGGGC |
| 42-43 | (4c) | 123 | tGGGAAtCAGTCACGCTGCTGGGTGCCCTTACTCCACCGTGGCGGtGtCTTATATCGGT |
| 44 | (4d) | 123 | AGGGAACAAGTCTACATGCTGGTGTCTCTCCACCCCACCGTGCTGCGCAACATCTGAAT |
| 44 | (4b) | 123 | GGAGAATACTTCTCGCTGCTGGGTGCCCTTGACCCCCACTGTGGCCGCCCTATCCCAAC |
| 41 | (5a) | 123 | agaTAAtGTCAGTAggTGCTGGGTcCAaATCACCCCACatTgTCAGCCCCaAccTCGGA |
| 45-50 | (6a) | 123 | CGATGATCGGTCCACCTGTTGGCATGCTGTGACCCCTGCCCACCCTGGCCATACCAAATGCTTCC |
| 51 | | | |

| 1-51 | consensus | | TG TGG    T    T CCC A    T  C |

| SEQ ID NO: | Genotype | | |
|---|---|---|---|
| 30-33 | (IV/2b) | 184 | GCaCTCACTCACAACCTGCGAaCaCAtGTCGAcATGATcGTAATGGCAGCTACGGTCTGCT |
| 34 | (2c) | 184 | GCTCTCACTAAGGCCCTGCTGCGAGCACACACATCATCGATATCATCGTCTGCTACGGTCTCTGTT |
| 26-29 | (III/2a) | 184 | GCcCTcACGCAGGGCTTGCGACGCACATCGACATGGTtGTGATGTCCGCCACGCTCTGCT |
| 35-39 | (V/3a) | 184 | GCAACCACCGCTTCGATACGCCAGTCATGTGGACCTCGATTGCTCGTCGGCCACgaTGTGCT |
| 9-25 | (II/1b) | 184 | gTCcCCACTCAGaCaATACGACgCcACGTCGATCGATTGCTCTGCTCGATCGATcTGCTtGTCgctTTCTgcT |
| 1-8 | (I/1a) | 184 | CTCCCCgCAaCGAaCGCAgCTtCGACGTCACATCGatCTGCTtGTCgGaACGCCACCCTCTgcT |
| 40 | (4a) | 184 | GCTCGCTTGAGTCGTTCCGGCAGCTTGAGCACTTAAtGGACTTAAtGGACTTAATGGCAGCCCACTTTGTGTT |
| 42-43 | (4c) | 184 | GCtCCGCTTGAcTCCCTCCGGAGACGTCACGTGATGGTtGGCGCCGTCGCGGCCGCCGCGCCGTACTgTATGCT |
| 44 | (4d) | 184 | GCTCCGCTTGAGTCTTTGAGATGCCAGGCATGGTCACGTAGACCTGATGGTCGGCCTGACTCTCTGCT |
| 44 | (4b) | 184 | GCACCGTTAGAGTCCATGCCAGGCATGGTCCGGAGGCCGTTGAcTACTTaGCGGaGGgCTGCcCTcTGCT |
| 41 | (5a) | 184 | GCGGTCACGCTCCTCTTCGGATCTtAgCCATGTGGATCTTCTTGCGGCCCGCAGTGGTTTGCT |
| 45-50 | (6a) | 184 | ACGCCCGCAACGGGATTCCGCAGGCATGTGGATCTTCTTGCGGCCCGCAGTGGTTTGCT |
| 51 | | | |

| 1-51 | consensus | | T G    T GA    T G     GC    T TG T |

FIGURE 1H-3

| SEQ ID NO: | Genotype | | |
|---|---|---|---|
| 30-33 | (IV/2b) | 245 | CGGCCTTGTATGTGGaGACgTgTGCGGGGCCGTGATGATcgTgTGTCGCAGGCTtTCATAaT |
| 34 | (2c) | 245 | CTGCCCTTTATGTGGTGGGGACGTGTGGCCGCGTGATGCTGGCGCTCAGGTCGTCGTCGT |
| 26-29 | (III/2a) | 245 | CcGCtCTtTACGTGGGGACcTCTGCGCGGCgGGTgATGCTCGCaGCcCAgATGTTCAtTgT |
| 35-39 | (V/3a) | 245 | CTGCGCTCTAcGTGGGtGATATGTGTGGGGCCGTTCTgTGGGACAAGCCTTCACGTT |
| 9-25 | (II/1b) | 245 | CCGctATGTAcGTGGGggAtCTcTGCGCGGaTCTGTtcTCCTCgTcTCCAGcTGTTCACctT |
| 1-8 | (I/1a) | 245 | CGGCCCTCTAcGTGGGGGACTGTGCGGGGTCTGTtCTGTGGtCAaCTGTTcACctT |
| 40 | (4a) | 245 | CTGCCCCTCTATGTGGGACCTCGCGGAGGTGCCTTCCTGATGGGCAGATGATCACTTT |
| 42-43 | (4c) | 245 | CtGCCCTCTACgTTGGaGAgATCTGTGCGGTgGTgCATTCTTGgTTGGcCAGATGTTcTCCTT |
| 44 | (4d) | 245 | CCGCCCTCTACATCGGAGACGTGTGTGTGGTGTTCTTGGTTCGTCAACTGTTCACCTT |
| 41 | (4b) | 245 | CCGCCTTCTACATTGGAGATCTGTGTGGAGGCGTCTTCCTAGTGGGCCAGCTGTTCGACTT |
| 45-50 | (5a) | 245 | CCGCgTATACGTCGGGACGCGTGCGGGCAGTGTTtTGGTAGGcCAaATGTTCAcCTA |
| 51 | (6a) | 245 | CATCCCTGTACATCGGGGACCTGTGTGCCTCTCTCTTTTGGCGGACACTATTCACCTT |
| 1-51 | consensus | | C T TA T GG GA TG GG T T CA T |

| SEQ ID NO: | Genotype | | |
|---|---|---|---|
| 30-33 | (IV/2b) | 306 | ATCGCCaGAACgCCACaACTTtACCCAagAGTGCAACTGTTCCATCTACCAAGGTCatATC |
| 34 | (2c) | 306 | GTCGCCACACACCATACGTTTGTCCAGGAATGCAACTGTTCCATATACCCGGCCGCATT |
| 26-29 | (III/2a) | 306 | CTCGCCGCaaCacCACTGTTGTTGTGCAAgAATGCAAtTGCTCCAtCTACCCtGGtACCATC |
| 35-39 | (V/3a) | 306 | CAGACCTCGTCGCCATCAAACgTCCAGACCTGTAACTGCTCGCTGTACCCAGGCCATCTT |
| 9-25 | (II/1b) | 306 | cTCgCCTCGCcCAGgCGCCGGCAtgaGACagtaACagCCAAgACTGTtCaaTCTATCCCGGcCacgTa |
| 1-8 | (I/1a) | 306 | cTTCTCCCAGgCGCCACTGGACTGGACAACGCCAaGACTGCAAGAGTGCAAtTGTTCtAtCTAtCCCgGCCATATa |
| 40 | (4a) | 306 | TCGGCCGCGTCGCCACTGGACTGGACGAGTGCAATTGTTCCATCTACACTGCCATAC |
| 42-43 | (4c) | 306 | CCAGGCCGCGACGCCACTACGCCGGCACTGGACTGCAATTGTTCCATCTAcGCaGGCAtaTC |
| 44 | (4d) | 306 | CCAACCTCGCCGCCGCCACTGGACTGGACTGCAACTGTTCAACTGCTCCATCTATCCACCATC |
| 41 | (4b) | 306 | CCGACCGCGCCGCCGCCAGCATacgGTgCAGGACTGCAATTACAGTGGCCATATC |
| 45-50 | (5a) | 306 | TAGgCCTCGCCaGCAGCAtactacgGTGCAGGACTGCAACTGTTCaTTACAGTGGCCATATC |
| 51 | (6a) | 306 | TCAGCCCGCCGTCATTGGACTGTGCAAGACTGTGCAAGACTGCAACTGCTCCATCTATACAGGCCACGTC |
| 1-51 | consensus | | CC C CA TG AA TG TC T TA GG T |

FIGURE 1H-4

| SEQ ID NO: | Genotype |  |
|---|---|---|
| 30-33 | (IV/2b) | 367 ACCGGCCACCGCATGGCAGTGGACACATGATGCTaAACTGGTCACCAACTCTtACCATGATCC |
| 34 | (2c) | 367 ACGGGACACCGCATGGCTTGGGATATGATGATGAACTGGTCGCCACTACCACCATGCTCC |
| 26-29 | (III/2a) | 367 ACtGGaCACCGTATGGCATGGACATGATGATGATGAACTGGTCGCCACggCCACaTGATCc |
| 35-39 | (V/3a) | 367 TCAGGACATGCaATGGCTTGGaGATATGATGATGATGAATTGGTCCCCGCtGTGGGTATGGTGG |
| 9-25 | (II/1b) | 367 tCAGGTCACCGCATGGCtTGGaTATGATGATGAACTGGTCaCtACAgCaGCccTaGTgg |
| 1-8 | (I/1a) | 367 ACGGGtCACCGCATGGCATGGGATATGATGATGATGAACTGGTCCCCtACgaCgGCgCtGGTag |
| 40 | (4a) | 367 ACCGGCCACAGGATGGCGTGGACATGATGATGATGAACTGGAGCCCTACCACCACTCTGCTCC |
| 42-43 | (4c) | 367 ACgGGCCACAGGATGGCATGGACATGATGATGATGAACTGGAGTCCCACAACCACCCTgCTtC |
| 44 | (4d) | 367 ACAGGACACAGGAATGCTTGGGACATGATGATGATGAATTGGAGCCCCACTGCGACGCTGGTCC |
| 41 | (4b) | 367 TCGGGCCACAGGATGGCCTGGGACATGATGATGATGAACTGGAGCCCTACCAGCGCGCTGATTA |
| 45-50 | (5a) | 367 ACCGGCCACCGGATGCGATGGCATGGACATGATGATGATGGTCACCtaCgACaGCCTTGgTGA |
| 51 | (6a) | 367 ACCGGCCACAGGATGGCTTGGGACATGATGATGATGAACTGGTCACCCACCAACCACTCTGGTCC |
| 1-51 | consensus | C GG CA G ATGGC TGGGA ATGATG T AA TGG CC C T T |

| SEQ ID NO: | Genotype |  |
|---|---|---|
| 30-33 | (IV/2b) | 428 TcGCCTAtGCcGCtcCGTGTtCCTGAgCTAGtCCTtgAaGTtGTCTTCGGCGGCCATTGGGG |
| 34 | (2c) | 428 TGGCGTACTTGGTGCGCATCCGGAAGTCATCTTGGATATTGTTACAGGAGTCATTGGGG |
| 26-29 | (III/2a) | 428 TGGCGTACGcGATGCGCGTTCCCGAGGTCATCaTAGACATCaTTaGCCGGGGCtCACTGGGG |
| 35-39 | (V/3a) | 428 TgGCGCACgTcCTGCGtTTGCCCCAGACCtTGTtCGACATAaTaGCcGGGGCCCATTGGGG |
| 9-25 | (II/1b) | 428 TaTCGCAgtTaCTCCGgaTCCaCAAGCTgTCGTGGAcaTGGTggCgGGGCCACTGGGG |
| 1-8 | (I/1a) | 428 TaGCtCAGCTGCTCcGaTCCtCgCAagCCATCTTGaACATGGTTGCGCCACTGGGG |
| 40 | (4a) | 428 TCGCCCAGATCATGAGGGTCCCCACAGCCTTTCTCGGTaGAtCTACTCgCTGGAGGGCACTGGGG |
| 42-43 | (4c) | 428 TCGCCCAGGTCATGAGGATCCCAGGCGCCATGTCCTAGTGACTCgCTTGCAGGCGGCCACTGGGG |
| 44 | (4d) | 428 TCGCCCAACTTATGAGGATCCCGATCCCTCTATCCTAGGTGACTGACTTGCTCACCGGTCACTGGGG |
| 41 | (4b) | 428 TGGCTCAGATCTTACGGATCCGGATtCCCCAGGTGGTCATtGACATCATtGCCGGGGCACTGGGG |
| 45-50 | (5a) | 428 TGGCCCAGtTGCTACGGATCCTGAGGGTACCTGAGATTTGTGCGAGTGTGATATTGGTGGCCATTGGGG |
| 51 | (6a) | 428 TATCTAGCATCTTGAGGGTACCTGAGATTTGTGCGAGTGTGATATTGGTGGCCATTGGGG |
| 1-51 | consensus | T C G T CC T T GG G CA TGGGG |

FIGURE 1H-5

| SEQ ID NO: | Genotype | | |
|---|---|---|---|
| 30-33 | (IV/2b) | 489 | cGTGGGTGTTTGGCTTGGCCTATTTCTCCATGCAGgGAGCGTGGGCCAAaGTCATtGCCATC |
| 34 | (2c) | 489 | TGTAATGTTTGGCCCTCGCTTGGCCTTACTTCTCCATGCAGGGATCGTGGGCGAAGGTCATCGTTATC |
| 26-29 | (III/2a) | 489 | CGTCaTGTTcGGCTtaGCCTAGCCTACTTCTTATGCAGGGAGCGTGGGCGAAaGTCGTTGTCATC |
| 35-39 | (V/3a) | 489 | CATCtTGGCGgGCGGGCCTtGCCTAGCTATTACTCCATCCATGGCCAACTGGGCTCAAGGTCGTATcaTC |
| 9-25 | (II/1b) | 489 | agTCCTgGCGGGGCCTtGCCCTACTATCCATGGtgGGgAACTGGGCTAAGGTttTgATTGTg |
| 1-8 | (I/1a) | 489 | AGTCCTaGCGGGCATAGCGTATTTCTCCATGGtGGGgAACTGGGCGAAGGTCCTggTaGTg |
| 40 | (4a) | 489 | CGTCCTCGCGGGCTTGGCGGCTTCAGCATGCAAGGCAAGCAATTGGGCCAAGGTAGTCCTGGTC |
| 42-43 | (4c) | 489 | cgTCCTTgTTgGGtTGGcGTACTTCagTaTGCAAGCTAATTGGGCCAAaGTCATcCTGGTC |
| 44 | (4d) | 489 | CATTCTGGTTGGCATAGCGTACTTCAGCATGCAAGCTAATTGGGCCAAGGTTATCCTGGTC |
| 41 | (4b) | 489 | AGTTCTCTGGTCgCGGCTCTAGCTTTCTTCAGCATGCAGAGTAACTGGGCGAAGGTCATCCTGGTC |
| 45-50 | (5a) | 489 | GGTCTTGTTcGCCGCCcGCCATaCTtcGCGTCGGCTaACTGGGCtAAGGTTgTgCTGGTc |
| 51 | (6a) | 489 | GATACTACTAGCCGTTGCCTACTTTGGCATGGCTGGCAACTGGCTAAAAGTTCTGGCTGTT | consensus   T     G     GC T    T                      TGG   AA GT      T

| SEQ ID NO: | Genotype | | |
|---|---|---|---|
| 30-33 | (IV/2b) | 550 | CTCCTtCTTGTcGCAGGAGTGGAtGCA |
| 34 | (2c) | 550 | CTCCTGCTGACTGCTGCTGGGGTGGAGGCG |
| 26-29 | (III/2a) | 550 | CTtCTGCTggCcGCTggGGTGGACGCG |
| 35-39 | (V/3a) | 550 | ATGgTTATGTTTTCAGGgGTCGAtGCC |
| 9-25 | (II/1b) | 550 | aTGCTACTcTTTGCcGGCGTtGAcGGg |
| 1-8 | (I/1a) | 550 | CTGtGCTGCTGTTgCCGGCGTcGAtGCG |
| 40 | (4a) | 550 | CTTTTCCTCTTGCTGTTGCCGCGGTAGACGCC |
| 42-43 | (4c) | 550 | CTTTTCCTtCTtCGCTGGAGTTGATGCC |
| 44 | (4d) | 550 | CTGTTCCTCTTTGCTcGCTGGAGTCGACGCT |
| 41 | (4b) | 550 | CTGTTCCTCTTTGCCGGGGTCGAGGGA |
| 45-50 | (5a) | 550 | CTATTCCTCTTTGCGGGGGTCGATGcC |
| 51 | (6a) | 550 | tTGTTtCTGTTTGCGGATGCC |
| | | 550 | CTGTTCCTATTTGCAGGGTTGAAGCA | consensus   T   T    T    C  GG GT GA G

FIGURE 2A-1

| SEQ ID NO: | Isolate | | |
|---|---|---|---|
| 56 | S14 | 1 | YQVRNSTGLYHVTNDCPNSSIVYEtADaILHaPGCVPCVREGNtSRCWVAMTPTVATRDGK |
| 52 | DK7 | 1 | YQVRNSTGLYHVTNDCPNSSIVYEAADAILHTPGCVPCVREGNvSRCWVAMTPTVATRDGK |
| 59 | US11 | 1 | YQVRNSTGLYHVTNDCPNSSIVYEAADAILHTPGCVPCVREGNaSRCWVAMTPTVATRDGK |
| 55 | DR4 | 1 | YQVRNSTGLYHVTNDCPNSSIVYEAADAILHTPGCVPCVREGNtSRCWVAVTPTVATRDGK |
| 54 | DR1 | 1 | HQVRNSTGLYHVTNDCPNSSIVYEAADAILHaPGCVPCVREGNASRCWVAVTPTVATRDGK |
| 53 | DK9 | 1 | HQVRNSTGLYHVTNDCPNSSIVYEAADAILHSPGCVPCVREGNASKCWVAVAPTVATRDGK |
| 58 | SW1 | 1 | YQVRNSSGLYHVTNDCPNSSIVYEAADAILHSPGCVPCVREdgApKCWVAVAPTVATRDGK |
| 57 | S18 | 1 | YQVRNSSGLYHVTNDCPNSSIVYETADAILHSPGCVPCVREgnAsrCWVpVAPTVATRDGK |
| | | 1 | YQVRNStGLYHVTNDCPNSSIVYETADtILHSPGCVPCVREgnasrCWVavtPTVATRDGK |
| 52-59 | consensus | | yQVRNStGLYHVTNDCPNSSIVYEaADaILH-PGCVPCVREgnasrCWVavtPTVATRDGK |

FIGURE 2A-2

| SEQ ID NO: | Isolate | | |
|---|---|---|---|
| 56 | S14 | 62 | LPatQLRRyIDLLVGSATLCSALYVGDLCGSVFLVGQLFTFSPRRlWTTQdCNCSIYPGHI |
| 52 | DK7 | 62 | LPTaQLRRHIDLLVGSATLCSALYVGDLCGSVFLVGQLFTFSPRRHWTTQGCNCSIYPGHI |
| 59 | US11 | 62 | LPTTQLRRHIDLLVGSATLCSALYVGDLCGSVFLVGQLFTFSPRRHWTTQGCNCSIYPGHI |
| 55 | DR4 | 62 | LPTTQLRRHIDLLVGSATLCSALYVGDLCGSVFLVGQLFTFSPRhHWTTQDCNCSIYPGHI |
| 54 | DR1 | 62 | LPTTQLRRHIDLLVGSATLCSALYVGDLCGSVFLVGQLFTFSPRRHWTTQDCNCSIYPGHI |
| 53 | DK9 | 62 | LPATQLRRHIDLLVGSATLCSALYVGDLCGSVFLVGQLFTFSPRRHWTTQDCNCSIYPGHI |
| 58 | SW1 | 62 | LPATQLRRHIDLLVGSATLCSALYVGDLCGSVFLVSQLFTFSPRRHWTTQDCNCSIYPGHI |
| 57 | S18 | 62 | LPATQLRRHIDLLVGSATLCSALYVGDLCGSVFLVSQLFTiSPRRHWTTQDCNCSIYPGHI |

52-59 consensus LP-tQLRRhIDLLVGSATLCSALYVGDLCGSVFLVgQLFtfSPRrhWTTQdCNCSIYPGHI

FIGURE 2A-3

| SEQ ID NO: | Isolate | |
|---|---|---|
| 56 | S14 | 123 TGHRMAWDMMMNWSPTTALVVAQLLRIPQAILDMIAGAHWGVLAGIAYFSMVGNWAKVLVV |
| 52 | DK7 | 123 TGHRMAWDMMMNWSPTTALVVAQLLRIPQAILDMIAGAHWGVLAGIAYFSMVGNWAKVLVV |
| 59 | US11 | 123 TGHRMAWDMMMNWSPTaALVVAQLLRIPQAILDMIAGAHWGVLAGIAYFSMVGNWAKVLVV |
| 55 | DR4 | 123 TGHRMAWDMMMNWSPTTALVVAQLLRIPQAILDMIAGAHWGVLAGIAYFSMVGNWAKVLVV |
| 54 | DR1 | 123 TGHRMAWDMMMNWSPTTALVMAQLLRIPQAILDMIAGAHWGVLAGIAYFSMVGNWAKVLVV |
| 53 | DK9 | 123 TGHRMAWDMMMNWSPTaALVMAQLLRIPQAILDMIAGAHWGVLAGIAYFSMVGNWAKVVVV |
| 58 | SW1 | 123 TGHRMAWDMMMNWSPTTALVvAQLLRIPQAVLDMIAGAHWGVLAGIAYFSMVGNWAKVLiV |
| 57 | S18 | 123 TGHRMAWDMMMNWSPTTALViAQLLRvPQAVLDMIAGAHWGVLAGIAYFSMaGNWAKVLlV |
| 52-59 | consensus | TGHRMAWDMMMNWSPTtALVvAQLLRiPQAiLDMIAGAHWGVLAGIAYFSMvGNWAKVlvv |

FIGURE 2A-4

| SEQ ID NO: | Isolate | | |
|---|---|---|---|
| 56 | S14  | 184 | LLLFAGVDA |
| 52 | DK7  | 184 | LLLFAGVDA |
| 59 | US11 | 184 | LLLFAGVDA |
| 55 | DR4  | 184 | LLLFAGVDA |
| 54 | DR1  | 184 | LLLFAGVDA |
| 53 | DK9  | 184 | LLLFtGVDA |
| 58 | SW1  | 184 | LLLFsGVDA |
| 57 | S18  | 184 | LLLFaGVDA |
| 52-59 | consensus | | LLLFaGVDA |

FIGURE 2B-1

| SEQ ID NO: | Isolate | | |
|---|---|---|---|
| 75 | T10 | 1 | YEVRNVSGmYHVTNDCSNSSIVfEAaDlIMHTPGCVPCVREgNsSRCWVALTPTLAARNtS |
| 62 | DK1 | 1 | YEVRNVSGvYHVTNDCSNSSIVYEAvDvIMHTPGCVPCVRENNhSRCWVALTPTLAARNAS |
| 64 | HK4 | 1 | hEVhNVSGiYHVTNDCSNSSIVYEAADMIMHTPGCVPCVRENNSSRCWVALTPTLAARNAS |
| 76 | US6 | 1 | YEVRNVSGmYHVTNDCSNSSIVYEAADMIMHTPGCVPCVRENNSSRCWVALTPTLAARNAS |
| 68 | IND8 | 1 | YEVRNVSGVYHVTNDCSNSSIVYEAADMIMHTPGCVPCVREGNfSsCWVALTPTLAARNAS |
| 67 | IND5 | 1 | YEVRNVSGVYHVTNDCSNSSIVYEAADMIMHTPGCVPCVREGNSSRCWVALTPTLAARNAS |
| 73 | SW2 | 1 | YEVRNVSGVYHVTNDCSNSSIVYETADMIMHTPGCVPCVREaNSSRCWVALTPTLAARNtS |
| 63 | HK3 | 1 | YEVRNVSGIYHVTNDCSNSsvVYETADMIMHTPGCVPCVRENNSSRCWVALTPTLAARNVS |
| 66 | HK8 | 1 | YEVRNVSGIYHVTNDCSNSSIVYETADMIMHTPGCmPCVRENNSSRCWVALTPTLAARNVS |
| 61 | D3 | 1 | YEVRNVSGVYqVTNDCSNSSIVYETADMIMHTPGCVPCVREdNSSRCWVALTPTLAARNsS |
| 74 | T3 | 1 | YEVRNVSGVYyYVTNDCSNSSIVYETADMIMHTPGCVPCVREsNSSRCWVALTPTLAARNAS |
| 65 | HK5 | 1 | YEVRNVSGVYHVTNDCSN1SIVYETtDMIMHTPGCVPCVRENNSSRCWVALaPTLAARNAS |
| 71 | S45 | 1 | YEVRNVSGaYHVTNDCSNSSIVYEAvDvI1HTPGCVPCVRENNSSRCWVALTPTLAARNSS |
| 72 | SA10 | 1 | YEVRNVSGmYHVTNDCSNSSIVYEAADMIMHTPGCVPCVRENNSSRCWVALTPTLAARNSS |
| 69 | P10 | 1 | YEVRNVSGVYHVTNDCSNSSIVYEAADMIMHTPGCVPCVRENNSSRCWVALTPTLAARNSS |
| 60 | D1 | 1 | YEVRNVSGVYHVTNDCSNSSIVYEtADMIMHTPGCVPCVREdNSSRCWVALTPTLAARNgn |
| 70 | S9 | 1 | YEVRNVSGaYHVTNDCSNSSIVYEaADvIMHTPGCVPCVqEgNSSqCWVALtPTLAARNat |
| 60-76 | consensus | | yEVrNVSGvYhVTNDCSNsSiVyEaaDmImHTPGCvPCVrEnNsSrCWVALtPTLAARNas |

FIGURE 2B-2

| SEQ ID NO: | Isolate | | |
|---|---|---|---|
| 75 | T10 | 62 | vPTTTIRRHVDLLVGAAAFCSAMYVGDLCGSVFLVSQLFTFSPRRHETlQDCNCSIYPGH1 |
| 62 | DK1 | 62 | IPTTTIRRHVDLLVGAAAFCSAMYVGDLCGSVFLVSQLFTFSPRRHETaQDCNCSIYPGHV |
| 64 | HK4 | 62 | IPTTTIRRHVDLLVGAAAFCSAMYVGDLCGSVFLVSQLFTFSPRRHETVQDCNCSIYPGHV |
| 76 | US6 | 62 | VPTTTIRRHVDLLVGAAtFCSAMYVGDLCGSVFLiSQLFTFSPRqHETVQDCNCSIYPGHV |
| 68 | IND8 | 62 | VPTTTIRRHVDLLVGAAAFCSAMYVGDLCGSVFLVSQLFTFSPRRHETVQDCNCSIYPGHV |
| 67 | IND5 | 62 | VsTTTIRhHVDLLVGAAAFCSAMYVGDLCGSVFLVSQLFTFSPRRHETVQDCNCSIYPGHV |
| 73 | SW2 | 62 | VPTTTIRRHVDLLVGAAAFCSvMYVGDLCGSVFLVSQLFTFSPRRHETVQDCNCSIYPGHV |
| 63 | HK3 | 62 | VPTTTIRRHVDLLVGAAAFCSAMYVGDLCGSVFLVSQLFTFSPRRHETVQDCNCSIYPGHV |
| 66 | HK8 | 62 | VPTTTIRRHVDLLVGAAAFCSAMYVGDLCGSVFLVSQLFTFSPRRHETVQDCNCSIYPGHV |
| 61 | D3 | 62 | VPTTTIRRHVDLLVGAAAFCSAMYVGDLCGSVFLVSQLFTFSPRRHETVQeCNCSIYPGHV |
| 74 | T3 | 62 | VPTkTIRRHVDLLVGAAAFCSAMYVGDLCGSVFLVSQLFTFSPRRHETVQDCNCSIYPGHV |
| 65 | HK5 | 62 | VPTTaIRRHVDLLVGAAAFCSAMYVGDLCGSVFLVSQLFTFSPRRHETVQDCNCSIYPGHV |
| 71 | S45 | 62 | VPTTTIRRHVDLLVGAAAFCSAMYVGDLCGSVFLVSQLFTFSPRRHETVQDCNCSIYPGHV |
| 72 | SA10 | 62 | VPTTTIRRHVDLLVGAAAFCSAMYVGDLCGSV1LVSQLFTFSPRRyETVQDCNCSIYPGrV |
| 69 | P10 | 62 | VPTTAIRRHVDLLVGAAAFCSAMYVGDLCGSVFLVSQLFTFSPRRHwTVQDCNCSIYPGHV |
| 60 | D1 | 62 | VPTTAIRRHVDLLVGAAAFCSAMYVGDLCGSVFLISQLFT1SPRRHETVQeCNCSIYPGHV |
| 70 | S9 | 62 | VPTTtIRRHVDLLVGAAvFCSaMYVGDLCGSVFLISQLFTiSPRRHETVQnCNCSIYPGHV |
| 60-76 | consensus | | vpTttIRrHVDLLVGAAaFCSaMYVGDLCGSVfLvSQLFTfSPRrheTvQdCNCSiYPGhv |

FIGURE 2B-3

| SEQ ID NO: | Isolate | | |
|---|---|---|---|
| 75 | T10 | 123 | SGHRMAWDMMMNWSPTTALVvSQLLRIPQAVmDMVtGAHWGVLAGLAYYSMAGNWAKVLIV |
| 62 | DK1 | 123 | SGHRMAWDMMMNWSPTTALV1SQLLRIPQAVvDMVAGAHWGVLAGLAYYSMAGNWAKVLIV |
| 64 | HK4 | 123 | SGHRMAWDMMMNWSPTAALVVSQLLRIPQAVMDMVAGAHWGVLAGLAYYSMVGNWAKVLIV |
| 76 | US6 | 123 | SGHRMAWDMMMNWSPTAALVVSQLLRIPQAVMDMVAGAHWGVLAGLAYYSMVGNWAKVLIV |
| 68 | IND8 | 123 | SGHRMAWDMMMNWSPTAALVVSQLLRIPQAVMDMVAGAHWGILAGLAYYSMVGNWAKVLIV |
| 67 | IND5 | 123 | SGHRMAWDMMMNWSPTAALVVSQLLRIPQAVMDMVAGAHWGILAGLAYYSMVGNWAKVLIV |
| 73 | SW2 | 123 | SGHRMAWDMMMNWSPTAALVVSQLLRIPQAVMDMVAGAHWGVLAGLAYYSMVGNWAKVLIV |
| 63 | HK3 | 123 | SGHRMAWDMMMNWSPTAALVVSQLLRIPQAVMDMVAGAHWGVLAGLAYYSMVGNWAKVLIV |
| 66 | HK8 | 123 | SGHRMAWDMMMNWSPTtALVVSQLLRIPQAiVDMVAGAHWGVLAGLAYYSMVGNWAKVLIV |
| 61 | D3 | 123 | SGHRMAWDMMMNWSPTaALVVSQLLRIPQAVVDMVAGAHWGVLAGLAYYSMVGNWAKVLIV |
| 74 | T3 | 123 | TGHRMAWDMMMNWSPTTALVVSQLLRIPQAVVDMVAGAHWGVLAGLAYYSMVGNWAKVLIV |
| 65 | HK5 | 123 | TGHRMAWDMMMNWSPTTALVVSQLLRIPQAVVDMVAGAHWGVLAGLAYYSMVGNWAKVLIV |
| 71 | S45 | 123 | TGHRMAWDMMMNWSPTTALVVSQLLRIPQAVVDMVAGAHWGVLAGLAYYSMVGNWAKVLIV |
| 72 | SA10 | 123 | TGHRMAWDMMMNWSPTTALVVSQLLRIPQAIVDMVAGAHWGVLAGLAYYSMVGNWAKVLIV |
| 69 | P10 | 123 | sGHRMAWDMMMNWSPTTALVVSQLLRIPQAIlDvVAGAHWGVLAGLAYYSMVGNWAKVLIV |
| 60 | D1 | 123 | TGHRMAWDMMMNWSPTTALVVSQLLRIPQAVMDMVAGAHWGVLAGLAYYSMVGNWAKVLIV |
| 70 | S9 | 123 | TGHRMAWDMMMNWSPTTALVVSQLLRIPQAVMDMVAGAHWGVLAGLAYYSMVGNWAKVLIV |
| 60-76 | consensus | | sGHRMAWDMMMNWSPTaALVvSQLLRiPQAvvDmVaGAHWGvLAGLAYYSMvGNWAKVLIV |

FIGURE 2B-4

| SEQ ID NO: | Isolate | | |
|---|---|---|---|
| 75 | T10 | 184 | mLLFAGVDG |
| 62 | DK1 | 184 | lLLFAGVDG |
| 64 | HK4 | 184 | mLLFAGVDG |
| 76 | US6 | 184 | lLLFAGVDG |
| 68 | IND8 | 184 | MLLFAGVDG |
| 67 | IND5 | 184 | MLLFAGVDG |
| 73 | SW2 | 184 | MLLFAGVDG |
| 63 | HK3 | 184 | MLLFAGVDG |
| 66 | HK8 | 184 | MLLFAGVDG |
| 61 | D3 | 184 | MLLFAGVDG |
| 74 | T3 | 184 | lLLFAGVDG |
| 65 | HK5 | 184 | MLLFAGVDG |
| 71 | S45 | 184 | MLLFAGVDG |
| 72 | SA10 | 184 | MLLFAGVDG |
| 69 | P10 | 184 | MLLFAGVDG |
| 60 | D1 | 184 | MLLFAGVDG |
| 70 | S9 | 184 | MLLFAGVDG |
| 60-76 | consensus | | mLLFAGVDG |

FIGURE 2C-1

| SEQ ID NO: | Isolate | | |
|---|---|---|---|
| 77 | T2 | 1 | AQVrNTsrgYMVTNDCSNeSITWQLQAAVLHVPGCiPCErlGNTSRCWIPVtPNVAVRQPG |
| 78 | T4 | 1 | AQVKNTtnSYMVTNDCSNDSITWQLQAAVLHVPGCVPCEktGNTSRCWIPVSPNVAVRQPG |
| 79 | T9 | 1 | AeVKNTSTSYMVTNDCSNDSITWQLQAAVLHVPGCVPCErVGNaSRCWIPVSPNVAVRPG |
| 80 | US10 | 1 | vqVKNTSTSYMVTNDCSNDSITWQLeAAVLHVPGCVPCEkVGNtSRCWIPVSPNVAVQRPG |
| 77-80 | consensus | | aqVkNTstsYMVTNDCSNdSITWQLqAAVLHVPGCvPCE-vGNtSRCWIPVsPNVAV--PG |

| SEQ ID NO: | Isolate | | |
|---|---|---|---|
| 77 | T2 | 62 | ALTQGLRTHIDMVVMSATLCSALYVGDLCGGVMLAAQMFIVSPrrHWFVQeCNCSIYPGTI |
| 78 | T4 | 62 | ALTQGLRTHIDMVVMSATLCSALYVGDLCGGVMLAAQMFIVSPQHHWFVQdCNCSIYPGTI |
| 79 | T9 | 62 | ALTQGLRTHIDMVVMSATLCSALYVGDLCGGVMLAAQMFIiSPQHHWFVQEeCNCSIYPGTI |
| 80 | US10 | 62 | ALTQGLRTHIDMVVMSATLCSALYVGDfCGGmMLAAQMFIvSPrHHsFVQECNCSIYPGTI |
| 77-80 | consensus | | ALTQGLRTHIDMVVMSATLCSALYVGDlCGGVMLAAQMFIvSP-hHwFVQeCNCSIYPGTI |

FIGURE 2C-2

| SEQ ID NO: | Isolate | | |
|---|---|---|---|
| 77 | T2 | 123 | TGHRMAWDMMMNWSPTATMILAYAMRVPEVIiDIigGAHWGVMFGLAYFSMQGAWAKViVI |
| 78 | T4 | 123 | TGHRMAWDMMMNWSPTATMILAYAMRVPEVIlDIvSGAHWGVMFGLAYFSMQGAWAKVVVI |
| 79 | T9 | 123 | TGHRMAWDMMMNWSPTtTMILAYAMRVPEVIIDIISGAHWGVMFGLAYFSMQGAWAKVVVI |
| 80 | US10 | 123 | TGHRMAWDMMMNWSPTaTlILAYvMRVPEVIIDDIISGAHWGV1FGLAYFSMQGAWAKVVVI |
| 77-80 | consensus | | TGHRMAWDMMMNWSPTaTmILAYaMRVPEVIiDIisGAHWGVmFGLAYFSMQGAWAKVvVI |

| SEQ ID NO: | Isolate | | |
|---|---|---|---|
| 77 | T2 | 184 | LLLAAGVDA |
| 78 | T4 | 184 | LLLAAGVDA |
| 79 | T9 | 184 | LLLtAGVDA |
| 80 | US10 | 184 | LLLaAGVDA |
| 77-80 | consensus | | LLLaAGVDA |

FIGURE 2D-1

| SEQ ID NO: | Isolate | | |
|---|---|---|---|
| 82 | DK11 | 1 | VEVRNtSSSYYATNDCSNnSITWQLTNAVLHLPGCVPCENDNGTLHCWIQVTPNVAVKHRG |
| 83 | SW3 | 1 | VEVRNiSSSYYATNDCSNsSITWQLTNAVLHLPGCVPCENDNGTLHCWIQVTPNVAVKHRG |
| 84 | T8 | 1 | VEVRNtSfSYYATNDCSNNsITWQLTNAVLHLPGCVPCENDNGTLRCWIQVTPNVAVKHRG |
| 81 | DK8 | 1 | VEVRNiSsSYYATNDCSNNSITWQLTdAVLHLPGCVPCENDNGTLRCWIQVTPNVAVKHRG |
| 81-84 | consensus | | VEVRN-SsSYYATNDCSNnSITWQLTnAVLHLPGCVPCENDNGTL-CWIQVTPNVAVKHRG |

| SEQ ID NO: | Isolate | | |
|---|---|---|---|
| 82 | DK11 | 62 | ALTHNLRAHiDMIVMAATVCSALYVGDvCGAVMIVSQAFIvSPEhhhFTQECNCSIYQGhI |
| 83 | SW3 | 62 | ALTHNLRAHVDMIVMAATVCSALYVGDmCGAVMIVSQAFIISPERHNFTQECNCSIYQGrI |
| 84 | T8 | 62 | ALTHNLRTHVDVIVMAATVCSALYVGDVCGAVMIaSQAFIISPERHNFTQECNCSIYQGHI |
| 81 | DK8 | 62 | ALTHNLRTHVDVIVMAATVCSALYVGDVCGAVMIvSQAlIISPERHNFTQECNCSIYQGHI |
| 81-84 | consensus | | ALTHNLR-HvD-IVMAATVCSALYVGDvCGAVMIvSQAfIiSPErHnFTQECNCSIYQGhI |

FIGURE 2D-2

| SEQ ID NO: | Isolate | | |
|---|---|---|---|
| 82 | DK11 | 123 | TGHRMAWDMMLNWSPTLTMILAYAARVPELVLEVVFGGHWGVVFGLAYFSMQGAWAKVIAI |
| 83 | SW3 | 123 | TGHRMAWDMMLNWSPTLTMILAYAARVPELVLEVVFGGHWGVVFGLAYFSMQGAWAKVIAI |
| 84 | T8 | 123 | TGHRMAWDMMLNWSPTLTMILAYAARVPELVLEVVFGGHWGVVFGLAYFSMQGAWAKVIAI |
| 81 | DK8 | 123 | TGHRMAWDMMLNWSPTLTMILAYAARVPELaLqVVFGGHWGVVFGLAYFSMQGAWAKVIAI |
| 81-84 | consensus | | TGHRMAWDMMLNWSPTLTMILAYAARVPELvLeVVFGGHWGVVFGLAYFSMQGAWAKVIAI |

| SEQ ID NO: | Isolate | | |
|---|---|---|---|
| 82 | DK11 | 184 | LLLVAGVDA |
| 83 | SW3 | 184 | LLLVAGVDA |
| 84 | T8 | 184 | LLLVAGVDA |
| 81 | DK8 | 184 | LLLVAGVDA |
| 81-84 | consensus | | LLLVAGVDA |

FIGURE 2E-1

| SEQ ID NO: | Isolate | |
|---|---|---|
| 86 | DK12 | 1 LEWRNVSGLYVLTNDCsNSSIVYEADDVILHTPGCVPCVQDGNTSTCWTSVTPTVAVRYVG |
| 87 | HK10 | 1 LEWRNVSGLYVLTNDCpNSSIVYEADDVILHTPGCVPCVQDGNTSTCWTSVTPTVAVRYVG |
| 88 | S2 | 1 LEWRNTSGLYVLTNDCSNSSIVYEADDVILHTPGCVPCVQDGNTSTCWTPVTPTVAVRYVG |
| 90 | S54 | 1 LEWRNTSGLYiLTNDCSNSSIVYEADDVILHTPGCVPCVQDGNTSTCWTPVTPTVAVRYVG |
| 89 | S52 | 1 LEWRNTSGLYvLTNDCSNSSIVYEADDVILHTPGCVPCVQDGNTSmCWTPVTPTVAVRYVG |
| 86-90 | consensus | LEWRNtSGLYvLTNDCsNSSIVYEADDVILHTPGCVPCVQDGNTStCWTpVTPTVAVRYVG |

| SEQ ID NO: | Isolate | |
|---|---|---|
| 86 | DK12 | 62 ATTASIRSHVDLLVGAATMCSALYVGDvCGAVFLVGQAFTFRPRRHQTVQTCNCSLYPGHL |
| 87 | HK10 | 62 ATTASIRSHVDLLVGAATMCSALYVGDMCGAVFLVGQAFTFRPRRHQTVQTCNCSLYPGHL |
| 88 | S2 | 62 ATTASIRSHVDLLVGAATMCSALYVGDMCGAVFLVGQAFTFRPRRHQTVQTCNCSLYPGHL |
| 90 | S54 | 62 ATTASIRSHVDLLVGAATLCSALYVGDMCGAVFLVGQAFTFRPRRHQTVQTCNCSLYPGHL |
| 89 | S52 | 62 ATTASIRSHVDLLVGAATLCSALYVGDMCGAVFLVGQAFTFRPRRHQTVQTCNCSLYPGHv |
| 86-90 | consensus | ATTASIRSHVDLLVGAATmCSALYVGDmCGAVFLVGQAFTFRPRRHQTVQTCNCSLYPGHl |

FIGURE 2E-2

| SEQ ID NO: | Isolate | | |
|---|---|---|---|
| 86 | DK12 | 123 | SGHRMAWDMMMNWSPAVGMVVAHVLRLPQTLFDIIAGAHWGImAGLAYYSMQGNWAKVAII |
| 87 | HK10 | 123 | SGHRMAWDMMMNWSPAVGMVVAHVLRLPQTLFDILAGAHWGILAGLAYYSMQGNWAKVAII |
| 88 | S2 | 123 | SGHRMAWDMMMNWSPAVGMVVAHVLRLPQTvFDIIAGAHWGILAGLAYYSMQGNWAKVAII |
| 90 | S54 | 123 | SGHRMAWDMMMNWSPAVGMVVAHILRLPQTLFDILAGAHWGILAGLAYYSMQGNWAKVAII |
| 89 | S52 | 123 | SGHRMAWDMMMNWSPAVGMVVAHILRLPQTLFDILAGAHWGILAGLAYYSMQGNWAKVAIv |
| 86-90 | consensus | | SGHRMAWDMMMNWSPAVGMVVAHvLRLPQTlFDIiAGAHWGIlAGLAYYSMQGNWAKVAIi |

| SEQ ID NO: | Isolate | | |
|---|---|---|---|
| 86 | DK12 | 184 | MVMFSGVDA |
| 87 | HK10 | 184 | MVMFSGVDA |
| 88 | S2 | 184 | MVMFSGVDA |
| 90 | S54 | 184 | MIMFSGVDA |
| 89 | S52 | 184 | MIMFSGVDA |
| 86-90 | consensus | | MvMFSGVDA |

FIGURE 2F-1

| SEQ ID NO: | Isolate | | |
|---|---|---|---|
| 93 | Z7 | 1 | VNYhNASGVYHiTNDCPNSSImYEAEHHILHLPGCVPCVReGNQSRCWVALTPTVAAPYIG |
| 94 | Z6 | 1 | VNYRNASGVYHVTNDCPNSSIVYEAEHqILHLPGC1PCVRvGNQSRCWVALTPTVAvsYIG |
| 93-94 consensus (Z6) | | | VNYrNASGVYHvTNDCPNSSIvYEAEHqILHLPGC1PCVRvGNQSRCWVALTPTVAvsYIG |

| SEQ ID NO: | Isolate | | |
|---|---|---|---|
| 93 | Z7 | 62 | APLESiRRHVDLMVGAATVCSALYIGDLCGGVFLVGQMFSFQPRRHWTTQDCNCSIYAGHV |
| 94 | Z6 | 62 | APLdSLRRHVDLMVGAATVCSALYvGDLCGGaFLVGQMFSFQPRRHWTTQDCNCSIYAGHI |
| 93-94 consensus (Z6) | | | APLdSlRRHVDLMVGAATVCSALYvGDLCGGaFLVGQMFSFQPRRHWTTQDCNCSIYAGHi |

| SEQ ID NO: | Isolate | | |
|---|---|---|---|
| 93 | Z7 | 123 | TGHRMAWDMMMNWSPTTTLvLAQVMRIPSTLVDLLTGGHWGiLiLiGvAYFCMQANWAKVILV |
| 94 | Z6 | 123 | TGHRMAWDMMMNWSPTTTL1LAQVMRIPSTLVDLLAGGHWGvLVG1AYFSMQANWAKVILV |
| 93-94 consensus (Z6) | | | TGHRMAWDMMMNWSPTTTL1LAQVMRIPSTLVDLLaGGHWGvLvG1AYFsMQANWAKVILV |

| SEQ ID NO: | Isolate | | |
|---|---|---|---|
| 93 | Z7 | 184 | LFLyAGVDA |
| 94 | Z6 | 184 | LFLFAGVDA |
| 93-94 consensus (Z6) | | | LFLfAGVDA |

FIGURE 2G-1

| SEQ ID NO: | Isolate | | |
|---|---|---|---|
| 98 | SA5 | 1 | VPYRNASGVYHVTNDCPNSSIVYEADNLILHAPGCVPCVKegNVSRCWVQITPTLSAPNLG |
| 100 | SA7 | 1 | VPYRNASGVYHVTNDCPNSSIVYEADNLILHAPGCVPCVRQnNVSRCWVQITPTLSAPNLG |
| 97 | SA4 | 1 | VPYRNASGVYHVTNDCPNSSIVYEADNLILHAPGCVPCVRQDNVSkCWVQITPTLSAPNLG |
| 96 | SA1 | 1 | VPYRNASGVYHVTNDCPNSSIVYEADNLILHAPGCVPCVRQDNVSRCWVQITPTLSAPNLG |
| 99 | SA6 | 1 | VPYRNASGVYHVTNDCPNSSIVYEADsLILHAPGCVPCVRQDNVSRCWVQITPTLSAPtfG |
| 101 | SA13 | 1 | VPYRNASGVYHVTNDCPNSSIVYEADDLILHAPGCVPCVRkDNVSRCWVhITPTLSAPSLG |
| | | 1 | VPYRNASGVYHVTNDCPNSSIVYEADDLILHAPGCVPCVRggNVSRCWVqITPTLSAPSLG |
| 96-101 | consensus | | VPYRNASGVYHVTNDCPNSSIVYEADnLILHAPGCVPCVrqdNVSrCWVqITPTLSAPnlG |

| SEQ ID NO: | Isolate | | |
|---|---|---|---|
| 98 | SA5 | 62 | AVTAPLRRvVDYLAGGAALCSALYVGDACGAVFLVGQMFtYRPRQHTTVQDCNCSIYSGHI |
| 100 | SA7 | 62 | AVTAPLRRAVDYLAGGAALCSALYVGDACGAVFLVGQMFsYRPRQHTTVQDCNCSIYSGHI |
| 97 | SA4 | 62 | AVTAPLRRAVDYLAGGAALCSALYVGDACGAVFLVGQMFTYRPRQHTTVQDCNCSIYSGHI |
| 96 | SA1 | 62 | AVTAPLRRAVDYLAGGAALCSALYVGDACGAVFLVGQMFTYRPRQHTTVQDCNCSIYSGHI |
| 99 | SA6 | 62 | AVTAPLRRAVDYLAGGAALCSALYVGDvCGAlFLVGQMFTYRPRQHaTVQDCNCSIYSGHI |
| 101 | SA13 | 62 | AVTAPLRRAVDYLAGGAALCSALYVGDaCGAVFLVGQMFTYsPRrHnvVQDCNCSIYSGHI |
| 96-101 | consensus | | AVTAPLRRaVDYLAGGAALCSALYVGDaCGAvFLVGQMFtYrPRqHttVQDCNCSIYSGHI |

FIGURE 2G-2

| SEQ ID NO: | Isolate | | |
|---|---|---|---|
| 98 | SA5 | 123 | TGHRMAWDMMMNWSPTTALVMAQvLRIPQVVIDIIAGGHWGVLFAvAYFASAANWAKVVLV |
| 100 | SA7 | 123 | TGHRMAWDMMMNWSPTTALVMAQLLRIPQVVIDIIAGGHWGVLFAAAYFASAANWAKVVLV |
| 97 | SA4 | 123 | TGHRMAWDMMMNWSPTTALVMAQLLRIPQVVIDIIAGGHWGVLFAAAYFASAANWAKVVLV |
| 96 | SA1 | 123 | TGHRMAWDMMMNWSPTTALLMAQMLRIPQVVIDIIAGGHWGVLFAAAYFASAANWAKViLV |
| 99 | SA6 | 123 | TGHRMAWDMMMNWSPaTALVMAQMLRIPQVVIDIIAGGHWGVLFAAAYFASAANWAKVVLV |
| 101 | SA13 | 123 | TGHRMAWDMMMNWSPtTALVMAQlLRIPQVVIDIIAGaHWGVLFAAAYyASAANWAKVVLV |
| 96-101 | consensus | | TGHRMAWDMMMNWSPtTALvMAQlLRIPQVVIDIIAGgHWGVLFAaAYFASAANWAKVvLV |

| SEQ ID NO: | Isolate | | |
|---|---|---|---|
| 98 | SA5 | 184 | LFLFAGVDg |
| 100 | SA7 | 184 | LFLFAGVDA |
| 97 | SA4 | 184 | LFLFAGVDA |
| 96 | SA1 | 184 | LFLFAGVDg |
| 99 | SA6 | 184 | LFLFAGVDA |
| 101 | SA13 | 184 | LFLFAGVDA |
| 96-101 | consensus | | LFLFAGVDa |

FIGURE 2H-1

| SEQ ID NO: | Genotype | |
|---|---|---|
| 81-84 | (IV/2b) | 1 VEVRNiSsSYYATNDCSNnSITWQLThAVLHLPGCVPCENDNGTLrCWIQVTPNVAVKHRG |
| 85 | (2c) | 1 VEVKDTGDSYMPTNDCSNSSIVWQLEGAVLHTPGCVPCERTANVSRCWVPVAPNLAISQPG |
| 77-80 | (III/2a) | 1 aqVkNTstsYMVTNDCSNdSITWQLqAAVLHVPGCvPCEkvGNtSRCWIPVsPNVAVqqPG |
| 86-90 | (V/3a) | 1 LEWRNtSGLYvLTNDCsNSSIVYEADDVILHTPGCVPCVQDGNTStCWTpVTPTVAVRYVG |
| 60-76 | (II/1b) | 1 yEVrNVSGvYhVTNDCSNnSSiVyEaaDmImHTPGCvPCVrEnNsSrCWVALtPTLAARNas |
| 52-59 | (I/1a) | 1 yQVRNStGLYHVTNDCPNSSIVYEaADaILHsPGCVPCVREgnasrCWVavtPTVATRDGK |
| 91 | (4a) | 1 EHYRNASGIYHITNDCPNSSIVYEADHHILHLPGCVPCVMTGNTSRCWTPVTPTVAVAHPG |
| 93-94 | (4c) | 1 VNYrNASGVYHVTNDCPNSSIVYEAEHqILHLPGClPCVRvGNQSRCWVALTPTVAvsYIG |
| 95 | (4d) | 1 YNYRNSSGVYHVTNDCPNSSIVYETDYHILHLPGCVPCVREGNKSTCWVSLTPTVAAQHLN |
| 92 | (4b) | 1 VHYRNASGVYHVTNDCPNTSIVYETEHHIMHLPGCVPCVRTENTSRCWPLTPTVAAPYPN |
| 96-101 | (5a) | 1 VPYRNASGVYHVTNDCPNSSIVYEADnLILHAPGCVPCVrqdNVSrCWVqITPTLSAPn1G |
| 102 | (6a) | 1 LTYGNSSGLYHLTNDCPNSSIVLEADAMILHLPGCLPCVRVDDRSTCWHAVTPTLAIPNAS |

52-102 consensus      Y   TNDC N S              H PGC PC        CW        P

| SEQ ID NO: | Genotype | |
|---|---|---|
| 81-84 | (IV/2b) | 62 ALTHNLRtHvDmIVMAATVCSALYVGDvCGAVMIvSQAfIiSPErHnFTQECNCSIYQGhI |
| 85 | (2c) | 62 ALTKGLRAHIDIIVMSATVCSALYvGDVCGALMLAAQVVVVSPQHHTFVQECNCSIYPGRI |
| 77-80 | (III/2a) | 62 ALTQGLRTHIDMVVMSATLCSALYVGD1CGGvMLAAQMFIvSPqhHwFVQeCNCSIYPGTI |
| 86-90 | (V/3a) | 62 ATTASIRSHVDLLVGAATmCGAVFLVGQAFTFRPRRHQTVQTCNCSLYPGH1 |
| 60-76 | (II/1b) | 62 vpTttIRrHVDLLVGAAaaFCSaMYVGDLCGSVFLVsQLFTfSPRrheTVQdCNCSiYPGhv |
| 52-59 | (I/1a) | 62 LPatQLRrHiDLLVGSATLCSALYVGDLCGSVFLVgQLFTfSPRrhWTTQdCNCSIYPGHI |
| 91 | (4a) | 62 APLESFRRHVDLMVGAATLCSALYVGDLCGGAFLMGQMITFRPRRHWTTQECNCSIYTGHI |
| 93-94 | (4c) | 62 APLdSlRRHVDLMVGAATLCSALYvGDLCGgaFLVGQMFSFQPRRHWTTQDCNCSIYAGHi |
| 95 | (4d) | 62 APLESLRRHVDLMVGGATLCSALYIGDVCGGVFLVGQLFTFQPRRHWTTQDCNCSIYTGHI |
| 92 | (4b) | 62 APLESMRRHVDLMVGAATMCSAFYIGDLCGGVFLVGQLFDFRPRRHWTTQDCNCSIYSGHI |
| 96-101 | (5a) | 62 AVTAPLRRaVDYLAGGAALCSALYVGDaCGAvFLVGQMFtYrPRqHttVQDCNCSIYSGHI |
| 102 | (6a) | 62 TPATGFRRHVDLLAGAAVVCSSLYIGDLCGSLFLAGQLFTFQPRRHWTVQDCNCSIYTGHV |

52-102 consensus     R     D     A   CS   Y GD CG        Q        Q     P        Q CNCS  Y G

FIGURE 2H-2

| SEQ ID NO: | Genotype | | |
|---|---|---|---|
| 81-84 | (IV/2b) | 123 | TGHRMAWDMMLNWSPTLTMILAYAARVPELvLeVVFGGHWGVVFGLAYFSMQGAWAKVIAI |
| 85 | (2c) | 123 | TGHRMAWDMMMNWSPTTTMLLAYLVRIPEVILDIVTGGHWGVVFGLAYFSMQGSWAKVIVI |
| 77-80 | (III/2a) | 123 | TGHRMAWDMMMNWSPTaTmILAyaMRVPEVIiDIisGAHWGVmFGLAYFSMQGAWAKVvVI |
| 86-90 | (V/3a) | 123 | SGHRMAWDMMMNWSPAVGMVVAHvLRLPQT1FDIiAGAHWGIlAGLAYYSMQGNWAKVAIi |
| 60-76 | (II/1b) | 123 | sGHRMAWDMMMNWSPTaAlVvSQLLRiPQAvvDmVaGAHWGVLAGLAYYSMvGNWAKVLIV |
| 52-59 | (I/1a) | 123 | TGHRMAWDMMMNWSPTtALVvAQLLRiPQAiLDMIAGAHWGVLAGIAYFSMvGNWAKVlvV |
| 91 | (4a) | 123 | TGHRMAWDMMMNWSPTTLLLAQIMRVPTAFLDMVAGGHWGVLAGLAYFSMQGNWAKVVLV |
| 93-94 | (4c) | 123 | TGHRMAWDMMMNWSPTTLlLAQVMRIPSTLvDLLaGGHWGVLvGlAYFsMQANWAKVILv |
| 95 | (4d) | 123 | TGHRMAWDMMMNWSPTATIVLAQLMRIPGAMVDLLAGGHWGILvGIAYFSMQANWAKVILv |
| 92 | (4b) | 123 | SGHRMAWDMMMNWSPTSALIMAQIlRIPSILGDLLTGGHWGVLAGLAFFSMQSNWAKVILv |
| 96-101 | (5a) | 123 | TGHRMAWDMMMNWSPtTALvMAQ1LRIPQVVIDIIAGghHWGVLFAaAYfASAANWAKVvLv |
| 102 | (6a) | 123 | TGHRMAWDMMMNWSPTTLVLSSILRVPEICASVIFGGHWGILLAVAYFGMAGNWLKVLAV |

| 52-102 | consensus | | GHRMAWDMM NWSP  R P  G HWG  A  W KV |

| SEQ ID NO: | Genotype | | |
|---|---|---|---|
| 81-84 | (IV/2b) | 184 | LLLVAGVDA |
| 85 | (2c) | 184 | LLLTAGVEA |
| 77-80 | (III/2a) | 184 | LLLaAGVDA |
| 86-90 | (V/3a) | 184 | MvMFSGVDA |
| 60-76 | (II/1b) | 184 | mLLFAGVDG |
| 52-59 | (I/1a) | 184 | LLLFaGVDA |
| 91 | (4a) | 184 | LFLFAGVDA |
| 93-94 | (4c) | 184 | LFlFAGVDA |
| 95 | (4d) | 184 | LFLFAGVDA |
| 92 | (4b) | 184 | LFLFAGVEG |
| 96-101 | (5a) | 184 | LFLFAGVDa |
| 102 | (6a) | 184 | LFLFAGVEA |

| 52-102 | consensus | | GV |

| Genotype | SEQ ID NO: 52-102 | Isolate | 290 gq(fftsPrrhwtvqdCNCSiypGhitGHRMAwDMMmNWSPttalvvaqlIRi 300 310 320 | 330 Pqavldmvagahwgvlagl 340 350 360 Ayfsmvgnwakvlivllfagvda 370 380 |
|---|---|---|---|---|
| IV/2b | 82 | DK11 | S-AFIyS-EhhhFT-E------I-q-hIT------ | ----TLTMILAYAA-V-ELVLEVVF-G---VVFGL-YFSMQGA-A--IAILLLVA--DA |
|  | 83 | SW3 | S-AFIIS-ERHHFT-E------I-q-rIT------ | ----TLTMILAYAA-V-ELVLEVVF-G---VVFGL-YFSMQGA-A--IAILLLVA--DA |
|  | 81 | DK8 | S-AIIIS-ERHHFT-E------I-q-HIT------ | ----TLTMILAYAA-V-ELaLqVVF-G---VVFGL-YFSMQGA-A--IAILLLVA--DA |
|  | 84 | T8 | S-AfIIS-ERHNFT-E------I-P-rIT------ | ----TLTMILAYAA-V-ELVLEVVF-G---VMFGL-YFSMQGA-A--IAILLLVA--DA |
| 2c | 85 | S83 | A-vvvVS-QHHtFV-E------I-P-rIT------ | -M--TtTMILAYLv-i-EVILDtVt-G---VMFGL-YFSMQGs-A--IVILLLtA--eA |
| III/2a | 78 | T4 | A-MFIVS-QHHHFV-d------I-P-TIT------ | -M--TATMILAYaM-V-EVILDIVS-A---VMFGL-YFSMQGA-A--VVILLLAA--DA |
|  | 80 | US10 | A-MFIVS-rHhsFV-E------I-P-TIT------ | -M--TATILAYM-V-EVIIDIIS-A---VLFGL-YFSMQGA-A--VVILLLAA--DA |
|  | 79 | T9 | A-MFIIS-qHHWFV-E------I-P-TIT------ | -M--TtTMILAYAM-V-EVIIDIIS-A---VMFGL-YFSMQGA-A--iVILLLtA--DA |
|  | 77 | T2 | A-MFIVS-RRHWFV-E------I-P-TIT------ | -M--TaTMILAYAM-V-EVIIDIg-A---VMFGL-YFSMQGA-A--IAILLLaA--DA |
| (V)/3a | 86 | DK12 | G-AFTFR-RRHQTV-T------L-P-HLS------ | -M--AVGHVVAHVL-I-QTLFDIA-A---IMAGL-YFSMQGN-A--AIMVMFS--DA |
|  | 87 | HK10 | G-AFTFR-RRHQTV-T------L-P-HLS------ | -M--AVGHVVAHVL-I-QTLFDIA-A---ILAGL-YFSMQGN-A--AIMVMFS--DA |
|  | 88 | S2 | G-AFTFR-RRHQTV-T------L-P-HLS------ | -M--AVGHVVARVL-I-QTVFDIA-A---ILAGL-YFSMQGN-A--AIMVMFS--DA |
|  | 90 | S54 | G-AFTFR-RRHQTV-T------L-P-HLS------ | -M--AVGHVVAHIL-I-QTLFDIA-A---ILAGL-YFSMQGN-A--AIMVMFS--DA |
|  | 89 | S52 | G-AFTFR-RRHQTV-T------L-P-HLS------ | -M--AVGHVVAHIL-I-QTLFDIA-A---IMAGL-YFSMQGN-A--AIMIMFS--DA |
| II/1b | 68 | IND8 | S-LFTFS-RRHETV-D------I-P-HVS------ | -M--TAALVVSQLL-I-QAVVDMVA-A---ILAGL-YYSMVGN-A--LIVMLLFA--DG |
|  | 67 | IND5 | S-LFTFS-RRHETV-D------I-P-HVS------ | -M--TAALVVSQLL-I-QAVVDMVA-A---ILAGL-YYSMVGN-A--LIVMLFA--DG |
|  | 73 | SW2 | S-LFTFS-RRHETV-D------I-P-HVS------ | -M--TAALVVSQLL-I-QAVVDMVA-A---VLAGL-YYSMVGN-A--LIVMLLFA--DG |
|  | 63 | HK3 | S-LFTFS-RRHETV-D------I-P-HVS------ | -M--TAALVVSQLL-I-QAVVDMVA-A---VLAGL-YYSMVGN-A--LIVMLLFA--DG |
|  | 66 | HK8 | S-LFTFS-RqHETV-D------I-P-HVS------ | -M--TAALVVSQLL-I-QAiVDMVA-A---VLAGL-YYSMVGN-A--LIVMLLFA--DG |
|  | 71 | S45 | S-LFTFS-RRHETV-D------I-P-HVT------ | -M--TCALVVSQLL-I-QAVVDMVA-A---VLAGL-YYSMVGN-A--LIVMLLFA--DG |
|  | 61 | D3 | S-LFTFS-RRHETV-e------I-P-HVT------ | -M--TAALVVSQLL-I-QAVVDMVA-A---VLAGL-YYSMVGN-A--LIVMLLFA--DG |
|  | 74 | T3 | S-LFTFS-RRHETV-D------I-P-HVT------ | -M--TAALVVSQLL-I-QAVVDMVA-A---VLAGL-YYSMAGN-A--LIVMLLFA--DG |
|  | 65 | HK5 | S-LFTFS-RRHETV-D------I-P-HVT------ | -M--TAALVVSQLL-I-QAVVDMVt-A---VLAGL-YYSMVGN-A--LIVMLLFA--DG |
|  | 64 | HK4 | S-LFTFS-RRHETL-D------I-P-HVS------ | -M--TAALVVSQLL-I-QAVVDMVA-A---VLAGL-YYSMVGN-A--LIVMLLFA--DG |
|  | 76 | US6 | S-LFTFS-RRHETV-D------I-P-HVT------ | -M--TAALVVSQLL-I-QAVVDMVA-A---VLAGL-YYSMVGN-A--LIVMLLFA--DG |
|  | 69 | P10 | S-LFTFS-RRYETV-D------I-P-HLS------ | -M--TTALVVSQLL-I-QAVDMVt-A---VLAGL-YYSMVGN-A--LIVMLLFA--DG |
|  | 72 | SA10 | S-LFTFS-RRHETL-D------I-rVt------ | -M--TTALVISQLL-I-QAVDMVA-A---VLAGL-YYSMVGN-A--LIVMLLFA--DG |
|  | 75 | T10 | S-LFTFS-RRHETV-D------I-P-HVS------ | -M--TTALVISQLL-I-QAVDMVA-A---VLAGL-YYSMVGN-A--LIVMLLFA--DG |
|  | 62 | DK1 | S-LFTFS-RRHEta-D------I-P-HVS------ | -M--TTALVVSQLL-I-QAVMDMVA-A---VLAGL-YYSMVGN-A--LIVMLLFA--DG |
|  | 70 | S9 | S-LFTiS-RRHETV-r------I-P-HVT------ | -M--TTALVVSQLL-I-QAYMDMIA-A---VLAGL-YYSMVGN-A--LIVMLLFA--DG |
|  | 60 | D1 | S-LFtLS-RRHETV-e------I-P-HVS------ | -M--TTALVVSQLL-I-QAYMDMIA-A---VLAGL-YYSMVGN-A--LIVLLLFA--DG |
| I/1a | 52 | DK7 | G-LFTFS-RRHWTT-G------I-P-HIT------ | -M--TTALVVAQLL-I-QAILDMIA-A---VLAGI-YFSMVGN-A--LVVLLLFA--DA |
|  | 59 | US11 | G-LFTFS-RRHWTT-G------I-P-HIT------ | -M--TTTLLLAQIM-I-QAILDMIA-A---VLAGI-YFSMVGN-A--LVVLLLFA--DA |
|  | 55 | DR4 | G-LFTFS-RRHWTT-D------I-P-HIT------ | -M--TTTLLLAQIM-V-QAILDMIA-A---VLAGI-YFSMVGN-A--VVVLLLFA--DA |
|  | 54 | DR1 | G-LFTFS-RRHWTT-D------I-P-HIT------ | -M--TTTLLLAQVM-V-QAILDMIA-A---VLAGI-YFSMVGN-A---VVLLLFS--DA |
|  | 53 | DK9 | G-LFTFS-RRHWTT-D------I-P-HIT------ | -M--TaALVMAQLL-V-QAILDMIA-A---VLAGI-YFSMVGN-A---LVLLLFA--DA |
|  | 58 | SW1 | g-LFTFS-RRHWTT-D------I-P-HIT------ | -M--TaALVMAQLL-V-QAILDMIA-A---VLAGI-YFSMVGN-A---LVLLLFs--DA |
|  | 56 | S14 | s-LFTFS-RRHWTT-D------I-P-HIT------ | -M--TTALVVAQLL-V-QAILDMIA-A---VLAGI-YFSMaGN-A---LVLLLFA--DA |
|  | 57 | S18 | s-LFTiS-RRHWTT-e------I-P-HIT------ | -M--TTALVIAQIM-V-QAVLDMIA-A---VLAGL-YFSMQGN-A---VLVLFLFA--DA |
| 4a | 91 | Z4 | G-MITFC-RRHWTT-e------I-t-HIT------ | -M--TTTLLLAQIM-V-tAfLDMIA-A---VLYGL-YFSMQAN-A--ILVLFLFA--DA |
| 4c | 93 | Z6 | G-MFSFQ-RRHWTT-D------I-A-HIT------ | -M--TTTLLVAQVM-I-STLVDLLA-G---VLiGv-YFCMQAN-A--ILVLFVA--DA |
|  | 94 | Z7 | G-MFSFQ-RRHWTT-D------I-A-HvT------ | -M--TTTLLVAQVM-I-STLVDLLT-G---VLiGv-YFCMQAN-A--ILVLFVA--DA |
| 4d | 95 | DK13 | G-LFtFQ-RRHWTT-D------I-t-HIT------ | -M--TaTLVLAQIM-I-gamvDLLa-G---iLvGi-YFSMQsN-A--ILVLFLFt--eG |
| 4b | 92 | Z1 | G-LFdFR-RRHWTI-D------I-p-Hvs------ | -M--TsALIMAQIL-I-silgDLLt-G---VLFAv-TFSMQsN-A--ILVLFLFK--eG |
| 5a | 98 | SA5 | G-MFtYR-RQHTTV-D------I-S-HIT------ | -M--TTALVMAQVL-L-QVVIDIIa---VLFAv-YFASAAN-A---VLFLFLFA--DG |
|  | 100 | SA7 | G-MFsYR-RQHTTV-D------I-S-HIT------ | -M--TTALVMAQLL-L-QVVIDIA-G---VLFAA-YFASAAN-A--VLFLFLFA--DG |
|  | 97 | SA4 | G-MFTYR-RQHTTV-D------I-S-HIT------ | -M--TTALLMAQLL-L-QVVIDIA-G---VLFAA-YFASAAN-A--VLFLFLFA--DG |
|  | 96 | SA1 | G-MFTYR-RQHTTV-D------I-S-HIT------ | -M--TTALLMAQML-L-QVVIDIA-G---VLFAA-YFASAAN-A--VLFLFLFA--DG |
|  | 99 | SA6 | G-MFTYR-RQhaTV-D------I-S-HIT------ | -M--aTALVMAQML-L-QVVIDIA-a---VLFAA-yASAAN-A--VLFLFLFA--DG |
|  | 101 | SA13 | G-MFTyS-RRhnvV-D------I-S-HIT------ | -M--TTALVMAQIL-L-QVVIDIA-a---VLFAA-YFASAAN-A--VLFLFLFA--DG |
| 6a | 102 | HK2 | G-LFtfq-RRHwTV-D------I-t-HvT------ | -M--TTtLVissiL-v-eicasvIf-g---iLLAv-YfgmAgN-t--LavLFLFA--eA |

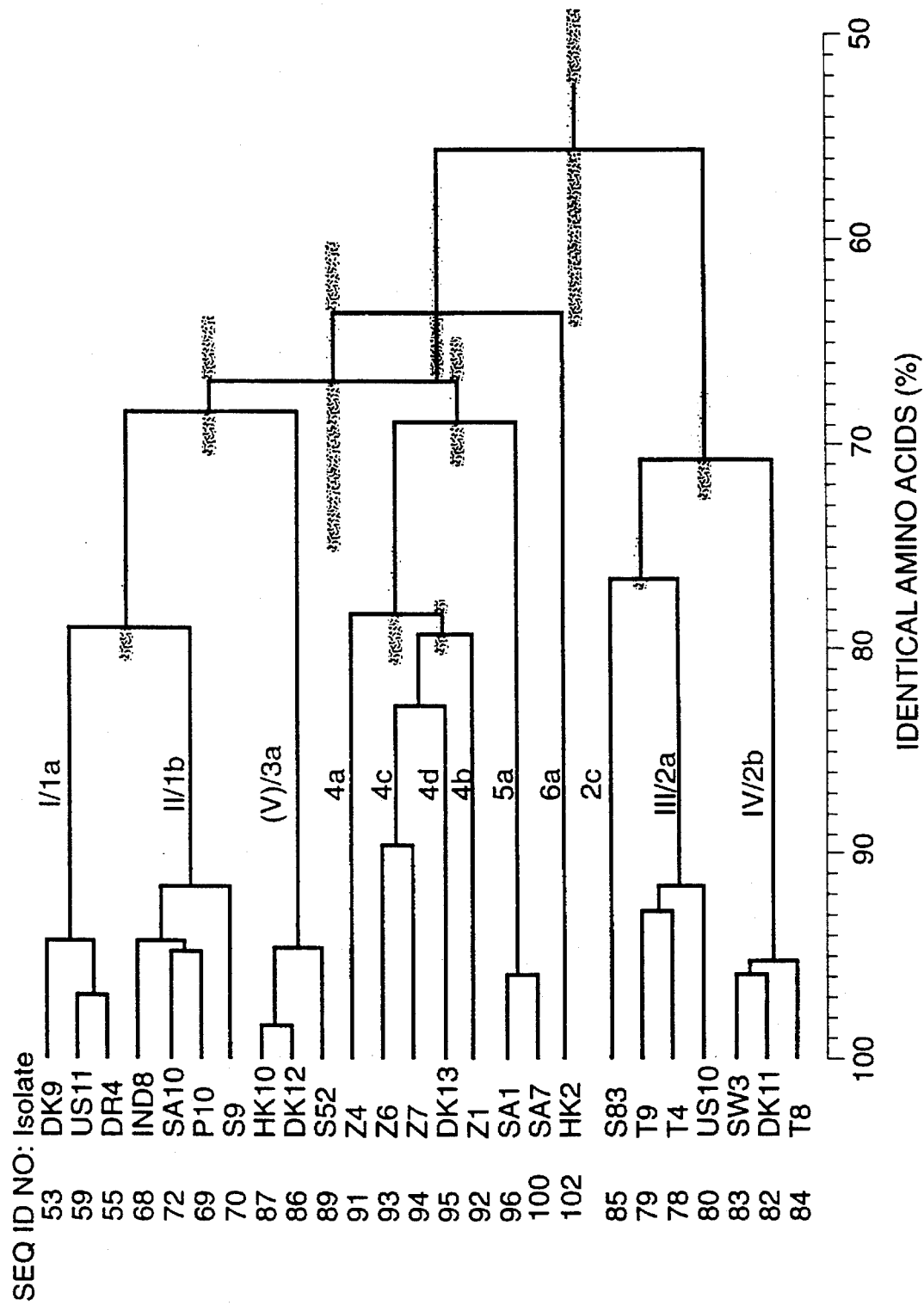

SEQUENCE LISTING ( 1 ) GENERAL INFORMATION:

( i i i ) NUMBER OF SEQUENCES: 159

( 2 ) INFORMATION FOR SEQ ID NO:1:

( i ) SEQUENCE CHARACTERISTICS:
  ( A ) LENGTH: 576 base pairs
  ( B ) TYPE: nucleic acid
  ( C ) STRANDEDNESS: single
  ( D ) TOPOLOGY: linear ( v i ) ORIGINAL SOURCE:
  ( A ) ORGANISM: homosapiens
  ( C ) INDIVIDUAL ISOLATE: DK7

( x i ) SEQUENCE DESCRIPTION: SEQ ID NO:1:

```
TAC CAA GTG CGC AAC TCC ACG GGG CTT TAC CAT GTC ACC          39
AAT GAT TGC CCT AAC TCG AGT ATC GTG TAC GAG GCG GCC          78
GAT GCC ATC CTG CAC ACT CCG GGG TGT GTC CCT TGC GTT         117
CGC GAG GGT AAC GTC TCG AGG TGT TGG GTG GCG ATG ACC         156
CCC ACG GTG GCC ACC AGG GAT GGC AAA CTC CCC ACA GCG         195
CAG CTT CGA CGT CAC ATC GAT CTG CTC GTC GGG AGT GCC         234
ACC CTC TGT TCG GCC CTC TAC GTG GGG GAC CTG TGC GGG         273
TCT GTC TTT CTT GTC GGT CAA CTG TTT ACC TTC TCT CCC         312
AGG CGC CAC TGG ACG ACG CAA GGC TGC AAT TGT TCT ATC         351
TAT CCT GGC CAT ATA ACG GGT CAC CGC ATG GCG TGG GAT         390
ATG ATG ATG AAC TGG TCC CCT ACC ACG GCG TTG GTA GTA         429
GCT CAG CTG CTC CGG ATC CCG CAA GCC ATC TTG GAC ATG         468
ATC GCT GGT GCT CAC TGG GGA GTC CTG GCG GGC ATA GCG         507
TAT TTT TCC ATG GTG GGG AAC TGG GCG AAG GTC CTG GTA         546
GTG CTG CTG CTA TTT GCC GGC GTC GAC GCG                     576
```

( 2 ) INFORMATION FOR SEQ ID NO:2:

( i ) SEQUENCE CHARACTERISTICS:
  ( A ) LENGTH: 576 base pairs
  ( B ) TYPE: nucleic acid
  ( C ) STRANDEDNESS: single
  ( D ) TOPOLOGY: linear ( v i ) ORIGINAL SOURCE:
  ( A ) ORGANISM: homosapiens
  ( C ) INDIVIDUAL ISOLATE: DK9

( x i ) SEQUENCE DESCRIPTION: SEQ ID NO:2:

```
TAC CAA GTA CGC AAC TCC TCG GGC CTC TAC CAT GTC ACC          39
AAT GAT TGC CCT AAC TCG AGT ATT GTG TAC GAG GCG GCC          78
GAT GCC ATC CTG CAT TCT CCA GGG TGT GTC CCT TGC GTT         117
CGC GAG GGT AAC GCC TCG AAA TGT TGG GTG GCG GTG GCC         156
CCC ACG GTG GCC ACC AGG GAC GGC AAG CTC CCC GCA ACG         195
CAG CTT CGA CGT CAC ATC GAT CTG CTT GTC GGG AGC GCC         234
ACC CTC TGC TCG GCC CTC TAT GTG GGG GAC TTG TGC GGG         273
```

| | | | | | | | | | | | | |
|---|---|---|---|---|---|---|---|---|---|---|---|---|
| TCT | GTC | TTC | CTT | GTC | GGC | CAA | CTG | TTC | ACC | TTC | TCC | CCC | 312 |
| AGA | CGC | CAC | TGG | ACA | ACG | CAA | GAC | TGC | AAC | TGT | TCT | ATC | 351 |
| TAC | CCC | GGC | CAT | ATT | ACG | GGT | CAT | CGC | ATG | GCG | TGG | GAT | 390 |
| ATG | ATG | ATG | AAC | TGG | TCC | CCT | ACA | GCA | GCG | CTG | GTA | ATG | 429 |
| GCG | CAG | CTG | CTC | AGG | ATC | CCG | CAG | GCC | ATC | TTG | GAC | ATG | 468 |
| ATC | GCT | GGT | GCC | CAC | TGG | GGA | GTC | CTA | GCG | GGC | ATA | GCG | 507 |
| TAT | TTC | TCC | ATG | GTG | GGG | AAC | TGG | GCG | AAG | GTC | GTG | GTG | 546 |
| GTA | CTG | TTG | CTG | TTT | ACC | GGC | GTC | GAT | GCG | | | | 576 |

(2) INFORMATION FOR SEQ ID NO:3:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DR1

(xi) SEQUENCE DESCRIPTION: SEQ ID NO:3:

| | | | | | | | | | | | | |
|---|---|---|---|---|---|---|---|---|---|---|---|---|
| CAC | CAA | GTG | CGC | AAC | TCT | ACA | GGG | CTT | TAC | CAT | GTC | ACC | 39 |
| AAT | GAT | TGC | CCT | AAT | TCG | AGT | ATT | GTG | TAC | GAG | GCG | GCC | 78 |
| GAT | GCC | ATC | CTG | CAC | GCG | CCG | GGG | TGT | GTC | CCT | TGC | GTT | 117 |
| CGC | GAG | GGT | AAC | GCC | TCG | AGG | TGT | TGG | GTG | GCG | GTG | ACC | 156 |
| CCC | ACG | GTG | GCC | ACC | AGG | GAC | GGC | AAA | CTC | CCC | ACA | ACG | 195 |
| CAG | CTT | CGA | CGT | CAC | ATC | GAC | CTG | CTT | GTC | GGG | AGC | GCC | 234 |
| ACC | CTC | TGC | TCG | GCC | CTC | TAC | GTG | GGG | GAC | CTG | TGC | GGG | 273 |
| TCT | GTC | TTC | CTT | GTC | GGT | CAA | CTG | TTC | ACC | TTT | TCT | CCC | 312 |
| AGG | CGC | CAC | TGG | ACA | ACG | CAA | GAC | TGC | AAT | TGT | TCT | ATC | 351 |
| TAT | CCC | GGC | CAT | ATA | ACG | GGA | CAC | CGT | ATG | GCA | TGG | GAT | 390 |
| ATG | ATG | ATG | AAC | TGG | TCC | CCT | ACG | ACA | GCG | CTG | GTA | ATG | 429 |
| GCT | CAG | CTG | CTC | CGG | ATC | CCA | CAA | GCC | ATC | TTG | GAC | ATG | 468 |
| ATC | GCT | GGA | GCC | CAC | TGG | GGA | GTC | CTA | GCG | GGC | ATA | GCG | 507 |
| TAT | TTC | TCC | ATG | GTG | GGG | AAC | TGG | GCG | AAG | GTC | GTG | GTA | 546 |
| GTG | CTG | TTG | CTG | TTT | GCC | GGC | GTT | GAT | GCG | | | | 576 |

(2) INFORMATION FOR SEQ ID NO:4:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DR4

(xi) SEQUENCE DESCRIPTION: SEQ ID NO:4:

| | | | | | | | | | | | | |
|---|---|---|---|---|---|---|---|---|---|---|---|---|
| CAC | CAA | GTG | CGC | AAC | TCT | ACA | GGG | CTT | TAC | CAT | GTC | ACC | 39 |
| AAT | GAT | TGC | CCT | AAT | TCG | AGT | ATT | GTG | TAC | GAG | GCG | GCC | 78 |

```
GAT GCC ATC CTG CAC ACG CCG GGG TGT GTC CCT TGC GTT        117
CGC GAG GGT AAC ACC TCG AGG TGT TGG GTG GCG GTG ACC        156
CCC ACG GTG GCC ACC AGG GAC GGC AAA CTC CCC ACA ACG        195
CAG CTC CGA CGT CAC ATC GAC CTG CTT GTC GGG AGC GCC        234
ACC CTC TGC TCG GCC CTC TAC GTG GGG GAC TTG TGC GGG        273
TCT GTC TTC CTT GTC GGT CAA CTG TTC ACC TTC TCT CCC        312
AGG CAC CAC TGG ACA ACG CAA GAC TGC AAT TGT TCC ATC        351
TAT CCC GGC CAT ATA ACG GGC CAC CGC ATG GCG TGG GAT        390
ATG ATG ATG AAC TGG TCC CCT ACG ACA GCG CTG GTA GTA        429
GCT CAG CTG CTC CGG ATC CCA CAA GCC ATC TTG GAC ATG        468
ATC GCT GGT GCC CAC TGG GGA GTC CTA GCG GGC ATA GCG        507
TAT TTC TCC ATG GTG GGG AAC TGG GCG AAG GTC CTG GTA        546
GTG CTG TTG CTG TTT GCC GGC GTT GAT GCG                    576
```

( 2 ) INFORMATION FOR SEQ ID NO:5:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S14

( x i ) SEQUENCE DESCRIPTION: SEQ ID NO:5:

```
TAC CAA GTG CGC AAC TCC ACG GGG CTT TAC CAT GTT ACC         39
AAT GAT TGC CCT AAC TCG AGT ATT GTG TAC GAG ACA GCT         78
GAT GCT ATC CTA CAC GCT CCG GGA TGT GTC CCT TGC GTT        117
CGT GAG GGT AAC ACC TCG AGG TGT TGG GTG GCG ATG ACC        156
CCC ACG GTG GCC ACC AGG GAC GGC AAA CTC CCC GCA ACG        195
CAG CTT CGA CGT TAC ATC GAT CTG CTT GTC GGG AGC GCC        234
ACC CTC TGT TCG GCC CTC TAC GTG GGG GAC TTG TGC GGG        273
TCT GTC TTT CTT GTC GGT CAG CTG TTT ACC TTC TCT CCC        312
AGG CGC CTC TGG ACG ACG CAA GAC TGC AAT TGT TCT ATC        351
TAT CCC GGC CAT ATA ACG GGT CAT CGC ATG GCA TGG GAT        390
ATG ATG ATG AAC TGG TCC CCT ACG ACG GCA CTG GTA GTA        429
GCT CAG CTG CTC CGG ATC CCA CAA GCC ATC TTG GAT ATG        468
ATC GCT GGT GCT CAC TGG GGA GTC CTA GCG GGC ATA GCG        507
TAT TTC TCC ATG GTG GGA AAC TGG GCG AAG GTC CTA GTG        546
GTG CTG CTG CTA TTC GCC GGC GTT GAC GCG                    576
```

( 2 ) INFORMATION FOR SEQ ID NO:6:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S18

( x i ) SEQUENCE DESCRIPTION: SEQ ID NO:6:

| | | | | | | | | | | | | |
|---|---|---|---|---|---|---|---|---|---|---|---|---|
| TAC | CAA | GTA | CGC | AAC | TCC | ACG | GGC | CTT | TAC | CAT | GTC | ACC | 39 |
| AAT | GAC | TGC | CCT | AAC | TCG | AGC | ATT | GTG | TAC | GAG | ACG | GCC | 78 |
| GAT | ACC | ATC | CTA | CAC | TCT | CCG | GGG | TGT | GTC | CCT | TGC | GTT | 117 |
| CGC | GAG | GGT | AAC | GCC | TCG | AGA | TGT | TGG | GTG | CCG | GTG | GCC | 156 |
| CCC | ACA | GTT | GCC | ACC | AGG | GAC | GGC | AAA | CTC | CCC | GCA | ACG | 195 |
| CAG | CTT | CGA | CGT | CAC | ATC | GAT | CTG | CTT | GTT | GGG | AGC | GCC | 234 |
| ACC | CTC | TGC | TCG | GCC | CTC | TAT | GTG | GGG | GAC | CTG | TGC | GGG | 273 |
| TCT | GTC | TTT | CTT | GTC | AGC | CAG | CTG | TTC | ACT | ATC | TCC | CCC | 312 |
| AGG | CGC | CAC | TGG | ACA | ACG | CAA | GAC | TGC | AAC | TGT | TCT | ATC | 351 |
| TAC | CCC | GGC | CAT | ATA | ACG | GGT | CAC | CGT | ATG | GCA | TGG | GAT | 390 |
| ATG | ATG | ATG | AAC | TGG | TCC | CCT | ACA | ACG | GCG | TTG | GTA | ATA | 429 |
| GCT | CAG | CTG | CTC | AGG | GTC | CCG | CAA | GCC | GTC | TTG | GAC | ATG | 468 |
| ATC | GCT | GGT | GCC | CAC | TGG | GGA | GTC | CTA | GCG | GGC | ATA | GCG | 507 |
| TAT | TTC | TCC | ATG | GCG | GGG | AAC | TGG | GCG | AAG | GTC | CTG | CTA | 546 |
| GTG | CTG | TTG | CTG | TTT | GCC | GGC | GTC | GAT | GCG | | | | 576 |

( 2 ) INFORMATION FOR SEQ ID NO:7:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SW1

( x i ) SEQUENCE DESCRIPTION: SEQ ID NO:7:

| | | | | | | | | | | | | |
|---|---|---|---|---|---|---|---|---|---|---|---|---|
| TAC | CAA | GTA | CGC | AAC | TCC | TCG | GGC | CTT | TAC | CAT | GTC | ACC | 39 |
| AAT | GAT | TGC | CCT | AAC | TCG | AGT | ATT | GTG | TAC | GAG | ACG | GCC | 78 |
| GAT | GCC | ATT | CTA | CAC | TCT | CCA | GGG | TGT | GTC | CCT | TGC | GTT | 117 |
| CGC | GAG | GAT | GGC | GCC | CCG | AAG | TGT | TGG | GTG | GCG | GTG | GCC | 156 |
| CCC | ACA | GTC | GCC | ACT | AGG | GAC | GGC | AAA | CTC | CCT | GCA | ACG | 195 |
| CAG | CTT | CGA | CGT | CAC | ATC | GAT | CTG | CTT | GTC | GGA | AGC | GCC | 234 |
| ACC | CTC | TGC | TCG | GCC | CTC | TAC | GTG | GGG | GAC | TTG | TGC | GGG | 273 |
| TCT | GTC | TTT | CTC | GTC | AGT | CAA | CTG | TTC | ACG | TTC | TCC | CCC | 312 |
| AGG | CGC | CAC | TGG | ACA | ACG | CAA | GAC | TGT | AAC | TGT | TCT | ATC | 351 |
| TAT | CCC | GGC | CAC | ATA | ACG | GGT | CAC | CGC | ATG | GCA | TGG | GAT | 390 |
| ATG | ATG | ATG | AAC | TGG | TCC | CCC | ACA | ACA | GCG | CTG | GTA | GTA | 429 |
| GCT | CAG | CTG | CTC | AGG | ATC | CCG | CAA | GCC | GTC | TTG | GAC | ATG | 468 |
| ATC | GCT | GGT | GCC | CAC | TGG | GGA | GTC | CTA | GCG | GGC | ATA | GCG | 507 |
| TAT | TTC | TCC | ATG | GTG | GGG | AAC | TGG | GCG | AAG | GTC | CTG | ATA | 546 |
| GTG | CTG | TTG | CTG | TTT | TCC | GGC | GTC | GAT | GCG | | | | 576 |

( 2 ) INFORMATION FOR SEQ ID NO:8:

( i ) SEQUENCE CHARACTERISTICS:
        ( A ) LENGTH: 576 base pairs (B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: US11

(xi) SEQUENCE DESCRIPTION: SEQ ID NO:8:

| TAC | CAA | GTA | CGC | AAC | TCC | ACG | GGG | CTT | TAC | CAT | GTC | ACC | 39 |
| AAT | GAT | TGC | CCT | AAC | TCG | AGT | ATT | GTG | TAC | GAG | GCG | GCC | 78 |
| GAT | GCC | ATC | CTG | CAC | ACT | CCG | GGG | TGT | GTT | CCT | TGC | GTT | 117 |
| CGC | GAG | GGT | AAC | GCT | TCG | AGG | TGT | TGG | GTG | GCG | ATG | ACC | 156 |
| CCC | ACG | GTG | GCC | ACC | AGG | GAC | GGC | AAA | CTC | CCC | ACA | ACG | 195 |
| CAA | CTT | CGA | CGT | CAC | ATC | GAT | CTG | CTT | GTC | GGG | AGC | GCC | 234 |
| ACC | CTC | TGT | TCG | GCC | CTC | TAC | GTG | GGG | GAC | CTG | TGC | GGG | 273 |
| TCT | GTC | TTT | CTT | GTC | GGT | CAA | CTG | TTT | ACC | TTC | TCT | CCC | 312 |
| AGA | CGC | CAC | TGG | ACG | ACG | CAG | GGC | TGC | AAT | TGT | TCT | ATC | 351 |
| TAT | CCC | GGC | CAT | ATA | ACG | GGT | CAC | CGC | ATG | GCA | TGG | GAT | 390 |
| ATG | ATG | ATG | AAC | TGG | TCC | CCT | ACG | GCG | GCG | TTG | GTG | GTA | 429 |
| GCT | CAG | CTG | CTC | CGG | ATC | CCA | CAA | GCC | ATC | TTG | GAC | ATG | 468 |
| ATC | GCT | GGT | GCT | CAC | TGG | GGA | GTC | CTA | GCG | GGC | ATA | GCG | 507 |
| TAT | TTC | TCC | ATG | GTG | GGG | AAC | TGG | GCG | AAG | GTC | CTG | GTA | 546 |
| GTG | CTG | CTG | CTA | TTT | GCC | GGC | GTC | GAC | GCG |     |     |     | 576 |

(2) INFORMATION FOR SEQ ID NO:9:

(i) SEQUENCE CHARACTERISTICS:
(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: D1

(xi) SEQUENCE DESCRIPTION: SEQ ID NO:9:

| TAT | GAA | GTG | CGC | AAC | GTG | TCC | GGG | GTG | TAC | CAT | GTC | ACG | 39 |
| AAC | GAC | TGT | TCC | AAC | TCG | AGC | ATT | GTG | TAT | GAG | ACA | GCG | 78 |
| GAC | ATG | ATC | ATG | CAC | ACC | CCG | GGT | GCG | TG | CCC | TGC | GTT | 117 |
| CGG | GAG | GAC | AAC | TCC | TCT | CGC | TGC | TGG | GTA | GCG | CTC | ACC | 156 |
| CCC | ACG | CTC | GCG | GCT | AGG | AAT | GGC | AAC | GTC | CCC | ACT | ACG | 195 |
| GCG | ATA | CGA | CGC | CAC | GTC | GAT | TTG | CTC | GTT | GGG | GCG | GCT | 234 |
| GCT | TTC | TGC | TCC | GCC | ATG | TAC | GTG | GGG | GAT | CTC | TGC | GGA | 273 |
| TCT | GTT | TTC | CTC | ATC | TCC | CAG | CTG | TTC | ACC | CTC | TCG | CCT | 312 |
| CGC | CGG | CAT | GAG | ACG | GTA | CAG | GAG | TGT | AAT | TGC | TCA | ATC | 351 |
| TAT | CCC | GGC | CAC | GTG | ACA | GGT | CAC | CGT | ATG | GCT | TGG | GAT | 390 |
| ATG | ATG | ATG | AAC | TGG | TCA | CCT | ACA | ACA | GCC | TTA | GTG | GTA | 429 |
| TCG | CAG | TTA | CTC | CGG | ATC | CCA | CAA | GCT | GTC | ATG | GAC | ATG | 468 |
| GTG | GCG | GGG | GCC | CAC | TGG | GGG | GTC | CTG | GCG | GGC | CTC | GCC | 507 |
| TAC | TAT | TCC | ATG | GTG | GGG | AAC | TGG | GCT | AAG | GTT | TTG | ATT | 546 |

GTG ATG CTA CTC TTT GCT GGC GTT GAC GGC          576

(2) INFORMATION FOR SEQ ID NO:10:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: D3

(xi) SEQUENCE DESCRIPTION: SEQ ID NO:10:

TAT GAA GTG CGC AAC GTG TCC GGG GTG TAC CAA GTC ACC          39
AAT GAC TGT TCC AAC TCG AGC ATC GTG TAT GAG ACA GCG          78
GAC ATG ATC ATG CAC ACC CCC GGG TGC GTG CCC TGC GTT          117
CGG GAG GAC AAC TCC TCT CGC TGC TGG GTA GCG CTC ACC          156
CCC ACG CTC GCG GCT AGG AAT AGC AGC GTC CCC ACT ACG          195
ACA ATA CGA CGC CAC GTC GAT TTG CTC GTT GGG GCG GCT          234
GCT TTC TGC TCC GCC ATG TAC GTG GGG GAT CTT TGC GGA          273
TCT GTT TTC CTC GTC TCC CAG CTG TTC ACC TTC TCG CCT          312
CGC CGG CAT GAG ACA GTA CAG GAA TGT AAC TGC TCA ATC          351
TAT CCC GGC CAC GTG ACA GGT CAC CGC ATG GCT TGG GAT          390
ATG ATG ATG AAC TGG TCG CCT ACA GCA GCC CTA GTG GTA          429
TCG CAG TTA CTC CGG ATC CCA CAA GCT GTC GTG GAC ATG          468
GTG GCG GGG GCC CAC TGG GGG GTC CTG GCG GGC CTC GCC          507
TAC TAT TCC ATG GTG GGG AAC TGG GCT AAG GTT TTG ATT          546
GTG ATG CTA CTC TTT GCT GGC GTC GAC GGC                      576

(2) INFORMATION FOR SEQ ID NO:11:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DK1

(xi) SEQUENCE DESCRIPTION: SEQ ID NO:11:

TAT GAA GTG CGC AAC GTG TCC GGG GTG TAC CAC GTC ACA          39
AAC GAC TGC TCC AAC TCA AGC ATC GTG TAT GAG GCA GTG          78
GAC GTG ATC ATG CAT ACC CCA GGG TGC GTG CCC TGC GTT          117
CGG GAG AAC AAC CAC TCC CGT TGC TGG GTA GCG CTC ACC          156
CCC ACG CTC GCG GCC AGG AAC GCC AGC ATC CCC ACT ACG          195
ACA ATA CGA CGC CAT GTC GAT TTG CTC GTT GGG GCG GCT          234
GCT TTC TGC TCC GCT ATG TAC GTG GGG GAC CTC TGC GGA          273
TCC GTT TTC CTC GTC TCT CAG CTG TTC ACC TTT TCA CCT          312
CGC CGG CAT GAG ACA GCA CAG GAC TGC AAC TGC TCA ATC          351
TAT CCC GGC CAC GTT TCA GGT CAC CGC ATG GCT TGG GAT          390
ATG ATG ATG AAC TGG TCA CCT ACA ACA GCC CTA GTG CTA          429

```
TCG CAG TTA CTC CGA ATC CCA CAA GCT GTC GTG GAC ATG        468

GTG GCG GGG GCC CAC TGG GGA GTC CTG GCG GGC CTC GCC        507

TAC TAC TCC ATG GCG GGG AAC TGG GCC AAG GTT TTA ATT        546

GTG TTG CTA CTC TTT GCC GGC GTT GAT GGG                    576
```

( 2 ) INFORMATION FOR SEQ ID NO:12:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK3

( x i ) SEQUENCE DESCRIPTION: SEQ ID NO:12:

```
TAT GAA GTG CGC AAC GTG TCC GGG ATA TAC CAT GTC ACG         39

AAC GAC TGC TCC AAC TCA AGC GTC GTG TAT GAG ACA GCA         78

GAC ATG ATC ATG CAT ACC CCT GGA TGC GTG CCC TGC GTA        117

CGG GAG AAC AAC TCC TCC CGC TGT TGG GTA GCG CTC ACT        156

CCC ACG CTC GCG GCC AGG AAC GTC AGC GTC CCC ACC ACG        195

ACA ATA CGA CGT CAC GTC GAC TTG CTC GTT GGG GCG GCT        234

GCC TTC TGC TCC GCT ATG TAC GTG GGG GAT CTC TGC GGA        273

TCT GTT TTC CTT GTC TCC CAG CTG TTC ACC TTC TCG CCT        312

CGC CGA CAC GAG ACA GTA CAG GAC TGC AAC TGC TCA CTC        351

TAT CCC GGC CAC GTA TCA GGT CAC CGC ATG GCT TGG GAT        390

ATG ATG ATG AAC TGG TCC CCT ACA GCA GCC CTA GTG GTG        429

TCG CAA TTA CTC CGG ATC CCG CAA GCT GTC GTG GAC ATG        468

GTG GCG GGG GCC CAC TGG GGA GTC CTA GCG GGC CTT GCC        507

TAC TAT TCC ATG GTG GGA AAC TGG GCT AAG GTT TTG ATT        546

GTG ATG CTA CTT TTT GCC GGC GTT GAT GGG                    576
```

( 2 ) INFORMATION FOR SEQ ID NO:13:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK4

( x i ) SEQUENCE DESCRIPTION: SEQ ID NO:13:

```
CAT GAA GTG CAC AAC GTA TCC GGG ATC TAC CAT GTC ACG         39

AAC GAC TGC TCC AAC TCA AGT ATT GTG TAT GAG GCA GCG         78

GAC ATG ATC ATG CAT ACC CCC GGG TGC GTG CCC TGC GTC        117

CGG GAG AAC AAC TCC TCC CGT TGC TGG GTA GCG CTC ACT        156

CCC ACG CTC GCG GCC AGG AAC GCC AGC ATC CCC ACT ACG        195

ACA ATA CGA CGC CAT GTC GAC TTG CTC GTT GGG GCG GCT        234

GCT TTC TGC TCC GCC ATG TAC GTG GGA GAT CTC TGC GGA        273
```

| | | | | | | | | | | | | |
|---|---|---|---|---|---|---|---|---|---|---|---|---|
|TCT|GTC|TTC|CTC|GTC|TCC|CAG|TTG|TTC|ACC|TTC|TCG|CCT|312|
|CGC|CGG|CAT|GAG|ACG|GTA|CAG|GAC|TGC|AAT|TGC|TCA|ATC|351|
|TAT|CCC|GGC|CAC|GTA|TCA|GGT|CAC|CGC|ATG|GCT|TGG|GAT|390|
|ATG|ATG|ATG|AAC|TGG|TCA|CCT|ACA|GCA|GCC|CTA|GTG|GTA|429|
|TCG|CAG|TTA|CTC|CGA|CTC|CCA|CAA|GCT|GTC|ATG|GAC|ATG|468|
|GTG|GCG|GGA|GCC|CAC|TGG|GGA|GTC|CTA|GCG|GGC|CTT|GCT|507|
|TAC|TAT|TCC|ATG|GTG|GGG|AAC|TGG|GCC|AAG|GTT|TTG|ATT|546|
|GTG|ATG|CTA|CTC|TTT|GCC|GGC|GTT|GAC|GGG| | | |576|

(2) INFORMATION FOR SEQ ID NO:14:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK5

(xi) SEQUENCE DESCRIPTION: SEQ ID NO:14:

| | | | | | | | | | | | | |
|---|---|---|---|---|---|---|---|---|---|---|---|---|
|TAT|GAA|GTG|CGC|AAC|GTG|TCC|GGG|GTA|TAC|CAT|GTC|ACG|39|
|AAC|GAC|TGC|TCC|AAC|TTA|AGC|ATC|GTG|TAC|GAG|ACA|ACG|78|
|GAC|ATG|ATC|ATG|CAC|ACC|CCT|GGG|TGC|GTG|CCC|TGC|GTT|117|
|CGG|GAA|AAC|AAC|TCC|TCC|CGT|TGT|TGG|GTA|GCG|CTC|GCC|156|
|CCC|ACG|CTC|GCG|GCC|AGG|AAC|GCC|AGC|GTC|CCC|ACC|ACG|195|
|GCA|ATA|CGA|CGC|CAC|GTC|GAC|TTG|CTC|GTT|GGG|GCG|GCT|234|
|GCT|TTC|TGC|TCC|GCT|ATG|TAC|GTG|GGG|GAT|CTT|TGC|GGA|273|
|TCT|GTT|TTC|CTC|GTC|TCC|CAG|CTG|TTC|ACC|TTC|TCG|CCT|312|
|CGC|CGA|CAC|GAG|ACG|GTA|CAG|GAC|TGC|AAC|TGC|TCA|ATC|351|
|TAT|CCC|GGC|CAC|GTA|ACA|GGT|CAC|CGC|ATG|GCT|TGG|GAT|390|
|ATG|ATG|ATG|AAC|TGG|TCA|CCT|ACA|ACA|GCC|CTA|GTG|GTG|429|
|TCG|CAG|TTA|CTC|CGG|ATC|CCG|CAA|GCT|GTC|GTG|GAC|ATG|468|
|GTA|GCG|GGG|GCC|CAC|TGG|GGG|GTC|CTG|GCG|GGC|CTT|GCC|507|
|TAC|TAT|TCC|ATG|GTG|GGA|AAC|TGG|GCT|AAG|GTT|TTG|ATT|546|
|GTG|ATG|CTA|CTT|TTT|GCC|GGC|GTT|GAT|GGG| | | |576|

(2) INFORMATION FOR SEQ ID NO:15:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK8

(xi) SEQUENCE DESCRIPTION: SEQ ID NO:15:

| | | | | | | | | | | | | |
|---|---|---|---|---|---|---|---|---|---|---|---|---|
|TAT|GAA|GTG|CGC|AAC|GTG|TCC|GGG|ATA|TAC|CAT|GTC|ACG|39|
|AAC|GAC|TGC|TCC|AAC|TCA|AGC|ATC|GTG|TAT|GAA|ACA|GCG|78|
|GAC|ATG|ATT|ATG|CAT|ACC|CCT|GGA|TGC|ATG|CCC|TGC|GTT|117|
|CGG|GAG|AAC|AAC|TCC|TCC|CGT|TGC|TGG|GTG|GCG|CTC|ACT|156|

| | | | | | | | | | | | | |
|---|---|---|---|---|---|---|---|---|---|---|---|---|
|CCC|ACG|CTC|GCG|GCT|AGG|AAT|GTC|AGC|GTC|CCC|ACT|ACG|195|
|ACA|ATA|CGA|CGC|CAC|GTC|GAC|TTG|CTC|GTT|GGG|GCG|GCT|234|
|GCT|TTC|TGC|TCC|GCT|ATG|TAC|GTG|GGG|GAT|CTC|TGC|GGA|273|
|TCT|GTT|TTC|CTC|GTC|TCC|CAG|CTG|TTC|ACC|TTT|TCG|CCT|312|
|CGC|CGA|CAC|GAG|ACG|GTA|CAG|GAC|TGC|AAC|TGC|TCA|ATC|351|
|TAT|CCC|GGC|CAC|GTA|TCA|GGT|CAC|CGC|ATG|GCT|TGG|GAT|390|
|ATG|ATG|ATG|AAC|TGG|TCG|CCC|ACA|ACA|GCC|CTA|GTG|GTG|429|
|TCG|CAG|TTA|CTC|CGG|ATC|CCG|CAA|GCT|ATC|GTG|GAC|ATG|468|
|GTG|GCG|GGG|GCC|CAC|TGG|GGA|GTC|CTA|GCG|GGC|CTT|GCC|507|
|TAC|TAT|TCC|ATG|GTG|GGC|AAC|TGG|GCT|AAG|GTT|TTG|ATT|546|
|GTG|ATG|CTA|CTG|TTT|GCC|GGC|GTT|GAT|GGG| | | |576|

( 2 ) INFORMATION FOR SEQ ID NO:16:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: IND5

( x i ) SEQUENCE DESCRIPTION: SEQ ID NO:16:

| | | | | | | | | | | | | |
|---|---|---|---|---|---|---|---|---|---|---|---|---|
|TAT|GAA|GTG|CGC|AAC|GTG|TCC|GGG|GTG|TAC|CAT|GTC|ACG|39|
|AAC|GAC|TGC|TCC|AAC|TCA|AGT|ATT|GTG|TAT|GAG|GCA|GCG|78|
|GAC|ATG|ATC|ATG|CAC|ACT|CCC|GGG|TGC|GTG|CCC|TGC|GTT|117|
|CGG|GAG|GGC|AAC|TCC|TCT|CGC|TGC|TGG|GTA|GCG|CTC|ACT|156|
|CCC|ACT|CTC|GCG|GCC|AGG|AAC|GCC|AGC|GTC|TCC|ACC|ACG|195|
|ACA|ATA|CGA|CAC|CAC|GTC|GAT|TTG|CTC|GTT|GGG|GCG|GCT|234|
|GCT|TTC|TGT|TCC|GCT|ATG|TAC|GTG|GGG|GAT|CTA|TGC|GGA|273|
|TCT|GTT|TTC|CTC|GTC|TCC|CAG|CTG|TTC|ACC|TTC|TCA|CCG|312|
|CGC|CGG|CAT|GAG|ACA|GTA|CAG|GAC|TGC|AAT|TGC|TCC|ATC|351|
|TAT|CCC|GGC|CAC|GTA|TCA|GGT|CAC|CGC|ATG|GCC|TGG|GAT|390|
|ATG|ATG|ATG|AAC|TGG|TCA|CCT|ACA|GCA|GCC|CTA|GTG|GTA|429|
|TCG|CAG|TTG|CTC|CGG|ATC|CCA|CAA|GCT|GTC|GTG|GAT|ATG|468|
|GTG|GCG|GGG|GCC|CAC|TGG|GGA|ATC|CTG|GCG|GGC|CTT|GCC|507|
|TAC|TAT|TCC|ATG|GTA|GGG|AAC|TGG|GCT|AAG|GTT|TTG|ATT|546|
|GTG|ATG|CTA|CTC|TTT|GCC|GGC|GTT|GAC|GGG| | | |576|

( 2 ) INFORMATION FOR SEQ ID NO:17:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: IND8

( x i ) SEQUENCE DESCRIPTION: SEQ ID NO:17:

| | | | | | | | | | | | | | |
|---|---|---|---|---|---|---|---|---|---|---|---|---|---|
| TAT | GAG | GTG | CGC | AAC | GTG | TCC | GGG | GTG | TAC | CAT | GTC | ACG | 39 |
| AAC | GAC | TGC | TCC | AAC | TCA | AGT | ATT | GTG | TAT | GAG | GCA | GCG | 78 |
| GAC | ATG | ATC | ATG | CAC | ACC | CCC | GGG | TGC | GTG | CCC | TGC | GTT | 117 |
| CGG | GAG | GGC | AAC | TTC | TCT | AGT | TGC | TGG | GTA | GCG | CTC | ACT | 156 |
| CCC | ACT | CTC | GCG | GCT | AGG | AAC | GCC | AGC | GTC | CCC | ACC | ACG | 195 |
| ACA | ATA | CGA | CGC | CAC | GTC | GAT | TTG | CTC | GTT | GGG | GCG | GCT | 234 |
| GCT | TTC | TGT | TCC | GCT | ATG | TAC | GTG | GGG | GAT | CTC | TGC | GGA | 273 |
| TCT | GTT | TTC | CTT | GTC | TCC | CAG | CTG | TTC | ACC | TTC | TCA | CCG | 312 |
| CGC | CGG | CAT | GAG | ACA | GTA | CAG | GAC | TGC | AAT | TGC | TCC | ATC | 351 |
| TAT | CCC | GGC | CAC | GTA | TCA | GGT | CAC | CGC | ATG | GCT | TGG | GAT | 390 |
| ATG | ATG | ATG | AAC | TGG | TCA | CCT | ACA | GCG | GCC | CTA | GTG | GTA | 429 |
| TCG | CAG | TTG | CTC | CGG | ATC | CCA | CAA | GCT | GTC | GTG | GAT | ATG | 468 |
| GTG | GCG | GGG | GCC | CAC | TGG | GGA | ATC | CTG | GCG | GGC | CTT | GCC | 507 |
| TAC | TAT | TCC | ATG | GTA | GGG | AAC | TGG | GCT | AAG | GTT | TTG | ATT | 546 |
| GTG | ATG | CTA | CTC | TTT | GCC | GGC | GTT | GAC | GGG | | | | 576 |

(2) INFORMATION FOR SEQ ID NO:18:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: P10

(xi) SEQUENCE DESCRIPTION: SEQ ID NO:18:

| | | | | | | | | | | | | | |
|---|---|---|---|---|---|---|---|---|---|---|---|---|---|
| TAT | GAA | GTG | CGC | AAC | GTG | TCC | GGG | GTG | TAC | CAT | GTC | ACG | 39 |
| AAC | GAC | TGC | TCC | AAC | TCA | AGT | ATT | GTG | TAT | GAG | GCA | GCG | 78 |
| GAC | ATG | ATA | ATG | CAC | ACC | CCC | GGG | TGC | GTG | CCC | TGT | GTT | 117 |
| CGG | GAG | AAC | AAC | TCC | TCC | CGC | TGC | TGG | GTA | GCG | CTC | ACT | 156 |
| CCC | ACA | CTC | GCG | GCT | AGG | AAT | TCC | AGC | GTC | CCA | ACT | ACG | 195 |
| GCA | ATA | CGA | CGC | CAT | GTC | GAT | TTG | CTC | GTT | GGG | GCG | GCT | 234 |
| GCT | TTC | TGC | TCC | GCT | ATG | TAC | GTG | GGG | GAT | CTC | TGC | GGA | 273 |
| TCT | GTT | CTC | CTC | GTC | TCC | CAG | CTG | TTC | ACC | TTC | TCA | CCT | 312 |
| CGC | CGG | CAT | TGG | ACA | GTA | CAG | GAC | TGC | AAT | TGT | TCA | ATC | 351 |
| TAT | CCT | GGC | CAC | GTA | TCA | GGT | CAC | CGC | ATG | GCT | TGG | GAT | 390 |
| ATG | ATG | ATG | AAC | TGG | TCG | CCC | ACA | GCA | GCC | CTA | GTG | GTG | 429 |
| TCG | CAG | CTA | CTC | CGG | ATC | CCA | CAA | GCT | ATC | TTG | GAT | GTG | 468 |
| GTG | GCG | GGG | GCC | CAC | TGG | GGA | GTC | CTG | GCG | GGC | CTT | GCC | 507 |
| TAC | TAT | TCC | ATG | GTG | GGG | AAC | TGG | GCT | AAG | GTC | TTG | ATT | 546 |
| GTG | ATG | CTA | CTC | TTT | GCC | GGC | GTT | GAC | GGA | | | | 576 |

(2) INFORMATION FOR SEQ ID NO:19:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
    (A) ORGANISM: homosapiens
    (C) INDIVIDUAL ISOLATE: S9

(xi) SEQUENCE DESCRIPTION: SEQ ID NO:19:

| | | | | | | | | | | | | |
|---|---|---|---|---|---|---|---|---|---|---|---|---|
| TAT | GAA | GTG | CGC | AAC | GTA | TCC | GGG | GCG | TAC | CAT | GTC | ACG | 39 |
| AAC | GAC | TGC | TCC | AAC | TCA | AGT | ATT | GTG | TAC | GAG | GCA | GCG | 78 |
| GAC | GTG | ATC | ATG | CAT | ACC | CCC | GGG | TGT | GTA | CCC | TGC | GTT | 117 |
| CAG | GAG | GGT | AAC | TCC | TCC | CAA | TGC | TGG | GTG | GCG | CTC | ACC | 156 |
| CCC | ACG | CTC | GCG | GCC | AGG | AAC | GCT | ACC | GTC | CCC | ACC | ACG | 195 |
| ACA | ATA | CGA | CGT | CAT | GTC | GAT | TTG | CTC | GTT | GGG | GCG | GCT | 234 |
| GTT | TTC | TGC | TCC | GCT | ATG | TAC | GTG | GGG | GAC | CTG | TGC | GGA | 273 |
| TCT | GTT | TTC | CTC | ATC | TCC | CAG | CTG | TTC | ACC | ATC | TCG | CCC | 312 |
| CGT | CGG | CAT | GAG | ACA | GTA | CAG | AAC | TGC | AAT | TGC | TCA | ATC | 351 |
| TAT | CCC | GGA | CAC | GTG | ACA | GGT | CAT | CGC | ATG | GCC | TGG | GAT | 390 |
| ATG | ATG | ATG | AAC | TGG | TCG | CCT | ACA | ACA | GCC | CTA | GTG | GTA | 429 |
| TCG | CAG | CTA | CTC | CGG | ATC | CCA | CAA | GCT | GTC | ATG | GAT | ATG | 468 |
| GTG | GCG | GGG | GCC | CAC | TGG | GGA | GTC | CTG | GCG | GGC | CTC | GCC | 507 |
| TAC | TAT | TCC | ATG | GTG | GGG | AAC | TGG | GCT | AAG | GTT | TTG | ATT | 546 |
| GTG | ATG | CTA | CTT | TTT | GCT | GGT | GTT | GAC | GGG | | | | 576 |

(2) INFORMATION FOR SEQ ID NO:20:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S45

(xi) SEQUENCE DESCRIPTION: SEQ ID NO:20:

| | | | | | | | | | | | | |
|---|---|---|---|---|---|---|---|---|---|---|---|---|
| TAT | GAA | GTG | CGC | AAC | GTG | TCC | GGG | GCG | TAC | CAT | GTC | ACG | 39 |
| AAC | GAC | TGC | TCC | AAC | TCA | AGC | ATT | GTG | TAT | GAG | GCA | GTG | 78 |
| GAC | GTG | ATC | CTG | CAC | ACC | CCT | GGG | TGT | GTG | CCC | TGC | GTT | 117 |
| CGG | GAG | AAC | AAC | TCC | TCC | CGT | TGC | TGG | GTG | GCG | CTC | ACT | 156 |
| CCC | ACG | CTC | GCG | GCC | AGG | AAC | TCC | AGC | GTC | CCC | ACT | ACG | 195 |
| ACA | ATA | CGA | CGT | CAC | GTC | GAT | TTG | CTC | GTT | GGG | GCG | GCT | 234 |
| GCT | TTC | TGC | TCC | GCT | ATG | TAC | GTG | GGG | GAT | CTC | TGC | GGA | 273 |
| TCT | GTT | TTC | CTT | GTT | TCC | CAG | CTG | TTC | ACC | TTC | TCG | CCT | 312 |
| CGT | CGG | CAT | GAG | ACA | GTA | CAG | GAC | TGC | AAC | TGT | TCA | ATC | 351 |
| TAT | CCC | GGC | CAC | GTA | ACA | GGT | CAC | CGC | ATG | GCT | TGG | GAT | 390 |
| ATG | ATG | ATG | AAC | TGG | TCG | CCT | ACA | GCA | GCC | TTA | GTG | GTA | 429 |
| TCG | CAG | TTA | CTC | CGG | ATC | CCA | CAA | GCT | GTC | GTG | GAC | ATG | 468 |
| GTG | GCG | GGG | GCC | CAC | TGG | GGA | GTC | CTG | GCG | GGC | CTT | GCC | 507 |
| TAC | TAT | TCC | ATG | GTG | GGG | AAC | TGG | GCT | AAG | GTT | CTG | ATT | 546 |
| GTG | ATG | CTA | CTC | TTT | GCC | GGC | GTT | GAC | GGG | | | | 576 |

( 2 ) INFORMATION FOR SEQ ID NO:21:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA10

( x i ) SEQUENCE DESCRIPTION: SEQ ID NO:21:

```
TAT GAA GTG CGC AAC GTG TCC GGG ATG TAC CAT GTC ACG        39
AAC GAC TGC TCC AAC TCA AGC ATT GTG TAT GAG GCA GCG        78
GAC ATG ATC ATG CAC ACC CCC GGG TGC GTG CCC TGC GTT       117
CGG GAG AAC AAC TCC TCC CGC TGC TGG GTA GCG CTC ACT       156
CCC ACG CTC GCG GCC AGG AAC TCC AGC GTC CCC ACT ACG       195
ACA ATA CGA CGC CAC GTC GAT TTG CTC GTT GGG GCG GCT       234
GCT TTC TGC TCC GCC ATG TAC GTG GGG GAC CTC TGC GGA       273
TCT GTT TTC CTT GTC TCC CAG CTG TTC ACC TTC TCG CCT       312
CGC CGG TAT GAG ACA GTA CAG GAC TGC AAT TGC TCA ATC       351
TAT CCC GGC CGC GTA ACA GGT CAC CGC ATG GCT TGG GAT       390
ATG ATG ATG AAC TGG TCA CCT ACA ACA GCT CTA GTA GTA       429
TCG CAG TTA CTC CGG ATC CCA CAA GCT ATC GTG GAC ATG       468
GTG GCG GGG GCC CAC TGG GGA GTC CTA GCG GGC CTT GCC       507
TAC TAT TCC ATG GTG GGG AAC TGG GCT AAG GTT TTG ATT       546
GTT ATG CTA CTC TTT GCC GGC GTT GAC GGG                    576
```

( 2 ) INFORMATION FOR SEQ ID NO:22:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SW2

( x i ) SEQUENCE DESCRIPTION: SEQ ID NO:22:

```
TAT GAA GTG CGC AAC GTG TCC GGG GTG TAT CAT GTC ACG        39
AAC GAC TGT TCC AAC TCA AGC ATT GTG TAT GAG ACA GCG        78
GAC ATG ATC ATG CAT ACC CCC GGG TGC GTG CCC TGC GTT       117
CGG GAG GCC AAC TCC TCC CGC TGC TGG GTA GCG CTC ACT       156
CCC ACG CTA GCA GCC AGG AAC ACC AGC GTC CCC ACT ACG       195
ACA ATA CGA CGC CAC GTC GAT TTG CTC GTT GGG GCG GCT       234
GCT TTC TGC TCC GTT ATG TAC GTG GGG GAT CTC TGC GGA       273
TCT GTT TTC CTC GTC TCC CAG CTG TTC ACT TTT TCA CCT       312
CGC CGG CAC GAG ACA GTA CAG GAC TGC AAC TGT TCC ATC       351
TAT CCC GGC CAC GTA TCA GGT CAC CGC ATG GCT TGG GAC       390
ATG ATG ATG AAC TGG TCA CCT ACA GCA GCC CTG GTG GTA       429
TCG CAG TTA CTC CGG ATC CCA CAA GCT GTC GTG GAC ATG       468
```

| | | | | | | | | | | | | |
|---|---|---|---|---|---|---|---|---|---|---|---|---|
|GTA|GCG|GGG|GCC|CAC|TGG|GGA|GTC|CTG|GCG|GGC|CTT|GCA|507|
|TAC|TAT|TCC|ATG|GTG|GGG|AAC|TGG|GCT|AAG|GTT|TTG|ATT|546|
|GTG|ATG|CTA|CTC|TTT|GCT|GGC|GTT|GAC|GGG| | | |576|

( 2 ) INFORMATION FOR SEQ ID NO:23:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T3

( x i ) SEQUENCE DESCRIPTION: SEQ ID NO:23:

| | | | | | | | | | | | | |
|---|---|---|---|---|---|---|---|---|---|---|---|---|
|TAC|GAA|GTG|CGC|AAC|GTG|TCC|GGG|GTG|TAC|TAT|GTC|ACG|39|
|AAC|GAC|TGT|TCC|AAC|TCA|AGC|ATT|GTG|TAT|GAG|ACA|GCG|78|
|GAC|ATG|ATC|ATG|CAC|ACC|CCT|GGG|TGC|GTG|CCC|TGC|GTT|117|
|CGG|GAG|AGC|AAT|TCC|TCC|CGC|TGC|TGG|GTA|GCG|CTT|ACT|156|
|CCC|ACG|CTC|GCG|GCC|AGG|AAC|GCC|AGC|GTC|CCC|ACT|AAG|195|
|ACA|ATA|CGA|CGT|CAC|GTC|GAC|TTG|CTC|GTT|GGG|GCG|GCT|234|
|GCT|TTC|TGT|TCC|GCT|ATG|TAC|GTG|GGG|GAT|CTC|TGC|GGA|273|
|TCT|GTT|TTC|CTC|GTC|TCC|CAG|CTG|TTC|ACT|TTC|TCG|CCT|312|
|CGC|CGG|CAT|GAG|ACA|GTA|CAG|GAC|TGC|AAC|TGC|TCA|ATC|351|
|TAT|CCC|GGC|CAC|GTA|ACA|GGT|CAC|CGT|ATG|GCT|TGG|GAT|390|
|ATG|ATG|ATG|AAC|TGG|TCG|CCC|ACA|ACG|GCA|CTA|GTG|GTG|429|
|TCG|CAG|TTG|CTC|CGG|ATC|CCA|CAA|GCT|GTC|GTG|GAC|ATG|468|
|GTG|GCG|GGG|GCC|CAC|TGG|GGA|GTC|CTG|GCG|GGC|CTT|GCC|507|
|TAC|TAT|TCC|ATG|GTG|GGG|AAC|TGG|GCT|AAG|GTT|TTG|ATT|546|
|GTG|CTG|CTA|CTC|TTT|GCC|GGC|GTT|GAT|GGG| | | |576|

( 2 ) INFORMATION FOR SEQ ID NO:24:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T10

( x i ) SEQUENCE DESCRIPTION: SEQ ID NO:24:

| | | | | | | | | | | | | |
|---|---|---|---|---|---|---|---|---|---|---|---|---|
|TAT|GAA|GTG|CGC|AAC|GTG|TCC|GGG|ATG|TAC|CAT|GTC|ACG|39|
|AAC|GAC|TGC|TCC|AAC|TCA|AGC|ATT|GTG|TTT|GAG|GCA|GCG|78|
|GAC|TTG|ATC|ATG|CAC|ACC|CCC|GGG|TGC|GTG|CCC|TGC|GTT|117|
|CGG|GAG|GGC|AAC|TCC|TCC|CGC|TGC|TGG|GTA|GCG|CTC|ACT|156|
|CCC|ACG|CTC|GCG|GCC|AGG|AAC|ACC|AGC|GTC|CCC|ACT|ACG|195|
|ACG|ATA|CGA|CGC|CAT|GTC|GAT|TTG|CTC|GTT|GGG|GCG|GCT|234|
|GCT|TTC|TGC|TCC|GCT|ATG|TAT|GTG|GGA|GAC|CTC|TGC|GGA|273|
|TCT|GTT|TTC|CTC|GTC|TCT|CAG|CTG|TTC|ACC|TTC|TCG|CCT|312|
|CGC|CGG|CAT|GAG|ACT|TTG|CAG|GAC|TGC|AAC|TGC|TCA|ATC|351|

```
TAT CCC GGC CAT CTG TCA GGT CAC CGC ATG GCT TGG GAC      390
ATG ATG ATG AAC TGG TCG CCT ACA ACA GCT CTA GTG GTG      429
TCG CAG TTA CTC CGG ATC CCA CAA GCT GTC ATG GAC ATG      468
GTG ACA GGG GCC CAC TGG GGA GTC CTG GCG GGC CTT GCC      507
TAC TAT TCC ATG GCG GGG AAC TGG GCT AAG GTT TTA ATT      546
GTG ATG CTA CTC TTT GCC GGC GTT GAT GGG                  576
```

( 2 ) INFORMATION FOR SEQ ID NO:25:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: US6

( x i ) SEQUENCE DESCRIPTION: SEQ ID NO:25:

```
TAT GAA GTG CGC AAC GTG TCC GGG ATG TAC CAT GTC ACG      39
AAC GAC TGC TCC AAC TCA AGC ATT GTG TAT GAG GCA GCG      78
GAC ATG ATC ATG CAC ACT CCC GGG TGC GTG CCC TGT GTT      117
CGG GAG AAC AAT TCC TCC CGC TGC TGG GTA GCG CTC ACT      156
CCC ACG CTC GCG GCC AGG AAC GCT AGC GTC CCC ACT ACG      195
ACA ATA CGA CGC CAC GTC GAT TTG CTC GTT GGG GCG GCT      234
ACT TTC TGC TCC GCT ATG TAC GTG GGG GAC CTC TGC GGG      273
TCC GTT TTC CTC ATC TCC CAG CTG TTC ACC TTC TCG CCT      312
CGT CAG CAT GAG ACA GTA CAG GAC TGC AAT TGT TCA ATC      351
TAT CCC GGC CAC GTA TCA GGT CAC CGC ATG GCT TGG GAT      390
ATG ATG ATG AAT TGG TCA CCT ACA GCA GCC CTA GTG GTA      429
TCG CAG TTA CTC CGG ATC CCA CAA GCT GTC ATG GAC ATG      468
GTG GCG GGG GCC CAC TGG GGA GTC CTG GCG GGC CTT GCC      507
TAC TAT TCC ATG GTG GGG AAC TGG GCT AAG GTT CTG ATT      546
GTG TTG CTA CTC TTT GCC GGC GTT GAC GGG                  576
```

( 2 ) INFORMATION FOR SEQ ID NO:26:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T2

( x i ) SEQUENCE DESCRIPTION: SEQ ID NO:26:

```
GCC CAA GTG AGG AAC ACC AGC CGC GGT TAC ATG GTG ACT      39
AAC GAC TGT TCC AAT GAG AGC ATC ACC TGG CAG CTC CAA      78
GCC GCG GTT CTC CAC GTC CCC GGG TGT ATC CCG TGT GAG      117
AGG CTG GGA AAT ACA TCC CGA TGC TGG ATA CCG GTC ACA      156
CCA AAC GTG GCC GTG CGG CAG CCC GGC GCT CTT ACG CAG      195
```

| | | | | | | | | | | | | |
|---|---|---|---|---|---|---|---|---|---|---|---|---|
| GGC | TTG | CGG | ACG | CAC | ATC | GAC | ATG | GTT | GTG | ATG | TCC | GCC | 234 |
| ACG | CTC | TGC | TCT | GCC | CTC | TAC | GTG | GGG | GAC | CTC | TGC | GGC | 273 |
| GGG | GTG | ATG | CTC | GCA | GCC | CAG | ATG | TTC | ATT | GTC | TCG | CCG | 312 |
| CGA | CGC | CAC | TGG | TTT | GTG | CAA | GAA | TGC | AAT | TGC | TCC | ATC | 351 |
| TAC | CCC | GGT | ACC | ATC | ACT | GGA | CAC | CGT | ATG | GCA | TGG | GAC | 390 |
| ATG | ATG | ATG | AAC | TGG | TCG | CCC | ACA | GCC | ACC | ATG | ATC | CTG | 429 |
| GCG | TAC | GCG | ATG | CGC | GTT | CCC | GAG | GTC | ATC | ATA | GAC | ATC | 468 |
| ATC | GGC | GGG | GCT | CAC | TGG | GGC | GTC | ATG | TTT | GGC | TTG | GCC | 507 |
| TAC | TTC | TCT | ATG | CAG | GGA | GCG | TGG | GCG | AAG | GTC | ATT | GTC | 546 |
| ATC | CTC | TTG | CTG | GCT | GCT | GGG | GTG | GAC | GCG | | | | 576 |

( 2 ) INFORMATION FOR SEQ ID NO:27:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T4

( x i ) SEQUENCE DESCRIPTION: SEQ ID NO:27:

| | | | | | | | | | | | | |
|---|---|---|---|---|---|---|---|---|---|---|---|---|
| GCA | CAA | GTG | AAG | AAC | ACC | ACT | AAC | AGC | TAC | ATG | GTG | ACC | 39 |
| AAC | GAC | TGT | TCT | AAT | GAC | AGC | ATC | ACT | TGG | CAG | CTC | CAG | 78 |
| GCC | GCG | GTC | CTC | CAC | GTC | CCC | GGG | TGT | GTC | CCG | TGC | GAG | 117 |
| AAA | ACG | GGA | AAT | ACA | TCT | CGG | TGC | TGG | ATA | CCG | GTT | TCA | 156 |
| CCA | AAC | GTG | GCC | GTG | CGG | CAG | CCC | GGC | GCC | CTC | ACG | CAG | 195 |
| GGC | TTG | CGG | ACG | CAC | ATT | GAC | ATG | GTT | GTG | ATG | TCC | GCC | 234 |
| ACG | CTC | TGC | TCT | GCT | CTT | TAC | GTG | GGG | GAC | CTC | TGC | GGC | 273 |
| GGG | GTG | ATG | CTC | GCA | GCC | CAG | ATG | TTC | ATC | GTC | TCG | CCG | 312 |
| CAA | CAT | CAC | TGG | TTT | GTG | CAA | GAC | TGC | AAT | TGC | TCT | ATC | 351 |
| TAC | CCT | GGC | ACC | ATC | ACT | GGA | CAC | CGT | ATG | GCA | TGG | GAT | 390 |
| ATG | ATG | ATG | AAC | TGG | TCG | CCC | ACG | GCC | ACC | ATG | ATC | CTG | 429 |
| GCG | TAC | GCG | ATG | CGC | GTT | CCC | GAG | GTC | ATC | TTA | GAC | ATC | 468 |
| GTT | AGC | GGG | GCA | CAC | TGG | GGC | GTC | ATG | TTC | GGC | TTG | GCC | 507 |
| TAC | TTC | TCT | ATG | CAG | GGA | GCG | TGG | GCG | AAA | GTC | GTT | GTC | 546 |
| ATC | CTT | CTG | CTG | GCC | GCT | GGG | GTG | GAC | GCG | | | | 576 |

( 2 ) INFORMATION FOR SEQ ID NO:28:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: T9

( x i ) SEQUENCE DESCRIPTION: SEQ ID NO:28:

| | | | | | | | | | | | | |
|---|---|---|---|---|---|---|---|---|---|---|---|---|
| GCC | GAA | GTG | AAG | AAC | ACC | AGT | ACC | AGC | TAC | ATG | GTG | ACA | 39 |
| AAT | GAC | TGT | TCC | AAC | GAC | AGC | ATC | ACC | TGG | CAA | CTC | CAG | 78 |

```
GCC GCG GTC CTC CAC GTC CCC GGG TGC GTC CCG TGC GAG        117

AGA GTT GGA AAC GCG TCG CGG TGC TGG ATA CCG GTC TCG        156

CCA AAC GTA GCT GTG CAG CGG CCT GGC GCC CTC ACG CAG        195

GGC TTG CGG ACG CAC ATC GAC ATG GTT GTG ATG TCC GCC        234

ACG CTC TGC TCC GCT CTC TAC GTG GGG GAT CTC TGC GGC        273

GGG GTA ATG CTC GCC GCT CAG ATG TTC ATT ATC TCG CCG        312

CAG CAC CAC TGG TTT GTG CAG GAA TGC AAC TGC TCC ATT        351

TAC CCT GGT ACC ATC ACT GGA CAC CGT ATG GCA TGG GAC        390

ATG ATG ATG AAC TGG TCG CCC ACA ACC ACC ATG ATC TTG        429

GCG TAC GCG ATG CGC GTT CCC GAG GTC ATC ATA GAC ATC        468

ATC AGC GGA GCT CAC TGG GGC GTC ATG TTC GGC CTA GCC        507

TAC TTC TCT ATG CAG GGA GCG TGG GCG AAG GTC GTT GTC        546

ATC CTG TTG CTC ACC GCT GGC GTG GAC GCG                    576
```

( 2 ) INFORMATION FOR SEQ ID NO:29:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: 10

( x i ) SEQUENCE DESCRIPTION: SEQ ID NO:29:

```
GTC CAA GTG AAA AAC ACC AGT ACC AGC TAT ATG GTG ACC        39

AAT GAC TGC TCC AAC GAC AGC ATC ACT TGG CAA CTT GAG        78

GCT GCG GTC CTC CAC GTT CCC GGG TGT GTC CCG TGC GAG        117

AAA GTG GGA AAT ACA TCT CGG TGC TGG ATA CCG GTC TCA        156

CCA AAT GTG GCC GTG CAG CGG CCT GGC GCC CTC ACG CAG        195

GGC TTG CGG ACT CAC ATC GAC ATG GTC GTG ATG TCC GCC        234

ACG CTC TGC TCC GCT CTT TAC GTG GGG GAC TTC TGC GGT        273

GGG ATG ATG CTC GCA GCC CAA ATG TTC ATT GTC TCG CCG        312

CGC CAC CAC TCG TTT GTG CAG GAA TGC AAC TGC TCC ATC        351

TAC CCC GGT ACC ATC ACC GGG CAC CGT ATG GCA TGG GAC        390

ATG ATG ATG AAC TGG TCG CCC ACG GCC ACT TTG ATC CTG        429

GCG TAC GTG ATG CGC GTT CCC GAG GTC ATC ATA GAC ATC        468

ATT AGC GGG GCG CAT TGG GGC GTC TTG TTC GGC TTA GCC        507

TAC TTC TCT ATG CAG GGA GCG TGG GCG AAA GTC GTT GTC        546

ATC CTT CTG CTA GCC GCT GGG GTG GAC GCG                    576
```

( 2 ) INFORMATION FOR SEQ ID NO:30:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens ( C ) INDIVIDUAL ISOLATE: DK8

( x i ) SEQUENCE DESCRIPTION: SEQ ID NO:30:

| | | | | | | | | | | | | |
|---|---|---|---|---|---|---|---|---|---|---|---|---|
| GTG | GAA | GTC | AGG | AAC | ATC | AGT | TCC | AGC | TAC | TAC | GCC | ACC | 39 |
| AAT | GAT | TGC | TCA | AAC | AAC | AGC | ATC | ACC | TGG | CAA | CTC | ACC | 78 |
| GAC | GCA | GTT | CTC | CAC | CTT | CCC | GGA | TGC | GTC | CCA | TGT | GAG | 117 |
| AAT | GAC | AAT | GGC | ACC | CTG | CGC | TGC | TGG | ATA | CAA | GTG | ACA | 156 |
| CCT | AAT | GTG | GCT | GTG | AAA | CAC | CGC | GGC | GCA | CTT | ACT | CAT | 195 |
| AAC | CTG | CGA | ACA | CAC | GTC | GAC | GTG | ATC | GTA | ATG | GCA | GCT | 234 |
| ACG | GTC | TGC | TCG | GCC | TTG | TAT | GTG | GGA | GAC | GTA | TGC | GGG | 273 |
| GCC | GTG | ATG | ATC | GTG | TCG | CAG | GCT | CTC | ATA | ATA | TCG | CCT | 312 |
| GAA | CGC | CAC | AAC | TTT | ACC | CAG | GAG | TGC | AAC | TGT | TCC | ATC | 351 |
| TAC | CAA | GGT | CAT | ATC | ACC | GGC | CAC | CGC | ATG | GCA | TGG | GAC | 390 |
| ATG | ATG | CTA | AAC | TGG | TCA | CCA | ACT | CTT | ACC | ATG | ATC | CTC | 429 |
| GCC | TAT | GCC | GCT | CGT | GTT | CCT | GAG | CTA | GCC | CTC | CAG | GTT | 468 |
| GTC | TTC | GGC | GGC | CAT | TGG | GGC | GTG | GTG | TTT | GGC | TTG | GCC | 507 |
| TAT | TTC | TCC | ATG | CAG | GGA | GCG | TGG | GCC | AAA | GTC | ATT | GCC | 546 |
| ATC | CTC | CTT | CTT | GTC | GCA | GGA | GTG | GAT | GCA | | | | 576 |

( 2 ) INFORMATION FOR SEQ ID NO:31:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK11

( x i ) SEQUENCE DESCRIPTION: SEQ ID NO:31:

| | | | | | | | | | | | | |
|---|---|---|---|---|---|---|---|---|---|---|---|---|
| GTG | GAA | GTC | AGG | AAC | ACC | AGT | TCT | AGT | TAC | TAC | GCC | ACC | 39 |
| AAT | GAT | TGC | TCA | AAC | AAC | AGC | ATC | ACC | TGG | CAA | CTC | ACC | 78 |
| AAC | GCA | GTT | CTC | CAC | CTT | CCC | GGA | TGC | GTC | CCA | TGT | GAG | 117 |
| AAT | GAC | AAT | GGC | ACC | CTG | CAC | TGC | TGG | ATA | CAA | GTG | ACA | 156 |
| CCT | AAT | GTG | GCT | GTG | AAA | CAC | CGC | GGC | GCA | CTC | ACT | CAC | 195 |
| AAC | CTG | CGA | GCA | CAT | ATA | GAT | ATG | ATT | GTA | ATG | GCA | GCT | 234 |
| ACG | GTC | TGC | TCG | GCC | TTG | TAT | GTG | GGA | GAC | GTG | TGC | GGG | 273 |
| GCC | GTG | ATG | ATC | GTG | TCG | CAG | GCT | TTC | ATA | GTA | TCG | CCA | 312 |
| GAA | CAC | CAC | CAC | TTT | ACC | CAA | GAG | TGC | AAC | TGT | TCC | ATC | 351 |
| TAC | CAA | GGT | CAC | ATC | ACC | GGC | CAC | CGC | ATG | GCA | TGG | GAC | 390 |
| ATG | ATG | CTT | AAC | TGG | TCA | CCA | ACT | CTC | ACC | ATG | ATC | CTC | 429 |
| GCC | TAT | GCC | GCC | CGT | GTT | CCT | GAG | CTA | GTC | CTT | GAA | GTC | 468 |
| GTC | TTC | GGT | GGT | CAT | TGG | GGT | GTG | GTG | TTT | GGC | TTG | GCC | 507 |
| TAT | TTC | TCC | ATG | CAG | GGA | GCG | TGG | GCC | AAG | GTC | ATT | GCC | 546 |
| ATC | CTC | CTT | CTT | GTA | GCA | GGA | GTG | GAT | GCA | | | | 576 |

( 2 ) INFORMATION FOR SEQ ID NO:32:

( i ) SEQUENCE CHARACTERISTICS:

(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: SW3

(xi) SEQUENCE DESCRIPTION: SEQ ID NO:32:

| | | | | | | | | | | | | |
|---|---|---|---|---|---|---|---|---|---|---|---|---|
| GTG | GAA | GTC | AGG | AAC | ATC | AGT | TCT | AGC | TAC | TAT | GCC | ACC | 39 |
| AAT | GAT | TGC | TCA | AAC | AGC | AGC | ATC | ACC | TGG | CAA | CTC | ACC | 78 |
| AAC | GCA | GTC | CTC | CAC | CTT | CCC | GGA | TGC | GTC | CCG | TGT | GAG | 117 |
| AAT | GAT | AAT | GGC | ACC | CTG | CAC | TGC | TGG | ATA | CAA | GTG | ACA | 156 |
| CCT | AAT | GTG | GCT | GTG | AAA | CAC | CGC | GGC | GCG | CTC | ACT | CAC | 195 |
| AAC | CTG | CGA | GCA | CAC | GTC | GAT | ATG | ATC | GTA | ATG | GCA | GCT | 234 |
| ACG | GTC | TGC | TCG | GCC | TTG | TAT | GTG | GGA | GAC | ATG | TGC | GGG | 273 |
| GCC | GTG | ATG | ATC | GTG | TCG | CAG | GCT | TTC | ATA | ATA | TCG | CCA | 312 |
| GAA | CGC | CAC | AAC | TTT | ACC | CAA | GAG | TGC | AAC | TGT | TCC | ATC | 351 |
| TAC | CAA | GGT | CGT | ATC | ACC | GGC | CAC | CGC | ATG | GCG | TGG | GAC | 390 |
| ATG | ATG | CTA | AAC | TGG | TCA | CCA | ACT | CTT | ACC | ATG | ATC | CTT | 429 |
| GCC | TAT | GCC | GCT | CGT | GTT | CCT | GAG | CTA | GTC | CTT | GAA | GTT | 468 |
| GTC | TTC | GGC | GGC | CAT | TGG | GGC | GTG | GTG | TTT | GGC | TTG | GCC | 507 |
| TAT | TTC | TCC | ATG | CAA | GGA | GCG | TGG | GCC | AAG | GTC | ATT | GCC | 546 |
| ATC | CTC | CTG | CTT | GTC | GCA | GGA | GTG | GAT | GCA | | | | 576 |

(2) INFORMATION FOR SEQ ID NO:33:

(i) SEQUENCE CHARACTERISTICS:
(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: T8

(xi) SEQUENCE DESCRIPTION: SEQ ID NO:33:

| | | | | | | | | | | | | |
|---|---|---|---|---|---|---|---|---|---|---|---|---|
| GTG | GAA | GTT | AGA | AAC | ACC | AGT | TTT | AGC | TAC | TAC | GCC | ACC | 39 |
| AAT | GAT | TGC | TCG | AAC | AAC | AGC | ATC | ACC | TGG | CAG | CTC | ACC | 78 |
| AAC | GCA | GTT | CTC | CAC | CTT | CCC | GGA | TGC | GTC | CCA | TGT | GAG | 117 |
| AAT | GAC | AAT | GGC | ACC | TTG | CGC | TGC | TGG | ATA | CAA | GTA | ACA | 156 |
| CCT | AAT | GTG | GCT | GTG | AAA | CAC | CGT | GGC | GCA | CTC | ACT | CAC | 195 |
| AAC | CTG | CGA | ACG | CAT | GTC | GAC | GTG | ATC | GTA | ATG | GCA | GCT | 234 |
| ACG | GTC | TGC | TCG | GCC | TTG | TAT | GTG | GGG | GAC | GTG | TGC | GGG | 273 |
| GCC | GTG | ATG | ATA | GCG | TCG | CAG | GCT | TTC | ATA | ATA | TCG | CCA | 312 |
| GAA | CGC | CAC | AAC | TTC | ACC | CAG | GAG | TGC | AAC | TGT | TCC | ATC | 351 |
| TAC | CAA | GGT | CAT | ATC | ACC | GGC | CAC | CGC | ATG | GCA | TGG | GAC | 390 |
| ATG | ATG | CTG | AAC | TGG | TCA | CCA | ACT | CTC | ACC | ATG | ATC | CTC | 429 |
| GCC | TAC | GCT | GCT | CGT | GTG | CCT | GAA | CTA | GTC | CTT | GAA | GTT | 468 |
| GTC | TTC | GGC | GGC | CAT | TGG | GGC | GTG | GTG | TTT | GGC | TTG | GCC | 507 |
| TAT | TTC | TCC | ATG | CAA | GGA | GCG | TGG | GCC | AAA | GTC | ATC | GCC | 546 |

```
ATC CTC CTC CTT GTC GCA GGA GTG GAC GCA              576
```

( 2 ) INFORMATION FOR SEQ ID NO:34:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S83

( x i ) SEQUENCE DESCRIPTION: SEQ ID NO:34:

```
GTG GAG GTC AAG GAC ACC GGC GAC TCC TAC ATG CCG ACC   39
AAC GAT TGC TCC AAC TCT AGT ATC GTT TGG CAG CTT GAA   78
GGA GCA GTG CTT CAT ACT CCT GGA TGC GTC CCT TGT GAG   117
CGT ACC GCC AAC GTC TCT CGA TGT TGG GTG CCG GTT GCC   156
CCC AAT CTC GCC ATA AGT CAA CCT GGC GCT CTC ACT AAG   195
GGC CTG CGA GCA CAC ATC GAT ATC ATC GTG ATG TCT GCT   234
ACG GTC TGT TCT GCC CTT TAT GTG GGG GAC GTG TGT GGC   273
GCG CTG ATG CTG GCC GCT CAG GTC GTC GTC GTG TCG CCA   312
CAA CAC CAT ACG TTT GTC CAG GAA TGC AAC TGT TCC ATA   351
TAC CCG GGC CGC ATT ACG GGA CAC CGC ATG GCT TGG GAT   390
ATG ATG ATG AAC TGG TCG CCC ACT ACC ACC ATG CTC CTG   429
GCG TAC TTG GTG CGC ATC CCG GAA GTC ATC TTG GAT ATT   468
GTT ACA GGA GGT CAT TGG GGT GTA ATG TTT GGC CTC GCT   507
TAC TTC TCC ATG CAG GGA TCG TGG GCG AAG GTC ATC GTT   546
ATC CTC CTG CTG ACT GCT GGG GTG GAG GCG               576
```

( 2 ) INFORMATION FOR SEQ ID NO:35:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: DK12

( x i ) SEQUENCE DESCRIPTION: SEQ ID NO:35:

```
TTA GAG TGG CGG AAT GTG TCC GGC CTC TAC GTC CTT ACC   39
AAC GAC TGT TCC AAT AGC AGT ATC GTG TAT GAG GCC GAT   78
GAC GTC ATT CTG CAC ACA CCT GGC TGT GTA CCT TGT GTT   117
CAG GAC GGC AAT ACA TCT ACG TGC TGG ACC TCA GTG ACG   156
CCT ACA GTG GCA GTC AGG TAC GTC GGA GCA ACC ACC GCT   195
TCG ATA CGC AGT CAT GTG GAC CTG CTA GTG GGC GCG GCC   234
ACG ATG TGC TCT GCG CTC TAC GTG GGT GAT GTG TGT GGG   273
GCC GTC TTC CTT GTG GGA CAA GCC TTC ACG TTC AGA CCT   312
CGT CGC CAT CAA ACA GTC CAG ACC TGT AAC TGC TCG CTG   351
TAC CCA GGC CAT CTT TCA GGA CAT CGA ATG GCT TGG GAT   390
```

```
ATG ATG ATG AAT TGG TCC CCC GCT GTG GGT ATG GTG GTA     429

GCG CAC GTC CTG CGT CTG CCC CAG ACC TTG TTC GAC ATA     468

ATA GCT GGG GCC CAT TGG GGC ATC ATG GCG GGC CTA GCC     507

TAT TAC TCC ATG CAG GGC AAC TGG GCC AAG GTC GCT ATC     546

ATC ATG GTT ATG TTT TCA GGA GTC GAT GCC                 576
```

( 2 ) INFORMATION FOR SEQ ID NO:36:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: HK10

( x i ) SEQUENCE DESCRIPTION: SEQ ID NO:36:

```
CTA GAG TGG CGG AAT GTG TCT GGC CTC TAT GTC CTT ACC     39

AAC GAC TGT CCC AAT AGC AGT ATT GTG TAT GAG GCC GAT     78

GAC GTC ATT CTG CAC ACA CCT GGC TGT GTA CCT TGT GTT     117

CAG GAC GGC AAT ACA TCC ACG TGC TGG ACC TCG GTG ACA     156

CCT ACA GTG GCA GTC AGG TAC GTC GGA GCA ACC ACC GCC     195

TCG ATA CGC AGT CAT GTG GAC CTG TTA GTG GGC GCG GCC     234

ACG ATG TGC TCT GCG CTC TAC GTG GGC GAT ATG TGT GGG     273

GCC GTC TTC CTC GTG GGA CAA GCC TTC ACG TTC AGA CCG     312

CGT CGC CAT CAA ACG GTC CAG ACC TGT AAC TGC TCG CTG     351

TAC CCA GGC CAC CTT TCA GGA CAT CGA ATG GCT TGG GAT     390

ATG ATG ATG AAT TGG TCC CCC GCC GTG GGT ATG GTG GTG     429

GCG CAC GTC CTG CGG TTG CCC CAG ACC TTG TTC GAC ATA     468

ATA GCC GGG GCC CAT TGG GGC ATC TTG GCA GGC CTA GCC     507

TAT TAC TCC ATG CAG GGC AAC TGG GCC AAG GTC GCT ATC     546

ATC ATG GTT ATG TTT TCA GGG GTC GAT GCC                 576
```

( 2 ) INFORMATION FOR SEQ ID NO:37:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S2

( x i ) SEQUENCE DESCRIPTION: SEQ ID NO:37:

```
CTA GAG TGG CGG AAT ACG TCT GGC CTC TAT GTC CTC ACC     39

AAC GAC TGT TCC AAT AGC AGT ATT GTG TAT GAG GCC GAT     78

GAC GTT ATT CTG CAC ACA CCT GGC TGT GTA CCT TGT GTT     117

CAG GAC GGT AAT ACA TCC ACG TGC TGG ACC CCA GTG ACA     156

CCT ACA GTG GCA GTC AGG TAT GTC GGA GCA ACC ACC GCT     195

TCG ATA CGC AGT CAT GTG GAC CTA TTG GTG GGC GCG GCC     234

ACT ATG TGC TCT GCG CTC TAC GTG GGT GAT ATG TGT GGG     273
```

| | | | | | | | | | | | | |
|---|---|---|---|---|---|---|---|---|---|---|---|---|
| GCC | GTC | TTT | CTC | GTG | GGA | CAA | GCC | TTC | ACG | TTC | AGA | CCT | 312 |
| CGT | CGC | CAT | CAA | ACG | GTC | CAG | ACC | TGT | AAC | TGC | TCG | CTG | 351 |
| TAC | CCA | GGC | CAT | CTT | TCA | GGA | CAT | CGC | ATG | GCT | TGG | GAT | 390 |
| ATG | ATG | ATG | AAT | TGG | TCC | CCC | GCT | GTG | GGT | ATG | GTG | GTG | 429 |
| GCG | CAC | GTT | CTG | CGT | TTG | CCC | CAG | ACC | GTG | TTC | GAC | ATA | 468 |
| ATA | GCC | GGG | GCC | CAT | TGG | GGC | ATC | TTG | GCG | GGC | CTA | GCC | 507 |
| TAT | TAC | TCC | ATG | CAA | GGC | AAC | TGG | GCC | AAG | GTC | GCT | ATC | 546 |
| ATC | ATG | GTT | ATG | TTT | TCA | GGG | GTC | GAC | GCC | | | | 576 |

( 2 ) INFORMATION FOR SEQ ID NO:38:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S52

( x i ) SEQUENCE DESCRIPTION: SEQ ID NO:38:

| | | | | | | | | | | | | |
|---|---|---|---|---|---|---|---|---|---|---|---|---|
| CTA | GAG | TGG | CGG | AAT | ACG | TCT | GGC | CTC | TAT | GTC | CTT | ACC | 39 |
| AAC | GAC | TGT | TCC | AAT | AGC | AGT | ATT | GTG | TAT | GAG | GCC | GAT | 78 |
| GAC | GTC | ATT | CTG | CAC | ACA | CCC | GGC | TGT | GTA | CCT | TGT | GTT | 117 |
| CAG | GAC | GGC | AAT | ACA | TCC | ATG | TGC | TGG | ACC | CCA | GTG | ACA | 156 |
| CCT | ACG | GTG | GCA | GTC | AGG | TAC | GTC | GGA | GCA | ACC | ACC | GCT | 195 |
| TCG | ATA | CGC | AGT | CAT | GTG | GAC | CTA | TTA | GTG | GGC | GCG | GCC | 234 |
| ACG | CTG | TGC | TCT | GCG | CTC | TAT | GTG | GGT | GAT | ATG | TGT | GGG | 273 |
| GCC | GTC | TTT | CTC | GTG | GGA | CAA | GCC | TTC | ACG | TTC | AGA | CCT | 312 |
| CGT | CGC | CAT | CAA | ACG | GTC | CAG | ACC | TGT | AAC | TGC | TCG | CTG | 351 |
| TAC | CCA | GGC | CAT | GTT | TCA | GGA | CAT | CGA | ATG | GCT | TGG | GAT | 390 |
| ATG | ATG | ATG | AAT | TGG | TCC | CCC | GCT | GTG | GGT | ATG | GTG | GTG | 429 |
| GCG | CAC | ATC | CTG | CGA | TTG | CCC | CAG | ACC | TTG | TTT | GAC | ATA | 468 |
| CTG | GCC | GGG | GCC | CAT | TGG | GGC | ATC | TTG | GCG | GGC | CTA | GCC | 507 |
| TAT | TAT | TCT | ATG | CAG | GGC | AAC | TGG | GCC | AAG | GTC | GCT | ATT | 546 |
| GTC | ATG | ATT | ATG | TTT | TCA | GGG | GTC | GAT | GCC | | | | 576 |

( 2 ) INFORMATION FOR SEQ ID NO:39:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: S54

( x i ) SEQUENCE DESCRIPTION: SEQ ID NO:39:

| | | | | | | | | | | | | |
|---|---|---|---|---|---|---|---|---|---|---|---|---|
| CTA | GAG | TGG | CGG | AAT | ACG | TCT | GGC | CTC | TAT | ATC | CTT | ACC | 39 |
| AAC | GAC | TGT | TCC | AAT | AGC | AGT | ATT | GTG | TAT | GAG | GCC | GAT | 78 |
| GAC | GTC | ATT | CTG | CAC | ACA | CCC | GGC | TGT | GTA | CCT | TGT | GTT | 117 |

```
CAG GAC GGC AAT ACA TCC ACG TGC TGG ACC CCA GTG ACA          156

CCT ACG GTG GCA GTC AGG TAC GTC GGA GCA ACC ACC GCT          195

TCG ATA CGC AGT CAT GTG GAC CTA TTA GTG GGC GCG GCC          234

ACG CTG TGC TCT GCG CTC TAT GTG GGT GAT ATG TGT GGG          273

GCC GTC TTT CTC GTG GGA CAA GCC TTC ACG TTC AGA CCT          312

CGT CGC CAT CAA ACG GTC CAG ACC TGT AAC TGC TCG CTG          351

TAC CCA GGC CAT CTT TCA GGA CAT CGA ATG GCT TGG GAT          390

ATG ATG ATG AAT TGG TCC CCC GCT GTG GGT ATG GTG GTG          429

GCG CAC ATC CTG CGA TTG CCC CAG ACC TTG TTT GAC ATA          468

CTG GCC GGG GCC CAT TGG GGC ATC TTG GCG GGC CTA GCC          507

TAT TAT TCT ATG CAG GGC AAC TGG GCC AAG GTC GCT ATC          546

ATC ATG ATT ATG TTT TCA GGG GTC GAT GCC                     576
```

( 2 ) INFORMATION FOR SEQ ID NO:40:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z4

( x i ) SEQUENCE DESCRIPTION: SEQ ID NO:40:

```
GAG CAC TAC CGG AAT GCT TCG GGC ATC TAT CAC ATC ACC           39

AAT GAT TGT CCG AAT TCC AGT ATA GTC TAT GAA GCT GAC           78

CAT CAC ATC CTA CAC TTG CCG GGG TGC GTA CCC TGT GTG          117

ATG ACT GGG AAC ACA TCG CGT TGC TGG ACG CCG GTG ACG          156

CCT ACA GTG GCT GTC GCA CAC CCG GGC GCT CCG CTT GAG          195

TCG TTC CGG CGA CAT GTG GAC TTA ATG GTA GGC GCG GCC          234

ACT TTG TGT TCT GCC CTC TAT GTT GGG GAC CTC TGC GGA          273

GGT GCC TTC CTG ATG GGG CAG ATG ATC ACT TTT CGG CCG          312

CGT CGC CAC TGG ACC ACG CAG GAG TGC AAT TGT TCC ATC          351

TAC ACT GGC CAT ATC ACC GGC CAC AGG ATG GCG TGG GAC          390

ATG ATG ATG AAC TGG AGC CCT ACC ACC ACT CTG CTC CTC          429

GCC CAG ATC ATG AGG GTC CCC ACA GCC TTT CTC GAC ATG          468

GTT GCC GGA GGC CAC TGG GGC GTC CTC GCG GGC TTG GCG          507

TAC TTC AGC ATG CAA GGC AAT TGG GCC AAG GTA GTC CTG          546

GTC CTT TTC CTC TTT GCT GGG GTA GAC GCC                      576
```

( 2 ) INFORMATION FOR SEQ ID NO:41:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z1

( x i ) SEQUENCE DESCRIPTION: SEQ ID NO:41:

```
GTG CAC TAC CGG AAT GCT TCG GGC GTC TAT CAT GTC ACC         39
AAT GAT TGC CCT AAC ACC AGC ATA GTG TAC GAG ACG GAG         78
CAC CAC ATC ATG CAC TTG CCA GGG TGT GTC CCC TGT GTG        117
CGG ACG GAG AAT ACT TCT CGC TGC TGG GTG CCC TTG ACC        156
CCC ACT GTG GCC GCG CCC TAT CCC AAC GCA CCG TTA GAG        195
TCC ATG CGC AGG CAT GTA GAC CTG ATG GTG GGT GCG GCT        234
ACT ATG TGT TCC GCC TTC TAC ATT GGA GAT CTG TGT GGA        273
GGC GTC TTC CTA GTG GGC CAG CTG TTC GAC TTC CGA CCG        312
CGC CGG CAC TGG ACC ACC CAG GAT TGC AAC TGC TCC ATC        351
TAT CCT GGT CAC GTC TCG GGC CAC AGG ATG GCC TGG GAC        390
ATG ATG ATG AAC TGG AGC CCT ACC AGC GCG CTG ATT ATG        429
GCT CAG ATC TTA CGG ATC CCC TCT ATC CTA GGT GAC TTG        468
CTC ACC GGG GGT CAC TGG GGA GTT CTT GCT GGT CTA GCT        507
TTC TTC AGC ATG CAG AGT AAC TGG GCG AAG GTC ATC CTG        546
GTC CTA TTC CTC TTT GCC GGG GTC GAG GGA                    576
```

( 2 ) INFORMATION FOR SEQ ID NO:42:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: Z6

( x i ) SEQUENCE DESCRIPTION: SEQ ID NO:42:

```
GTT AAC TAT CGC AAT GCC TCG GGC GTC TAT CAC GTC ACC         39
AAC GAC TGC CCG AAC TCG AGC ATA GTG TAT GAG GCC GAA         78
CAC CAG ATC TTA CAC CTC CCA GGG TGC TTG CCC TGT GTG        117
AGG GTT GGG AAT CAG TCA CGC TGC TGG GTG GCC CTT ACT        156
CCC ACC GTG GCG GTG TCT TAT ATC GGT GCT CCG CTT GAC        195
TCC CTC CGG AGA CAT GTG GAC CTG ATG GTG GGC GCC GCT        234
ACT GTA TGC TCT GCC CTC TAC GTT GGA GAT CTG TGC GGT        273
GGT GCA TTC TTG GTT GGC CAG ATG TTC TCC TTC CAG CCG        312
CGA CGC CAC TGG ACT ACG CAG GAC TGC AAT TGT TCT ATC        351
TAC GCA GGG CAT ATC ACG GGC CAC AGG ATG GCA TGG GAC        390
ATG ATG ATG AAC TGG AGT CCC ACA ACC ACC CTG CTT CTC        429
GCC CAG GTC ATG AGG ATC CCT AGC ACT CTG GTA GAT CTA        468
CTC GCT GGA GGG CAC TGG GGC GTC CTT GTT GGG TTG GCG        507
TAC TTC AGT ATG CAA GCT AAT TGG GCC AAA GTC ATC CTG        546
GTC CTT TTC CTC TTC GCT GGA GTT GAT GCC                    576
```

( 2 ) INFORMATION FOR SEQ ID NO:43:

( i ) SEQUENCE CHARACTERISTICS:
        ( A ) LENGTH: 576 base pairs
        ( B ) TYPE: nucleic acid
        ( C ) STRANDEDNESS: single (D) TOPOLOGY: linear (vi) ORIGINAL SOURCE:
(A) ORGANISM: homosapiens
(C) INDIVIDUAL ISOLATE: Z7

(xi) SEQUENCE DESCRIPTION: SEQ ID NO:43:

| | | | | | | | | | | | | |
|---|---|---|---|---|---|---|---|---|---|---|---|---|
| GTC | AAC | TAT | CAC | AAT | GCC | TCG | GGC | GTC | TAT | CAC | ATC | ACC | 39 |
| AAC | GAC | TGC | CCG | AAC | TCG | AGC | ATA | ATG | TAT | GAG | GCC | GAA | 78 |
| CAC | CAC | ATC | CTA | CAC | CTC | CCA | GGG | TGC | GTA | CCC | TGT | GTG | 117 |
| AGG | GAG | GGG | AAC | CAG | TCA | CGC | TGC | TGG | GTG | GCC | CTT | ACT | 156 |
| CCC | ACC | GTG | GCG | GCG | CCT | TAT | ATC | GGT | GCA | CCG | CTT | GAA | 195 |
| TCC | ATC | CGG | AGA | CAT | GTG | GAC | CTG | ATG | GTA | GGC | GCT | GCT | 234 |
| ACA | GTG | TGC | TCC | GCT | CTC | TAC | ATT | GGG | GAC | CTG | TGC | GGT | 273 |
| GGC | GTA | TTT | TTG | GTT | GGT | CAG | ATG | TTT | TCT | TTC | CAG | CCG | 312 |
| CGA | CGC | CAC | TGG | ACT | ACG | CAG | GAC | TGC | AAT | TGT | TCC | ATC | 351 |
| TAT | GCG | GGG | CAC | GTT | ACA | GGC | CAC | AGA | ATG | GCA | TGG | GAC | 390 |
| ATG | ATG | ATG | AAC | TGG | AGT | CCC | ACA | ACC | ACC | TTG | GTC | CTC | 429 |
| GCC | CAG | GTT | ATG | AGG | ATC | CCT | AGC | ACT | CTG | GTG | GAC | CTA | 468 |
| CTC | ACT | GGA | GGG | CAC | TGG | GGT | ATC | CTT | ATC | GGG | GTG | GCA | 507 |
| TAC | TTC | TGC | ATG | CAA | GCT | AAT | TGG | GCC | AAG | GTC | ATT | CTG | 546 |
| GTC | CTT | TTC | CTC | TAC | GCT | GGA | GTT | GAT | GCC | | | | 576 |

(2) INFORMATION FOR SEQ ID NO:44:

(i) SEQUENCE CHARACTERISTICS:
(A) LENGTH: 576 base pairs
(B) TYPE: nucleic acid
(C) STRANDEDNESS: single
(D) TOPOLOGY: linear (vi) ORIGINAL SOURCE:
(A) ORGANISM: homosapiens
(C) INDIVIDUAL ISOLATE: DK13

(xi) SEQUENCE DESCRIPTION: SEQ ID NO:44:

| | | | | | | | | | | | | |
|---|---|---|---|---|---|---|---|---|---|---|---|---|
| TAC | AAC | TAT | CGC | AAC | AGC | TCG | GGT | GTC | TAC | CAT | GTC | ACC | 39 |
| AAC | GAT | TGC | CCG | AAC | TCG | AGC | ATA | GTC | TAT | GAA | ACC | GAT | 78 |
| TAC | CAC | ATC | TTA | CAC | CTC | CCG | GGA | TGC | GTT | CCT | TGC | GTG | 117 |
| AGG | GAA | GGG | AAC | AAG | TCT | ACA | TGC | TGG | GTG | TCT | CTC | ACC | 156 |
| CCC | ACC | GTG | GCT | GCG | CAA | CAT | CTG | AAT | GCT | CCG | CTT | GAG | 195 |
| TCT | TTG | AGA | CGT | CAC | GTG | GAT | CTG | ATG | GTG | GGC | GGC | GCC | 234 |
| ACT | CTC | TGC | TCC | GCC | CTC | TAC | ATC | GGA | GAC | GTG | TGT | GGG | 273 |
| GGT | GTG | TTC | TTG | GTC | GGT | CAA | CTG | TTC | ACC | TTC | CAA | CCT | 312 |
| CGC | CGC | CAC | TGG | ACC | ACC | CAA | GAC | TGC | AAT | TGT | TCC | ATC | 351 |
| TAC | ACA | GGA | CAT | ATC | ACA | GGA | CAC | AGA | ATG | GCT | TGG | GAC | 390 |
| ATG | ATG | ATG | AAT | TGG | AGC | CCC | ACT | GCG | ACG | CTG | GTC | CTC | 429 |
| GCC | CAA | CTT | ATG | AGG | ATC | CCA | GGC | GCC | ATG | GTC | GAC | CTG | 468 |
| CTT | GCA | GGC | GGC | CAC | TGG | GGC | ATT | CTG | GTT | GGC | ATA | GCG | 507 |
| TAC | TTC | AGC | ATG | CAA | GCT | AAT | TGG | GCC | AAG | GTT | ATC | CTG | 546 |
| GTC | CTG | TTT | CTC | TTT | GCT | GGA | GTC | GAC | GCT | | | | 576 |

( 2 ) INFORMATION FOR SEQ ID NO:45:

( i ) SEQUENCE CHARACTERISTICS:
    ( A ) LENGTH: 576 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: SA1

( x i ) SEQUENCE DESCRIPTION: SEQ ID NO:45:

| | | | | | | | | | | | | | |
|---|---|---|---|---|---|---|---|---|---|---|---|---|---|
| GTT | CCC | TAC | CGG | AAT | GCC | TCT | GGG | GTT | TAC | CAT | GTC | ACC | 39 |
| AAT | GAC | TGC | CCA | AAC | TCC | TCC | ATA | GTC | TAC | GAG | GCT | GAT | 78 |
| AGC | CTG | ATC | TTG | CAC | GCA | CCT | GGC | TGC | GTG | CCC | TGT | GTC | 117 |
| AGG | CAA | GAT | AAT | GTC | AGT | AGG | TGC | TGG | GTC | CAA | ATC | ACC | 156 |
| CCC | ACA | CTG | TCA | GCC | CCG | ACC | TTC | GGA | GCG | GTC | ACG | GCT | 195 |
| CCT | CTT | CGG | AGG | GCC | GTT | GAC | TAC | TTA | GCG | GGA | GGA | GCT | 234 |
| GCT | CTC | TGC | TCC | GCA | CTA | TAC | GTC | GGC | GAC | GCG | TGC | GGG | 273 |
| GCA | GTG | TTT | CTG | GTA | GGC | CAA | ATG | TTC | ACC | TAT | AGG | CCT | 312 |
| CGC | CAG | CAT | ACC | ACA | GTG | CAG | GAC | TGC | AAC | TGT | TCC | ATT | 351 |
| TAC | AGT | GGC | CAT | ATC | ACC | GGC | CAC | CGG | ATG | GCT | TGG | GAC | 390 |
| ATG | ATG | ATG | AAT | TGG | TCA | CCT | ACG | ACA | GCC | TTG | CTG | ATG | 429 |
| GCC | CAG | ATG | CTA | CGG | ATC | CCC | CAG | GTG | GTC | ATA | GAC | ATC | 468 |
| ATA | GCC | GGG | GGC | CAC | TGG | GGG | GTC | TTG | TTT | GCC | GCC | GCA | 507 |
| TAC | TTT | GCG | TCG | GCC | GCC | AAC | TGG | GCT | AAG | GTA | GTG | CTG | 546 |
| GTT | CTG | TTC | CTG | TTT | GCG | GGG | GTC | GAT | GGC | | | | 576 |

( 2 ) INFORMATION FOR SEQ ID NO:46:

( i ) SEQUENCE CHARACTERISTICS:
    ( A ) LENGTH: 576 base pairs
    ( B ) TYPE: nucleic acid
    ( C ) STRANDEDNESS: single
    ( D ) TOPOLOGY: linear ( v i ) ORIGINAL SOURCE:
    ( A ) ORGANISM: homosapiens
    ( C ) INDIVIDUAL ISOLATE: SA4

( x i ) SEQUENCE DESCRIPTION: SEQ ID NO:46:

| | | | | | | | | | | | | | |
|---|---|---|---|---|---|---|---|---|---|---|---|---|---|
| GTT | CCC | TAC | CGA | AAC | GCC | TCT | GGG | GTT | TAT | CAT | GTC | ACC | 39 |
| AAT | GAT | TGC | CCA | AAC | TCT | TCC | ATA | GTT | TAC | GAG | GCT | GAT | 78 |
| AAC | CTG | ATC | TTG | CAT | GCA | CCT | GGT | TGC | GTG | CCT | TGT | GTC | 117 |
| AGG | CAA | GAT | AAT | GTC | AGT | AAG | TGC | TGG | GTC | CAA | ATC | ACC | 156 |
| CCC | ACG | TTG | TCA | GCC | CCG | AAT | CTC | GGA | GCG | GTC | ACG | GCT | 195 |
| CCT | CTT | CGG | AGG | GCC | GTT | GAC | TAC | TTA | GCG | GGA | GGG | GCT | 234 |
| GCC | CTC | TGC | TCC | GCA | CTA | TAC | GTC | GGG | GAC | GCG | TGC | GGG | 273 |
| GCA | GTG | TTT | TTG | GTA | GGC | CAA | ATG | TTC | ACC | TAT | AGG | CCT | 312 |
| CGC | CAG | CAC | ACT | ACG | GTG | CAA | GAC | TGC | AAT | TGC | TCT | ATT | 351 |
| TAC | AGT | GGC | CAT | ATC | ACC | GGC | CAC | CGG | ATG | GCA | TGG | GAC | 390 |
| ATG | ATG | ATG | AAT | TGG | TCA | CCT | ACG | ACG | GCC | TTG | CTG | ATG | 429 |
| GCC | CAG | TTG | CTA | CGG | ATT | CCC | CAG | GTG | GTC | ATC | GAC | ATC | 468 |

| | | | | | | | | | | | | |
|---|---|---|---|---|---|---|---|---|---|---|---|---|
| ATT | GCC | GGG | GGC | CAC | TGG | GGG | GTC | TTG | TTT | GCC | GCC | GCA | 507 |
| TAT | TTC | GCG | TCA | GCG | GCT | AAC | TGG | GCT | AAG | GTT | ATA | CTG | 546 |
| GTC | TTG | TTT | CTG | TTT | GCG | GGG | GTC | GAT | GCC | | | | 576 |

( 2 ) INFORMATION FOR SEQ ID NO:47:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA5

( x i ) SEQUENCE DESCRIPTION: SEQ ID NO:47:

| | | | | | | | | | | | | |
|---|---|---|---|---|---|---|---|---|---|---|---|---|
| GTC | CCC | TAC | CGA | AAT | GCC | TCT | GGG | GTT | TAT | CAT | GTC | ACC | 39 |
| AAT | GAT | TGC | CCA | AAC | TCT | TCC | ATA | GTC | TAC | GAG | GCT | GAT | 78 |
| AAC | CTG | ATT | CTG | CAC | GCA | CCT | GGT | TGC | GTG | CCC | TGT | GTC | 117 |
| AAG | GAA | GGT | AAT | GTC | AGT | AGG | TGC | TGG | GTC | CAA | ATC | ACC | 156 |
| CCC | ACA | TTG | TCA | GCC | CCG | AAC | CTC | GGA | GCG | GTC | ACG | GCT | 195 |
| CCT | CTT | CGG | AGG | GTC | GTT | GAC | TAC | TTA | GCG | GGA | GGG | GCT | 234 |
| GCC | CTC | TGC | TCC | GCA | CTA | TAC | GTC | GGG | GAC | GCG | TGC | GGG | 273 |
| GCA | GTG | TTC | TTG | GTA | GGC | CAA | ATG | TTC | ACC | TAT | AGG | CCT | 312 |
| CGC | CAG | CAT | ACT | ACG | GTG | CAG | GAC | TGC | AAC | TGT | TCC | ATT | 351 |
| TAC | AGC | GGC | CAT | ATC | ACC | GGC | CAC | CGA | ATG | GCA | TGG | GAC | 390 |
| ATG | ATG | ATG | AAT | TGG | TCA | CCT | ACG | ACA | GCC | TTG | GTG | ATG | 429 |
| GCC | CAG | GTG | CTA | CGG | ATT | CCC | CAA | GTG | GTC | ATT | GAC | ATC | 468 |
| ATT | GCC | GGG | GGC | CAC | TGG | GGG | GTC | TTG | TTC | GCC | GTC | GCA | 507 |
| TAC | TTC | GCG | TCA | GCG | GCT | AAC | TGG | GCT | AAG | GTT | GTG | CTG | 546 |
| GTC | CTG | TTT | CTG | TTT | GCG | GGG | GTC | GAT | GGC | | | | 576 |

( 2 ) INFORMATION FOR SEQ ID NO:48:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA6

( x i ) SEQUENCE DESCRIPTION: SEQ ID NO:48:

| | | | | | | | | | | | | |
|---|---|---|---|---|---|---|---|---|---|---|---|---|
| GTT | CCT | TAC | CGG | AAT | GCC | TCT | GGG | GTG | TAT | CAT | GTT | ACC | 39 |
| AAT | GAT | TGC | CCA | AAC | TCT | TCC | ATA | GTC | TAT | GAG | GCT | GAT | 78 |
| GAC | CTG | ATC | CTA | CAC | GCA | CCT | GGC | TGC | GTG | CCC | TGT | GTC | 117 |
| CGG | AAG | GAT | AAT | GTC | AGT | AGA | TGC | TGG | GTT | CAT | ATC | ACC | 156 |
| CCC | ACA | CTA | TCA | GCC | CCG | AGC | CTC | GGA | GCG | GTC | ACG | GCT | 195 |
| CCT | CTT | CGG | AGG | GCC | GTT | GAT | TAC | TTG | GCG | GGA | GGG | GCC | 234 |
| GCC | CTG | TGC | TCC | GCG | TTA | TAC | GTC | GGA | GAC | GTG | TGC | GGG | 273 |
| GCA | TTG | TTT | TTG | GTA | GGC | CAA | ATG | TTC | ACC | TAT | AGG | CCT | 312 |

| | | | | | | | | | | | | |
|---|---|---|---|---|---|---|---|---|---|---|---|---|
| CGC | CAG | CAT | GCT | ACG | GTA | CAG | GAC | TGC | AAC | TGC | TCC | ATT | 351 |
| TAC | AGT | GGC | CAT | ATC | ACT | GGC | CAC | CGG | ATG | GCA | TGG | GAC | 390 |
| ATG | ATG | ATG | AAT | TGG | TCA | CCC | GCG | ACA | GCC | TTG | GTG | ATG | 429 |
| GCC | CAA | ATG | CTA | CGG | ATT | CCC | CAG | GTG | GTC | ATT | GAC | ATC | 468 |
| ATT | GCC | GGG | GGC | CAC | TGG | GGG | GTC | TTG | TTC | GCC | GCT | GCA | 507 |
| TAC | TTC | GCG | TCG | GCG | GCT | AAC | TGG | GCT | AAG | GTT | GTG | CTG | 546 |
| GTC | TTG | TTT | CTG | TTT | GCG | GGG | GTT | GAT | GCC | | | | 576 |

( 2 ) INFORMATION FOR SEQ ID NO:49:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA7

( x i ) SEQUENCE DESCRIPTION: SEQ ID NO:49:

| | | | | | | | | | | | | |
|---|---|---|---|---|---|---|---|---|---|---|---|---|
| GTC | CCC | TAC | CGA | AAT | GCC | TCC | GGG | GTT | TAT | CAT | GTC | ACC | 39 |
| AAT | GAT | TGC | CCG | AAC | TCT | TCC | ATA | GTC | TAT | GAG | GCT | GAC | 78 |
| AAC | CTG | ATC | CTG | CAC | GCA | CCT | GGT | TGC | GTG | CCC | TGT | GTC | 117 |
| AGA | CAA | AAT | AAT | GTC | AGT | AGG | TGC | TGG | GTC | CAA | ATC | ACC | 156 |
| CCC | ACA | TTG | TCA | GCC | CCG | AAC | CTC | GGA | GCG | GTC | ACG | GCT | 195 |
| CCT | CTT | CGG | AGG | GCC | GTT | GAC | TAC | CTA | GCG | GGA | GGG | GCT | 234 |
| GCC | CTC | TGC | TCC | GCG | CTA | TAC | GTC | GGG | GAC | GCG | TGC | GGG | 273 |
| GCA | GTG | TTT | TTG | GTA | GGC | CAG | ATG | TTC | AGC | TAT | AGG | CCT | 312 |
| CGC | CAG | CAC | ACT | ACG | GTG | CAG | GAC | TGC | AAC | TGT | TCC | ATT | 351 |
| TAC | AGT | GGC | CAT | ATC | ACC | GGC | CAC | CGA | ATG | GCA | TGG | GAC | 390 |
| ATG | ATG | ATG | AAT | TGG | TCA | CCT | ACG | ACA | GCC | TTG | GTG | ATG | 429 |
| GCC | CAG | TTG | CTA | CGG | ATT | CCC | CAG | GTG | GTC | ATC | GAC | ATC | 468 |
| ATT | GCC | GGG | GGC | CAC | TGG | GGG | GTC | TTG | TTC | GCC | GCC | GCA | 507 |
| TAT | TTC | GCG | TCA | GCG | GCT | AAC | TGG | GCT | AAG | GTT | GTG | CTG | 546 |
| GTC | TTG | TTT | CTG | TTT | GCG | GGG | GTC | GAT | GCC | | | | 576 |

( 2 ) INFORMATION FOR SEQ ID NO:50:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homosapiens
        ( C ) INDIVIDUAL ISOLATE: SA13

( x i ) SEQUENCE DESCRIPTION: SEQ ID NO:50:

| | | | | | | | | | | | | |
|---|---|---|---|---|---|---|---|---|---|---|---|---|
| GTT | CCC | TAC | CGA | AAT | GCC | TCT | GGG | GTT | TAT | CAT | GTC | ACC | 39 |
| AAT | GAT | TGC | CCA | AAC | TCT | TCC | ATC | GTC | TAC | GAG | GCT | GAT | 78 |
| GAC | CTG | ATC | TTA | CAC | GCA | CCT | GGT | TGC | GTG | CCC | TGT | GTT | 117 |
| AGG | CAG | GGT | AAT | GTC | AGT | AGG | TGC | TGG | GTC | CAG | ATC | ACC | 156 |
| CCC | ACA | CTG | TCA | GCC | CCG | AGC | CTC | GGA | GCG | GTC | ACG | GCT | 195 |

```
CCT CTT CGG AGG GCC GTT GAC TAC TTA GCG GGG GGG GCT          234

GCC CTT TGC TCC GCG TTA TAC GTC GGA GAC GCG TGC GGG          273

GCA GTG TTT TTG GTA GGT CAA ATG TTC ACC TAT AGC CCT          312

CGC CGG CAT AAT GTT GTG CAG GAC TGC AAC TGT TCC ATT          351

TAC AGT GGC CAC ATC ACC GGC CAC CGG ATG GCA TGG GAC          390

ATG ATG ATG AAT TGG TCA CCT ACA ACA GCT TTG GTG ATG          429

GCC CAG TTG TTA CGG ATT CCC CAG GTG GTC ATT GAC ATC          468

ATT GCC GGG GCC CAC TGG GGG GTC TTG TTC GCC GCC GCA          507

TAC TAC GCG TCG GCG GCT AAC TGG GCC AAG GTT GTG CTG          546

GTC CTG TTT CTG TTT GCG GGG GTC GAT GCC                      576
```

(2) INFORMATION FOR SEQ ID NO:51:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK2

(xi) SEQUENCE DESCRIPTION: SEQ ID NO:51:

```
CTT ACC TAC GGC AAC TCC AGT GGG CTA TAC CAT CTC ACA           39

AAT GAT TGC CCC AAC TCC AGC ATC GTG CTG GAG GCG GAT           78

GCT ATG ATC TTG CAT TTG CCT GGA TGC TTG CCT TGT GTG          117

AGG GTC GAT GAT CGG TCC ACC TGT TGG CAT GCT GTG ACC          156

CCC ACC CTG GCC ATA CCA AAT GCT TCC ACG CCC GCA ACG          195

GGA TTC CGC AGG CAT GTG GAT CTT CTT GCG GGC GCC GCA          234

GTG GTT TGC TCA TCC CTG TAC ATC GGG GAC CTG TGT GGC          273

TCT CTC TTT TTG GCG GGA CAA CTA TTC ACC TTT CAG CCC          312

CGC CGT CAT TGG ACT GTG CAA GAC TGC AAC TGC TCC ATC          351

TAT ACA GGC CAC GTC ACC GGC CAC AGG ATG GCT TGG GAC          390

ATG ATG ATG AAC TGG TCA CCC ACA ACC ACT CTG GTC CTA          429

TCT AGC ATC TTG AGG GTA CCT GAG ATT TGT GCG AGT GTG          468

ATA TTT GGT GGC CAT TGG GGG ATA CTA CTA GCC GTT GCC          507

TAC TTT GGC ATG GCT GGC AAC TGG CTA AAA GTT CTG GCT          546

GTT CTG TTC CTA TTT GCA GGG GTT GAA GCA                      576
```

(2) INFORMATION FOR SEQ ID NO:52:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK7

(xi) SEQUENCE DESCRIPTION: SEQ ID NO:52:

```
Tyr Gln Val Arg Asn Ser Thr Gly Leu Tyr His Val Thr Asn Asp
            5                   10                      15
```

| | | | | | | | | | | | | | | |
|---|---|---|---|---|---|---|---|---|---|---|---|---|---|---|
|Cys|Pro|Asn|Ser|Ser<br>20|Ile|Val|Tyr|Glu|Ala<br>25|Ala|Asp|Ala|Ile|Leu<br>30|
|His|Thr|Pro|Gly|Cys<br>35|Val|Pro|Cys|Val|Arg<br>40|Glu|Gly|Asn|Val|Ser<br>45|
|Arg|Cys|Trp|Val|Ala<br>50|Met|Thr|Pro|Thr|Val<br>55|Ala|Thr|Arg|Asp|Gly<br>60|
|Lys|Leu|Pro|Thr|Ala<br>65|Gln|Leu|Arg|Arg|His<br>70|Ile|Asp|Leu|Leu|Val<br>75|
|Gly|Ser|Ala|Thr|Leu<br>80|Cys|Ser|Ala|Leu|Tyr<br>85|Val|Gly|Asp|Leu|Cys<br>90|
|Gly|Ser|Val|Phe|Leu<br>95|Val|Gly|Gln|Leu|Phe<br>100|Thr|Phe|Ser|Pro|Arg<br>105|
|Arg|His|Trp|Thr|Thr<br>110|Gln|Gly|Cys|Asn|Cys<br>115|Ser|Ile|Tyr|Pro|Gly<br>120|
|His|Ile|Thr|Gly|His<br>125|Arg|Met|Ala|Trp|Asp<br>130|Met|Met|Met|Asn|Trp<br>135|
|Ser|Pro|Thr|Thr|Ala<br>140|Leu|Val|Val|Ala|Gln<br>145|Leu|Leu|Arg|Ile|Pro<br>150|
|Gln|Ala|Ile|Leu|Asp<br>155|Met|Ile|Ala|Gly|Ala<br>160|His|Trp|Gly|Val|Leu<br>165|
|Ala|Gly|Ile|Ala|Tyr<br>170|Phe|Ser|Met|Val|Gly<br>175|Asn|Trp|Ala|Lys|Val<br>180|
|Leu|Val|Val|Leu|Leu<br>185|Leu|Phe|Ala|Gly|Val<br>190|Asp|Ala| | | |

( 2 ) INFORMATION FOR SEQ ID NO:53:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK9

( x i ) SEQUENCE DESCRIPTION: SEQ ID NO:53:

| | | | | | | | | | | | | | | |
|---|---|---|---|---|---|---|---|---|---|---|---|---|---|---|
|Tyr|Gln|Val|Arg|Asn<br>5|Ser|Ser|Gly|Leu|Tyr<br>10|His|Val|Thr|Asn|Asp<br>15|
|Cys|Pro|Asn|Ser|Ser<br>20|Ile|Val|Tyr|Glu|Ala<br>25|Ala|Asp|Ala|Ile|Leu<br>30|
|His|Ser|Pro|Gly|Cys<br>35|Val|Pro|Cys|Val|Arg<br>40|Glu|Gly|Asn|Ala|Ser<br>45|
|Lys|Cys|Trp|Val|Ala<br>50|Val|Ala|Pro|Thr|Val<br>55|Ala|Thr|Arg|Asp|Gly<br>60|
|Lys|Leu|Pro|Ala|Thr<br>65|Gln|Leu|Arg|Arg|His<br>70|Ile|Asp|Leu|Leu|Val<br>75|
|Gly|Ser|Ala|Thr|Leu<br>80|Cys|Ser|Ala|Leu|Tyr<br>85|Val|Gly|Asp|Leu|Cys<br>90|
|Gly|Ser|Val|Phe|Leu<br>95|Val|Gly|Gln|Leu|Phe<br>100|Thr|Phe|Ser|Pro|Arg<br>105|
|Arg|His|Trp|Thr|Thr<br>110|Gln|Asp|Cys|Asn|Cys<br>115|Ser|Ile|Tyr|Pro|Gly<br>120|
|His|Ile|Thr|Gly|His<br>125|Arg|Met|Ala|Trp|Asp<br>130|Met|Met|Met|Asn|Trp<br>135|
|Ser|Pro|Thr|Ala|Ala<br>140|Leu|Val|Met|Ala|Gln<br>145|Leu|Leu|Arg|Ile|Pro<br>150|
|Gln|Ala|Ile|Leu|Asp|Met|Ile|Ala|Gly|Ala|His|Trp|Gly|Val|Leu|

|   |   |   |   | 155 |   |   |   |   | 160 |   |   |   | 165 |
|---|---|---|---|---|---|---|---|---|---|---|---|---|---|

Ala Gly Ile Ala Tyr Phe Ser Met Val Gly Asn Trp Ala Lys Val
                170                 175             180

Val Val Val Leu Leu Leu Phe Thr Gly Val Asp Ala
                185             190

( 2 ) INFORMATION FOR SEQ ID NO:54:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DR1

( x i ) SEQUENCE DESCRIPTION: SEQ ID NO:54:

His Gln Val Arg Asn Ser Thr Gly Leu Tyr His Val Thr Asn Asp
                5                   10              15

Cys Pro Asn Ser Ser Ile Val Tyr Glu Ala Ala Asp Ala Ile Leu
                20                  25              30

His Ala Pro Gly Cys Val Pro Cys Val Arg Glu Gly Asn Ala Ser
                35                  40              45

Arg Cys Trp Val Ala Val Thr Pro Thr Val Ala Thr Arg Asp Gly
                50                  55              60

Lys Leu Pro Thr Thr Gln Leu Arg Arg His Ile Asp Leu Leu Val
                65                  70              75

Gly Ser Ala Thr Leu Cys Ser Ala Leu Tyr Val Gly Asp Leu Cys
                80                  85              90

Gly Ser Val Phe Leu Val Gly Gln Leu Phe Thr Phe Ser Pro Arg
                95                  100             105

Arg His Trp Thr Thr Gln Asp Cys Asn Cys Ser Ile Tyr Pro Gly
                110                 115             120

His Ile Thr Gly His Arg Met Ala Trp Asp Met Met Met Asn Trp
                125                 130             135

Ser Pro Thr Thr Ala Leu Val Met Ala Gln Leu Leu Arg Ile Pro
                140                 145             150

Gln Ala Ile Leu Asp Met Ile Ala Gly Ala His Trp Gly Val Leu
                155                 160             165

Ala Gly Ile Ala Tyr Phe Ser Met Val Gly Asn Trp Ala Lys Val
                170                 175             180

Val Val Val Leu Leu Leu Phe Ala Gly Val Asp Ala
                185             190

( 2 ) INFORMATION FOR SEQ ID NO:55:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DR4

( x i ) SEQUENCE DESCRIPTION: SEQ ID NO:55:

His Gln Val Arg Asn Ser Thr Gly Leu Tyr His Val Thr Asn Asp
                5                   10              15

Cys Pro Asn Ser Ser Ile Val Tyr Glu Ala Ala Asp Ala Ile Leu
                20                  25              30

His Thr Pro Gly Cys Val Pro Cys Val Arg Glu Gly Asn Thr Ser
                35                  40                  45

Arg Cys Trp Val Ala Val Thr Pro Thr Val Ala Thr Arg Asp Gly
                50                  55                  60

Lys Leu Pro Thr Thr Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

His His Trp Thr Thr Gln Asp Cys Asn Cys Ser Ile Tyr Pro Gly
               110                 115                 120

His Ile Thr Gly His Arg Met Ala Trp Asp Met Met Met Asn Trp
               125                 130                 135

Ser Pro Thr Thr Ala Leu Val Val Ala Gln Leu Leu Arg Ile Pro
               140                 145                 150

Gln Ala Ile Leu Asp Met Ile Ala Gly Ala His Trp Gly Val Leu
               155                 160                 165

Ala Gly Ile Ala Tyr Phe Ser Met Val Gly Asn Trp Ala Lys Val
               170                 175                 180

Leu Val Val Leu Leu Leu Phe Ala Gly Val Asp Ala
               185                 190

( 2 ) INFORMATION FOR SEQ ID NO:56:

( i ) SEQUENCE CHARACTERISTICS:
( A ) LENGTH: 192 amino acids
( B ) TYPE: amino acid
( C ) STRANDEDNESS: unknown
( D ) TOPOLOGY: unknown ( v i ) ORIGINAL SOURCE:
( A ) ORGANISM: homosapiens
( C ) INDIVIDUAL ISOLATE: S14

( x i ) SEQUENCE DESCRIPTION: SEQ ID NO:56:

Tyr Gln Val Arg Asn Ser Thr Gly Leu Tyr His Val Thr Asn Asp
                 5                  10                  15

Cys Pro Asn Ser Ser Ile Val Tyr Glu Thr Ala Asp Ala Ile Leu
                20                  25                  30

His Ala Pro Gly Cys Val Pro Cys Val Arg Glu Gly Asn Thr Ser
                35                  40                  45

Arg Cys Trp Val Ala Met Thr Pro Thr Val Ala Thr Arg Asp Gly
                50                  55                  60

Lys Leu Pro Ala Thr Gln Leu Arg Arg Tyr Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

Arg Leu Trp Thr Thr Gln Asp Cys Asn Cys Ser Ile Tyr Pro Gly
               110                 115                 120

His Ile Thr Gly His Arg Met Ala Trp Asp Met Met Met Asn Trp
               125                 130                 135

Ser Pro Thr Thr Ala Leu Val Val Ala Gln Leu Leu Arg Ile Pro
               140                 145                 150

Gln Ala Ile Leu Asp Met Ile Ala Gly Ala His Trp Gly Val Leu
               155                 160                 165

Ala Gly Ile Ala Tyr Phe Ser Met Val Gly Asn Trp Ala Lys Val
               170                 175                 180

```
Leu  Val  Val  Leu  Leu  Leu  Phe  Ala  Gly  Val  Asp  Ala
               185                 190
```

( 2 ) INFORMATION FOR SEQ ID NO:57:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S18

( x i ) SEQUENCE DESCRIPTION: SEQ ID NO:57:

```
Tyr  Gln  Val  Arg  Asn  Ser  Thr  Gly  Leu  Tyr  His  Val  Thr  Asn  Asp
                    5                        10                        15

Cys  Pro  Asn  Ser  Ser  Ile  Val  Tyr  Glu  Thr  Ala  Asp  Thr  Ile  Leu
                    20                       25                        30

His  Ser  Pro  Gly  Cys  Val  Pro  Cys  Val  Arg  Glu  Gly  Asn  Ala  Ser
                    35                       40                        45

Arg  Cys  Trp  Val  Pro  Val  Ala  Pro  Thr  Val  Ala  Thr  Arg  Asp  Gly
                    50                       55                        60

Lys  Leu  Pro  Ala  Thr  Gln  Leu  Arg  Arg  His  Ile  Asp  Leu  Leu  Val
                    65                       70                        75

Gly  Ser  Ala  Thr  Leu  Cys  Ser  Ala  Leu  Tyr  Val  Gly  Asp  Leu  Cys
                    80                       85                        90

Gly  Ser  Val  Phe  Leu  Val  Ser  Gln  Leu  Phe  Thr  Ile  Ser  Pro  Arg
                    95                       100                       105

Arg  His  Trp  Thr  Thr  Gln  Asp  Cys  Asn  Cys  Ser  Ile  Tyr  Pro  Gly
                    110                      115                       120

His  Ile  Thr  Gly  His  Arg  Met  Ala  Trp  Asp  Met  Met  Met  Asn  Trp
                    125                      130                       135

Ser  Pro  Thr  Thr  Ala  Leu  Val  Ile  Ala  Gln  Leu  Leu  Arg  Val  Pro
                    140                      145                       150

Gln  Ala  Val  Leu  Asp  Met  Ile  Ala  Gly  Ala  His  Trp  Gly  Val  Leu
                    155                      160                       165

Ala  Gly  Ile  Ala  Tyr  Phe  Ser  Met  Ala  Gly  Asn  Trp  Ala  Lys  Val
                    170                      175                       180

Leu  Leu  Val  Leu  Leu  Leu  Phe  Ala  Gly  Val  Asp  Ala
                    185                      190
```

( 2 ) INFORMATION FOR SEQ ID NO:58:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SW1

( x i ) SEQUENCE DESCRIPTION: SEQ ID NO:58:

```
Tyr  Gln  Val  Arg  Asn  Ser  Ser  Gly  Leu  Tyr  His  Val  Thr  Asn  Asp
                    5                        10                        15

Cys  Pro  Asn  Ser  Ser  Ile  Val  Tyr  Glu  Thr  Ala  Asp  Ala  Ile  Leu
                    20                       25                        30

His  Ser  Pro  Gly  Cys  Val  Pro  Cys  Val  Arg  Glu  Asp  Gly  Ala  Pro
                    35                       40                        45

Lys  Cys  Trp  Val  Ala  Val  Ala  Pro  Thr  Val  Ala  Thr  Arg  Asp  Gly
```

```
Lys Leu Pro Ala Thr     Gln Leu Arg Arg His     Ile Asp Leu Leu Val
                65                      70                      75

Gly Ser Ala Thr Leu     Cys Ser Ala Leu Tyr     Val Gly Asp Leu Cys
                80                      85                      90

Gly Ser Val Phe Leu     Val Ser Gln Leu Phe     Thr Phe Ser Pro Arg
                95                      100                     105

Arg His Trp Thr Thr     Gln Asp Cys Asn Cys     Ser Ile Tyr Pro Gly
                110                     115                     120

His Ile Thr Gly His     Arg Met Ala Trp Asp     Met Met Met Asn Trp
                125                     130                     135

Ser Pro Thr Thr Ala     Leu Val Val Ala Gln     Leu Leu Arg Ile Pro
                140                     145                     150

Gln Ala Val Leu Asp     Met Ile Ala Gly Ala     His Trp Gly Val Leu
                155                     160                     165

Ala Gly Ile Ala Tyr     Phe Ser Met Val Gly     Asn Trp Ala Lys Val
                170                     175                     180

Leu Ile Val Leu Leu     Leu Phe Ser Gly Val     Asp Ala
                185                     190
```

(2) INFORMATION FOR SEQ ID NO:59:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: US11

(xi) SEQUENCE DESCRIPTION: SEQ ID NO:59:

```
Tyr Gln Val Arg Asn     Ser Thr Gly Leu Tyr     His Val Thr Asn Asp
                5                       10                      15

Cys Pro Asn Ser Ser     Ile Val Tyr Glu Ala     Ala Asp Ala Ile Leu
                20                      25                      30

His Thr Pro Gly Cys     Val Pro Cys Val Arg     Glu Gly Asn Ala Ser
                35                      40                      45

Arg Cys Trp Val Ala     Met Thr Pro Thr Val     Ala Thr Arg Asp Gly
                50                      55                      60

Lys Leu Pro Thr Thr     Gln Leu Arg Arg His     Ile Asp Leu Leu Val
                65                      70                      75

Gly Ser Ala Thr Leu     Cys Ser Ala Leu Tyr     Val Gly Asp Leu Cys
                80                      85                      90

Gly Ser Val Phe Leu     Val Gly Gln Leu Phe     Thr Phe Ser Pro Arg
                95                      100                     105

Arg His Trp Thr Thr     Gln Gly Cys Asn Cys     Ser Ile Tyr Pro Gly
                110                     115                     120

His Ile Thr Gly His     Arg Met Ala Trp Asp     Met Met Met Asn Trp
                125                     130                     135

Ser Pro Thr Ala Ala     Leu Val Val Ala Gln     Leu Leu Arg Ile Pro
                140                     145                     150

Gln Ala Ile Leu Asp     Met Ile Ala Gly Ala     His Trp Gly Val Leu
                155                     160                     165

Ala Gly Ile Ala Tyr     Phe Ser Met Val Gly     Asn Trp Ala Lys Val
                170                     175                     180

Leu Val Val Leu Leu     Leu Phe Ala Gly Val     Asp Ala
                185                     190
```

( 2 ) INFORMATION FOR SEQ ID NO:60:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: D1

( x i ) SEQUENCE DESCRIPTION: SEQ ID NO:60:

```
Tyr Glu Val Arg Asn Val Ser Gly Val Tyr His Val Thr Asn Asp
                  5                  10                  15

Cys Ser Asn Ser Ser Ile Val Tyr Glu Thr Ala Asp Met Ile Met
                 20                  25                  30

His Thr Pro Gly Cys Val Pro Cys Val Arg Glu Asp Asn Ser Ser
                 35                  40                  45

Arg Cys Trp Val Ala Leu Thr Pro Thr Leu Ala Ala Arg Asn Gly
                 50                  55                  60

Asn Val Pro Thr Thr Ala Ile Arg Arg His Val Asp Leu Leu Val
                 65                  70                  75

Gly Ala Ala Ala Phe Cys Ser Ala Met Tyr Val Gly Asp Leu Cys
                 80                  85                  90

Gly Ser Val Phe Leu Ile Ser Gln Leu Phe Thr Leu Ser Pro Arg
                 95                 100                 105

Arg His Glu Thr Val Gln Glu Cys Asn Cys Ser Ile Tyr Pro Gly
                110                 115                 120

His Val Thr Gly His Arg Met Ala Trp Asp Met Met Met Asn Trp
                125                 130                 135

Ser Pro Thr Thr Ala Leu Val Val Ser Gln Leu Leu Arg Ile Pro
                140                 145                 150

Gln Ala Val Met Asp Met Val Ala Gly Ala His Trp Gly Val Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

( 2 ) INFORMATION FOR SEQ ID NO:61:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: D3

( x i ) SEQUENCE DESCRIPTION: SEQ ID NO:61:

```
Tyr Glu Val Arg Asn Val Ser Gly Val Tyr Gln Val Thr Asn Asp
                  5                  10                  15

Cys Ser Asn Ser Ser Ile Val Tyr Glu Thr Ala Asp Met Ile Met
                 20                  25                  30

His Thr Pro Gly Cys Val Pro Cys Val Arg Glu Asp Asn Ser Ser
                 35                  40                  45

Arg Cys Trp Val Ala Leu Thr Pro Thr Leu Ala Ala Arg Asn Ser
                 50                  55                  60

Ser Val Pro Thr Thr Thr Ile Arg Arg His Val Asp Leu Leu Val
                 65                  70                  75
```

```
Gly  Ala  Ala  Ala  Phe  Cys  Ser  Ala  Met  Tyr  Val  Gly  Asp  Leu  Cys
                    80                  85                            90

Gly  Ser  Val  Phe  Leu  Val  Ser  Gln  Leu  Phe  Thr  Phe  Ser  Pro  Arg
                    95                 100                           105

Arg  His  Glu  Thr  Val  Gln  Glu  Cys  Asn  Cys  Ser  Ile  Tyr  Pro  Gly
                   110                 115                           120

His  Val  Thr  Gly  His  Arg  Met  Ala  Trp  Asp  Met  Met  Met  Asn  Trp
                   125                 130                           135

Ser  Pro  Thr  Ala  Ala  Leu  Val  Val  Ser  Gln  Leu  Leu  Arg  Ile  Pro
                   140                 145                           150

Gln  Ala  Val  Val  Asp  Met  Val  Ala  Gly  Ala  His  Trp  Gly  Val  Leu
                   155                 160                           165

Ala  Gly  Leu  Ala  Tyr  Tyr  Ser  Met  Val  Gly  Asn  Trp  Ala  Lys  Val
                   170                 175                           180

Leu  Ile  Val  Met  Leu  Leu  Phe  Ala  Gly  Val  Asp  Gly
                   185                 190
```

( 2 ) INFORMATION FOR SEQ ID NO:62:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK1

( x i ) SEQUENCE DESCRIPTION: SEQ ID NO:62:

```
Tyr  Glu  Val  Arg  Asn  Val  Ser  Gly  Val  Tyr  His  Val  Thr  Asn  Asp
                     5                  10                            15

Cys  Ser  Asn  Ser  Ser  Ile  Val  Tyr  Glu  Ala  Val  Asp  Val  Ile  Met
                    20                  25                            30

His  Thr  Pro  Gly  Cys  Val  Pro  Cys  Val  Arg  Glu  Asn  Asn  His  Ser
                    35                  40                            45

Arg  Cys  Trp  Val  Ala  Leu  Thr  Pro  Thr  Leu  Ala  Ala  Arg  Asn  Ala
                    50                  55                            60

Ser  Ile  Pro  Thr  Thr  Thr  Ile  Arg  Arg  His  Val  Asp  Leu  Leu  Val
                    65                  70                            75

Gly  Ala  Ala  Ala  Phe  Cys  Ser  Ala  Met  Tyr  Val  Gly  Asp  Leu  Cys
                    80                  85                            90

Gly  Ser  Val  Phe  Leu  Val  Ser  Gln  Leu  Phe  Thr  Phe  Ser  Pro  Arg
                    95                 100                           105

Arg  His  Glu  Thr  Ala  Gln  Asp  Cys  Asn  Cys  Ser  Ile  Tyr  Pro  Gly
                   110                 115                           120

His  Val  Ser  Gly  His  Arg  Met  Ala  Trp  Asp  Met  Met  Met  Asn  Trp
                   125                 130                           135

Ser  Pro  Thr  Thr  Ala  Leu  Val  Leu  Ser  Gln  Leu  Leu  Arg  Ile  Pro
                   140                 145                           150

Gln  Ala  Val  Val  Asp  Met  Val  Ala  Gly  Ala  His  Trp  Gly  Val  Leu
                   155                 160                           165

Ala  Gly  Leu  Ala  Tyr  Tyr  Ser  Met  Val  Gly  Asn  Trp  Ala  Lys  Val
                   170                 175                           180

Leu  Ile  Val  Leu  Leu  Leu  Phe  Ala  Gly  Val  Asp  Gly
                   185                 190
```

( 2 ) INFORMATION FOR SEQ ID NO:63:

( i ) SEQUENCE CHARACTERISTICS:

(A) LENGTH: 192 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK3

(xi) SEQUENCE DESCRIPTION: SEQ ID NO:63:

| Tyr | Glu | Val | Arg | Asn | Val | Ser | Gly | Ile | Tyr | His | Val | Thr | Asn | Asp |
|---|---|---|---|---|---|---|---|---|---|---|---|---|---|---|
| | | | | 5 | | | | | 10 | | | | | 15 |
| Cys | Ser | Asn | Ser | Ser | Val | Val | Tyr | Glu | Thr | Ala | Asp | Met | Ile | Met |
| | | | | 20 | | | | | 25 | | | | | 30 |
| His | Thr | Pro | Gly | Cys | Val | Pro | Cys | Val | Arg | Glu | Asn | Asn | Ser | Ser |
| | | | | 35 | | | | | 40 | | | | | 45 |
| Arg | Cys | Trp | Val | Ala | Leu | Thr | Pro | Thr | Leu | Ala | Ala | Arg | Asn | Val |
| | | | | 50 | | | | | 55 | | | | | 60 |
| Ser | Val | Pro | Thr | Thr | Thr | Ile | Arg | Arg | His | Val | Asp | Leu | Leu | Val |
| | | | | 65 | | | | | 70 | | | | | 75 |
| Gly | Ala | Ala | Ala | Phe | Cys | Ser | Ala | Met | Tyr | Val | Gly | Asp | Leu | Cys |
| | | | | 80 | | | | | 85 | | | | | 90 |
| Gly | Ser | Val | Phe | Leu | Val | Ser | Gln | Leu | Phe | Thr | Phe | Ser | Pro | Arg |
| | | | | 95 | | | | | 100 | | | | | 105 |
| Arg | His | Glu | Thr | Val | Gln | Asp | Cys | Asn | Cys | Ser | Leu | Tyr | Pro | Gly |
| | | | | 110 | | | | | 115 | | | | | 120 |
| His | Val | Ser | Gly | His | Arg | Met | Ala | Trp | Asp | Met | Met | Met | Asn | Trp |
| | | | | 125 | | | | | 130 | | | | | 135 |
| Ser | Pro | Thr | Ala | Ala | Leu | Val | Val | Ser | Gln | Leu | Leu | Arg | Ile | Pro |
| | | | | 140 | | | | | 145 | | | | | 150 |
| Gln | Ala | Val | Val | Asp | Met | Val | Ala | Gly | Ala | His | Trp | Gly | Val | Leu |
| | | | | 155 | | | | | 160 | | | | | 165 |
| Ala | Gly | Leu | Ala | Tyr | Tyr | Ser | Met | Val | Gly | Asn | Trp | Ala | Lys | Val |
| | | | | 170 | | | | | 175 | | | | | 180 |
| Leu | Ile | Val | Met | Leu | Leu | Phe | Ala | Gly | Val | Asp | Gly | | | |
| | | | | 185 | | | | | 190 | | | | | |

(2) INFORMATION FOR SEQ ID NO:64:

(i) SEQUENCE CHARACTERISTICS:
(A) LENGTH: 192 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK4

(xi) SEQUENCE DESCRIPTION: SEQ ID NO:64:

| His | Glu | Val | His | Asn | Val | Ser | Gly | Ile | Tyr | His | Val | Thr | Asn | Asp |
|---|---|---|---|---|---|---|---|---|---|---|---|---|---|---|
| | | | | 5 | | | | | 10 | | | | | 15 |
| Cys | Ser | Asn | Ser | Ser | Ile | Val | Tyr | Glu | Ala | Ala | Asp | Met | Ile | Met |
| | | | | 20 | | | | | 25 | | | | | 30 |
| His | Thr | Pro | Gly | Cys | Val | Pro | Cys | Val | Arg | Glu | Asn | Asn | Ser | Ser |
| | | | | 35 | | | | | 40 | | | | | 45 |
| Arg | Cys | Trp | Val | Ala | Leu | Thr | Pro | Thr | Leu | Ala | Ala | Arg | Asn | Ala |
| | | | | 50 | | | | | 55 | | | | | 60 |
| Ser | Ile | Pro | Thr | Thr | Thr | Ile | Arg | Arg | His | Val | Asp | Leu | Leu | Val |
| | | | | 65 | | | | | 70 | | | | | 75 |
| Gly | Ala | Ala | Ala | Phe | Cys | Ser | Ala | Met | Tyr | Val | Gly | Asp | Leu | Cys |
| | | | | 80 | | | | | 85 | | | | | 90 |

```
Gly  Ser  Val  Phe  Leu  Val  Ser  Gln  Leu  Phe  Thr  Phe  Ser  Pro  Arg
                    95                  100                           105

Arg  His  Glu  Thr  Val  Gln  Asp  Cys  Asn  Cys  Ser  Ile  Tyr  Pro  Gly
                    110                 115                           120

His  Val  Ser  Gly  His  Arg  Met  Ala  Trp  Asp  Met  Met  Met  Asn  Trp
                    125                 130                           135

Ser  Pro  Thr  Ala  Ala  Leu  Val  Val  Ser  Gln  Leu  Leu  Arg  Leu  Pro
                    140                 145                           150

Gln  Ala  Val  Met  Asp  Met  Val  Ala  Gly  Ala  His  Trp  Gly  Val  Leu
                    155                 160                           165

Ala  Gly  Leu  Ala  Tyr  Tyr  Ser  Met  Val  Gly  Asn  Trp  Ala  Lys  Val
                    170                 175                           180

Leu  Ile  Val  Met  Leu  Leu  Phe  Ala  Gly  Val  Asp  Gly
                    185                 190
```

( 2 ) INFORMATION FOR SEQ ID NO:65:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: HK5

( x i ) SEQUENCE DESCRIPTION: SEQ ID NO:65:

```
Tyr  Glu  Val  Arg  Asn  Val  Ser  Gly  Val  Tyr  His  Val  Thr  Asn  Asp
                    5                   10                            15

Cys  Ser  Asn  Leu  Ser  Ile  Val  Tyr  Glu  Thr  Thr  Asp  Met  Ile  Met
                    20                  25                            30

His  Thr  Pro  Gly  Cys  Val  Pro  Cys  Val  Arg  Glu  Asn  Asn  Ser  Ser
                    35                  40                            45

Arg  Cys  Trp  Val  Ala  Leu  Ala  Pro  Thr  Leu  Ala  Ala  Arg  Asn  Ala
                    50                  55                            60

Ser  Val  Pro  Thr  Thr  Ala  Ile  Arg  Arg  His  Val  Asp  Leu  Leu  Val
                    65                  70                            75

Gly  Ala  Ala  Ala  Phe  Cys  Ser  Ala  Met  Tyr  Val  Gly  Asp  Leu  Cys
                    80                  85                            90

Gly  Ser  Val  Phe  Leu  Val  Ser  Gln  Leu  Phe  Thr  Phe  Ser  Pro  Arg
                    95                  100                           105

Arg  His  Glu  Thr  Val  Gln  Asp  Cys  Asn  Cys  Ser  Ile  Tyr  Pro  Gly
                    110                 115                           120

His  Val  Thr  Gly  His  Arg  Met  Ala  Trp  Asp  Met  Met  Met  Asn  Trp
                    125                 130                           135

Ser  Pro  Thr  Thr  Ala  Leu  Val  Val  Ser  Gln  Leu  Leu  Arg  Ile  Pro
                    140                 145                           150

Gln  Ala  Val  Val  Asp  Met  Val  Ala  Gly  Ala  His  Trp  Gly  Val  Leu
                    155                 160                           165

Ala  Gly  Leu  Ala  Tyr  Tyr  Ser  Met  Val  Gly  Asn  Trp  Ala  Lys  Val
                    170                 175                           180

Leu  Ile  Val  Met  Leu  Leu  Phe  Ala  Gly  Val  Asp  Gly
                    185                 190
```

( 2 ) INFORMATION FOR SEQ ID NO:66:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown (vi) ORIGINAL SOURCE:
    (A) ORGANISM: homosapiens
    (C) INDIVIDUAL ISOLATE: HK8

(xi) SEQUENCE DESCRIPTION: SEQ ID NO:66:

| | | | | | | | | | | | | | | |
|---|---|---|---|---|---|---|---|---|---|---|---|---|---|---|
| Tyr | Glu | Val | Arg | Asn | Val | Ser | Gly | Ile | Tyr | His | Val | Thr | Asn | Asp |
| | | | | 5 | | | | | 10 | | | | | 15 |
| Cys | Ser | Asn | Ser | Ser | Ile | Val | Tyr | Glu | Thr | Ala | Asp | Met | Ile | Met |
| | | | | 20 | | | | | 25 | | | | | 30 |
| His | Thr | Pro | Gly | Cys | Met | Pro | Cys | Val | Arg | Glu | Asn | Asn | Ser | Ser |
| | | | | 35 | | | | | 40 | | | | | 45 |
| Arg | Cys | Trp | Val | Ala | Leu | Thr | Pro | Thr | Leu | Ala | Ala | Arg | Asn | Val |
| | | | | 50 | | | | | 55 | | | | | 60 |
| Ser | Val | Pro | Thr | Thr | Thr | Ile | Arg | Arg | His | Val | Asp | Leu | Leu | Val |
| | | | | 65 | | | | | 70 | | | | | 75 |
| Gly | Ala | Ala | Ala | Phe | Cys | Ser | Ala | Met | Tyr | Val | Gly | Asp | Leu | Cys |
| | | | | 80 | | | | | 85 | | | | | 90 |
| Gly | Ser | Val | Phe | Leu | Val | Ser | Gln | Leu | Phe | Thr | Phe | Ser | Pro | Arg |
| | | | | 95 | | | | | 100 | | | | | 105 |
| Arg | His | Glu | Thr | Val | Gln | Asp | Cys | Asn | Cys | Ser | Ile | Tyr | Pro | Gly |
| | | | | 110 | | | | | 115 | | | | | 120 |
| His | Val | Ser | Gly | His | Arg | Met | Ala | Trp | Asp | Met | Met | Met | Asn | Trp |
| | | | | 125 | | | | | 130 | | | | | 135 |
| Ser | Pro | Thr | Thr | Ala | Leu | Val | Val | Ser | Gln | Leu | Leu | Arg | Ile | Pro |
| | | | | 140 | | | | | 145 | | | | | 150 |
| Gln | Ala | Ile | Val | Asp | Met | Val | Ala | Gly | Ala | His | Trp | Gly | Val | Leu |
| | | | | 155 | | | | | 160 | | | | | 165 |
| Ala | Gly | Leu | Ala | Tyr | Tyr | Ser | Met | Val | Gly | Asn | Trp | Ala | Lys | Val |
| | | | | 170 | | | | | 175 | | | | | 180 |
| Leu | Ile | Val | Met | Leu | Leu | Phe | Ala | Gly | Val | Asp | Gly | | | |
| | | | | 185 | | | | | 190 | | | | | |

(2) INFORMATION FOR SEQ ID NO:67:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: IND5

(xi) SEQUENCE DESCRIPTION: SEQ ID NO:67:

| | | | | | | | | | | | | | | |
|---|---|---|---|---|---|---|---|---|---|---|---|---|---|---|
| Tyr | Glu | Val | Arg | Asn | Val | Ser | Gly | Val | Tyr | His | Val | Thr | Asn | Asp |
| | | | | 5 | | | | | 10 | | | | | 15 |
| Cys | Ser | Asn | Ser | Ser | Ile | Val | Tyr | Glu | Ala | Ala | Asp | Met | Ile | Met |
| | | | | 20 | | | | | 25 | | | | | 30 |
| His | Thr | Pro | Gly | Cys | Val | Pro | Cys | Val | Arg | Glu | Gly | Asn | Ser | Ser |
| | | | | 35 | | | | | 40 | | | | | 45 |
| Arg | Cys | Trp | Val | Ala | Leu | Thr | Pro | Thr | Leu | Ala | Ala | Arg | Asn | Ala |
| | | | | 50 | | | | | 55 | | | | | 60 |
| Ser | Val | Ser | Thr | Thr | Thr | Ile | Arg | His | His | Val | Asp | Leu | Leu | Val |
| | | | | 65 | | | | | 70 | | | | | 75 |
| Gly | Ala | Ala | Ala | Phe | Cys | Ser | Ala | Met | Tyr | Val | Gly | Asp | Leu | Cys |
| | | | | 80 | | | | | 85 | | | | | 90 |
| Gly | Ser | Val | Phe | Leu | Val | Ser | Gln | Leu | Phe | Thr | Phe | Ser | Pro | Arg |
| | | | | 95 | | | | | 100 | | | | | 105 |
| Arg | His | Glu | Thr | Val | Gln | Asp | Cys | Asn | Cys | Ser | Ile | Tyr | Pro | Gly |

|  | | | | | | | | | | | | | | |
|---|---|---|---|---|---|---|---|---|---|---|---|---|---|---|
| His | Val | Ser | Gly | His<br>125 | Arg | Met | Ala | Trp | Asp<br>130 | Met | Met | Met | Asn | Trp<br>135 |
| Ser | Pro | Thr | Ala | Ala<br>140 | Leu | Val | Val | Ser | Gln<br>145 | Leu | Leu | Arg | Ile | Pro<br>150 |
| Gln | Ala | Val | Val | Asp<br>155 | Met | Val | Ala | Gly | Ala<br>160 | His | Trp | Gly | Ile | Leu<br>165 |
| Ala | Gly | Leu | Ala | Tyr<br>170 | Tyr | Ser | Met | Val | Gly<br>175 | Asn | Trp | Ala | Lys | Val<br>180 |
| Leu | Ile | Val | Met | Leu<br>185 | Leu | Phe | Ala | Gly | Val<br>190 | Asp | Gly | | | |

(2) INFORMATION FOR SEQ ID NO:68:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: IND8

(xi) SEQUENCE DESCRIPTION: SEQ ID NO:68:

|  | | | | | | | | | | | | | | |
|---|---|---|---|---|---|---|---|---|---|---|---|---|---|---|
| Tyr | Glu | Val | Arg | Asn<br>5 | Val | Ser | Gly | Val | Tyr<br>10 | His | Val | Thr | Asn | Asp<br>15 |
| Cys | Ser | Asn | Ser | Ser<br>20 | Ile | Val | Tyr | Glu | Ala<br>25 | Ala | Asp | Met | Ile | Met<br>30 |
| His | Thr | Pro | Gly | Cys<br>35 | Val | Pro | Cys | Val | Arg<br>40 | Glu | Gly | Asn | Phe | Ser<br>45 |
| Ser | Cys | Trp | Val | Ala<br>50 | Leu | Thr | Pro | Thr | Leu<br>55 | Ala | Ala | Arg | Asn | Ala<br>60 |
| Ser | Val | Pro | Thr | Thr<br>65 | Thr | Ile | Arg | Arg | His<br>70 | Val | Asp | Leu | Leu | Val<br>75 |
| Gly | Ala | Ala | Ala | Phe<br>80 | Cys | Ser | Ala | Met | Tyr<br>85 | Val | Gly | Asp | Leu | Cys<br>90 |
| Gly | Ser | Val | Phe | Leu<br>95 | Val | Ser | Gln | Leu | Phe<br>100 | Thr | Phe | Ser | Pro | Arg<br>105 |
| Arg | His | Glu | Thr | Val<br>110 | Gln | Asp | Cys | Asn | Cys<br>115 | Ser | Ile | Tyr | Pro | Gly<br>120 |
| His | Val | Ser | Gly | His<br>125 | Arg | Met | Ala | Trp | Asp<br>130 | Met | Met | Met | Asn | Trp<br>135 |
| Ser | Pro | Thr | Ala | Ala<br>140 | Leu | Val | Val | Ser | Gln<br>145 | Leu | Leu | Arg | Ile | Pro<br>150 |
| Gln | Ala | Val | Val | Asp<br>155 | Met | Val | Ala | Gly | Ala<br>160 | His | Trp | Gly | Ile | Leu<br>165 |
| Ala | Gly | Leu | Ala | Tyr<br>170 | Tyr | Ser | Met | Val | Gly<br>175 | Asn | Trp | Ala | Lys | Val<br>180 |
| Leu | Ile | Val | Met | Leu<br>185 | Leu | Phe | Ala | Gly | Val<br>190 | Asp | Gly | | | |

(2) INFORMATION FOR SEQ ID NO:69:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: P10

( x i ) SEQUENCE DESCRIPTION: SEQ ID NO:69:

| | | | | | | | | | | | | | | |
|---|---|---|---|---|---|---|---|---|---|---|---|---|---|---|
| Tyr | Glu | Val | Arg | Asn<br>5 | Val | Ser | Gly | Val | Tyr<br>10 | His | Val | Thr | Asn | Asp<br>15 |
| Cys | Ser | Asn | Ser | Ser<br>20 | Ile | Val | Tyr | Glu | Ala<br>25 | Ala | Asp | Met | Ile | Met<br>30 |
| His | Thr | Pro | Gly | Cys<br>35 | Val | Pro | Cys | Val | Arg<br>40 | Glu | Asn | Asn | Ser | Ser<br>45 |
| Arg | Cys | Trp | Val | Ala<br>50 | Leu | Thr | Pro | Thr | Leu<br>55 | Ala | Ala | Arg | Asn | Ser<br>60 |
| Ser | Val | Pro | Thr | Thr<br>65 | Ala | Ile | Arg | Arg | His<br>70 | Val | Asp | Leu | Leu | Val<br>75 |
| Gly | Ala | Ala | Ala | Phe<br>80 | Cys | Ser | Ala | Met | Tyr<br>85 | Val | Gly | Asp | Leu | Cys<br>90 |
| Gly | Ser | Val | Leu | Leu<br>95 | Val | Ser | Gln | Leu | Phe<br>100 | Thr | Phe | Ser | Pro | Arg<br>105 |
| Arg | His | Trp | Thr | Val<br>110 | Gln | Asp | Cys | Asn | Cys<br>115 | Ser | Ile | Tyr | Pro | Gly<br>120 |
| His | Val | Ser | Gly | His<br>125 | Arg | Met | Ala | Trp | Asp<br>130 | Met | Met | Met | Asn | Trp<br>135 |
| Ser | Pro | Thr | Ala | Ala<br>140 | Leu | Val | Val | Ser | Gln<br>145 | Leu | Leu | Arg | Ile | Pro<br>150 |
| Gln | Ala | Ile | Leu | Asp<br>155 | Val | Val | Ala | Gly | Ala<br>160 | His | Trp | Gly | Val | Leu<br>165 |
| Ala | Gly | Leu | Ala | Tyr<br>170 | Tyr | Ser | Met | Val | Gly<br>175 | Asn | Trp | Ala | Lys | Val<br>180 |
| Leu | Ile | Val | Met | Leu<br>185 | Leu | Phe | Ala | Gly | Val<br>190 | Asp | Gly | | | |

( 2 ) INFORMATION FOR SEQ ID NO:70:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S9

( x i ) SEQUENCE DESCRIPTION: SEQ ID NO:70:

| | | | | | | | | | | | | | | |
|---|---|---|---|---|---|---|---|---|---|---|---|---|---|---|
| Tyr | Glu | Val | Arg | Asn<br>5 | Val | Ser | Gly | Ala | Tyr<br>10 | His | Val | Thr | Asn | Asp<br>15 |
| Cys | Ser | Asn | Ser | Ser<br>20 | Ile | Val | Tyr | Glu | Ala<br>25 | Ala | Asp | Val | Ile | Met<br>30 |
| His | Thr | Pro | Gly | Cys<br>35 | Val | Pro | Cys | Val | Gln<br>40 | Glu | Gly | Asn | Ser | Ser<br>45 |
| Gln | Cys | Trp | Val | Ala<br>50 | Leu | Thr | Pro | Thr | Leu<br>55 | Ala | Ala | Arg | Asn | Ala<br>60 |
| Thr | Val | Pro | Thr | Thr<br>65 | Thr | Ile | Arg | Arg | His<br>70 | Val | Asp | Leu | Leu | Val<br>75 |
| Gly | Ala | Ala | Val | Phe<br>80 | Cys | Ser | Ala | Met | Tyr<br>85 | Val | Gly | Asp | Leu | Cys<br>90 |
| Gly | Ser | Val | Phe | Leu<br>95 | Ile | Ser | Gln | Leu | Phe<br>100 | Thr | Ile | Ser | Pro | Arg<br>105 |
| Arg | His | Glu | Thr | Val<br>110 | Gln | Asn | Cys | Asn | Cys<br>115 | Ser | Ile | Tyr | Pro | Gly<br>120 |
| His | Val | Thr | Gly | His<br>125 | Arg | Met | Ala | Trp | Asp<br>130 | Met | Met | Met | Asn | Trp<br>135 |

| Ser | Pro | Thr | Thr | Ala | Leu | Val | Val | Ser | Gln | Leu | Leu | Arg | Ile | Pro |
| | | | | 140 | | | | | 145 | | | | | 150 |

| Gln | Ala | Val | Met | Asp | Met | Val | Ala | Gly | Ala | His | Trp | Gly | Val | Leu |
| | | | | 155 | | | | | 160 | | | | | 165 |

| Ala | Gly | Leu | Ala | Tyr | Tyr | Ser | Met | Val | Gly | Asn | Trp | Ala | Lys | Val |
| | | | | 170 | | | | | 175 | | | | | 180 |

| Leu | Ile | Val | Met | Leu | Leu | Phe | Ala | Gly | Val | Asp | Gly |
| | | | | 185 | | | | | 190 | | |

( 2 ) INFORMATION FOR SEQ ID NO:71:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S45

( x i ) SEQUENCE DESCRIPTION: SEQ ID NO:71:

| Tyr | Glu | Val | Arg | Asn | Val | Ser | Gly | Ala | Tyr | His | Val | Thr | Asn | Asp |
| | | | | 5 | | | | | 10 | | | | | 15 |

| Cys | Ser | Asn | Ser | Ser | Ile | Val | Tyr | Glu | Ala | Val | Asp | Val | Ile | Leu |
| | | | | 20 | | | | | 25 | | | | | 30 |

| His | Thr | Pro | Gly | Cys | Val | Pro | Cys | Val | Arg | Glu | Asn | Asn | Ser | Ser |
| | | | | 35 | | | | | 40 | | | | | 45 |

| Arg | Cys | Trp | Val | Ala | Leu | Thr | Pro | Thr | Leu | Ala | Ala | Arg | Asn | Ser |
| | | | | 50 | | | | | 55 | | | | | 60 |

| Ser | Val | Pro | Thr | Thr | Thr | Ile | Arg | Arg | His | Val | Asp | Leu | Leu | Val |
| | | | | 65 | | | | | 70 | | | | | 75 |

| Gly | Ala | Ala | Ala | Phe | Cys | Ser | Ala | Met | Tyr | Val | Gly | Asp | Leu | Cys |
| | | | | 80 | | | | | 85 | | | | | 90 |

| Gly | Ser | Val | Phe | Leu | Val | Ser | Gln | Leu | Phe | Thr | Phe | Ser | Pro | Arg |
| | | | | 95 | | | | | 100 | | | | | 105 |

| Arg | His | Glu | Thr | Val | Gln | Asp | Cys | Asn | Cys | Ser | Ile | Tyr | Pro | Gly |
| | | | | 110 | | | | | 115 | | | | | 120 |

| His | Val | Thr | Gly | His | Arg | Met | Ala | Trp | Asp | Met | Met | Met | Asn | Trp |
| | | | | 125 | | | | | 130 | | | | | 135 |

| Ser | Pro | Thr | Ala | Ala | Leu | Val | Val | Ser | Gln | Leu | Leu | Arg | Ile | Pro |
| | | | | 140 | | | | | 145 | | | | | 150 |

| Gln | Ala | Val | Val | Asp | Met | Val | Ala | Gly | Ala | His | Trp | Gly | Val | Leu |
| | | | | 155 | | | | | 160 | | | | | 165 |

| Ala | Gly | Leu | Ala | Tyr | Tyr | Ser | Met | Val | Gly | Asn | Trp | Ala | Lys | Val |
| | | | | 170 | | | | | 175 | | | | | 180 |

| Leu | Ile | Val | Met | Leu | Leu | Phe | Ala | Gly | Val | Asp | Gly |
| | | | | 185 | | | | | 190 | | |

( 2 ) INFORMATION FOR SEQ ID NO:72:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA10

( x i ) SEQUENCE DESCRIPTION: SEQ ID NO:72:

| Tyr | Glu | Val | Arg | Asn | Val | Ser | Gly | Met | Tyr | His | Val | Thr | Asn | Asp |

|     |     |     |     |     |     |     |     |     |     |     |     |     |     |     |
|---|---|---|---|---|---|---|---|---|---|---|---|---|---|---|
| Cys | Ser | Asn | Ser | Ser | Ile | Val | Tyr | Glu | Ala | Ala | Asp | Met | Ile | Met |
|     |     |     |     | 20  |     |     |     | 25  |     |     |     |     |     | 30  |
| His | Thr | Pro | Gly | Cys | Val | Pro | Cys | Val | Arg | Glu | Asn | Asn | Ser | Ser |
|     |     |     |     | 35  |     |     |     | 40  |     |     |     |     |     | 45  |
| Arg | Cys | Trp | Val | Ala | Leu | Thr | Pro | Thr | Leu | Ala | Ala | Arg | Asn | Ser |
|     |     |     |     | 50  |     |     |     | 55  |     |     |     |     |     | 60  |
| Ser | Val | Pro | Thr | Thr | Thr | Ile | Arg | Arg | His | Val | Asp | Leu | Leu | Val |
|     |     |     |     | 65  |     |     |     | 70  |     |     |     |     |     | 75  |
| Gly | Ala | Ala | Ala | Phe | Cys | Ser | Ala | Met | Tyr | Val | Gly | Asp | Leu | Cys |
|     |     |     |     | 80  |     |     |     | 85  |     |     |     |     |     | 90  |
| Gly | Ser | Val | Phe | Leu | Val | Ser | Gln | Leu | Phe | Thr | Phe | Ser | Pro | Arg |
|     |     |     |     | 95  |     |     |     | 100 |     |     |     |     |     | 105 |
| Arg | Tyr | Glu | Thr | Val | Gln | Asp | Cys | Asn | Cys | Ser | Ile | Tyr | Pro | Gly |
|     |     |     |     | 110 |     |     |     | 115 |     |     |     |     |     | 120 |
| Arg | Val | Thr | Gly | His | Arg | Met | Ala | Trp | Asp | Met | Met | Met | Asn | Trp |
|     |     |     |     | 125 |     |     |     | 130 |     |     |     |     |     | 135 |
| Ser | Pro | Thr | Thr | Ala | Leu | Val | Val | Ser | Gln | Leu | Leu | Arg | Ile | Pro |
|     |     |     |     | 140 |     |     |     | 145 |     |     |     |     |     | 150 |
| Gln | Ala | Ile | Val | Asp | Met | Val | Ala | Gly | Ala | His | Trp | Gly | Val | Leu |
|     |     |     |     | 155 |     |     |     | 160 |     |     |     |     |     | 165 |
| Ala | Gly | Leu | Ala | Tyr | Tyr | Ser | Met | Val | Gly | Asn | Trp | Ala | Lys | Val |
|     |     |     |     | 170 |     |     |     | 175 |     |     |     |     |     | 180 |
| Leu | Ile | Val | Met | Leu | Leu | Phe | Ala | Gly | Val | Asp | Gly |     |     |     |
|     |     |     |     | 185 |     |     |     | 190 |     |     |     |     |     |     |

( 2 ) INFORMATION FOR SEQ ID NO:73:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SW2

( x i ) SEQUENCE DESCRIPTION: SEQ ID NO:73:

|     |     |     |     |     |     |     |     |     |     |     |     |     |     |     |
|---|---|---|---|---|---|---|---|---|---|---|---|---|---|---|
| Tyr | Glu | Val | Arg | Asn | Val | Ser | Gly | Val | Tyr | His | Val | Thr | Asn | Asp |
|     |     |     |     | 5   |     |     |     | 10  |     |     |     |     |     | 15  |
| Cys | Ser | Asn | Ser | Ser | Ile | Val | Tyr | Glu | Thr | Ala | Asp | Met | Ile | Met |
|     |     |     |     | 20  |     |     |     | 25  |     |     |     |     |     | 30  |
| His | Thr | Pro | Gly | Cys | Val | Pro | Cys | Val | Arg | Glu | Ala | Asn | Ser | Ser |
|     |     |     |     | 35  |     |     |     | 40  |     |     |     |     |     | 45  |
| Arg | Cys | Trp | Val | Ala | Leu | Thr | Pro | Thr | Leu | Ala | Ala | Arg | Asn | Thr |
|     |     |     |     | 50  |     |     |     | 55  |     |     |     |     |     | 60  |
| Ser | Val | Pro | Thr | Thr | Thr | Ile | Arg | Arg | His | Val | Asp | Leu | Leu | Val |
|     |     |     |     | 65  |     |     |     | 70  |     |     |     |     |     | 75  |
| Gly | Ala | Ala | Ala | Phe | Cys | Ser | Val | Met | Tyr | Val | Gly | Asp | Leu | Cys |
|     |     |     |     | 80  |     |     |     | 85  |     |     |     |     |     | 90  |
| Gly | Ser | Val | Phe | Leu | Val | Ser | Gln | Leu | Phe | Thr | Phe | Ser | Pro | Arg |
|     |     |     |     | 95  |     |     |     | 100 |     |     |     |     |     | 105 |
| Arg | His | Glu | Thr | Val | Gln | Asp | Cys | Asn | Cys | Ser | Ile | Tyr | Pro | Gly |
|     |     |     |     | 110 |     |     |     | 115 |     |     |     |     |     | 120 |
| His | Val | Ser | Gly | His | Arg | Met | Ala | Trp | Asp | Met | Met | Met | Asn | Trp |
|     |     |     |     | 125 |     |     |     | 130 |     |     |     |     |     | 135 |
| Ser | Pro | Thr | Ala | Ala | Leu | Val | Val | Ser | Gln | Leu | Leu | Arg | Ile | Pro |
|     |     |     |     | 140 |     |     |     | 145 |     |     |     |     |     | 150 |

Gln Ala Val Val Asp Met Val Ala Gly Ala His Trp Gly Val Leu
                    155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185             190

( 2 ) INFORMATION FOR SEQ ID NO:74:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T3

( x i ) SEQUENCE DESCRIPTION: SEQ ID NO:74:

Tyr Glu Val Arg Asn Val Ser Gly Val Tyr Tyr Val Thr Asn Asp
                5                   10                  15

Cys Ser Asn Ser Ser Ile Val Tyr Glu Thr Ala Asp Met Ile Met
                20                  25                  30

His Thr Pro Gly Cys Val Pro Cys Val Arg Glu Ser Asn Ser Ser
                35                  40                  45

Arg Cys Trp Val Ala Leu Thr Pro Thr Leu Ala Ala Arg Asn Ala
                50                  55                  60

Ser Val Pro Thr Lys Thr Ile Arg Arg His Val Asp Leu Leu Val
                65                  70                  75

Gly Ala Ala Ala Phe Cys Ser Ala Met Tyr Val Gly Asp Leu Cys
                80                  85                  90

Gly Ser Val Phe Leu Val Ser Gln Leu Phe Thr Phe Ser Pro Arg
                95                  100                 105

Arg His Glu Thr Val Gln Asp Cys Asn Cys Ser Ile Tyr Pro Gly
                110                 115                 120

His Val Thr Gly His Arg Met Ala Trp Asp Met Met Met Asn Trp
                125                 130                 135

Ser Pro Thr Thr Ala Leu Val Val Ser Gln Leu Leu Arg Ile Pro
                140                 145                 150

Gln Ala Val Val Asp Met Val Ala Gly Ala His Trp Gly Val Leu
                155                 160                 165

Ala Gly Leu Ala Tyr Tyr Ser Met Val Gly Asn Trp Ala Lys Val
                170                 175                 180

Leu Ile Val Leu Leu Leu Phe Ala Gly Val Asp Gly
                185             190

( 2 ) INFORMATION FOR SEQ ID NO:75:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T10

( x i ) SEQUENCE DESCRIPTION: SEQ ID NO:75:

Tyr Glu Val Arg Asn Val Ser Gly Met Tyr His Val Thr Asn Asp
                5                   10                  15

Cys Ser Asn Ser Ser Ile Val Phe Glu Ala Ala Asp Leu Ile Met
                20                  25                  30

His Thr Pro Gly Cys Val Pro Cys Val Arg Glu Gly Asn Ser Ser
                    35                    40                    45

Arg Cys Trp Val Ala Leu Thr Pro Thr Leu Ala Ala Arg Asn Thr
                    50                    55                    60

Ser Val Pro Thr Thr Thr Ile Arg Arg His Val Asp Leu Leu Val
                    65                    70                    75

Gly Ala Ala Ala Phe Cys Ser Ala Met Tyr Val Gly Asp Leu Cys
                    80                    85                    90

Gly Ser Val Phe Leu Val Ser Gln Leu Phe Thr Phe Ser Pro Arg
                    95                    100                   105

Arg His Glu Thr Leu Gln Asp Cys Asn Cys Ser Ile Tyr Pro Gly
                    110                   115                   120

His Leu Ser Gly His Arg Met Ala Trp Asp Met Met Met Asn Trp
                    125                   130                   135

Ser Pro Thr Thr Ala Leu Val Val Ser Gln Leu Leu Arg Ile Pro
                    140                   145                   150

Gln Ala Val Met Asp Met Val Thr Gly Ala His Trp Gly Val Leu
                    155                   160                   165

Ala Gly Leu Ala Tyr Tyr Ser Met Ala Gly Asn Trp Ala Lys Val
                    170                   175                   180

Leu Ile Val Met Leu Leu Phe Ala Gly Val Asp Gly
                    185                   190

( 2 ) INFORMATION FOR SEQ ID NO:76:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: US6

( x i ) SEQUENCE DESCRIPTION: SEQ ID NO:76:

Tyr Glu Val Arg Asn Val Ser Gly Met Tyr His Val Thr Asn Asp
                    5                     10                    15

Cys Ser Asn Ser Ser Ile Val Tyr Glu Ala Ala Asp Met Ile Met
                    20                    25                    30

His Thr Pro Gly Cys Val Pro Cys Val Arg Glu Asn Asn Ser Ser
                    35                    40                    45

Arg Cys Trp Val Ala Leu Thr Pro Thr Leu Ala Ala Arg Asn Ala
                    50                    55                    60

Ser Val Pro Thr Thr Thr Ile Arg Arg His Val Asp Leu Leu Val
                    65                    70                    75

Gly Ala Ala Thr Phe Cys Ser Ala Met Tyr Val Gly Asp Leu Cys
                    80                    85                    90

Gly Ser Val Phe Leu Ile Ser Gln Leu Phe Thr Phe Ser Pro Arg
                    95                    100                   105

Gln His Glu Thr Val Gln Asp Cys Asn Cys Ser Ile Tyr Pro Gly
                    110                   115                   120

His Val Ser Gly His Arg Met Ala Trp Asp Met Met Met Asn Trp
                    125                   130                   135

Ser Pro Thr Ala Ala Leu Val Val Ser Gln Leu Leu Arg Ile Pro
                    140                   145                   150

Gln Ala Val Met Asp Met Val Ala Gly Ala His Trp Gly Val Leu
                    155                   160                   165

Ala Gly Leu Ala Tyr Tyr Ser Met Val Gly Asn Trp Ala Lys Val 170                                    175                               180
Leu  Ile  Val  Leu  Leu  Leu  Phe  Ala  Gly  Val  Asp  Gly
                              185                      190

(2) INFORMATION FOR SEQ ID NO:77:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T2

(xi) SEQUENCE DESCRIPTION: SEQ ID NO:77:

Ala  Gln  Val  Arg  Asn  Thr  Ser  Arg  Gly  Tyr  Met  Val  Thr  Asn  Asp
                    5                         10                         15

Cys  Ser  Asn  Glu  Ser  Ile  Thr  Trp  Gln  Leu  Gln  Ala  Ala  Val  Leu
                    20                        25                         30

His  Val  Pro  Gly  Cys  Ile  Pro  Cys  Glu  Arg  Leu  Gly  Asn  Thr  Ser
                    35                        40                         45

Arg  Cys  Trp  Ile  Pro  Val  Thr  Pro  Asn  Val  Ala  Val  Arg  Gln  Pro
                    50                        55                         60

Gly  Ala  Leu  Thr  Gln  Gly  Leu  Arg  Thr  His  Ile  Asp  Met  Val  Val
                    65                        70                         75

Met  Ser  Ala  Thr  Leu  Cys  Ser  Ala  Leu  Tyr  Val  Gly  Asp  Leu  Cys
                    80                        85                         90

Gly  Gly  Val  Met  Leu  Ala  Ala  Gln  Met  Phe  Ile  Val  Ser  Pro  Arg
                    95                        100                        105

Arg  His  Trp  Phe  Val  Gln  Glu  Cys  Asn  Cys  Ser  Ile  Tyr  Pro  Gly
                    110                       115                        120

Thr  Ile  Thr  Gly  His  Arg  Met  Ala  Trp  Asp  Met  Met  Met  Asn  Trp
                    125                       130                        135

Ser  Pro  Thr  Ala  Thr  Met  Ile  Leu  Ala  Tyr  Ala  Met  Arg  Val  Pro
                    140                       145                        150

Glu  Val  Ile  Ile  Asp  Ile  Ile  Gly  Gly  Ala  His  Trp  Gly  Val  Met
                    155                       160                        165

Phe  Gly  Leu  Ala  Tyr  Phe  Ser  Met  Gln  Gly  Ala  Trp  Ala  Lys  Val
                    170                       175                        180

Ile  Val  Ile  Leu  Leu  Leu  Ala  Ala  Gly  Val  Asp  Ala
                    185                       190

(2) INFORMATION FOR SEQ ID NO:78:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T4

(xi) SEQUENCE DESCRIPTION: SEQ ID NO:78:

Ala  Gln  Val  Lys  Asn  Thr  Thr  Asn  Ser  Tyr  Met  Val  Thr  Asn  Asp
                    5                         10                         15

Cys  Ser  Asn  Asp  Ser  Ile  Thr  Trp  Gln  Leu  Gln  Ala  Ala  Val  Leu
                    20                        25                         30

His  Val  Pro  Gly  Cys  Val  Pro  Cys  Glu  Lys  Thr  Gly  Asn  Thr  Ser
                    35                        40                         45

```
Arg Cys Trp Ile Pro Val Ser Pro Asn Val Ala Val Arg Gln Pro
                50                  55                  60

Gly Ala Leu Thr Gln Gly Leu Arg Thr His Ile Asp Met Val Val
                65                  70                  75

Met Ser Ala Thr Leu Cys Ser Ala Leu Tyr Val Gly Asp Leu Cys
                80                  85                  90

Gly Gly Val Met Leu Ala Ala Gln Met Phe Ile Val Ser Pro Gln
                95                  100                 105

His His Trp Phe Val Gln Asp Cys Asn Cys Ser Ile Tyr Pro Gly
                110                 115                 120

Thr Ile Thr Gly His Arg Met Ala Trp Asp Met Met Met Asn Trp
                125                 130                 135

Ser Pro Thr Ala Thr Met Ile Leu Ala Tyr Ala Met Arg Val Pro
                140                 145                 150

Glu Val Ile Leu Asp Ile Val Ser Gly Ala His Trp Gly Val Met
                155                 160                 165

Phe Gly Leu Ala Tyr Phe Ser Met Gln Gly Ala Trp Ala Lys Val
                170                 175                 180

Val Val Ile Leu Leu Leu Ala Ala Gly Val Asp Ala
                185                 190
```

( 2 ) INFORMATION FOR SEQ ID NO:79:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: T9

( x i ) SEQUENCE DESCRIPTION: SEQ ID NO:79:

```
Ala Glu Val Lys Asn Thr Ser Thr Ser Tyr Met Val Thr Asn Asp
                5                   10                  15

Cys Ser Asn Asp Ser Ile Thr Trp Gln Leu Gln Ala Ala Val Leu
                20                  25                  30

His Val Pro Gly Cys Val Pro Cys Glu Arg Val Gly Asn Ala Ser
                35                  40                  45

Arg Cys Trp Ile Pro Val Ser Pro Asn Val Ala Val Gln Arg Pro
                50                  55                  60

Gly Ala Leu Thr Gln Gly Leu Arg Thr His Ile Asp Met Val Val
                65                  70                  75

Met Ser Ala Thr Leu Cys Ser Ala Leu Tyr Val Gly Asp Leu Cys
                80                  85                  90

Gly Gly Val Met Leu Ala Ala Gln Met Phe Ile Ile Ser Pro Gln
                95                  100                 105

His His Trp Phe Val Gln Glu Cys Asn Cys Ser Ile Tyr Pro Gly
                110                 115                 120

Thr Ile Thr Gly His Arg Met Ala Trp Asp Met Met Met Asn Trp
                125                 130                 135

Ser Pro Thr Thr Thr Met Ile Leu Ala Tyr Ala Met Arg Val Pro
                140                 145                 150

Glu Val Ile Ile Asp Ile Ile Ser Gly Ala His Trp Gly Val Met
                155                 160                 165

Phe Gly Leu Ala Tyr Phe Ser Met Gln Gly Ala Trp Ala Lys Val
                170                 175                 180

Val Val Ile Leu Leu Leu Thr Ala Gly Val Asp Ala
                185                 190
```

( 2 ) INFORMATION FOR SEQ ID NO:80:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: US10

( x i ) SEQUENCE DESCRIPTION: SEQ ID NO:80:

```
Val Gln Val Lys Asn Thr Ser Thr Ser Tyr Met Val Thr Asn Asp
                  5                  10                 15
Cys Ser Asn Asp Ser Ile Thr Trp Gln Leu Glu Ala Ala Val Leu
                 20                  25                 30
His Val Pro Gly Cys Val Pro Cys Glu Lys Val Gly Asn Thr Ser
                 35                  40                 45
Arg Cys Trp Ile Pro Val Ser Pro Asn Val Ala Val Gln Arg Pro
                 50                  55                 60
Gly Ala Leu Thr Gln Gly Leu Arg Thr His Ile Asp Met Val Val
                 65                  70                 75
Met Ser Ala Thr Leu Cys Ser Ala Leu Tyr Val Gly Asp Phe Cys
                 80                  85                 90
Gly Gly Met Met Leu Ala Ala Gln Met Phe Ile Val Ser Pro Arg
                 95                 100                105
His His Ser Phe Val Gln Glu Cys Asn Cys Ser Ile Tyr Pro Gly
                110                 115                120
Thr Ile Thr Gly His Arg Met Ala Trp Asp Met Met Met Asn Trp
                125                 130                135
Ser Pro Thr Ala Thr Leu Ile Leu Ala Tyr Val Met Arg Val Pro
                140                 145                150
Glu Val Ile Ile Asp Ile Ile Ser Gly Ala His Trp Gly Val Leu
                155                 160                165
Phe Gly Leu Ala Tyr Phe Ser Met Gln Gly Ala Trp Ala Lys Val
                170                 175                180
Val Val Ile Leu Leu Leu Ala Ala Gly Val Asp Ala
                185                 190
```

( 2 ) INFORMATION FOR SEQ ID NO:81:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK8

( x i ) SEQUENCE DESCRIPTION: SEQ ID NO:81:

```
Val Glu Val Arg Asn Ile Ser Ser Ser Tyr Tyr Ala Thr Asn Asp
                  5                  10                 15
Cys Ser Asn Asn Ser Ile Thr Trp Gln Leu Thr Asp Ala Val Leu
                 20                  25                 30
His Leu Pro Gly Cys Val Pro Cys Glu Asn Asp Asn Gly Thr Leu
                 35                  40                 45
Arg Cys Trp Ile Gln Val Thr Pro Asn Val Ala Val Lys His Arg
                 50                  55                 60
Gly Ala Leu Thr His Asn Leu Arg Thr His Val Asp Val Ile Val
```

```
                               65              70                75
Met Ala Ala Thr Val Cys Ser Ala Leu Tyr Val Gly Asp Val Cys
                  80              85                90
Gly Ala Val Met Ile Val Ser Gln Ala Leu Ile Ile Ser Pro Glu
                  95             100               105
Arg His Asn Phe Thr Gln Glu Cys Asn Cys Ser Ile Tyr Gln Gly
                 110             115               120
His Ile Thr Gly His Arg Met Ala Trp Asp Met Met Leu Asn Trp
                 125             130               135
Ser Pro Thr Leu Thr Met Ile Leu Ala Tyr Ala Ala Arg Val Pro
                 140             145               150
Glu Leu Ala Leu Gln Val Val Phe Gly Gly His Trp Gly Val Val
                 155             160               165
Phe Gly Leu Ala Tyr Phe Ser Met Gln Gly Ala Trp Ala Lys Val
                 170             175               180
Ile Ala Ile Leu Leu Leu Val Ala Gly Val Asp Ala
                 185             190
```

( 2 ) INFORMATION FOR SEQ ID NO:82:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: DK11

( x i ) SEQUENCE DESCRIPTION: SEQ ID NO:82:

```
Val Glu Val Arg Asn Thr Ser Ser Ser Tyr Tyr Ala Thr Asn Asp
                  5              10                15
Cys Ser Asn Asn Ser Ile Thr Trp Gln Leu Thr Asn Ala Val Leu
                 20              25                30
His Leu Pro Gly Cys Val Pro Cys Glu Asn Asp Asn Gly Thr Leu
                 35              40                45
His Cys Trp Ile Gln Val Thr Pro Asn Val Ala Val Lys His Arg
                 50              55                60
Gly Ala Leu Thr His Asn Leu Arg Ala His Ile Asp Met Ile Val
                 65              70                75
Met Ala Ala Thr Val Cys Ser Ala Leu Tyr Val Gly Asp Val Cys
                 80              85                90
Gly Ala Val Met Ile Val Ser Gln Ala Phe Ile Val Ser Pro Glu
                 95             100               105
His His His Phe Thr Gln Glu Cys Asn Cys Ser Ile Tyr Gln Gly
                110             115               120
His Ile Thr Gly His Arg Met Ala Trp Asp Met Met Leu Asn Trp
                125             130               135
Ser Pro Thr Leu Thr Met Ile Leu Ala Tyr Ala Ala Arg Val Pro
                140             145               150
Glu Leu Val Leu Glu Val Val Phe Gly Gly His Trp Gly Val Val
                155             160               165
Phe Gly Leu Ala Tyr Phe Ser Met Gln Gly Ala Trp Ala Lys Val
                170             175               180
Ile Ala Ile Leu Leu Leu Val Ala Gly Val Asp Ala
                185             190
```

( 2 ) INFORMATION FOR SEQ ID NO:83:

(i) SEQUENCE CHARACTERISTICS:
  (A) LENGTH: 192 amino acids
  (B) TYPE: amino acid
  (C) STRANDEDNESS: unknown
  (D) TOPOLOGY: unknown (vi) ORIGINAL SOURCE:
  (A) ORGANISM: homosapiens
  (C) INDIVIDUAL ISOLATE: SW3

(xi) SEQUENCE DESCRIPTION: SEQ ID NO:83:

| | | | | | | | | | | | | | | |
|---|---|---|---|---|---|---|---|---|---|---|---|---|---|---|
|Val|Glu|Val|Arg|Asn|Ile|Ser|Ser|Ser|Tyr|Tyr|Ala|Thr|Asn|Asp|
| | | | |5| | | | |10| | | | |15|
|Cys|Ser|Asn|Ser|Ser|Ile|Thr|Trp|Gln|Leu|Thr|Asn|Ala|Val|Leu|
| | | | |20| | | | |25| | | | |30|
|His|Leu|Pro|Gly|Cys|Val|Pro|Cys|Glu|Asn|Asp|Asn|Gly|Thr|Leu|
| | | | |35| | | | |40| | | | |45|
|His|Cys|Trp|Ile|Gln|Val|Thr|Pro|Asn|Val|Ala|Val|Lys|His|Arg|
| | | | |50| | | | |55| | | | |60|
|Gly|Ala|Leu|Thr|His|Asn|Leu|Arg|Ala|His|Val|Asp|Met|Ile|Val|
| | | | |65| | | | |70| | | | |75|
|Met|Ala|Ala|Thr|Val|Cys|Ser|Ala|Leu|Tyr|Val|Gly|Asp|Met|Cys|
| | | | |80| | | | |85| | | | |90|
|Gly|Ala|Val|Met|Ile|Val|Ser|Gln|Ala|Phe|Ile|Ile|Ser|Pro|Glu|
| | | | |95| | | | |100| | | | |105|
|Arg|His|Asn|Phe|Thr|Gln|Glu|Cys|Asn|Cys|Ser|Ile|Tyr|Gln|Gly|
| | | | |110| | | | |115| | | | |120|
|Arg|Ile|Thr|Gly|His|Arg|Met|Ala|Trp|Asp|Met|Met|Leu|Asn|Trp|
| | | | |125| | | | |130| | | | |135|
|Ser|Pro|Thr|Leu|Thr|Met|Ile|Leu|Ala|Tyr|Ala|Ala|Arg|Val|Pro|
| | | | |140| | | | |145| | | | |150|
|Glu|Leu|Val|Leu|Glu|Val|Val|Phe|Gly|Gly|His|Trp|Gly|Val|Val|
| | | | |155| | | | |160| | | | |165|
|Phe|Gly|Leu|Ala|Tyr|Phe|Ser|Met|Gln|Gly|Ala|Trp|Ala|Lys|Val|
| | | | |170| | | | |175| | | | |180|
|Ile|Ala|Ile|Leu|Leu|Leu|Val|Ala|Gly|Val|Asp|Ala| | | |
| | | | |185| | | | |190| | | | | |

(2) INFORMATION FOR SEQ ID NO:84:

(i) SEQUENCE CHARACTERISTICS:
  (A) LENGTH: 192 amino acids
  (B) TYPE: amino acid
  (C) STRANDEDNESS: unknown
  (D) TOPOLOGY: unknown (vi) ORIGINAL SOURCE:
  (A) ORGANISM: homosapiens
  (C) INDIVIDUAL ISOLATE: T8

(xi) SEQUENCE DESCRIPTION: SEQ ID NO:84:

| | | | | | | | | | | | | | | |
|---|---|---|---|---|---|---|---|---|---|---|---|---|---|---|
|Val|Glu|Val|Arg|Asn|Thr|Ser|Phe|Ser|Tyr|Tyr|Ala|Thr|Asn|Asp|
| | | | |5| | | | |10| | | | |15|
|Cys|Ser|Asn|Asn|Ser|Ile|Thr|Trp|Gln|Leu|Thr|Asn|Ala|Val|Leu|
| | | | |20| | | | |25| | | | |30|
|His|Leu|Pro|Gly|Cys|Val|Pro|Cys|Glu|Asn|Asp|Asn|Gly|Thr|Leu|
| | | | |35| | | | |40| | | | |45|
|Arg|Cys|Trp|Ile|Gln|Val|Thr|Pro|Asn|Val|Ala|Val|Lys|His|Arg|
| | | | |50| | | | |55| | | | |60|
|Gly|Ala|Leu|Thr|His|Asn|Leu|Arg|Thr|His|Val|Asp|Val|Ile|Val|
| | | | |65| | | | |70| | | | |75|
|Met|Ala|Ala|Thr|Val|Cys|Ser|Ala|Leu|Tyr|Val|Gly|Asp|Val|Cys|
| | | | |80| | | | |85| | | | |90|

Gly Ala Val Met Ile Ala Ser Gln Ala Phe Ile Ile Ser Pro Glu
                  95              100              105

Arg His Asn Phe Thr Gln Glu Cys Asn Cys Ser Ile Tyr Gln Gly
                110              115              120

His Ile Thr Gly His Arg Met Ala Trp Asp Met Met Leu Asn Trp
                125              130              135

Ser Pro Thr Leu Thr Met Ile Leu Ala Tyr Ala Ala Arg Val Pro
                140              145              150

Glu Leu Val Leu Glu Val Val Phe Gly Gly His Trp Gly Val Val
                155              160              165

Phe Gly Leu Ala Tyr Phe Ser Met Gln Gly Ala Trp Ala Lys Val
                170              175              180

Ile Ala Ile Leu Leu Leu Val Ala Gly Val Asp Ala
                185              190

( 2 ) INFORMATION FOR SEQ ID NO:85:

( i ) SEQUENCE CHARACTERISTICS:
            ( A ) LENGTH: 192 amino acids
            ( B ) TYPE: amino acid
            ( C ) STRANDEDNESS: unknown
            ( D ) TOPOLOGY: unknown ( v i ) ORIGINAL SOURCE:
            ( A ) ORGANISM: homosapiens
            ( C ) INDIVIDUAL ISOLATE: S83

( x i ) SEQUENCE DESCRIPTION: SEQ ID NO:85:

Val Glu Val Lys Asp Thr Gly Asp Ser Tyr Met Pro Thr Asn Asp
                5                10               15

Cys Ser Asn Ser Ser Ile Val Trp Gln Leu Glu Gly Ala Val Leu
                20               25               30

His Thr Pro Gly Cys Val Pro Cys Glu Arg Thr Ala Asn Val Ser
                35               40               45

Arg Cys Trp Val Pro Val Ala Pro Asn Leu Ala Ile Ser Gln Pro
                50               55               60

Gly Ala Leu Thr Lys Gly Leu Arg Ala His Ile Asp Ile Ile Val
                65               70               75

Met Ser Ala Thr Val Cys Ser Ala Leu Tyr Val Gly Asp Val Cys
                80               85               90

Gly Ala Leu Met Leu Ala Ala Gln Val Val Val Val Ser Pro Gln
                95               100              105

His His Thr Phe Val Gln Glu Cys Asn Cys Ser Ile Tyr Pro Gly
                110              115              120

Arg Ile Thr Gly His Arg Met Ala Trp Asp Met Met Met Asn Trp
                125              130              135

Ser Pro Thr Thr Thr Met Leu Leu Ala Tyr Leu Val Arg Ile Pro
                140              145              150

Glu Val Ile Leu Asp Ile Val Thr Gly Gly His Trp Gly Val Met
                155              160              165

Phe Gly Leu Ala Tyr Phe Ser Met Gln Gly Ser Trp Ala Lys Val
                170              175              180

Ile Val Ile Leu Leu Leu Thr Ala Gly Val Glu Ala
                185              190

( 2 ) INFORMATION FOR SEQ ID NO:86:

( i ) SEQUENCE CHARACTERISTICS:
            ( A ) LENGTH: 192 amino acids
            ( B ) TYPE: amino acid
            ( C ) STRANDEDNESS: unknown (D) TOPOLOGY: unknown (vi) ORIGINAL SOURCE:
(A) ORGANISM: homosapiens
(C) INDIVIDUAL ISOLATE: DK12

(xi) SEQUENCE DESCRIPTION: SEQ ID NO:86:

| | | | | | | | | | | | | | | |
|---|---|---|---|---|---|---|---|---|---|---|---|---|---|---|
| Leu | Glu | Trp | Arg | Asn<br>5 | Val | Ser | Gly | Leu | Tyr<br>10 | Val | Leu | Thr | Asn | Asp<br>15 |
| Cys | Ser | Asn | Ser | Ser<br>20 | Ile | Val | Tyr | Glu | Ala<br>25 | Asp | Asp | Val | Ile | Leu<br>30 |
| His | Thr | Pro | Gly | Cys<br>35 | Val | Pro | Cys | Val | Gln<br>40 | Asp | Gly | Asn | Thr | Ser<br>45 |
| Thr | Cys | Trp | Thr | Ser<br>50 | Val | Thr | Pro | Thr | Val<br>55 | Ala | Val | Arg | Tyr | Val<br>60 |
| Gly | Ala | Thr | Thr | Ala<br>65 | Ser | Ile | Arg | Ser | His<br>70 | Val | Asp | Leu | Leu | Val<br>75 |
| Gly | Ala | Ala | Thr | Met<br>80 | Cys | Ser | Ala | Leu | Tyr<br>85 | Val | Gly | Asp | Val | Cys<br>90 |
| Gly | Ala | Val | Phe | Leu<br>95 | Val | Gly | Gln | Ala | Phe<br>100 | Thr | Phe | Arg | Pro | Arg<br>105 |
| Arg | His | Gln | Thr | Val<br>110 | Gln | Thr | Cys | Asn | Cys<br>115 | Ser | Leu | Tyr | Pro | Gly<br>120 |
| His | Leu | Ser | Gly | His<br>125 | Arg | Met | Ala | Trp | Asp<br>130 | Met | Met | Met | Asn | Trp<br>135 |
| Ser | Pro | Ala | Val | Gly<br>140 | Met | Val | Val | Ala | His<br>145 | Val | Leu | Arg | Leu | Pro<br>150 |
| Gln | Thr | Leu | Phe | Asp<br>155 | Ile | Ile | Ala | Gly | Ala<br>160 | His | Trp | Gly | Ile | Met<br>165 |
| Ala | Gly | Leu | Ala | Tyr<br>170 | Tyr | Ser | Met | Gln | Gly<br>175 | Asn | Trp | Ala | Lys | Val<br>180 |
| Ala | Ile | Ile | Met | Val<br>185 | Met | Phe | Ser | Gly | Val<br>190 | Asp | Ala | | | |

(2) INFORMATION FOR SEQ ID NO:87:

(i) SEQUENCE CHARACTERISTICS:
(A) LENGTH: 192 amino acids
(B) TYPE: amino acid
(C) STRANDEDNESS: unknown
(D) TOPOLOGY: unknown (vi) ORIGINAL SOURCE:
(A) ORGANISM: homosapiens
(C) INDIVIDUAL ISOLATE: HK10

(xi) SEQUENCE DESCRIPTION: SEQ ID NO:87:

| | | | | | | | | | | | | | | |
|---|---|---|---|---|---|---|---|---|---|---|---|---|---|---|
| Leu | Glu | Trp | Arg | Asn<br>5 | Val | Ser | Gly | Leu | Tyr<br>10 | Val | Leu | Thr | Asn | Asp<br>15 |
| Cys | Pro | Asn | Ser | Ser<br>20 | Ile | Val | Tyr | Glu | Ala<br>25 | Asp | Asp | Val | Ile | Leu<br>30 |
| His | Thr | Pro | Gly | Cys<br>35 | Val | Pro | Cys | Val | Gln<br>40 | Asp | Gly | Asn | Thr | Ser<br>45 |
| Thr | Cys | Trp | Thr | Ser<br>50 | Val | Thr | Pro | Thr | Val<br>55 | Ala | Val | Arg | Tyr | Val<br>60 |
| Gly | Ala | Thr | Thr | Ala<br>65 | Ser | Ile | Arg | Ser | His<br>70 | Val | Asp | Leu | Leu | Val<br>75 |
| Gly | Ala | Ala | Thr | Met<br>80 | Cys | Ser | Ala | Leu | Tyr<br>85 | Val | Gly | Asp | Met | Cys<br>90 |
| Gly | Ala | Val | Phe | Leu<br>95 | Val | Gly | Gln | Ala | Phe<br>100 | Thr | Phe | Arg | Pro | Arg<br>105 |

```
Arg His Gln Thr Val Gln Thr Cys Asn Cys Ser Leu Tyr Pro Gly
                 110                 115                 120

His Leu Ser Gly His Arg Met Ala Trp Asp Met Met Met Asn Trp
                 125                 130                 135

Ser Pro Ala Val Gly Met Val Val Ala His Val Leu Arg Leu Pro
                 140                 145                 150

Gln Thr Leu Phe Asp Ile Ile Ala Gly Ala His Trp Gly Ile Leu
                 155                 160                 165

Ala Gly Leu Ala Tyr Tyr Ser Met Gln Gly Asn Trp Ala Lys Val
                 170                 175                 180

Ala Ile Ile Met Val Met Phe Ser Gly Val Asp Ala
                 185                 190
```

( 2 ) INFORMATION FOR SEQ ID NO:88:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S2

( x i ) SEQUENCE DESCRIPTION: SEQ ID NO:88:

```
Leu Glu Trp Arg Asn Thr Ser Gly Leu Tyr Val Leu Thr Asn Asp
                 5                   10                  15

Cys Ser Asn Ser Ser Ile Val Tyr Glu Ala Asp Asp Val Ile Leu
                 20                  25                  30

His Thr Pro Gly Cys Val Pro Cys Val Gln Asp Gly Asn Thr Ser
                 35                  40                  45

Thr Cys Trp Thr Pro Val Thr Pro Thr Val Ala Val Arg Tyr Val
                 50                  55                  60

Gly Ala Thr Thr Ala Ser Ile Arg Ser His Val Asp Leu Leu Val
                 65                  70                  75

Gly Ala Ala Thr Met Cys Ser Ala Leu Tyr Val Gly Asp Met Cys
                 80                  85                  90

Gly Ala Val Phe Leu Val Gly Gln Ala Phe Thr Phe Arg Pro Arg
                 95                  100                 105

Arg His Gln Thr Val Gln Thr Cys Asn Cys Ser Leu Tyr Pro Gly
                 110                 115                 120

His Leu Ser Gly His Arg Met Ala Trp Asp Met Met Met Asn Trp
                 125                 130                 135

Ser Pro Ala Val Gly Met Val Val Ala His Val Leu Arg Leu Pro
                 140                 145                 150

Gln Thr Val Phe Asp Ile Ile Ala Gly Ala His Trp Gly Ile Leu
                 155                 160                 165

Ala Gly Leu Ala Tyr Tyr Ser Met Gln Gly Asn Trp Ala Lys Val
                 170                 175                 180

Ala Ile Ile Met Val Met Phe Ser Gly Val Asp Ala
                 185                 190
```

( 2 ) INFORMATION FOR SEQ ID NO:89:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens ( C ) INDIVIDUAL ISOLATE: S52

( x i ) SEQUENCE DESCRIPTION: SEQ ID NO:89:

| | | | | | | | | | | | | | | |
|---|---|---|---|---|---|---|---|---|---|---|---|---|---|---|
| Leu | Glu | Trp | Arg | Asn<br>5 | Thr | Ser | Gly | Leu | Tyr<br>10 | Val | Leu | Thr | Asn | Asp<br>15 |
| Cys | Ser | Asn | Ser | Ser<br>20 | Ile | Val | Tyr | Glu | Ala<br>25 | Asp | Asp | Val | Ile | Leu<br>30 |
| His | Thr | Pro | Gly | Cys<br>35 | Val | Pro | Cys | Val | Gln<br>40 | Asp | Gly | Asn | Thr | Ser<br>45 |
| Met | Cys | Trp | Thr | Pro<br>50 | Val | Thr | Pro | Thr | Val<br>55 | Ala | Val | Arg | Tyr | Val<br>60 |
| Gly | Ala | Thr | Thr | Ala<br>65 | Ser | Ile | Arg | Ser | His<br>70 | Val | Asp | Leu | Leu | Val<br>75 |
| Gly | Ala | Ala | Thr | Leu<br>80 | Cys | Ser | Ala | Leu | Tyr<br>85 | Val | Gly | Asp | Met | Cys<br>90 |
| Gly | Ala | Val | Phe | Leu<br>95 | Val | Gly | Gln | Ala | Phe<br>100 | Thr | Phe | Arg | Pro | Arg<br>105 |
| Arg | His | Gln | Thr | Val<br>110 | Gln | Thr | Cys | Asn | Cys<br>115 | Ser | Leu | Tyr | Pro | Gly<br>120 |
| His | Val | Ser | Gly | His<br>125 | Arg | Met | Ala | Trp | Asp<br>130 | Met | Met | Met | Asn | Trp<br>135 |
| Ser | Pro | Ala | Val | Gly<br>140 | Met | Val | Val | Ala | His<br>145 | Ile | Leu | Arg | Leu | Pro<br>150 |
| Gln | Thr | Leu | Phe | Asp<br>155 | Ile | Leu | Ala | Gly | Ala<br>160 | His | Trp | Gly | Ile | Leu<br>165 |
| Ala | Gly | Leu | Ala | Tyr<br>170 | Tyr | Ser | Met | Gln | Gly<br>175 | Asn | Trp | Ala | Lys | Val<br>180 |
| Ala | Ile | Val | Met | Ile<br>185 | Met | Phe | Ser | Gly | Val<br>190 | Asp | Ala | | | |

( 2 ) INFORMATION FOR SEQ ID NO:90:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: S54

( x i ) SEQUENCE DESCRIPTION: SEQ ID NO:90:

| | | | | | | | | | | | | | | |
|---|---|---|---|---|---|---|---|---|---|---|---|---|---|---|
| Leu | Glu | Trp | Arg | Asn<br>5 | Thr | Ser | Gly | Leu | Tyr<br>10 | Ile | Leu | Thr | Asn | Asp<br>15 |
| Cys | Ser | Asn | Ser | Ser<br>20 | Ile | Val | Tyr | Glu | Ala<br>25 | Asp | Asp | Val | Ile | Leu<br>30 |
| His | Thr | Pro | Gly | Cys<br>35 | Val | Pro | Cys | Val | Gln<br>40 | Asp | Gly | Asn | Thr | Ser<br>45 |
| Thr | Cys | Trp | Thr | Pro<br>50 | Val | Thr | Pro | Thr | Val<br>55 | Ala | Val | Arg | Tyr | Val<br>60 |
| Gly | Ala | Thr | Thr | Ala<br>65 | Ser | Ile | Arg | Ser | His<br>70 | Val | Asp | Leu | Leu | Val<br>75 |
| Gly | Ala | Ala | Thr | Leu<br>80 | Cys | Ser | Ala | Leu | Tyr<br>85 | Val | Gly | Asp | Met | Cys<br>90 |
| Gly | Ala | Val | Phe | Leu<br>95 | Val | Gly | Gln | Ala | Phe<br>100 | Thr | Phe | Arg | Pro | Arg<br>105 |
| Arg | His | Gln | Thr | Val<br>110 | Gln | Thr | Cys | Asn | Cys<br>115 | Ser | Leu | Tyr | Pro | Gly<br>120 |
| His | Leu | Ser | Gly | His | Arg | Met | Ala | Trp | Asp | Met | Met | Met | Asn | Trp |

|  |  |  |  | 125 |  |  |  |  | 130 |  |  |  |  | 135 |
|---|---|---|---|---|---|---|---|---|---|---|---|---|---|---|

Ser Pro Ala Val Gly Met Val Val Ala His Ile Leu Arg Leu Pro
                    140                 145                 150

Gln Thr Leu Phe Asp Ile Leu Ala Gly Ala His Trp Gly Ile Leu
                    155                 160                 165

Ala Gly Leu Ala Tyr Tyr Ser Met Gln Gly Asn Trp Ala Lys Val
                    170                 175                 180

Ala Ile Ile Met Ile Met Phe Ser Gly Val Asp Ala
                    185                 190

(2) INFORMATION FOR SEQ ID NO:91:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z4

(xi) SEQUENCE DESCRIPTION: SEQ ID NO:91:

Glu His Tyr Arg Asn Ala Ser Gly Ile Tyr His Ile Thr Asn Asp
                    5                   10                  15

Cys Pro Asn Ser Ser Ile Val Tyr Glu Ala Asp His His Ile Leu
                    20                  25                  30

His Leu Pro Gly Cys Val Pro Cys Val Met Thr Gly Asn Thr Ser
                    35                  40                  45

Arg Cys Trp Thr Pro Val Thr Pro Thr Val Ala Val Ala His Pro
                    50                  55                  60

Gly Ala Pro Leu Glu Ser Phe Arg Arg His Val Asp Leu Met Val
                    65                  70                  75

Gly Ala Ala Thr Leu Cys Ser Ala Leu Tyr Val Gly Asp Leu Cys
                    80                  85                  90

Gly Gly Ala Phe Leu Met Gly Gln Met Ile Thr Phe Arg Pro Arg
                    95                  100                 105

Arg His Trp Thr Thr Gln Glu Cys Asn Cys Ser Ile Tyr Thr Gly
                    110                 115                 120

His Ile Thr Gly His Arg Met Ala Trp Asp Met Met Met Asn Trp
                    125                 130                 135

Ser Pro Thr Thr Thr Leu Leu Leu Ala Gln Ile Met Arg Val Pro
                    140                 145                 150

Thr Ala Phe Leu Asp Met Val Ala Gly Gly His Trp Gly Val Leu
                    155                 160                 165

Ala Gly Leu Ala Tyr Phe Ser Met Gln Gly Asn Trp Ala Lys Val
                    170                 175                 180

Val Leu Val Leu Phe Leu Phe Ala Gly Val Asp Ala
                    185                 190

(2) INFORMATION FOR SEQ ID NO:92:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z1

(xi) SEQUENCE DESCRIPTION: SEQ ID NO:92:

```
Val His Tyr Arg Asn Ala Ser Gly Val Tyr His Val Thr Asn Asp
                  5                  10                  15

Cys Pro Asn Thr Ser Ile Val Tyr Glu Thr Glu His His Ile Met
                 20                  25                  30

His Leu Pro Gly Cys Val Pro Cys Val Arg Thr Glu Asn Thr Ser
                 35                  40                  45

Arg Cys Trp Val Pro Leu Thr Pro Thr Val Ala Ala Pro Tyr Pro
                 50                  55                  60

Asn Ala Pro Leu Glu Ser Met Arg Arg His Val Asp Leu Met Val
                 65                  70                  75

Gly Ala Ala Thr Met Cys Ser Ala Phe Tyr Ile Gly Asp Leu Cys
                 80                  85                  90

Gly Gly Val Phe Leu Val Gly Gln Leu Phe Asp Phe Arg Pro Arg
                 95                 100                 105

Arg His Trp Thr Thr Gln Asp Cys Asn Cys Ser Ile Tyr Pro Gly
                110                 115                 120

His Val Ser Gly His Arg Met Ala Trp Asp Met Met Met Asn Trp
                125                 130                 135

Ser Pro Thr Ser Ala Leu Ile Met Ala Gln Ile Leu Arg Ile Pro
                140                 145                 150

Ser Ile Leu Gly Asp Leu Leu Thr Gly Gly His Trp Gly Val Leu
                155                 160                 165

Ala Gly Leu Ala Phe Phe Ser Met Gln Ser Asn Trp Ala Lys Val
                170                 175                 180

Ile Leu Val Leu Phe Leu Phe Ala Gly Val Glu Gly
                185                 190
```

( 2 ) INFORMATION FOR SEQ ID NO:93:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: Z6

( x i ) SEQUENCE DESCRIPTION: SEQ ID NO:93:

```
Val Asn Tyr Arg Asn Ala Ser Gly Val Tyr His Val Thr Asn Asp
                  5                  10                  15

Cys Pro Asn Ser Ser Ile Val Tyr Glu Ala Glu His Gln Ile Leu
                 20                  25                  30

His Leu Pro Gly Cys Leu Pro Cys Val Arg Val Gly Asn Gln Ser
                 35                  40                  45

Arg Cys Trp Val Ala Leu Thr Pro Thr Val Ala Val Ser Tyr Ile
                 50                  55                  60

Gly Ala Pro Leu Asp Ser Leu Arg Arg His Val Asp Leu Met Val
                 65                  70                  75

Gly Ala Ala Thr Val Cys Ser Ala Leu Tyr Val Gly Asp Leu Cys
                 80                  85                  90

Gly Gly Ala Phe Leu Val Gly Gln Met Phe Ser Phe Gln Pro Arg
                 95                 100                 105

Arg His Trp Thr Thr Gln Asp Cys Asn Cys Ser Ile Tyr Ala Gly
                110                 115                 120

His Ile Thr Gly His Arg Met Ala Trp Asp Met Met Met Asn Trp
                125                 130                 135

Ser Pro Thr Thr Thr Leu Leu Leu Ala Gln Val Met Arg Ile Pro
                140                 145                 150
```

Ser Thr Leu Val Asp Leu Leu Ala Gly Gly His Trp Gly Val Leu
                155                 160                 165

Val Gly Leu Ala Tyr Phe Ser Met Gln Ala Asn Trp Ala Lys Val
                170                 175                 180

Ile Leu Val Leu Phe Leu Phe Ala Gly Val Asp Ala
                185                 190

( 2 ) INFORMATION FOR SEQ ID NO:94:

( i ) SEQUENCE CHARACTERISTICS:
    ( A ) LENGTH: 192 amino acids
    ( B ) TYPE: amino acid
    ( C ) STRANDEDNESS: unknown
    ( D ) TOPOLOGY: unknown ( v i ) ORIGINAL SOURCE:
    ( A ) ORGANISM: homosapiens
    ( C ) INDIVIDUAL ISOLATE: Z7

( x i ) SEQUENCE DESCRIPTION: SEQ ID NO:94:

Val Asn Tyr His Asn Ala Ser Gly Val Tyr His Ile Thr Asn Asp
                  5                  10                  15

Cys Pro Asn Ser Ser Ile Met Tyr Glu Ala Glu His His Ile Leu
                 20                  25                  30

His Leu Pro Gly Cys Val Pro Cys Val Arg Glu Gly Asn Gln Ser
                 35                  40                  45

Arg Cys Trp Val Ala Leu Thr Pro Thr Val Ala Ala Pro Tyr Ile
                 50                  55                  60

Gly Ala Pro Leu Glu Ser Ile Arg Arg His Val Asp Leu Met Val
                 65                  70                  75

Gly Ala Ala Thr Val Cys Ser Ala Leu Tyr Ile Gly Asp Leu Cys
                 80                  85                  90

Gly Gly Val Phe Leu Val Gly Gln Met Phe Ser Phe Gln Pro Arg
                 95                 100                 105

Arg His Trp Thr Thr Gln Asp Cys Asn Cys Ser Ile Tyr Ala Gly
                110                 115                 120

His Val Thr Gly His Arg Met Ala Trp Asp Met Met Met Asn Trp
                125                 130                 135

Ser Pro Thr Thr Thr Leu Val Leu Ala Gln Val Met Arg Ile Pro
                140                 145                 150

Ser Thr Leu Val Asp Leu Leu Thr Gly Gly His Trp Gly Ile Leu
                155                 160                 165

Ile Gly Val Ala Tyr Phe Cys Met Gln Ala Asn Trp Ala Lys Val
                170                 175                 180

Ile Leu Val Leu Phe Leu Tyr Ala Gly Val Asp Ala
                185                 190

( 2 ) INFORMATION FOR SEQ ID NO:95:

( i ) SEQUENCE CHARACTERISTICS:
    ( A ) LENGTH: 192 amino acids
    ( B ) TYPE: amino acid
    ( C ) STRANDEDNESS: unknown
    ( D ) TOPOLOGY: unknown ( v i ) ORIGINAL SOURCE:
    ( A ) ORGANISM: homosapiens
    ( C ) INDIVIDUAL ISOLATE: DK13

( x i ) SEQUENCE DESCRIPTION: SEQ ID NO:95:

Tyr Asn Tyr Arg Asn Ser Ser Gly Val Tyr His Val Thr Asn Asp
                  5                  10                  15

Cys Pro Asn Ser Ser Ile Val Tyr Glu Thr Asp Tyr His Ile Leu

|     | 20  |     |     |     |     | 25  |     |     |     |     | 30  |     |     |     |
|-----|-----|-----|-----|-----|-----|-----|-----|-----|-----|-----|-----|-----|-----|-----|
| His | Leu | Pro | Gly | Cys | Val | Pro | Cys | Val | Arg | Glu | Gly | Asn | Lys | Ser |
|     |     |     |     | 35  |     |     |     |     | 40  |     |     |     |     | 45  |
| Thr | Cys | Trp | Val | Ser | Leu | Thr | Pro | Thr | Val | Ala | Ala | Gln | His | Leu |
|     |     |     |     | 50  |     |     |     |     | 55  |     |     |     |     | 60  |
| Asn | Ala | Pro | Leu | Glu | Ser | Leu | Arg | Arg | His | Val | Asp | Leu | Met | Val |
|     |     |     |     | 65  |     |     |     |     | 70  |     |     |     |     | 75  |
| Gly | Gly | Ala | Thr | Leu | Cys | Ser | Ala | Leu | Tyr | Ile | Gly | Asp | Val | Cys |
|     |     |     |     | 80  |     |     |     |     | 85  |     |     |     |     | 90  |
| Gly | Gly | Val | Phe | Leu | Val | Gly | Gln | Leu | Phe | Thr | Phe | Gln | Pro | Arg |
|     |     |     |     | 95  |     |     |     |     | 100 |     |     |     |     | 105 |
| Arg | His | Trp | Thr | Thr | Gln | Asp | Cys | Asn | Cys | Ser | Ile | Tyr | Thr | Gly |
|     |     |     |     | 110 |     |     |     |     | 115 |     |     |     |     | 120 |
| His | Ile | Thr | Gly | His | Arg | Met | Ala | Trp | Asp | Met | Met | Met | Asn | Trp |
|     |     |     |     | 125 |     |     |     |     | 130 |     |     |     |     | 135 |
| Ser | Pro | Thr | Ala | Thr | Leu | Val | Leu | Ala | Gln | Leu | Met | Arg | Ile | Pro |
|     |     |     |     | 140 |     |     |     |     | 145 |     |     |     |     | 150 |
| Gly | Ala | Met | Val | Asp | Leu | Leu | Ala | Gly | Gly | His | Trp | Gly | Ile | Leu |
|     |     |     |     | 155 |     |     |     |     | 160 |     |     |     |     | 165 |
| Val | Gly | Ile | Ala | Tyr | Phe | Ser | Met | Gln | Ala | Asn | Trp | Ala | Lys | Val |
|     |     |     |     | 170 |     |     |     |     | 175 |     |     |     |     | 180 |
| Ile | Leu | Val | Leu | Phe | Leu | Phe | Ala | Gly | Val | Asp | Ala |     |     |     |
|     |     |     |     | 185 |     |     |     |     | 190 |     |     |     |     |     |

( 2 ) INFORMATION FOR SEQ ID NO:96:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA1

( x i ) SEQUENCE DESCRIPTION: SEQ ID NO:96:

| Val | Pro | Tyr | Arg | Asn | Ala | Ser | Gly | Val | Tyr | His | Val | Thr | Asn | Asp |
|-----|-----|-----|-----|-----|-----|-----|-----|-----|-----|-----|-----|-----|-----|-----|
|     |     |     |     | 5   |     |     |     |     | 10  |     |     |     |     | 15  |
| Cys | Pro | Asn | Ser | Ser | Ile | Val | Tyr | Glu | Ala | Asp | Ser | Leu | Ile | Leu |
|     |     |     |     | 20  |     |     |     |     | 25  |     |     |     |     | 30  |
| His | Ala | Pro | Gly | Cys | Val | Pro | Cys | Val | Arg | Gln | Asp | Asn | Val | Ser |
|     |     |     |     | 35  |     |     |     |     | 40  |     |     |     |     | 45  |
| Arg | Cys | Trp | Val | Gln | Ile | Thr | Pro | Thr | Leu | Ser | Ala | Pro | Thr | Phe |
|     |     |     |     | 50  |     |     |     |     | 55  |     |     |     |     | 60  |
| Gly | Ala | Val | Thr | Ala | Pro | Leu | Arg | Arg | Ala | Val | Asp | Tyr | Leu | Ala |
|     |     |     |     | 65  |     |     |     |     | 70  |     |     |     |     | 75  |
| Gly | Gly | Ala | Ala | Leu | Cys | Ser | Ala | Leu | Tyr | Val | Gly | Asp | Ala | Cys |
|     |     |     |     | 80  |     |     |     |     | 85  |     |     |     |     | 90  |
| Gly | Ala | Val | Phe | Leu | Val | Gly | Gln | Met | Phe | Thr | Tyr | Arg | Pro | Arg |
|     |     |     |     | 95  |     |     |     |     | 100 |     |     |     |     | 105 |
| Gln | His | Thr | Thr | Val | Gln | Asp | Cys | Asn | Cys | Ser | Ile | Tyr | Ser | Gly |
|     |     |     |     | 110 |     |     |     |     | 115 |     |     |     |     | 120 |
| His | Ile | Thr | Gly | His | Arg | Met | Ala | Trp | Asp | Met | Met | Met | Asn | Trp |
|     |     |     |     | 125 |     |     |     |     | 130 |     |     |     |     | 135 |
| Ser | Pro | Thr | Thr | Ala | Leu | Leu | Met | Ala | Gln | Met | Leu | Arg | Ile | Pro |
|     |     |     |     | 140 |     |     |     |     | 145 |     |     |     |     | 150 |
| Gln | Val | Val | Ile | Asp | Ile | Ile | Ala | Gly | Gly | His | Trp | Gly | Val | Leu |
|     |     |     |     | 155 |     |     |     |     | 160 |     |     |     |     | 165 |

```
Phe  Ala  Ala  Ala  Tyr  Phe  Ala  Ser  Ala  Ala  Asn  Trp  Ala  Lys  Val
                    170                 175                           180

Val  Leu  Val  Leu  Phe  Leu  Phe  Ala  Gly  Val  Asp  Gly
                    185                 190
```

(2) INFORMATION FOR SEQ ID NO:97:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA4

(xi) SEQUENCE DESCRIPTION: SEQ ID NO:97:

```
Val  Pro  Tyr  Arg  Asn  Ala  Ser  Gly  Val  Tyr  His  Val  Thr  Asn  Asp
                    5                   10                            15

Cys  Pro  Asn  Ser  Ser  Ile  Val  Tyr  Glu  Ala  Asp  Asn  Leu  Ile  Leu
                    20                  25                            30

His  Ala  Pro  Gly  Cys  Val  Pro  Cys  Val  Arg  Gln  Asp  Asn  Val  Ser
                    35                  40                            45

Lys  Cys  Trp  Val  Gln  Ile  Thr  Pro  Thr  Leu  Ser  Ala  Pro  Asn  Leu
                    50                  55                            60

Gly  Ala  Val  Thr  Ala  Pro  Leu  Arg  Arg  Ala  Val  Asp  Tyr  Leu  Ala
                    65                  70                            75

Gly  Gly  Ala  Ala  Leu  Cys  Ser  Ala  Leu  Tyr  Val  Gly  Asp  Ala  Cys
                    80                  85                            90

Gly  Ala  Val  Phe  Leu  Val  Gly  Gln  Met  Phe  Thr  Tyr  Arg  Pro  Arg
                    95                  100                           105

Gln  His  Thr  Thr  Val  Gln  Asp  Cys  Asn  Cys  Ser  Ile  Tyr  Ser  Gly
                    110                 115                           120

His  Ile  Thr  Gly  His  Arg  Met  Ala  Trp  Asp  Met  Met  Met  Asn  Trp
                    125                 130                           135

Ser  Pro  Thr  Thr  Ala  Leu  Leu  Met  Ala  Gln  Leu  Leu  Arg  Ile  Pro
                    140                 145                           150

Gln  Val  Val  Ile  Asp  Ile  Ile  Ala  Gly  Gly  His  Trp  Gly  Val  Leu
                    155                 160                           165

Phe  Ala  Ala  Ala  Tyr  Phe  Ala  Ser  Ala  Ala  Asn  Trp  Ala  Lys  Val
                    170                 175                           180

Ile  Leu  Val  Leu  Phe  Leu  Phe  Ala  Gly  Val  Asp  Ala
                    185                 190
```

(2) INFORMATION FOR SEQ ID NO:98:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA5

(xi) SEQUENCE DESCRIPTION: SEQ ID NO:98:

```
Val  Pro  Tyr  Arg  Asn  Ala  Ser  Gly  Val  Tyr  His  Val  Thr  Asn  Asp
                    5                   10                            15

Cys  Pro  Asn  Ser  Ser  Ile  Val  Tyr  Glu  Ala  Asp  Asn  Leu  Ile  Leu
                    20                  25                            30

His  Ala  Pro  Gly  Cys  Val  Pro  Cys  Val  Lys  Glu  Gly  Asn  Val  Ser
                    35                  40                            45
```

```
Arg  Cys  Trp  Val  Gln  Ile  Thr  Pro  Thr  Leu  Ser  Ala  Pro  Asn  Leu
                    50                       55                            60

Gly  Ala  Val  Thr  Ala  Pro  Leu  Arg  Arg  Val  Val  Asp  Tyr  Leu  Ala
                    65                       70                            75

Gly  Gly  Ala  Ala  Leu  Cys  Ser  Ala  Leu  Tyr  Val  Gly  Asp  Ala  Cys
                    80                       85                            90

Gly  Ala  Val  Phe  Leu  Val  Gly  Gln  Met  Phe  Thr  Tyr  Arg  Pro  Arg
                    95                       100                          105

Gln  His  Thr  Thr  Val  Gln  Asp  Cys  Asn  Cys  Ser  Ile  Tyr  Ser  Gly
                    110                      115                          120

His  Ile  Thr  Gly  His  Arg  Met  Ala  Trp  Asp  Met  Met  Met  Asn  Trp
                    125                      130                          135

Ser  Pro  Thr  Thr  Ala  Leu  Val  Met  Ala  Gln  Val  Leu  Arg  Ile  Pro
                    140                      145                          150

Gln  Val  Val  Ile  Asp  Ile  Ile  Ala  Gly  Gly  His  Trp  Gly  Val  Leu
                    155                      160                          165

Phe  Ala  Val  Ala  Tyr  Phe  Ala  Ser  Ala  Ala  Asn  Trp  Ala  Lys  Val
                    170                      175                          180

Val  Leu  Val  Leu  Phe  Leu  Phe  Ala  Gly  Val  Asp  Gly
                    185                      190
```

(2) INFORMATION FOR SEQ ID NO:99:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA6

(xi) SEQUENCE DESCRIPTION: SEQ ID NO:99:

```
Val  Pro  Tyr  Arg  Asn  Ala  Ser  Gly  Val  Tyr  His  Val  Thr  Asn  Asp
                    5                        10                            15

Cys  Pro  Asn  Ser  Ser  Ile  Val  Tyr  Glu  Ala  Asp  Asp  Leu  Ile  Leu
                    20                       25                            30

His  Ala  Pro  Gly  Cys  Val  Pro  Cys  Val  Arg  Lys  Asp  Asn  Val  Ser
                    35                       40                            45

Arg  Cys  Trp  Val  His  Ile  Thr  Pro  Thr  Leu  Ser  Ala  Pro  Ser  Leu
                    50                       55                            60

Gly  Ala  Val  Thr  Ala  Pro  Leu  Arg  Arg  Ala  Val  Asp  Tyr  Leu  Ala
                    65                       70                            75

Gly  Gly  Ala  Ala  Leu  Cys  Ser  Ala  Leu  Tyr  Val  Gly  Asp  Val  Cys
                    80                       85                            90

Gly  Ala  Leu  Phe  Leu  Val  Gly  Gln  Met  Phe  Thr  Tyr  Arg  Pro  Arg
                    95                       100                          105

Gln  His  Ala  Thr  Val  Gln  Asp  Cys  Asn  Cys  Ser  Ile  Tyr  Ser  Gly
                    110                      115                          120

His  Ile  Thr  Gly  His  Arg  Met  Ala  Trp  Asp  Met  Met  Met  Asn  Trp
                    125                      130                          135

Ser  Pro  Ala  Thr  Ala  Leu  Val  Met  Ala  Gln  Met  Leu  Arg  Ile  Pro
                    140                      145                          150

Gln  Val  Val  Ile  Asp  Ile  Ile  Ala  Gly  Gly  His  Trp  Gly  Val  Leu
                    155                      160                          165

Phe  Ala  Ala  Ala  Tyr  Phe  Ala  Ser  Ala  Ala  Asn  Trp  Ala  Lys  Val
                    170                      175                          180

Val  Leu  Val  Leu  Phe  Leu  Phe  Ala  Gly  Val  Asp  Ala
                    185                      190
```

( 2 ) INFORMATION FOR SEQ ID NO:100:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA7

( x i ) SEQUENCE DESCRIPTION: SEQ ID NO:100:

```
Val Pro Tyr Arg Asn Ala Ser Gly Val Tyr His Val Thr Asn Asp
              5                  10                      15
Cys Pro Asn Ser Ser Ile Val Tyr Glu Ala Asp Asn Leu Ile Leu
             20                  25                      30
His Ala Pro Gly Cys Val Pro Cys Val Arg Gln Asn Asn Val Ser
             35                  40                      45
Arg Cys Trp Val Gln Ile Thr Pro Thr Leu Ser Ala Pro Asn Leu
             50                  55                      60
Gly Ala Val Thr Ala Pro Leu Arg Arg Ala Val Asp Tyr Leu Ala
             65                  70                      75
Gly Gly Ala Ala Leu Cys Ser Ala Leu Tyr Val Gly Asp Ala Cys
             80                  85                      90
Gly Ala Val Phe Leu Val Gly Gln Met Phe Ser Tyr Arg Pro Arg
             95                 100                     105
Gln His Thr Thr Val Gln Asp Cys Asn Cys Ser Ile Tyr Ser Gly
            110                 115                     120
His Ile Thr Gly His Arg Met Ala Trp Asp Met Met Met Asn Trp
            125                 130                     135
Ser Pro Thr Thr Ala Leu Val Met Ala Gln Leu Leu Arg Ile Pro
            140                 145                     150
Gln Val Val Ile Asp Ile Ile Ala Gly Gly His Trp Gly Val Leu
            155                 160                     165
Phe Ala Ala Ala Tyr Phe Ala Ser Ala Ala Asn Trp Ala Lys Val
            170                 175                     180
Val Leu Val Leu Phe Leu Phe Ala Gly Val Asp Ala
            185                 190
```

( 2 ) INFORMATION FOR SEQ ID NO:101:

( i ) SEQUENCE CHARACTERISTICS:
        ( A ) LENGTH: 192 amino acids
        ( B ) TYPE: amino acid
        ( C ) STRANDEDNESS: unknown
        ( D ) TOPOLOGY: unknown ( v i ) ORIGINAL SOURCE:
        ( A ) ORGANISM: homosapiens
        ( C ) INDIVIDUAL ISOLATE: SA13

( x i ) SEQUENCE DESCRIPTION: SEQ ID NO:101:

```
Val Pro Tyr Arg Asn Ala Ser Gly Val Tyr His Val Thr Asn Asp
              5                  10                      15
Cys Pro Asn Ser Ser Ile Val Tyr Glu Ala Asp Asp Leu Ile Leu
             20                  25                      30
His Ala Pro Gly Cys Val Pro Cys Val Arg Gln Gly Asn Val Ser
             35                  40                      45
Arg Cys Trp Val Gln Ile Thr Pro Thr Leu Ser Ala Pro Ser Leu
             50                  55                      60
```

| | | | | | | | | | | | | | | |
|---|---|---|---|---|---|---|---|---|---|---|---|---|---|---|
|Gly|Ala|Val|Thr|Ala<br>65|Pro|Leu|Arg|Arg|Ala<br>70|Val|Asp|Tyr|Leu|Ala<br>75|
|Gly|Gly|Ala|Ala|Leu<br>80|Cys|Ser|Ala|Leu|Tyr<br>85|Val|Gly|Asp|Ala|Cys<br>90|
|Gly|Ala|Val|Phe|Leu<br>95|Val|Gly|Gln|Met|Phe<br>100|Thr|Tyr|Ser|Pro|Arg<br>105|
|Arg|His|Asn|Val|Val<br>110|Gln|Asp|Cys|Asn|Cys<br>115|Ser|Ile|Tyr|Ser|Gly<br>120|
|His|Ile|Thr|Gly|His<br>125|Arg|Met|Ala|Trp|Asp<br>130|Met|Met|Met|Asn|Trp<br>135|
|Ser|Pro|Thr|Thr|Ala<br>140|Leu|Val|Met|Ala|Gln<br>145|Leu|Leu|Arg|Ile|Pro<br>150|
|Gln|Val|Val|Ile|Asp<br>155|Ile|Ile|Ala|Gly|Ala<br>160|His|Trp|Gly|Val|Leu<br>165|
|Phe|Ala|Ala|Ala|Tyr<br>170|Tyr|Ala|Ser|Ala|Ala<br>175|Asn|Trp|Ala|Lys|Val<br>180|
|Val|Leu|Val|Leu|Phe<br>185|Leu|Phe|Ala|Gly|Val<br>190|Asp|Ala| | | |

(2) INFORMATION FOR SEQ ID NO:102:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK2

(xi) SEQUENCE DESCRIPTION: SEQ ID NO:102:

| | | | | | | | | | | | | | | |
|---|---|---|---|---|---|---|---|---|---|---|---|---|---|---|
|Leu|Thr|Tyr|Gln|Asn<br>1|Ser|Ser|Gln|Leu|Tyr<br>10|His|Leu|Thr|Asn|Asp<br>15|
|Cys|Pro|Asn|Ser|Ser<br>20|Ile|Val|Leu|Glu|Ala<br>25|Asp|Ala|Met|Ile|Leu<br>30|
|His|Leu|Pro|Gln|Cys<br>35|Leu|Pro|Cys|Val|Arg<br>40|Val|Asp|Asp|Arg|Ser<br>45|
|Thr|Cys|Trp|His|Ala<br>50|Val|Thr|Pro|Thr|Leu<br>55|Ala|Ile|Pro|Asn|Ala<br>60|
|Ser|Thr|Pro|Ala|Thr<br>65|Gln|Phe|Arg|Arg|His<br>70|Val|Asp|Leu|Leu|Ala<br>75|
|Gln|Ala|Ala|Val|Val<br>80|Cys|Ser|Ser|Leu|Tyr<br>85|Ile|Gln|Asp|Leu|Cys<br>90|
|Gln|Ser|Leu|Phe|Leu<br>95|Ala|Gln|Gln|Leu|Phe<br>100|Thr|Phe|Gln|Pro|Arg<br>105|
|Arg|His|Trp|Thr|Val<br>110|Gln|Asp|Cys|Asn|Cys<br>115|Ser|Ile|Tyr|Thr|Gln<br>120|
|His|Val|Thr|Gln|His<br>125|Arg|Met|Ala|Trp|Asp<br>130|Met|Met|Met|Asn|Trp<br>135|
|Ser|Pro|Thr|Thr|Thr<br>140|Leu|Val|Leu|Ser|Ser<br>145|Ile|Leu|Arg|Val|Pro<br>150|
|Glu|Ile|Cys|Ala|Ser<br>155|Val|Ile|Phe|Gln|Gln<br>160|His|Trp|Gln|Ile|Leu<br>165|
|Leu|Ala|Val|Ala|Tyr<br>170|Phe|Gln|Met|Ala|Gln<br>175|Asn|Trp|Leu|Lys|Val<br>180|
|Leu|Ala|Val|Leu|Phe<br>185|Leu|Phe|Ala|Gln|Val<br>190|Glu|Ala| | | |

(2) INFORMATION FOR SEQ ID NO:103:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:103:

GCGTCCGGGT TCTGGAAGAC GGCGTGAACT ATGCAACAGG    40

( 2 ) INFORMATION FOR SEQ ID NO:104:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:104:

AGGCTTTCAT TGCAGTTCAA GGCCGTGCTA TTGATGTGCC    40

( 2 ) INFORMATION FOR SEQ ID NO:105:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:105:

AAGACGGCGT GAACTATGCA ACAGGGAACC TTCCTGGTTG    40

( 2 ) INFORMATION FOR SEQ ID NO:106:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:106:

AGTTCAAGGC CGTGCTATTG ATGTGCCAAC TGCCGTTGGT    40

( 2 ) INFORMATION FOR SEQ ID NO:107:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:107:

AAGACGGCGT GAATTCTGCA ACAGGGAACC TTCCTGGTTG    40

( 2 ) INFORMATION FOR SEQ ID NO:108:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:108:

AGTTCAAGGC CGTGGAATTC ATGTGCCAAC TGCCGTTGGT    40

( 2 ) INFORMATION FOR SEQ ID NO:109:

( i ) SEQUENCE CHARACTERISTICS:
    ( A ) LENGTH: 42 base pairs
    ( B ) TYPE: nucleic acid
    ( C ) STRANDEDNESS: single (D) TOPOLOGY: linear (xi) SEQUENCE DESCRIPTION: SEQ ID NO:109:

ARCTYCGACG TYACATCGAY CTGCTYGTYG GRAGYGCCAC CC 42

(2) INFORMATION FOR SEQ ID NO:110:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:110:

RCARGCCRTC TTGGAYATGA TCGCTGGWGC Y 31

(2) INFORMATION FOR SEQ ID NO:111:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:111:

CRATACGACR YCAYGTCGAY TTGCTCGTTG GGGCGGCTRY YT 42

(2) INFORMATION FOR SEQ ID NO:112:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:112:

RCAAGCTRTC RTGGAYRTGG TRRCRGGRGC C 31

(2) INFORMATION FOR SEQ ID NO:113:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:113:

TTGCGGACKC ACATYGACAT GGTYGTGATG TCCGCCACGC 40

(2) INFORMATION FOR SEQ ID NO:114:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:114:

GATGCGCGTT CCCGAGGTCA TCWTAGACAT CRTYRGCGGR GCD 43

(2) INFORMATION FOR SEQ ID NO:115:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:115:

AATGGCACCY TGCRCTGCTG GATACAAGTR ACACCTAATG TGGCTGTGAA 50

ACAC                                                                54

( 2 ) INFORMATION FOR SEQ ID NO:116:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

TGARCTAGYC CTYSARGTYG TCTTCGGYGG Y                                  31

( 2 ) INFORMATION FOR SEQ ID NO:117:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

GCCAACGTCT CTCGATGTTG GGTGCCGGTT GCCCCAATC TCGCCATAAG               50

TCAA                                                                54

( 2 ) INFORMATION FOR SEQ ID NO:118:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:118:

AAGGGCCTGC GAGCACACAT CGATATCATC GTGATGTCTG CTACGG                  46

( 2 ) INFORMATION FOR SEQ ID NO:119:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:119:

TTGGTGCGCA TCCCGGAAGT CATCTTGGAT ATTGTTACAG GAGGT                   45

( 2 ) INFORMATION FOR SEQ ID NO:120:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:120:

AGTCAGGTAY GTCGGAGCAA CCACCGCYTC GATACGCAGT                         40

( 2 ) INFORMATION FOR SEQ ID NO:121:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:121:

AGCCTTCACG TTCAGACCKC GTCGCCATCA AACRGTCCAG ACCTGT                  46

( 2 ) INFORMATION FOR SEQ ID NO:122:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:122:

```
TCCCCCGCYG  TGGGTATGGT  GGTRGCGCAC  RTYCTGCGDY  TGCCCCAGAC      50

CKTGTTYGAC  ATAMTRGCYG  GGGCC                                   75
```

( 2 ) INFORMATION FOR SEQ ID NO:123:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:123:

```
ACGCCGGTGA  CGCCTACAGT  GGCTGTCGCA  CACCCGGGC                   39
```

( 2 ) INFORMATION FOR SEQ ID NO:124:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:124:

```
ATGAGGGTCC  CCACAGCCTT  TCTCGACATG  GTTGCCGGAG  GC              42
```

( 2 ) INFORMATION FOR SEQ ID NO:125:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:125:

```
CGCGCCCTAT  CCCAACGCAC  CGTTAGAGTC  CATGCGCAGG                  40
```

( 2 ) INFORMATION FOR SEQ ID NO:126:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:126:

```
TCAGATCTTA  CGGATCCCCT  CTATCCTAGG  TGACTTGCTC  ACCGGGGGT       49
```

( 2 ) INFORMATION FOR SEQ ID NO:127:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:127:

```
CAGTCACGCT  GCTGGGTGGC  CCTTACTCCC  ACCGTGGCGG  YGYCTTATAT      50

CGGT                                                            54
```

( 2 ) INFORMATION FOR SEQ ID NO:128:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

```
TAGCACTCTG GTRGAYCTAC TCRCTGGAGG G                           31
```

( 2 ) INFORMATION FOR SEQ ID NO:129:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

```
AAGTCTACAT GCTGGGTGTC TCTCACCCCC ACCGTGGCTG CGCAACATCT       50

GAAT                                                         54
```

( 2 ) INFORMATION FOR SEQ ID NO:130:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

```
AGGCGCCATG GTCGACCTGC TTGCAGGCGG C                           31
```

( 2 ) INFORMATION FOR SEQ ID NO:131:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

```
TCAGCCCCGA VYYTCGGAGC GGTCACGGCT CCTCTTCGGA GGG              43
```

( 2 ) INFORMATION FOR SEQ ID NO:132:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

```
TGYTACGGAT YCCCCARGTG GTCATHGACA TCATWGCCGG GGSC             44
```

( 2 ) INFORMATION FOR SEQ ID NO:133:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

```
CATACCAAAT GCTTCCACGC CCGCAACGGG ATTCCGCAGG                  40
```

( 2 ) INFORMATION FOR SEQ ID NO:134:

( i ) SEQUENCE CHARACTERISTICS:

(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:134:

TCTTCTTGCG GGCGCCGCAG TGGTTTGCTC ATCCCTG                37

(2) INFORMATION FOR SEQ ID NO:135:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:135:

ATCTAGCATC TTGAGGGTAC CTGAGATTTG TGCGAGTGTG ATATTTGGTG    50
GC                                                       52

(2) INFORMATION FOR SEQ ID NO:136:

(i) SEQUENCE CHARACTERISTICS:
(A) LENGTH: 33 amino acids
(B) TYPE: amino acid
(C) STRANDEDNESS: unknown
(D) TOPOLOGY: unknown (xi) SEQUENCE DESCRIPTION: SEQ ID NO:136:

Trp Ile Gln Val Thr Pro Asn Val Ala Val Lys His Arg Gly Ala
                  5                  10                  15
Leu Thr His Asn Leu Arg Xaa His Xaa Asp Xaa Ile Val Met Ala
                 20                  25                  30
Ala Thr Val (2) INFORMATION FOR SEQ ID NO:137:

(i) SEQUENCE CHARACTERISTICS:
(A) LENGTH: 33 amino acids
(B) TYPE: amino acid
(C) STRANDEDNESS: unknown
(D) TOPOLOGY: unknown (xi) SEQUENCE DESCRIPTION: SEQ ID NO:137:

Trp Val Pro Val Ala Pro Asn Leu Ala Ile Ser Gln Pro Gly Ala
                  5                  10                  15
Leu Thr Lys Gly Leu Arg Ala His Ile Asp Ile Ile Val Met Ser
                 20                  25                  30
Ala Thr Val (2) INFORMATION FOR SEQ ID NO:138:

(i) SEQUENCE CHARACTERISTICS:
(A) LENGTH: 33 amino acids
(B) TYPE: amino acid
(C) STRANDEDNESS: unknown
(D) TOPOLOGY: unknown (xi) SEQUENCE DESCRIPTION: SEQ ID NO:138:

Trp Ile Pro Val Xaa Pro Asn Val Ala Val Xaa Xaa Pro Gly Ala
                  5                  10                  15
Leu Thr Gln Gly Leu Arg Thr His Ile Asp Met Val Val Met Ser
                 20                  25                  30
Ala Thr Leu (2) INFORMATION FOR SEQ ID NO:139:

( i ) SEQUENCE CHARACTERISTICS:
    ( A ) LENGTH: 33 amino acids
    ( B ) TYPE: amino acid
    ( C ) STRANDEDNESS: unknown
    ( D ) TOPOLOGY: unknown ( x i ) SEQUENCE DESCRIPTION: SEQ ID NO:139:

```
Trp Thr Xaa Val Thr Pro Thr Val Ala Val Arg Tyr Val Gly Ala
                  5                  10                   15
Thr Thr Ala Ser Ile Arg Ser His Val Asp Leu Leu Val Gly Ala
                 20                  25                   30
Ala Thr Xaa
```

( 2 ) INFORMATION FOR SEQ ID NO:140:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:140:

```
Trp Val Ala Leu Xaa Pro Thr Leu Ala Ala Arg Asn Xaa Xaa Xaa
                  5                  10                   15
Xaa Thr Xaa Xaa Ile Arg Xaa His Val Asp Leu Leu Val Gly Ala
                 20                  25                   30
Ala Xaa Phe
```

( 2 ) INFORMATION FOR SEQ ID NO:141:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:141:

```
Trp Val Xaa Xaa Xaa Pro Thr Val Ala Thr Arg Asp Gly Lys Leu
                  5                  10                   15
Pro Xaa Xaa Gln Leu Arg Arg Xaa Ile Asp Leu Leu Val Gly Ser
                 20                  25                   30
Ala Thr Leu
```

( 2 ) INFORMATION FOR SEQ ID NO:142:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:142:

```
Trp Thr Pro Val Thr Pro Thr Val Ala Val Ala His Pro Gly Ala
                  5                  10                   15
Pro Leu Glu Ser Phe Arg Arg His Val Asp Leu Met Val Gly Ala
                 20                  25                   30
Ala Thr Leu
```

( 2 ) INFORMATION FOR SEQ ID NO:143:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:143:

Trp Val Ala Leu Thr Pro Thr Val Ala Xaa Xaa Tyr Ile Gly Ala
                 5                  10                      15

Pro Leu Xaa Ser Xaa Arg Arg His Val Asp Leu Met Val Gly Ala
                20                  25                      30

Ala Thr Val ( 2 ) INFORMATION FOR SEQ ID NO:144:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:144:

Trp Val Ser Leu Thr Pro Thr Val Ala Ala Gln His Leu Asn Ala
                 5                  10                      15

Pro Leu Glu Ser Leu Arg Arg His Val Asp Leu Met Val Gly Gly
                20                  25                      30

Ala Thr Leu ( 2 ) INFORMATION FOR SEQ ID NO:145:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:145:

Trp Val Pro Leu Thr Pro Thr Val Ala Ala Pro Tyr Pro Asn Ala
                 5                  10                      15

Pro Leu Glu Ser Met Arg Arg His Val Asp Leu Met Val Gly Ala
                20                  25                      30

Ala Thr Met ( 2 ) INFORMATION FOR SEQ ID NO:146:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:146:

Trp Val Xaa Ile Thr Pro Thr Leu Ser Ala Pro Xaa Xaa Gly Ala
                 5                  10                      15

Val Thr Ala Pro Leu Arg Arg Xaa Val Asp Tyr Leu Ala Gly Gly
                20                  25                      30

Ala Ala Leu ( 2 ) INFORMATION FOR SEQ ID NO:147:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:147:

Trp His Ala Val Thr Pro Thr Leu Ala Ile Pro Asn Ala Ser Thr
                 5                  10                      15

Pro Ala Thr Gly Phe Arg Arg His Val Asp Leu Leu Ala Gly Ala
                20                  25                      30

Ala Val Val ( 2 ) INFORMATION FOR SEQ ID NO:148:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:148:

Thr Leu Thr Met Ile Leu Ala Tyr Ala Ala Arg Val Pro Glu Leu
                5                        10                    15

Xaa Leu Xaa Val Val Phe Gly Gly
                20

( 2 ) INFORMATION FOR SEQ ID NO:149:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:149:

Thr Thr Thr Met Leu Leu Ala Tyr Leu Val Arg Ile Pro Glu Val
                5                        10                    15

Ile Leu Asp Ile Val Thr Gly Gly
                20

( 2 ) INFORMATION FOR SEQ ID NO:150:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:150:

Thr Xaa Thr Xaa Ile Leu Ala Tyr Xaa Met Arg Val Pro Glu Val
                5                        10                    15

Ile Xaa Asp Ile Xaa Xaa Gly Ala
                20

( 2 ) INFORMATION FOR SEQ ID NO:151:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:151:

Ala Val Gly Met Val Val Ala His Xaa Leu Arg Leu Pro Gln Thr
                5                        10                    15

Xaa Phe Asp Ile Xaa Ala Gly Ala
                20

( 2 ) INFORMATION FOR SEQ ID NO:152:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:152:

Thr Xaa Ala Leu Val Xaa Ser Gln Leu Leu Arg Xaa Pro Gln Ala

Xaa Xaa Asp Xaa Val Xaa Gly Ala
                            20

( 2 ) INFORMATION FOR SEQ ID NO:153:

( i ) SEQUENCE CHARACTERISTICS:
                ( A ) LENGTH: 23 amino acids
                ( B ) TYPE: amino acid
                ( C ) STRANDEDNESS: unknown
                ( D ) TOPOLOGY: unknown ( x i ) SEQUENCE DESCRIPTION: SEQ ID NO:153:

Thr Xaa Ala Leu Val Xaa Ala Gln Leu Leu Arg Xaa Pro Gln Ala
                  5                    10                   15

Xaa Leu Asp Met Ile Ala Gly Ala
                   20

( 2 ) INFORMATION FOR SEQ ID NO:154:

( i ) SEQUENCE CHARACTERISTICS:
                ( A ) LENGTH: 23 amino acids
                ( B ) TYPE: amino acid
                ( C ) STRANDEDNESS: unknown
                ( D ) TOPOLOGY: unknown ( x i ) SEQUENCE DESCRIPTION: SEQ ID NO:154:

Thr Thr Thr Leu Leu Leu Ala Gln Ile Met Arg Val Pro Thr Ala
                  5                    10                   15

Phe Leu Asp Met Val Ala Gly Gly
                   20

( 2 ) INFORMATION FOR SEQ ID NO:155:

( i ) SEQUENCE CHARACTERISTICS:
                ( A ) LENGTH: 23 amino acids
                ( B ) TYPE: amino acid
                ( C ) STRANDEDNESS: unknown
                ( D ) TOPOLOGY: unknown ( x i ) SEQUENCE DESCRIPTION: SEQ ID NO:155:

Thr Thr Thr Leu Xaa Leu Ala Gln Val Met Arg Ile Pro Ser Thr
                  5                    10                   15

Leu Val Asp Leu Leu Xaa Gly Gly
                   20

( 2 ) INFORMATION FOR SEQ ID NO:156:

( i ) SEQUENCE CHARACTERISTICS:
                ( A ) LENGTH: 23 amino acids
                ( B ) TYPE: amino acid
                ( C ) STRANDEDNESS: unknown
                ( D ) TOPOLOGY: unknown ( x i ) SEQUENCE DESCRIPTION: SEQ ID NO:156:

Thr Ala Thr Leu Val Leu Ala Gln Leu Met Arg Ile Pro Gly Ala
                  5                    10                   15

Met Val Asp Leu Leu Ala Gly Gly
                   20

( 2 ) INFORMATION FOR SEQ ID NO:157:

( i ) SEQUENCE CHARACTERISTICS:
                ( A ) LENGTH: 23 amino acids
                ( B ) TYPE: amino acid
                ( C ) STRANDEDNESS: unknown
                ( D ) TOPOLOGY: unknown ( x i ) SEQUENCE DESCRIPTION: SEQ ID NO:157:

Thr Ser Ala Leu Ile Met Ala Gln Ile Leu Arg Ile Pro Ser Ile
                  5                   10                  15

Leu Gly Asp Leu Leu Thr Gly Gly
                20

( 2 ) INFORMATION FOR SEQ ID NO:158:

( i ) SEQUENCE CHARACTERISTICS:
       ( A ) LENGTH: 23 amino acids
       ( B ) TYPE: amino acid
       ( C ) STRANDEDNESS: unknown
       ( D ) TOPOLOGY: unknown ( x i ) SEQUENCE DESCRIPTION: SEQ ID NO:158:

Xaa Thr Ala Leu Xaa Met Ala Gln Xaa Leu Arg Ile Pro Gln Val
                  5                   10                  15

Val Ile Asp Ile Ile Ala Gly Xaa
                20

( 2 ) INFORMATION FOR SEQ ID NO:159:

( i ) SEQUENCE CHARACTERISTICS:
       ( A ) LENGTH: 23 amino acids
       ( B ) TYPE: amino acid
       ( C ) STRANDEDNESS: unknown
       ( D ) TOPOLOGY: unknown ( x i ) SEQUENCE DESCRIPTION: SEQ ID NO:159:

Thr Thr Thr Leu Val Leu Ser Ser Ile Leu Arg Val Pro Glu Ile
                  5                   10                  15

Cys Ala Ser Val Ile Phe Gly Gly
                20

NUCLEOTIDE AND DEDUCED AMINO ACID SEQUENCES OF THE ENVELOPE 1 GENE OF 51 ISOLATES OF HEPATITIS C VIRUS AND THE USE OF REAGENTS DERIVED FROM THESE SEQUENCES IN DIAGNOSTIC METHODS AND VACCINES

FIELD OF INVENTION

The present invention is in the field of hepatitis virology. The invention relates to the complete nucleotide and deduced amino acid sequences of the envelope 1 (E1) gene of 51 hepatitis C virus (HCV) isolates from around the world and the grouping of these isolates into twelve distinct HCV genotypes. More specifically, this invention relates to oligonucleotides, peptides and recombinant proteins derived from the envelope 1 gene sequences of the 51 isolates of hepatitis C virus and to diagnostic methods and vaccines which employ these reagents.

BACKGROUND OF INVENTION

Hepatitis C, originally called non-A, non-B hepatitis, was first described in 1975 as a disease serologically distinct from hepatitis A and hepatitis B (Feinstone, S. M. et al. (1975) N. Engl. J. Med. 292:767–770). Although hepatitis C was (and is) the leading type of transfusion-associated hepatitis as well as an important part of community-acquired hepatitis, little progress was made in understanding the disease until the recent identification of hepatitis C virus (HCV) as the causative agent of hepatitis C via the cloning and sequencing of the HCV genome (Choo, A. L. et al. (1989) Science 288:359–362). The sequence information generated by this study resulted in the characterization of HCV as a small, enveloped, positive-stranded RNA virus and led to the demonstration that HCV is a major cause of both acute and chronic hepatitis worldwide (Weiner, A. J. et al. (1990) Lancet 335:1–3). These observations, combined with studies showing that over 50% of acute cases of hepatitis C progress to chronicity with 20% of these resulting in cirrhosis and an undetermined proportion progressing to liver cancer, have led to tremendous efforts by investigators within the hepatitis C field to develop diagnostic assays and vaccines which can detect and prevent hepatitis C infection.

The cloning and sequencing of the HCV genome by Choo et al. (1989) has permitted the development of serologic tests which can detect HCV or antibody to HCV (Kuo, G. et al. (1989) Science 244:362–364). In addition, the work of Choo et al. has also allowed the development of methods for detecting HCV infection via amplification of HCV RNA sequences by reverse transcription and cDNA polymerase chain reaction (RT-PCR) using primers derived from the HCV genomic sequence (Weiner, A. J. et al.). However, although the development of these diagnostic methods has resulted in improved diagnosis of HCV infection, only approximately 60% of cases of hepatitis C are associated with a factor identified as contributing to transmission of HCV (Alter, M. J. et al. (1989) JAMA 262:1201–1205). This observation suggests that effective control of hepatitis C transmission is likely to occur only via universal pediatric vaccination as has been initiated recently for hepatitis B virus. Unfortunately, attempts to date to protect chimpanzees from hepatitis C infection via administration of recombinant vaccines have had only limited success. Moreover, the apparent genetic heterogeneity of HCV, as indicated by the recent assignment of all available HCV isolates to one of four genotypes, I–IV (Okamoto, H. et al. (1992) J. Gen. Virol; 73:673–679), presents additional hurdles which must be overcome in order to develop accurate and effective diagnostic assays and vaccines.

For example, one possible obstacle to the development of effective hepatitis C vaccines would arise if the observed genetic heterogeneity of HCV reflects serologic heterogeneity. In such a case, the most genetically diverse strains of HCV may then represent different serotypes of HCV with the result being that infection with one strain may not protect against infection with another. Indeed, the inability of one strain to protect against infection with another strain was recently noted by both Farci et al. (Farci, P. et al. (1992) Science 258:135–140) and Prince et al. (Prince, A. M. et al. (1992) J. Infect. Dis. 165:438–443), each of whom presented evidence that while infection with one strain of HCV does modify the degree of the hepatitis C associated with the reinfection, it does not protect against reinfection with a closely related strain. The genetic heterogeneity among different HCV strains also increases the difficulty encountered in developing RT-PCR assays to detect HCV infection since such heterogeneity often results in false-negative results because of primer and template mismatch. In addition, currently used serologic tests for detection of HCV or for detection of antibody to HCV are not sufficiently well developed to detect all of the HCV genotypes which might exist in a given blood sample. Finally, in terms of choosing the proper treatment modality to combat hepatitis infection, the inability of presently available serologic assays to distinguish among the various genotypes of HCV represents a significant shortcoming in that recent reports suggest that an HCV-infected patient's response to therapy might be related to the genotype of the infectious virus (Yoshioka, K. et al. (1992) Hepatology 16:293–299; Kanai, K. et al. (1992) Lancet 339:1543; Lan, J. Y. N. et al. (1992) Hepatology 16:209A). Indeed, the data presented in the above studies suggest that the closely related genotypes I and II are less responsive to interferon therapy than are the closely related genotypes III and IV. Moreover, preliminary data by Pozzato et al. (Pozzato, G. et al. (1991) Lancet 338:509) suggests that different genotypes may be associated with different types or degrees of clinical disease. Taken together, these studies suggest that before effective vaccines against HCV infection can be developed, and indeed, before more accurate and effective methods for diagnosis and treatment of HCV infection can be produced, one must obtain a greater knowledge about the genetic and serologic diversity of HCV isolates.

In a recent attempt to gain an understanding of the extent of genetic heterogeneity among HCV strains, Bukh et al. carried out a detailed analysis of HCV isolates via the use of PCR technology to amplify different regions of the HCV genome (Bukh, J. et al. (1992a) Proc. Natl. Acad. Sci. 89:187–191). Following PCR amplification, the 5'-noncoding (5' NC) portion of the genomes of various HCV isolates were sequenced and it was found that primer pairs designed from conserved regions of the 5' NC region of the HCV genome were more sensitive for detecting the presence of HCV than were primer pairs representing other portions of the genome (Bukh, J. et al. (1992b) Proc. Natl. Acad. Sci. U.S.A. 89:4942–4946). In addition, the authors noted that although many of the HCV isolates examined could be classified into the four genotypes described by Okamoto et al. (1992), other previously undescribed genotypes emerged based on genetic heterogeneity observed in the 5' NC region of the various isolates. One of the most prominent of these newly noted genotypes comprised a group of related viruses that contained the most genetically divergent 5' NC regions of those studied. This group of viruses, tentatively classified as a fifth genotype, are very similar to strains recently described by others (Cha, T. -A et al. (1992) Proc. Natl. Acad. Sci. U.S.A. 89:7144–7148; Chan, S-W. et al. (1992) J. Gen. Virol., 73:1131–1141 and Lee, C-H et al. (1992) J. Clin. Microbio. 30:1602–1604). In addition, at least four more putative genotypes were identified thereby providing evidence that the genetic heterogeneity of HCV was more extensive than previously appreciated.

However, while the studies of Bukh et al. (1992a and b) provided new and useful information on the genetic heterogeneity of HCV, it is widely appreciated by those skilled in the art that the three structural genes of HCV, core (C), envelope (E1) and envelope 2/nonstructural 1 (E2/NS1) are the most important for the development of serologic diagnostics and vaccines since it is the product of these genes that constitutes the hepatitis C virion. Thus, a determination of the nucleotide sequence of one or all of the structural genes of a variety of HCV isolates would be useful in designing reagents for use in diagnostic assays and vaccines since a demonstration of genetic heterogeneity in a structural gene(s) of HCV isolates might suggest that some of the HCV genotypes represent distinct serotypes of HCV based upon the previously observed relationship between genetic heterogeneity and serologic heterogeneity among another group of single-stranded, positive-sense RNA viruses, the picornaviruses (Ruechert, R. R. "Picornaviridae and their replication", in Fields, B. N. et al., eds. Virology, New York: Raven Press, Ltd. (1990) 507–548).

SUMMARY OF INVENTION

The present invention relates to 51 cDNAs, each encoding the complete nucleotide sequence of the envelope 1 (E1) gene of an isolate of human hepatitis C virus (HCV).

The present invention also relates to the nucleic acid and deduced amino acid sequences of these E1 cDNAs.

It is an object of this invention to provide synthetic nucleic acid sequences capable of directing production of recombinant E1 proteins, as well as equivalent natural nucleic acid sequences. Such natural nucleic acid sequences may be isolated from a cDNA or genomic library from which the gene capable of directing synthesis of the E1 proteins may be identified and isolated. For purposes of this application, nucleic acid sequence refers to RNA, DNA, cDNA or any synthetic variant thereof which encodes for peptides.

The invention also relates to the method of preparing recombinant E1 proteins derived from the E1 cDNA sequences by cloning the nucleic acid and inserting the cDNA into an expression vector and expressing the recombinant protein in a host cell.

The invention also relates to isolated and substantially purified recombinant E1 proteins and analogs thereof encoded by the E1 cDNAs.

The invention further relates to the use of recombinant E1 proteins as diagnostic agents and as vaccines.

The invention also relates to the use of single-stranded antisense poly- or oligonucleotides derived from the E1 cDNAs to inhibit the expression of the hepatitis C E1 gene.

The invention further relates to multiple computer-generated alignments of the nucleotide and deduced amino acid sequences of the 51 E1 cDNAs. These multiple sequence alignments serve to highlight regions of homology and non-homology between different sequences and hence, can be used by one skilled in the art to design peptides and oligonucleotides useful as reagents in diagnostic assays and vaccines.

The invention therefore also relates to purified and isolated peptides and analogs thereof derived from E1 CDNA sequences.

The invention further relates to the use of these peptides as diagnostic agents and vaccines.

The present invention also encompasses methods of detecting antibodies specific for hepatitis C virus in biological samples. The methods of detecting HCV or antibodies to HCV disclosed in the present invention are useful for diagnosis of infection and disease caused by HCV and for monitoring the progression of such disease. Such methods are also useful for monitoring the efficacy of therapeutic agents during the course of treatment of HCV infection and disease in a mammal.

The invention also provides a kit for the detection of antibodies specific for HCV in a biological sample where said kit contains at least one purified and isolated peptide derived from the E1 cDNA sequences.

The invention further provides isolated and purified genotype-specific oligonucleotides and analogs thereof derived from E1 cDNA sequences.

The invention also relates to a method for detecting the presence of hepatitis C virus in a mammal, said method comprising analyzing the RNA of a mammal for the presence of hepatitis C virus. The invention further relates to a method for determining the genotype of hepatitis C virus present in a mammal. This method is useful in determining the proper course of treatment for an HCV-infected patient.

The invention also provides a diagnostic kit for the detection of hepatitis C virus in a biological sample. The kit comprises purified and isolated nucleic acid sequences useful as primers for reverse-transcription polymerase chain reaction (RT-PCR) analysis of RNA for the presence of hepatitis C virus.

The invention further provides a diagnostic kit for the determination of the genotype of a hepatitis C virus present in a mammal. The kit comprises purified and isolated nucleic acid sequences useful as primers for RT-PCR analysis of RNA for the presence of HCV in a biological sample and purified and isolated nucleic acid sequences useful as hybridization probes in determining the genotype of the HCV isolate detected in PCR.

This invention also relates to pharmaceutical compositions for use in prevention or treatment of hepatitis C in a mammal.

DESCRIPTION OF FIGURES

Figure 1B-7:
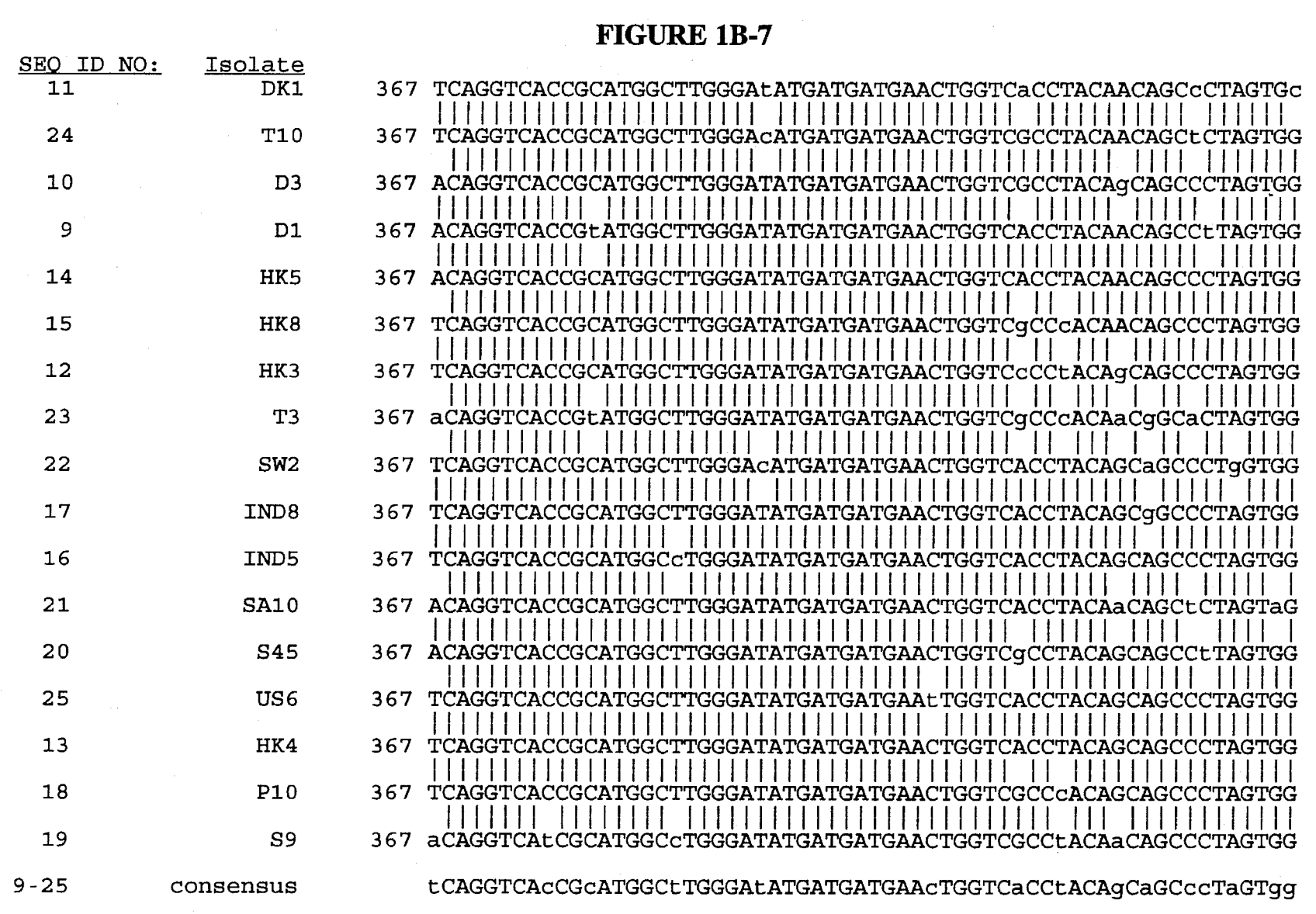
Figure 1H-1:
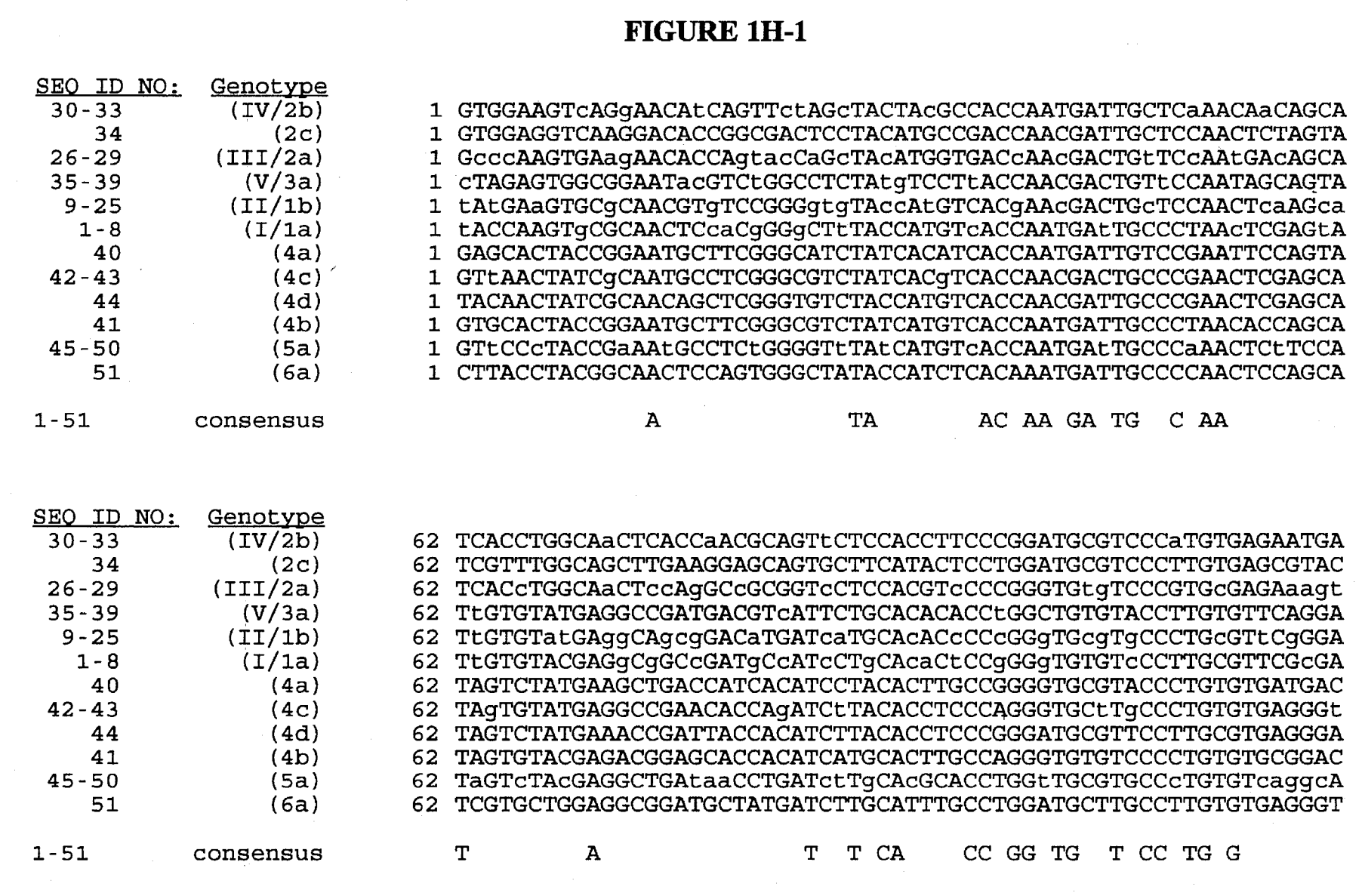

FIGS. 1A-1 through 1H-5 show computer generated sequence alignments of the nucleotide sequences of the 51 HCV E1 cDNAs. The single letter abbreviations used for the nucleotides shown in FIGS. 1A-1 through 1H-5 are those standardly used in the art. FIGS. 1A-1 through 1A-10 show the alignment of SEQ ID NOs:1–8 to produce a consensus sequence for genotype I/1a. FIGS. 1B-1 through 1B-10 show the alignment of SEQ ID NOs:9–25 to produce a consensus sequence for genotype II/1b. FIGS. 1C-1 through 1C-5 show the alignment of SEQ ID NOs:26–29 to produce a consensus sequence for genotype III/2a. FIGS. 1D- through 1D-5 show the alignment of SEQ ID NOs:30–33 to produce a consensus sequence for genotype IV/2b. FIGS. 1E-1 through 1E-5 show the alignment of SEQ ID NOs:35–39 to produce a consensus sequence for genotype V/3a. FIGS. 1F-1 through 1F-3 show the computer alignment of SEQ ID NOs:42–43 to produce a consensus sequence for genotype 4C. FIGS. 1G-1 through 1G-5 show the alignment of SEQ ID NOs:45–50 to produce a consensus sequence for genotype 5a. The nucleotides shown in capital letters in the consensus sequences of FIGS. 1A-1 through 1G-5 are those conserved within a genotype while nucleotides shown in lower case letters in the consensus sequences are those variable within a genotype. In addition, in FIGS. 1A-1 through 1E-5 and 1G-1 through 1G-5, when the lower case letter is shown in a consensus sequence, the lower case letter represents the nucleotide found most frequently in the sequences aligned to produce the consensus sequence. In FIG. 1E-1 through 1E-5 the lower case letters shown in the consensus sequence are nucleotides in SEQ ID NO:42 which differ from nucleotides found in the same positions in SEQ ID NO:43. Finally, a hyphen at a nucleotide position in the consensus sequences in FIGS. 1A-1 through 1G-5 indicates that two nucleotides were found in equal numbers at that position in the aligned sequences. In the aligned sequences, nucleotides are shown in lower case letters if they differed from the nucleotides of both adjacent isolates. FIGS. 1H-1 through 1H-5 show the alignment of the consensus sequences of FIGS. 1A-1 through 1G-5 with SEQ ID NO:34 (genotype 2c), SEQ ID NO:40 (genotype 4a), SEQ ID NO:41 (genotype 4b), SEQ ID NO:44 (genotype 4d) and SEQ ID NO:51 (genotype 6a) to produce a consensus sequence for all twelve genotypes. This consensus sequence is shown as the bottom line of FIGS. 1H-1 through 1H-5 where the nucleotides shown in capital letters are conserved among all genotypes and a blank space indicates that the nucleotide at that position is not conserved among all genotypes.

FIGS. 2A-1 through 2H-2 show computer alignments of the deduced amino acid sequences of the 51 HCV E1 cDNAs. The single letter abbreviations used for the amino acids shown in FIGS. 2A–H follow the conventional amino acid shorthand for the twenty naturally occurring amino acids. FIGS. 2A-1 through 2A-4 show the alignment of SEQ ID NOs:52–59 to produce a consensus sequence for genotype I/1a. FIGS. 2B-1 through 2C-2 show the alignment of SEQ ID NOs:60–76 to produce a consensus sequence for genotype II/1b. FIGS. 2C-1 and 2C-2 show the alignment of SEQ ID NOs:77–80 to produce a consensus sequence for genotype III/2a. FIGS. 2D-1 and 2D-2 show the alignment of SEQ ID NOs:81–84 to produce a consensus sequence for genotype IV/2b. FIGS. 2E-1 and 2E-2 show the alignment of SEQ ID NOs:86–90 to produce a consensus sequence for genotype V/3a. FIG. 2F shows the computer alignment of SEQ ID NOS:93–94 to produce a consensus sequence for genotype 4c. FIG. 2G-1 and 2E-2 show the alignment of SEQ ID NOs:96–101 to produce a consensus sequence for genotype 5a. The amino acids shown in capital letters in the consensus sequences of FIGS. 2A-1 through 2G-2 are those conserved within a genotype while amino acids shown in lower case letters in the consensus sequences are those variable within a genotype. In addition, in FIGS. 2A-1 through 2E-2 and 2G-1 through 2G-2 when the lower case letter is shown in a consensus sequence, the letter represents the amino acid found most frequently in the sequences aligned to produce the consensus sequence. In FIG. 2F-1, the lower case letters shown in the consensus sequence are amino acids in SEQ ID NO:93 which differ from amino acids found in the same positions in SEQ ID NO:94. Finally, a hyphen at an amino acid position in the consensus sequences of FIGS. 2A-1 through 2G-2 indicates that two amino acids were found in equal numbers at that position in the aligned sequences. In the aligned sequences, amino acids are shown in lower case letters if they differed from the amino acids of both adjacent isolates. FIGS. 2H-1 and 2H-2 show the alignment of the consensus sequences of FIGS. 2A-1 through 2G-2 with SEQ ID NO:85 (genotype 2c), SEQ ID NO:91 (genotype 4a), SEQ ID NO:92 (genotype 4b), SEQ ID NO:95 (genotype 4d) and SEQ ID NO:102 (genotype 6a) to produce a consensus sequence for all twelve genotypes. This consensus sequence is shown as the bottom line of FIGS. 2H-1 and 2H-2 where the amino acids shown in capital letters are conserved among all genotypes and a blank space indicates that the amino acid at that position is not conserved among all genotypes.

FIGS. 3A and 3B show multiple sequence alignment of the deduced amino acid sequence of the E1 gene of 51 HCV isolates collected worldwide. The consensus sequence of the E1 protein is shown in boldface (top). In the consensus sequence cysteine residues are highlighted with stars, potential N-linked glycosylation sites are underlined, and invariant amino acids are capitalized, whereas variable amino acids are shown in lower case letters. In the alignment, amino acids are shown in lower case letters if they differed from the amino acid of both adjacent isolates. Amino acid residues shown in bold print in the alignment represent residues which at that position in the amino acid sequence are genotype-specific. Amino acids that were invariant among all HCV isolates are shown as hyphens (-) in the alignment. Amino acid positions correspond to those of the HCV prototype sequence (HCV-1, Choo, L. et al. (1991) Proc. Natl. Acad. Sci. USA 88:2451–2455) with the first amino acid of the E1 protein at position 192. The grouping of isolates into 12 genotypes (I/1a, II/1b, III/2a, IV/2b, V/3a, 2c, 4a, 4b, 4c, 4d, 5a and 6a) is indicated.

FIG. 4 shows a dendrogram of the genetic relatedness of the twelve genotypes of HCV based on the percent amino acid identity of the E1 gene of the HCV genome. The twelve genotypes shown are designated as I/1a, II/1b, III/2a, IV/2b, V/3a, 2c, 4a, 4b, 4c, 4d, 5a and 6a. The shaded bars represent a range showing the maximum and minimum homology between the amino acid sequence of any one isolate of the genotype indicated and the amino acid sequence of any other isolate.

FIG. 5 shows the distribution of the complete E1 gene sequence of 74 HCV isolates into the twelve HCV genotypes in the 12 countries studied. For 51 of these HCV isolates, including 8 isolates of genotype I/1a, 17 isolates of genotype II/1b and 26 isolates comprising the additional 10 genotypes, the complete E1 gene sequence was determined. In the remaining 23 isolates, all of genotypes I/1a and II/1b, the genotype assignment was based on only a partial E1 gene sequence. The partially sequenced isolates did not represent additional genotypes in any of the 12 countries. The number of isolates of a particular genotype is given in each of the 12 countries studied. For ease of viewing, those genotypes designated by two terms (e.g., I/1a) are indicated by the latter term (e.g. 1a). The designations used for each country are: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z). National borders depicted in this figure represent those existing at the time of sampling.

DETAILED DESCRIPTION OF INVENTION

Figure 5:
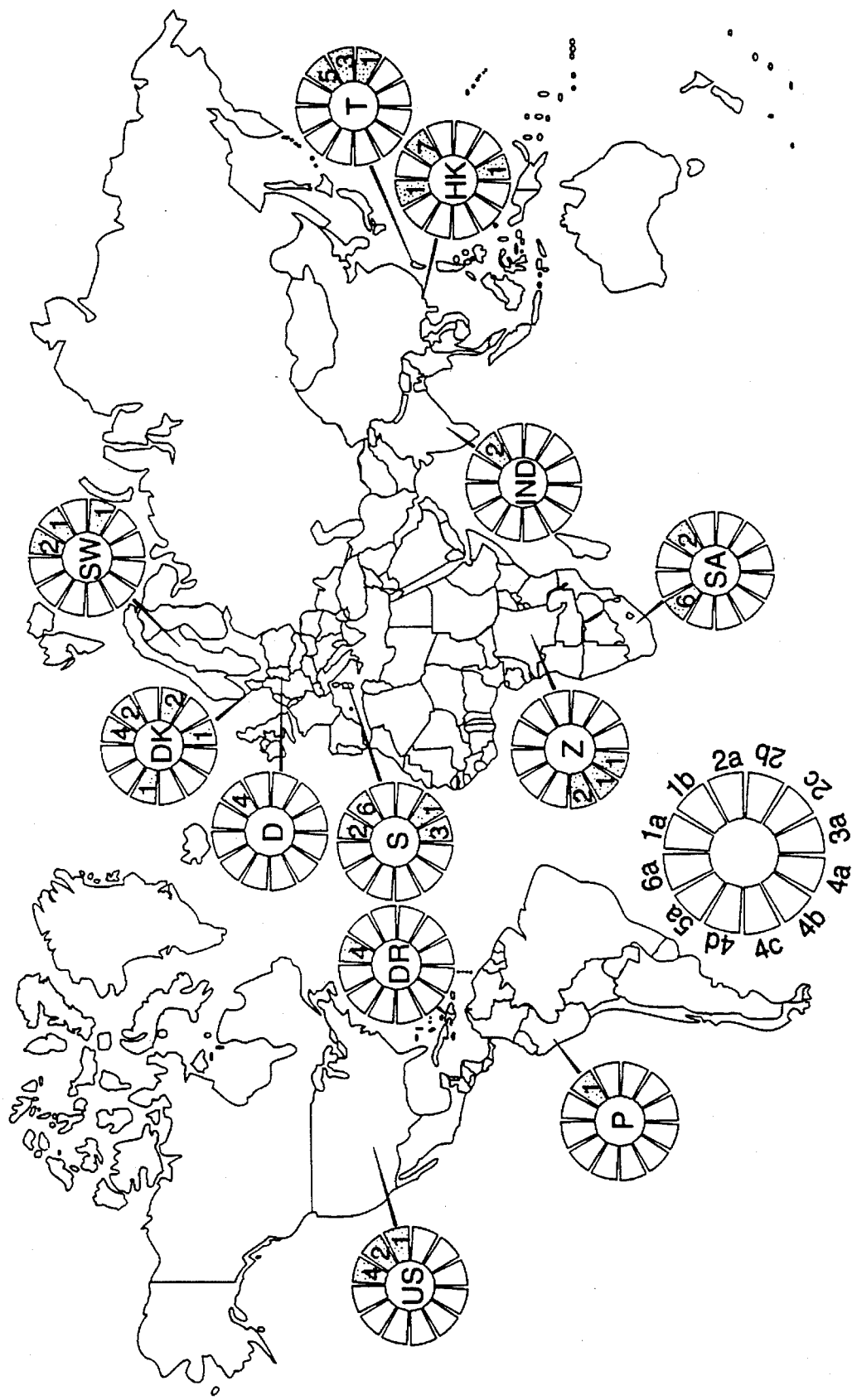

The present invention relates to 51 cDNAs, each encoding the complete nucleotide sequence of the envelope 1 (E1)

gene of an isolate of human hepatitis C virus (HCV). The cDNAs of the present invention were obtained as follows. Viral RNA was extracted from serum collected from humans infected with hepatitis C virus and the viral RNA was then reverse transcribed and amplified by polymerase chain reaction using primers deduced from the sequence of the HCV strain H-77 (Ogata, N. et al. (1991) Proc. Natl. Acad. Sci. U.S.A. 88:3392–3396). The amplified cDNA was then isolated by gel electrophoresis and sequenced.

The present invention further relates to the nucleotide sequences of the cDNAs encoding the E1 gene of the 51 HCV isolates. These nucleotide sequences are shown in the sequence listing as SEQ ID NO:1 through SEQ ID NO:51.

The abbreviations used for the nucleotides are those standardly used in the art.

The deduced amino acid sequence of each of SEQ ID NO:1 through SEQ ID NO:51 are presented in the sequence listing as SEQ ID NO:52 through SEQ ID NO:102 where the amino acid sequence in SEQ ID NO:52 is deduced from the nucleotide sequence shown in SEQ ID NO:1, the amino acid sequence shown in SEQ ID NO:53 is deduced from the nucleotide sequence shown in SEQ ID NO:2 and so on. The deduced amino acid sequence of each of SEQ ID Nos:52–102 starts at nucleotide 1 of the corresponding sequence shown in SEQ ID NOs:1–51 and extends 595 nucleotides.

The three letter abbreviations used in SEQ ID Nos:52–102 follow the conventional amino acid shorthand for the twenty naturally occurring amino acids.

Preferably, the E1 proteins or peptides of the present invention are substantially homologous to, and most preferably biologically equivalent to, the native HCV E1 proteins or peptides. By "biologically equivalent" as used throughout the specification and claims, it is meant that the compositions are immunogenicically equivalent to the native E1 proteins or peptides. The E1 proteins or peptides of the present invention may also stimulate the production of protective antibodies upon injection into a mammal that would serve to protect the mammal upon challenge with HCV. By "substantially homologous" as used throughout the ensuing specification and claims to describe E1 proteins and peptides, it is meant a degree of homology in the amino acid sequence to the native E1 proteins or peptides. Preferably the degree of homology is in excess of 90, preferably in excess of 95, with a particularly preferred group of proteins being in excess of 99 homologous with the native E1 proteins or peptides.

Variations are contemplated in the cDNA sequences shown in SEQ ID NO:1 through SEQ ID NO:51 which will result in a DNA sequence that is capable of directing production of analogs of the corresponding envelope 1 (E1) protein shown in SEQ ID NO:52 through SEQ ID NO:102. It should be noted that the DNA sequences set forth above represent a preferred embodiment of the present invention. Due to the degeneracy of the genetic code, it is to be understood that numerous choices of nucleotides may be made that will lead to a DNA sequence capable of directing production of the instant E1 protein or its analogs. As such, DNA sequences which are functionally equivalent to the sequence set forth above or which are functionally equivalent to sequences that would direct production of analogs of the E1 proteins produced pursuant to the amino acid sequences set forth above, are intended to be encompassed within the present invention.

The term analog as used throughout the specification or claims to describe the E1 proteins or peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the native E1 protein or peptide.

"Chemical derivative" refers to an E1 protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The E1 protein or peptide of the present invention also includes any protein or peptide having one or more additions and/or deletions or residues relative to the sequence of a peptide whose sequence is shown herein, so long as the peptide is biologically equivalent to the native E1 protein or peptide.

The present invention also includes a recombinant DNA method for the manufacture of HCV E1 proteins. In this method, natural or synthetic nucleic acid sequences may be used to direct the production of E1 proteins.

In one embodiment of the invention, the method comprises:

(a) preparation of a nucleic acid sequence capable of directing a host organism to produce HCV E1 protein;

(b) cloning the nucleic acid sequence into a vector capable of being transferred into and replicated in a host organism, such vector containing operational elements for the nucleic acid sequence;

(c) transferring the vector containing the nucleic acid and operational elements into a host organism capable of expressing the protein;

(d) culturing the host organism under conditions appropriate for amplification of the vector and expression of the protein; and (e) harvesting the protein.

In another embodiment of the invention, the method for the recombinant DNA synthesis of an HCV E1 protein encoded by any one of the nucleic acid sequences shown in SEQ ID NOs:1–51 comprises:

(a) culturing a transformed or transfected host organism containing a nucleic acid sequence capable of directing the host organism to produce a protein, under conditions such that the protein is produced, said protein exhibiting substantial homology to a native E1 protein isolated from HCV having the amino acid sequence according to any one of the amino acid sequences shown in SEQ ID NOs:52–102 or combinations thereof.

In one embodiment, the RNA sequence of an HCV isolate was isolated and cloned to cDNA as follows. Viral RNA is extracted from a biological sample collected from human subjects infected with hepatitis C and the viral RNA is then reverse transcribed and amplified by polymerase chain reaction using primers deduced from the sequence of HCV strain H-77 (Ogata et al. (1991)). Preferred primer sequences are shown as SEQ ID NOs:103–108 in the sequence listing. Once amplified, the PCR fragments are isolated by gel electrophoresis and sequenced.

The vectors contemplated for use in the present invention include any vectors into which a nucleic acid sequence as described above can be inserted, along with any preferred or required operational elements, and which vector can then be subsequently transferred into a host organism and replicated in such organisms. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable markers and at least one promoter sequence capable of initiating transcription of the nucleic acid sequence.

In construction of the recombinant for expression cloning vector of the present invention, it should additionally be noted that multiple copies of the nucleic acid sequence and its attendant operational elements may be inserted into each vector. In such an embodiment, the host organism would produce greater amounts per vector of the desired E1 protein. The number of multiple copies of the DNA sequence which may be inserted into the vector is limited only by the ability of the resultant vector due to its size, to be transferred into and replicated and transcribed in an appropriate host microorganism.

In another embodiment, restriction digest fragments containing a coding sequence for E1 proteins can be inserted into a suitable expression vector that functions in prokaryotic or eukaryotic cells. By suitable is meant that the vector is capable of carrying and expressing a complete nucleic acid sequence coding for E1 protein. Preferred expression vectors are those that function in a eukaryotic cell. Examples of such vectors include but are not limited to vaccinia virus vectors, adenovirus or herpes viruses. A preferred vector is the baculovirus transfer vector, pBlueBac.

In yet another embodiment, the selected recombinant expression vector may then be transfected into a suitable eukaryotic cell system for purposes of expressing the recombinant protein. Such eukaryotic cell systems include but are not limited to cell lines such as HeLa, MRC-5 or Cv-1. A preferred eukaryotic cell system is SF9 insect cells.

The expressed recombinant protein may be detected by methods known in the art including, but not limited to, Coomassie blue staining and Western blotting.

The present invention also relates to substantially purified and isolated recombinant E1 proteins. In one embodiment, the recombinant protein expressed by the SF9 cells can be obtained as a crude lysate or it can be purified by standard protein purification procedures known in the art which may include differential precipitation, molecular sieve chromatography, ion-exchange chromatography, isoelectric focusing, gel electrophoresis and affinity and immunoaffinity chromatography. The recombinant protein may be purified by passage through a column containing a resin which has bound thereto antibodies specific for the open reading frame (ORF) protein.

The present invention further relates to the use of recombinant E1 proteins as diagnostic agents and vaccines. In one embodiment, the expressed recombinant proteins of this invention can be used in immunoassays for diagnosing or prognosing hepatitis C in a mammal. For the purposes of the present invention, "mammal" as used throughout the specification and claims, includes, but is not limited to humans, chimpanzees, other primates and the like. In a preferred embodiment, the immunoassay is useful in diagnosing hepatitis C infection in humans.

Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Methods in Immunodiagnosis*, 2nd Edition, Rose and Bigazzi, eds., John Wiley and Sons, 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art (Oellerich, M. 1984. *J. Clin. Chem. Clin.* BioChem 22:895–904) Biological samples appropriate for such detection assays include, but are not limited to serum, liver, saliva, lymphocytes or other mononuclear cells.

In a preferred embodiment, test serum is reacted with a solid phase reagent having surface-bound recombinant HCV E1 protein as an antigen. The solid surface reagent can be prepared by known techniques for attaching protein to solid support material. These attachment methods include non-specific adsorption of the protein to the support or covalent attachment of the protein to a reactive group on the support. After reaction of the antigen with anti-HCV antibody, unbound serum components are removed by washing and the antigen-antibody complex is reacted with a secondary antibody such as labelled anti-human antibody. The label may be an enzyme which is detected by incubating the solid support in the presence of a suitable fluorimetric or calorimetric reagent. Other detectable labels may also be used, such as radiolabels or colloidal gold, and the like.

The HCV E1 protein and analogs thereof may be prepared in the form of a kit, alone, or in combinations with other reagents such as secondary antibodies, for use in immunoassays.

In yet another embodiment the recombinant E1 proteins or analogs thereof can be used as a vaccine to protect mammals against challenge with Hepatitis C. The vaccine, which acts as an immunogen, may be a cell, cell lysate from cells transfected with a recombinant expression vector or a culture supernatant containing the expressed protein. Alternatively, the immunogen is a partially or substantially purified recombinant protein.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving the solid active ingredient in water containing physiologically compatible substances such as sodium chloride (e.g. 0.1– 2.0 m), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are preferably incorporated in an amount of 0.11–10,000 parts by weight per part by weight of immunogens. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or adsorb the proteins or their derivatives. The controlled delivery may be exercised by selecting appropriate macromolecules (for example polyester, polyamino acids, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen or immunogens (i.e. the E1 protein may be administered alone or in combination with the E1 proteins derived from other isolates of HCV) can be used in a suitable diluent such as saline or water, or complete or incomplete adjuvants. Further, the immunogen(s) may or may not be bound to a carrier to make the protein(s) immunogenic. Examples of such carrier molecules include but are not limited to bovine serum albumin (BSA), keyhole limpet hemocyanin (KLH), tetanus toxoid, and the like. The immunogen(s) can be administered by any route appropriate for antibody production such as intravenous, intraperitoneal, intramuscular, subcutaneous, and the like. The immunogen(s) may be administered once or at periodic intervals until a significant titer of anti-HCV antibody is produced. The antibody may be detected in the serum using an immunoassay.

The administration of the immunogen(s) of the present invention may be for either a prophylactic or therapeutic purpose. When provided prophylactically, the immunogen(s) is provided in advance of any exposure to HCV or in advance of any symptom of any symptoms due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV. The therapeutic administration of the immunogen(s) serves to attenuate the infection or disease.

In addition to use as a vaccine, the compositions can be used to prepare antibodies to HCV E1 proteins. The antibodies can be used directly as antiviral agents. To prepare antibodies, a host animal is immunized using the E1 proteins native to the virus particle bound to a carrier as described above for vaccines. The host serum or plasma is collected following an appropriate time interval to provide a composition comprising antibodies reactive with the E1 protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80:15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedleret al. 1988 J. Immunol. 141:4053, all incorporated herein by reference).

The antibodies or antigen binding fragments may also be produced by genetic engineering. The technology for expression of both heavy and light cain genes in *E. coli* is the subject of the PCT patent applications; publication number WO 901443, WO 901443, and WO 9014424 and in Huse et al., 1989 Science 246:1275–1281.

The antibodies can also be used as a means of enhancing the immune response. The antibodies can be administered in amount similar to those used for other therapeutic administrations of antibody. For example, normal immune globulin is administered at 0.02–0.1 ml/1b body weight during the early incubation period of other viral diseases such as rabies, measles, and hepatitis B to interfere with viral entry into cells. Thus, antibodies reactive with the HCV E1 protein can be passively administered alone or in conjunction with another antiviral agent to a host infected with an HCV to enhance the immune response and/or the effectiveness of an antiviral drug.

Alternatively, anti-HCV E1 antibodies can be induced by administered anti-idiotype antibodies as immunogens. Conveniently, a purified anti-HCV E1 antibody preparation prepared as described above is used to induce anti-idiotype antibody in a host animal, the composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-HCV E1 antibodies, or by affinity chromatography using anti-HCV E1 antibodies bound to the affinity matrix. The anti-idiotype antibodies produced are similar in conformation to the authentic HCV E1 protein and may be used to prepare an HCV vaccine rather than using an HCV E1 protein.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

The HCV E1 proteins of the invention are also intended for use in producing antiserum designed for pre- or post-exposure prophylaxis. Here an E1 protein, or mixture of E1 proteins is formulated with a suitable adjuvant and administered by injection to human volunteers, according to known methods for producing human antisera. Antibody response to the injected proteins is monitored, during a several-week period following immunization, by periodic serum sampling to detect the presence of anti-HCV E1 serum antibodies, using an immunoassay as described herein.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

For both in vivo use of antibodies to HCV virus-like particles and proteins and anti-idiotype antibodies and diagnostic use, it may be preferable to use monoclonal antibodies. Monoclonal anti-HCV E1 protein antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., New York, N.Y., pp. 56–97). To produce a human-human hybridoma, a human lymphocyte donor is selected. A donor known to be infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-E1 antibodies, the antibodies must bind to HCV E1 protein. For monoclonal anti-idiotype antibodies, the antibodies must bind to anti-E1 protein antibodies. Cells producing antibodies of the desired specify are selected.

The present invention also relates to the use of single-stranded antisense poly- or oligonucleotides derived from nucleotide sequences substantially homologous to those shown in SEQ ID NOs:1–51 to inhibit the expression of hepatitis C E1 genes. By substantially homologous as used throughout the specification and claims to describe the nucleic acid sequences of the present invention, is meant a level of homology between the nucleic acid sequence and the SEQ ID NOs. referred to in that sentence. Preferably, the level of homology is in excess of 80%, more preferably in excess of 90%, with a preferred nucleic acid sequence being in excess of 95% homologous with the DNA sequence shown in the indicated SEQ ID NO. These anti-sense poly- or oligonucleotides can be either DNA or RNA. The targeted sequence is typically messenger RNA and more preferably, a single sequence required for processing or translation of the RNA. The anti-sense poly- or oligonucleotides can be conjugated to a polycation such as polylysine as disclosed in Lemaitre, M. et al. ((1989) Proc. Natl. Acad. Sci. USA 84:648–652) and this conjugate can be administrated to a mammal in an amount sufficient to hybridize to and inhibit the function of the messenger RNA.

The present invention further relates to multiple computer-generated alignments of the nucleotide and deduced amino acid sequences shown in SEQ ID NOs:1–102. Computer analysis of the nucleotide sequences shown in SEQ ID NOs.:1–51 and of the deduced amino acid sequences shown in SEQ ID NOs:52–102 can be carried out using commercially available computer programs known to one skilled in the art.

In one embodiment, computer analysis of SEQ ID NOs.:1–51 by the program GENALIGN (Intelligenetics, Inc. Mountainview, Calif.) results in distribution of the 51 sequences into twelve genotypes based upon the degree of variation of the sequences. For the purposes of the present invention, the nucleotide sequence identity of E1 cDNAs of HCV isolates of the same genotype is in the range of about 85% to about 100% whereas the identity of E1 cDNA sequences of different genotypes is in the range of about 50% to about 80%.

The grouping of SEQ ID NOs.:1–51 into twelve HCV genotypes is shown below.

| SEQ ID NOs: | Genotypes |
| --- | --- |
| 1–8 | I/1a |
| 9–25 | II/1b |
| 26–29 | III/2a |
| 30–33 | IV/2b |
| 34 | 2c |
| 35–39 | V/3a |
| 40 | 4a |
| 41 | 4b |
| 42–43 | 4c |
| 44 | 4d |
| 45–50 | 5a |
| 51 | 6a |

For those genotypes containing more than one E1 nucleotide sequence, computer alignment of the constituent nucleotide sequences of the genotype was conducted using GENALIGN in order to produce a consensus sequence for each genotype. These alignments and their resultant consensus sequences are shown in FIGS. 1A-1 through 1G-5 for the seven genotypes (I/1a, II/1b, III/2a, IV/2b, V/3a, 4c and 5a) which comprise more than one nucleotide sequence. Further alignment of the consensus sequences of FIGS. 1A-1 through 1G-5 with SEQ ID NO:34 (genotype 2c), SEQ ID NO:40 (genotype 4a), SEQ ID NO:41 (genotype 4b), SEQ ID NO:44 (genotype 4d) and SEQ ID NO:51 (genotype 6a) produces a consensus sequence for all twelve genotypes as shown in FIGS. 1H-1 through 1H-5. The multiple alignments of nucleotide sequences shown in FIGS. 1A-1 through 1H-5 serve to highlight regions of homology and non-homology between different sequences and hence, can be used by one skilled in the art to design oligonucleotides useful as reagents in diagnostic assays for HCV.

Examples of purified and isolated oligonucleotide sequences provided by the present invention are shown as SEQ ID NOs:109–135. The oligonucleotides shown in SEQ ID NOs:109–135 are useful as "genotype-specific" primers and probes since these oligonucleotides can hybridize specifically to the nucleotide sequence of the E1 gene of HCV isolates belonging to a single genotype. The genotype-specificity of the oligonucleotides shown in SEQ ID NOs:109–135 is as follows: SEQ ID NOs:109–110 are specific for genotype I/1a; SEQ ID NOs:111–112 are specific for genotype II/1b; SEQ ID NOs:113–114 are specific for genotype III/2a; SEQ ID NOs:115–116 are specific for genotype IV/2b; SEQ ID NOs:117–119 are specific for genotype 2c; SEQ ID NOs:120–122 are specific for genotype V/3a; SEQ ID NOs:123–124 are specific for genotype 4a; SEQ ID NOs:125–125 are specific for genotype 4b; SEQ ID NOs:127–128 are specific for genotype 4c; SEQ ID NOs:129–130 are specific for genotype 4d; SEQ ID NOs:131–132 are specific for genotype 5a and SEQ ID NOs:133–135 are specific for genotype 6a.

The oligonucleotides of this invention can be synthesized using any of the known methods of oligonucleotide synthesis (e.g., the phosphodiester method of Agarwal et al. 1972, Agnew. Chem. Int. Ed. Engl. 11:451, the phosphotriester method of Hsiung et al. 1979, Nucleic Acids Res 6:1371, or the automated diethylphosphoramidite method of Baeucage et al. 1981, Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In a preferred embodiment, SEQ ID NO:103 through SEQ ID NO:135 are synthetic oligonucleotides.

The present invention also relates to a method for detecting the presence of HCV in a mammal, said method comprising analyzing the RNA of a mammal for the presence of hepatitis C virus.

The RNA to be analyzed can be isolated from serum, liver, saliva, lymphocytes or other mononuclear cells as viral RNA, whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J. M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412). A preferred method of isolating RNA is extraction of viral RNA by the quanidium-phenol-chloroform method of Bukh et al. (1992a).

The methods for analyzing the RNA for the presence of HCV include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W. H. Freeman and Company, New York). A preferred method is RT-PCR. In this method, the RNA can be reverse transcribed to first strand cDNA using a primer or primers derived from the nucleotide sequences shown in SEQ ID NOs:1–51. A preferred primer for reverse transcription is that shown in SEQ ID NO:104. Once the cDNAs are synthesized, PCR amplification is carried out using pairs of primers designed to hybridize with sequences in the HCV E1 cDNA which are an appropriate distance apart (at least about 50 nucleotides) to permit amplification of the cDNA and subsequent detection of the amplification product. Each primer of a pair is a single-stranded oligonucleotide of about 20 to about 60 bases in length where one primer (the "upstream" primer) is complementary to the original RNA and the second primer (the "downstream" primer) is complementary to the first strand of cDNA generated by reverse transcriptions of the RNA. The target sequence is generally about 100 to about 300 base pairs long but can be as large as 500–1500 base pairs. Optimization of the amplification reaction to obtain sufficiently specific hybridization to the E1 nucleotide sequence is well within the skill in the art and is preferably achieved by adjusting the annealing temperature.

In one embodiment, the primer pairs selected to amplify E1 cDNAs are universal primers. By "universal", as used to describe primers throughout the claims and specification, is meant those primer pairs which can amplify E1 gene fragments derived from an HCV isolate belonging to any one of the twelve genotypes of HCV described herein. Purified and isolated universal primers are used in Example 1 of the present invention and are shown as SEQ ID NOs:103–108 where SEQ ID NOs:103 and 104 represent one pair of primers, SEQ ID NOs:105 and 106 represent a second pair of primers and SEQ ID NOs:107–108 represent a third pair of primers.

In an alternative embodiment, primer pairs selected to amplify E1 cDNAs are genotype-specific primers. In the present invention, genotype-specific primer pairs can readily be derived from the following genotype-specific nucleotide domains: nucleotides 197–238 and 450–480 of the consensus sequence of genotype I/1a shown in FIGS. 1A-4 and 1A-8; nucleotides 197–238 and 450–480 of the consensus sequence of genotype II/1b shown in FIGS. 1B-4 and 1B-8; nucleotides 199–238 and 438–480 of the consensus sequence of genotype III/2a shown in FIGS. 1C-2 and 1C-4; nucleotides 124–177 and 450–480 of the consensus sequence of genotype IV/2b shown in FIGS. 1D-2 and 1D-4; nucleotides 124–177, 193–238 and 436–480 of SEQ ID NO:34 (genotype 2C); nucleotides 168–207, 294–339 and 406–480 of the consensus sequence of genotype V/3a shown in FIGS. 1E-2, 1E-3 and 1E-4; nucleotides 145–183 and 439–480 of SEQ ID NO:40 (genotype 4a); nucleotides 168–207 and 432–480 of SEQ ID NO:41 (genotype 4b); nucleotides 130–183 and 450–480 of the consensus sequence of genotype 4c shown in FIGS. 1F-1 and 1F-2; nucleotides 130–183 and 450–480 of SEQ ID NO:44 (genotype 4d); nucleotides 166–208 and 437–480 of the consensus sequence of genotype 5a shown in FIGS. 1G-2 and 1G-4 and nucleotides 168–207, 216–252 and 429–480 of SEQ ID NO:51 (genotype 6a). One skilled in the art would readily appreciate that in a pair of genotype-specific primers, each primer is derived from different genotype-specific nucleotide domains indicated above for a given genotype. Also, as described earlier, it is understood by one skilled in the art that each pair of primers comprises one primer which is complementary to the original viral RNA and the other which is complementary to the first strand of cDNA generated by reverse transcription of the viral RNA. For example, in a pair of genotype-specific primers for genotype 4b, one primer would have a nucleotide sequence derived from region 168–207 of SEQ ID NO:40 and the other primer would have a nucleotide sequence which is the complement of region 432–480 of SEQ ID NO:40. One skilled in the art would readily recognize that such genotype specific domains would also be useful in designing oligonucleotides for use as genotype-specific hybridization probes. Indeed, the sequences of such genotype-specific hybridization probes are disclosed later in the specification.

The amplification products of PCR can be detected either directly or indirectly. In one embodiment, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be detected by agarose gel electrophoresis followed by ethidum bromide staining and visualization under ultraviolet light or via direct sequencing of the PCR-products.

In yet another embodiment, unlabelled amplification products can be detected via hybridization with labelled nucleic acid probes radioactively labelled or, labelled with biotin, in methods known to one skilled in the art such as dot and slot blot hybridization (Kafatos, F. C. et al. (1979) or filter hybridization (Hollander, M. C. et al. (1990)).

In one embodiment, the nucleic acid sequences used as probes are selected from, and substantially homologous to, SEQ ID NOs:1–51. Such probes are useful as universal probes in that they can detect in PCR-amplification products of E1 cDNAs of an HCV isolate belonging to any of the twelve HCV genotypes disclosed herein. The size of these probes can range from about 200 to about 500 nucleotides.

In an alternative embodiment, the present invention relates to a method for determining the genotype of a hepatitis C virus present in a mammal where said method comprises:

(a) amplifying RNA of a mammal via RT-PCR to produce amplification products;

(b) contacting said products with at least one genotype-specific oligonucleotide; and (c) detecting complexes of said products which bind to said oligonucleotide(s).

In this method, one embodiment of said amplification step is carried out using the universal primers (SEQ ID NO:103 through SEQ ID NO:108) as disclosed above. In step (b) of this method, the nucleic acid sequences used as probes are substantially homologous to the sequences shown in SEQ ID NOs:109–135. The probes disclosed in SEQ ID NOs.:109–135 are useful in specifically detecting PCR-amplification products of E1 cDNAs of HCV isolates belonging to one of the twelve HCV genotypes disclosed herein. In a preferred embodiment, probes having sequences substantially homologous to the sequences shown in SEQ ID NOs:109–135 are used alone or in combination with other probes specific to the same genotype.

For example, a probe having a sequence according to SEQ ID NO:109 can be used alone or in combination with a probe having a sequence according to SEQ ID NO:110. The probes derived from SEQ ID NOs:109–135 can range in size from about 30 to about 70 nucleotides and can be synthesized as described earlier.

The nucleic acid sequence used as a probe to detect PCR amplification products of the present invention can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. (1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:126–131; Erickson, P. F. et al. (1982) *J. of Immunology Methods*, 51:241–249; Matthaei, F. S. et al. (1986) *Anal. Biochem.*, 157:123–128) and methods which allow detection by fluorescence using commercially available products.

The present invention also relates to computer analysis of the amino acid sequences shown in SEQ ID NOs:52–102 by the program GENALIGN. This analysis groups the 51 amino acid sequences shown in SEQ ID NOs:52–102 into the twelve genotypes disclosed earlier in this application based upon the degree of variation of the amino acid sequences. For the purposes of the present invention, the amino acid sequence identity of E1 amino acid sequences of the same genotype ranges from about 85% to about 100% whereas the identity of E1 sequences of different genotypes ranges from about 45% to about 80%.

The grouping of SEQ ID NOs:52–102 into the twelve HCV genotypes is shown below:

| SEQ ID NOs: | Genotypes |
| --- | --- |
| 52–59 | I/1a |
| 60–76 | II/1b |
| 77–80 | III/2a |
| 81–84 | IV/2b |
| 85 | 2c |
| 86–90 | V/3a |
| 91 | 4a |
| 92 | 4b |
| 93–94 | 4c |
| 95 | 4d |
| 96–101 | 5a |
| 102 | 6a |

For those genotypes containing more than one E1 amino acid sequence, computer alignment of the constituent sequences of each genotype was conducted using the computer program GENALIGN in order to produce a consensus sequence for each genotype. These alignments and their resultant consensus sequences are shown in FIGS. 2A-1 through 2G-2 for the seven genotypes (I/1a, II/1b, III/2a, IV/2b, V/3a, 4c and 5a) which comprise more than one sequence. Further alignment of the consensus sequences shown in FIGS. 2A–G with the amino acid sequences of SEQ ID NO:85 (genotype 2c); SEQ ID NO:91 (genotype 4a); SEQ ID NO:92 (genotype 4b); SEQ ID NO:95 (genotype 4d) and SEQ ID NO:102 (genotype 6a) to produce a consensus amino acid sequence for all twelve genotypes is shown in FIGS. 2H-1 and and 2H-2. The multiple alignment of E1 amino acid sequences shown in FIGS. 2A–H serves to highlight regions of homology and non-homology between amino acid sequences and hence, these alignments can readily be used by one skilled in the art to derive peptides useful in assays and vaccines for the diagnosis and prevention of HCV infection. Examples of purified and isolated peptides are provided by the present invention are shown as SEQ ID NOs:136–159. These peptides are derived from two regions of the amino acid sequences shown in FIGS. 2A-1 through 2H-2, amino acids 48–80 and amino acids 138–160. The peptides shown in SEQ ID NOs. 136–159 are useful as genotype-specific diagnostic reagents since they are capable of detecting an immune response specific to HCV isolates belonging to a single genotype. The genotype-specificity of the peptides shown in SEQ ID NOs:136–159 are as follows: SEQ ID NOs:136 and 148 are specific for genotype IV/2b; SEQ ID NOs:137 and 149 are specific for genotype 2c; SEQ ID NOs:138 and 150 are specific for genotype III/2a; SEQ ID NOs:139 and 151 are specific for genotype V/a; SEQ ID NOs:140 and 152 are specific for genotype II/1b; SEQ ID NOs:141 and 153 are specific for genotype I/1a; SEQ ID NOs:142 and 154 are specific for genotype 4a; SEQ ID NOs:143 and 155 are specific for genotype 4c; SEQ ID NOs:144 and 156 are specific for genotype 4d; SEQ ID NOs:145 and 157 are specific for genotype 4b; SEQ ID NOs:146 and 158 are specific for genotype 5a and SEQ ID NOs:147 and 159 are specific for genotype 6a. In SEQ ID NO:136, Xaa at position 22 is a residue of Ala or Thr, Xaa at position 24 is a residue of Val or Ile, Xaa at position 26 is a residue of Val or Met; in SEQ ID NO:138, Xaa at position 5 is a Ser or Thr residue, Xaa at position 11 is an Arg or Gln residue, Xaa at position 12 is an Arg or Gln residue; in SEQ ID NO:139, Xaa at position 3 is a Pro or Ser residue, Xaa at position 33 is a Leu or Met residue; in SEQ ID NO:140, Xaa at position 5 is a Thr or Ala residue, Xaa at position 13 is a Gly, Ala, Ser, Val or Thr residue, Xaa at position 14 is a Ser, Thr or Asn residue, Xaa at position 15 is a Val or Ile residue, Xaa at position 16 is a Pro or Ser residue, Xaa at position 18 is a Thr or Lys residue, Xaa at position 19 is a Thr or Ala residue, Xaa at position 22 is an Arg or His residue, Xaa at position 32 is an Ala, Val or Thr residue; in SEQ ID NO:141, Xaa at position 3 is an Ala or Pro residue, Xaa at position 4 is a Val or Met residue, Xaa at position 5 is a Thr or Ala residue, Xaa at position 17 is a Thr or Ala residue, Xaa at position 18 is a Thr or Ala residue, Xaa at position 23 is a His or Tyr residue; in SEQ ID NO:143, Xaa at position 10 is a Val or Ala residue, Xaa at position 11 is a Ser or Pro residue, Xaa at position 18 is an Asp or Glu residue Xaa at position 20 is a Leu or Ile residue; in SEQ ID NO:146, Xaa at position 3 is a Gln or His residue, Xaa at position 12 is an Asn, Ser or Thr residue, Xaa at position 13 is a Leu or Phe residue, Xaa at position 23 is an Ala or Val residue; in SEQ ID NO:148, Xaa at position 16 is a Val or Ala residue, Xaa at position 18 is a Glu or Gln residue; in SEQ ID NO:150, Xaa at position 2 is an Ala or Thr residue, Xaa at position 4 is a Met or Leu residue, Xaa at position 9 is an Ala or Val residue, Xaa at position 17 is an Ile or Leu residue, Xaa at position 20 is an Ile or Val residue, Xaa at position 21 is a Ser or Gly residue; in SEQ ID NO:151, Xaa at position 9 is a Val or Ile residue, Xaa at position 16 is a Leu or Val residue, Xaa at position 20 is an Ile or Leu residue; in SEQ ID NO:152, Xaa at position 2 is an Ala or Thr residue, Xaa at position 6 is a Val or Leu residue, Xaa at position 12 is an Ile or Leu residue, Xaa at position 16 is a Val or Ile residue, Xaa at position 17 is a Val, Leu or Met residue, Xaa at position 19 is a Met or Val residue, Xaa at position 21 is an Ala or Thr residue; in SEQ ID NO:153, Xaa at position 2 is a Thr or Ala residue, Xaa at position 6 is a Val, Ile or Met residue, Xaa at position 12 is an Ile or Val residue, Xaa at position 16 is a Ile or Val residue; in SEQ ID NO:155, Xaa at position 5 is a Leu or Val residue, Xaa at position 21 is a Thr or Ala residue; in SEQ ID NO:158, Xaa at position 1 is a Thr or Ala residue, Xaa at position 5 is a Val or Leu residue, Xaa at position 9 is a Leu, Met or Val residue, Xaa at position 23 is a Gly or Ala residue.

Those skilled in the art would be aware that the peptides of the present invention or analogs thereof can be synthesized by automated instruments sold by a variety of manufacturers or can be commercially custom-ordered and prepared. The term analog has been described earlier in the specification and for purposes of describing the peptides of the present invention, analogs can further include branched or non-linear arrangements of the peptide sequences shown in SEQ ID NOs:136–159.

Alternatively, peptides can be expressed from nucleic acid sequences where such sequences can be DNA, cDNA, RNA or any variant thereof which is capable of directing protein synthesis. In one embodiment, restriction digest fragments containing a coding sequence for a peptide can be inserted into a suitable expression vector that functions in prokaryotic or eukaryotic cells. Such restriction digest fragments may be obtained from clones isolated from prokaryotic or eukaryotic sources which encode the peptide sequence.

Suitable expression vectors and methods of isolating clones encoding the peptide sequences of the present invention have previously been described.

The preferred size of the peptides of the present invention is from about 8 to about 100 amino acids in length.

The present invention further relates to the use of the peptides shown in SEQ ID NOs:136–159 in methods of detecting antibodies specific for HCV in biological samples. In one embodiment, at least one peptide specific for a single genotype to be used in previously described immunoassays to detect antibodies specific for a single genotype of HCV. A preferred immunoassay is ELISA.

It is understood by one skilled in the art that the diagnostic assays described herein using genotype-specific oligonucleotides or genotype-specific peptides ca be useful in assisting one skilled in the art to choose a course of therapy for the HCV-infected individual.

In an alternative embodiment, a mixture of peptides can be used in an immunoassay to detect antibodies to any of the twelve genotypes of HCV. The mixture of peptides as disclosed herein, comprises at least one peptide selected from SEQ ID NOs:140–141 and 152–153; one peptide selected from SEQ ID NOs:136, 138, 148 and 150; one peptide selected from SEQ ID NOs:142–145 and 154–157; one peptide selected from SEQ ID NOs:146 and 158; one peptide selected from SEQ ID NOs:139 and 151; one peptide selected from SEQ ID NOs:138 and 150 and one peptide selected from SEQ ID NOs:140 and 159. In a preferred embodiment, the peptides of the present invention can be used in an ELISA assay as described previously for E1 proteins.

The peptides or analogs thereof may be prepared in the form of a kit, alone or in combinations with other reagents such as secondary antibodies, for use in immunoassay. In addition, since genotype-specific peptides shown in SEQ ID NOs:136–159 are derived from two variable regions in the E1 protein, amino acids 48–80 (SEQ ID NOs:136–147) and amino acids 138–160 (SEQ ID NOs:148–159), one skilled in the art would recognize that these peptides would be useful as vaccines against hepatitis C. In the present invention, a peptide from SEQ ID NOs:136–159 can be used alone or in combination with other peptides shown therein as immunogens in the vaccine. Formulations suitable for administering the peptide(s) of the present invention, routes of administration, pharmaceutical compositions comprising the peptides and so forth are the same as those previously described for recombinant E1 proteins. In addition, as described for E1 proteins, the peptide(s) can also be used to prepare antibodies to HCV-E1 protein.

The peptides of the present invention may also be supplied in the form of a kit, alone, or in the form of a pharmaceutical composition as described above for E1 proteins recombinant.

Any articles or patents referenced herein are incorporated by reference. The following examples illustrate various aspects of the invention but are in no way intended to limit the scope thereof.

MATERIALS

Serum used in these examples was obtained from 84 anti-HCV positive individuals that were previously found to be positive for HCV RNA in a cDNA PCR assay with primer set a from the 5' NC region of the HCV genome (Bukh, J. et al. (1992 (b)) Natl. Acad. Sci. USA 89:4942–4946). These samples were from 12 countries: Denmark (DK); Dominican Republic (DR); Germany (D); Hong Kong (HK); India (IND); Sardinia, Italy (S) ; Peru (P) ; South Africa (SA); Sweden (SW); Taiwan (T); United States (US); and Zaire (Z) .

EXAMPLE 1

Identification of the DNA Sequence of the E1 Gene of 51 Isolates of HCV via RT-PCR Analysis of Viral RNA Using Universal Primers Viral RNA was extracted from 100 μl of serum by the guanidinium-phenol-chloroform method and the final RNA solution was divided into 10 equal aliquots and stored at −80° C. as described (Bukh, et al. (1992 (a)). The sequences of the synthetic oligonucleotides used in the RT-PCR assay, deduced from the sequence of HCV strain H-77 (Ogata, N. et al. (1991) Proc. Natl. Acad. Sci. USA 88:3392–3396), are shown as SEQ ID NOs:103–108. One aliquot of the final RNA solution, equivalent to 10 μl of serum, was used for cDNA synthesis that was performed in a 20 μl reaction mixture using avian myeloblastosis virus reverse transcriptase (Promega, Madison, Wis.) and SEQ ID NO:104 as a primer. The resulting cDNA was amplified in a "nested" PCR assay by Taq DNA polymerase (Amplitaq, Perkin-Elmer/Cetus) as described previously (Bukh et al. (1992a)) with primer set e (SEQ ID NOs:103–106). Precautions were taken to avoid contamination with exogenous HCV nucleic acid (Bukh et al. 1992a)), and negative controls (normal, uninfected serum) were interspersed between every test sample in both the RNA extraction and cDNA PCR procedures. No false positive results were observed in the analysis. In most instances, amplified DNA (first or second PCR products) was reamplified with primers SEQ ID NO:107 and SEQ ID NO:108 prior to sequencing since these two primers contained EcoR1 sites which would facilitate future cloning of the E1 gene. Amplified DNA was purified by gel electrophoresis followed by glass-milk extraction (Geneclean, BIO 101, LaJolla, Calif.) and both strands were sequenced directly by the dideoxy-nucleotide chain termination method (Bachman, B. et al. (1990) Nucl. Acids Res. 18:1309)) with phage T7 DNA polymerase (Sequenase, United States Biochemicals, Cleveland, Ohio), [alpha $^{33}$S]dATP (Amersham, Arlington Heights, Ill.) or [alpha $^{33}$P] dATP (Amersham or DuPont, Wilmington, Del.) and sequencing primers. RNA extracted from serum containing HCV strain H-77, previously sequenced by Ogata, N. et al. (1991), was amplified with primer set e (SEQ ID NOs:103–106) and sequenced in parallel as a control. The nucleotide sequences of the envelope 1 (E1) gene of all 51 HCV isolates are shown as SEQ ID NOs:1–51. In all 51 HCV isolates, the E1 gene was exactly 576 nucleotides in length and did not have any in-frame stop codons.

EXAMPLE 2

Computer Analysis of the Nucleotide and Deduced Amino Acid Sequences of the E1 Gene of the 51 HCV Isolates Multiple computer-generated alignments of the nucleotide (SEQ ID NOs:1–51, FIGS. 1A-1 through 2H-2) and deduced amino acid sequences (SEQ ID NOs:52–102, FIGS. 2A-1 through 2H-2) of the cDNAs of the 51 HCV isolates constructed using the computer program GENALIGN (Miller, R. H. et al. (1990) Proc. Natl. Acad. Sci. USA 87:2057–2061) resulted in the 51 HCV isolates being divided into twelve genotypes based upon the degree of variation of the E1 gene sequence as shown in table 1.

of 27 amino acids invariant among all 51 HCV isolates. It is possible that the 5' and 3' ends of this domain are conserved

TABLE 1

Biochemistry: Bukh et al.
Percent nucleotide (nt) and amino acid (aa) sequence identify of the E1 gene among the 12 HCV genotypes.

| | I/1a | II/1b | III/2a | IV/2b | 2c | (V)/3a | 4a | 4b | 4c | 4d | 5a | 6a | nt: |
|---|---|---|---|---|---|---|---|---|---|---|---|---|---|
| | 89.9–97.6 | 72.0–76.2 | 59.2–63.7 | 56.1–58.3 | 60.8–62.8 | 63.0–66.3 | 63.9–67.2 | 64.9–66.8 | 62.7–64.4 | 67.7–69.4 | 62.3–67.2 | 62.2–63.9 | I/1a |
| aa: | | 88.9–97.9 | 58.3–62.2 | 53.8–57.5 | 60.1–61.5 | 63.9–67.2 | 60.9–63.7 | 63.4–65.8 | 61.6–65.1 | 63.0–65.5 | 62.2–66.5 | 61.6–63.0 | II/1b |
| I/1a | 91.1–98.4 | | 88.0–91.3 | 69.1–71.0 | 72.7–73.6 | 58.0–60.8 | 61.5–62.7 | 59.9–60.4 | 59.7–63.4 | 58.7–61.3 | 56.6–60.8 | 55.0–56.8 | III/2a |
| II/1b | 75.5–80.7 | 90.1–97.9 | | 92.7–95.0 | 67.5–68.9 | 56.3–58.3 | 58.9–60.8 | 56.4–57.6 | 57.1–59.9 | 57.5–59.0 | 53.5–56.6 | 53.6–55.2 | IV/2b |
| III/2a | 58.3–64.6 | 52.6–56.8 | 89.1–92.7 | | — | 57.5–58.2 | 59.2 | 58.5 | 58.0–58.3 | 58.9 | 56.9–57.1 | 57.6 | 2c |
| IV/2b | 54.2–56.8 | 51.0–54.2 | 69.3–72.9 | 93.8–96.4 | | 93.8–99.1 | 64.4–65.3 | 62.7–64.1 | 60.9–62.5 | 62.3–63.9 | 61.8–64.4 | 58.0–58.9 | (V)/3a |
| 2c | 56.3–60.4 | 52.6–55.7 | 74.5–77.1 | 67.7–69.8 | — | | — | 74.8 | 75.5–78.0 | 74.8 | 62.8–64.6 | 62.0 | 4a |
| (V)/3a | 64.1–68.8 | 66.7–70.8 | 54.7–58.9 | 54.2–56.8 | 52.1–53.6 | 94.3–98.4 | | — | 74.0–74.8 | 72.0 | 63.9–64.6 | 62.7 | 4b |
| 4a | 69.3–73.4 | 64.6–67.2 | 62.0–63.0 | 58.9–60.4 | 58.3 | 66.1–68.8 | — | | 90.1 | 77.6–78.6 | 62.7–64.8 | 63.0–64.4 | 4c |
| 4b | 66.7–69.3 | 66.1–70.3 | 53.6–56.3 | 52.1–53.1 | 53.6 | 62.0–64.6 | 76.0 | — | | — | 64.4–66.1 | 64.1 | 4d |
| 4c | 66.1–72.9 | 64.6–69.3 | 55.2–61.5 | 54.2–58.3 | 54.7–58.3 | 63.0–65.6 | 77.1–81.3 | 79.2–80.2 | 89.6 | | 90.1–95.7 | 60.6–63.2 | 5a |
| 4d | 73.4–75.5 | 66.7–70.3 | 56.3–58.9 | 55.2–55.7 | 54.2 | 63.5–64.6 | 78.1 | 77.6 | 82.8 | — | | — | 6a |
| 5a | 66.1–73.4 | 64.1–70.3 | 52.6–57.3 | 50.5–53.1 | 54.2–56.3 | 60.4–64.1 | 67.2–68.2 | 65.1–67.2 | 67.7–71.4 | 69.3–71 | 92.7–97.4 | | |
| 6a | 64.6–65.6 | 62.5–65.6 | 49.0–51.0 | 49.0–50.5 | 50.5 | 57.8–58.9 | 66.1 | 62.5 | 66.1–67.2 | 66.7 | 62.0–63.5 | — | |

Nucleotide sequences analyzed in compiling the above table are shown SEQ ID NOs: 1–51 while the amino acid sequences analyzed are shown in SEQ ID NOs: 52–102. The grouping of SEQ ID NOs: into genotypes is previously described in the specification.

The nucleotide and amino acid sequence identity of HCV isolates of the same genotype was in the range of 88.0–99.1% and 89.1–98.4%, respectively, whereas that of HCV isolates of different genotypes was in the range of 53.5–78.6% and 49.0–82.8%, respectively. The latter differences are similar to those found when comparing the envelope gene sequences of the various serotypes of the related flaviviruses, as well as other RNA viruses. When microheterogenicity in a sequence was observed, defined as more than one prominent nucleotide at a specific position, the nucleotide that was identical to that of the HCV prototype (HCV1, Choo et al. (1989)) was reported if possible. Alternatively, the nucleotide that was identical to the most closely related isolate is shown.

Figure 3A:
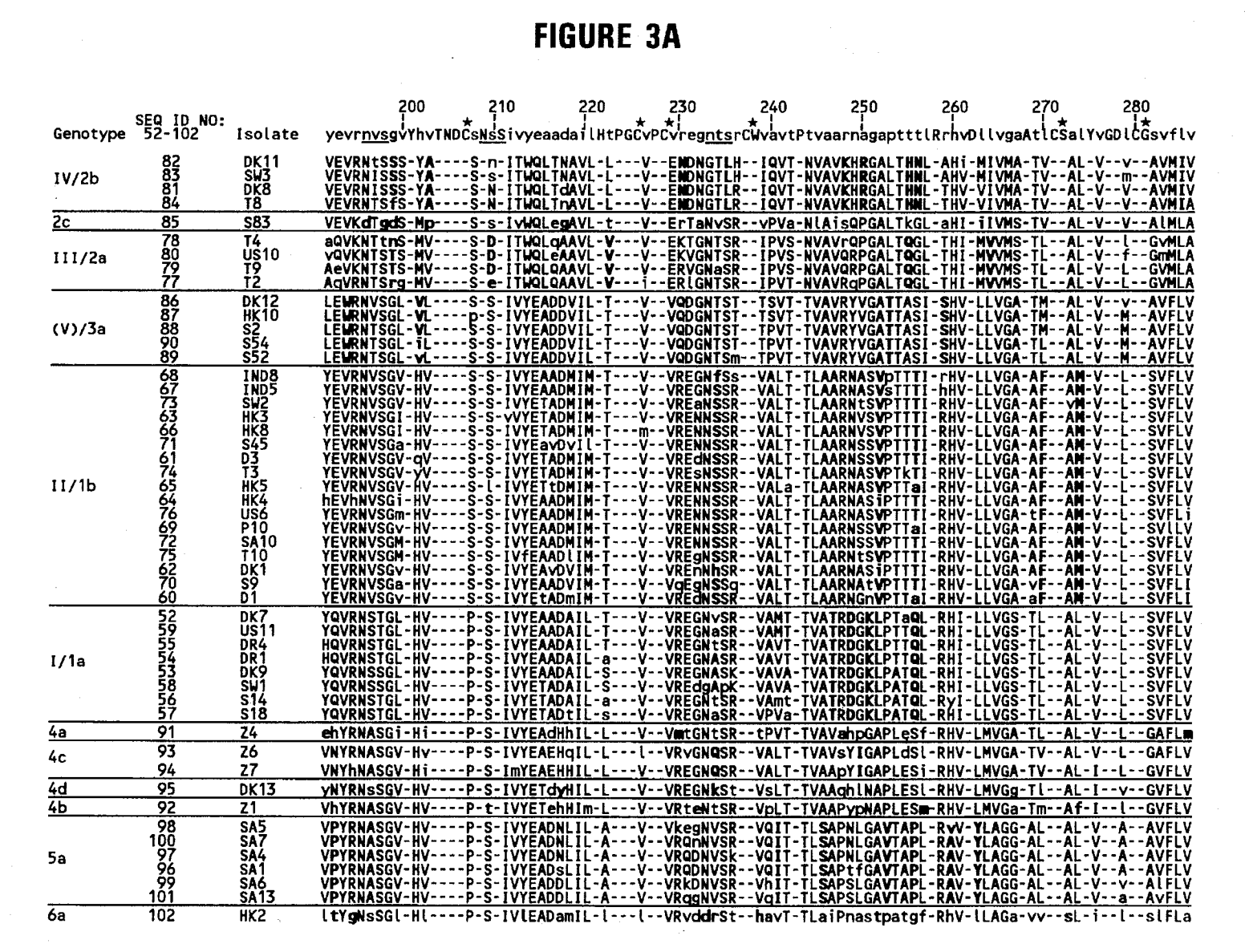

Analysis of the consensus sequence of the E1 protein of the 51 HCV isolates from this study demonstrated that a total of 60 (30.3%) of the 192 amino acids of the E1 protein were invariant among these isolates (FIGS. 3A and 3B). Most impressive, all 8 cysteine residues as well as 6 of 8 proline residues were invariant. The most abundant amino acids (e.g. alanine, valine and leucine) showed a very low degree of conservation. The consensus sequence of the E1 protein contained 5 potential N-linked glycosylation sites. Three sites at positions 209, 305 and 325 were maintained in all 51 HCV isolates. A site at position 196 was maintained in all isolates except the sole isolate of genotype 2c. Also, a site at position 234 was maintained in all isolates except one isolate of genotype I/1a, all four isolates of genotype IV/2b and the sole isolate of 6a. Conversely, only genotype IV/2b isolates had a potential glycosylation site at position 233. Further analysis revealed a highly conserved amino acid domain (aa 302–328) in the E1 protein with 20 (74.1%) of 27 amino acids invariant among all 51 HCV isolates. It is possible that the 5' and 3' ends of this domain are conserved due to important cysteine residues and N-linked glycosylation sites. The central sequence, 5'-GHRMAWDMM-3' (aa 315–323), may be conserved due to additional functional constraints on the protein structure. Finally, although the amino acid sequence surrounding the putative E1 protein cleavage site was variable, an amino acid doublet (GV) at position 380 was invariant among all HCV isolates.

A dendrogram of the genetic relatedness of the E1 protein of selected HCV isolates representing the 12 genotypes is shown in FIG. 4. This dendrogram was constructed using the program CLUSTAL (Weiner, A. J. et al. (1991) Virology 180:842–848) and had a limit of 25 sequences. The scale showing percent identity was added based upon manual calculation. From the 51 HCV isolates for which the complete sequence of the E1 gene region was obtained, 25 isolates representing the twelve genotypes were selected for analysis as follows. Among isolates with genotype I/1a (SEQ ID NOs:52–59), as well as among isolates with genotype II/1b (SEQ ID NOs:60–76) the two isolates with the lowest amino acid identity within each genotype were included. Among isolates of genotype IV/2b, isolate DK8 (SEQ ID NO:81) that has an amino acid identity of 96.4% to isolate T8 (SEQ ID NO:84) was excluded. Among isolates of genotype V/3a, isolates S2 (SEQ ID NO:88) and S54 (SEQ ID NO:90) that both shared 97.9% of the amino acids of isolates HK10 (SEQ ID NO:87) and S52 (SEQ ID NO:89) were excluded. Finally, among isolates of genotype VI, isolates SA4 (SEQ ID NO:97) and SA5 (SEQ ID NO:98) with an amino acid identity to isolate SA7 (SEQ ID NO:100) of 96.4% and 95.8%, respectively were excluded. This dendrogram in combination with the analysis of the E1 gene sequence of 51 HCV isolates in Table 1 demonstrates extensive heterogeneity of this important gene.

The worldwide distribution of the 12 genotypes among 74 HCV isolates is depicted in FIG. 5. The complete E1 gene sequence was determined in 51 of these HCV isolates (SEQ ID NOs:1–51), including 8 isolates of genotype I/1a, 17 isolates of genotype II/1b and 26 isolates comprising genotypes III/2a, IV/2b, 2c, 3a, 4a–4d, 5a and 6a. In the remaining 23 isolates, all of genotypes I/1a and II/1b, the genotype assignment was based on a partial E1 gene sequence since they did not represent additional genotypes in any of the 12 countries. The number of isolates of a particular genotype is given in each of the 12 countries studied. Of the twelve genotypes, genotypes I/1a and II/1b were the most common accounting for 48 (65%) of the 74 isolates. Analysis of the E1 gene sequences available in the GenBank data base at the time of this study revealed that all 44 such sequences were of genotypes I/1a, II/1b, III/2a and IV/2b. Thus, based upon E1 gene analysis, 8 new genotypes of HCV have been identified.

Also of interest, different HCV genotypes were frequently found in the same country, with the highest number of genotypes (five) being detected in Denmark. Of the twelve genotypes, genotypes I/1a, II/1b, III/2a, IV/2b and V/3a were widely distributed with genotype II/1b being identified in 11 of 12 countries studied (Zaire was the only exception). In addition, while genotypes I/1a and II/1b were predominant in the Americas, Europe and Asia, several new genotypes were predominant in Africa.

It was also found that genotypes I/1a, II/1b, III/2a, IV/2b and V/3a of HCV were widely distributed around the world, whereas genotypes 2c, 4a, 4b, 4d, 5a and 6a were identified only in discreet geographical regions. For example, the majority of isolates in South Africa comprised a new genotype (5a) and all isolates in Zaire comprised 3 new closely related genotypes (4a, 4b, 4c). These genotypes were not identified outside Africa.

EXAMPLE 3

Detection by ELISA Based on Antigen from Insect Cells Expressing Complete E1 Protein Expression of E1 protein in SF9 cells. A cDNA (SEQ ID NO:1) encoding the complete E1 protein of SEQ ID NO:52 is subcloned into pBlueBac—Transfer vector (Invitrogen) using standard subcloning procedures. The resultant recombinant expression vector is cotransfected into SF9 insect cells (Invitrogen) by the Ca precipitation method according to the Invitrogen protocol.

ELISA Based on Infected SF9 cells. $5 \times 10^6$ SF9 cells infected with the above-described recombinant expression vector are resuspended in 1 ml of 10 mM Tris-HCl, pH 7.5, 0.15M NaCl and are then frozen and thawed 3 times. 10 ul of this suspension is dissolved in 10 ml of carbonate buffer (pH 9.6) and used to cover one flexible microtiter assay plate (Falcon). Serum samples are diluted 1:20, 1:400 and 1:8000, or 1:100, 1:1000 and 1:10000. Blocking and washing solutions for use in the ELISA assay are PBS containing 10% fetal calf serum and 0.5% gelatin (blocking solution) and PBS with 0.05% Tween −20 (Sigma, St.Louis, Mo.) (washing solution). As a secondary antibody, peroxidase-conjugated goat IgG fraction to human IgG or horse radish peroxidase-labelled goat anti-Old or anti-New World monkey immunoglobulin is used. The results are determined by measuring the optical density (O.D.) at 405 nm.

To determine if insect cells-derived E1 protein representing genotype I/a of HCV could detect anti-HCV antibody in chimpanzees infected with genotype I/1a of HCV, three infected chimpanzees are examined. The serum of all 3 chimpanzees are found to seroconvert to anti-HCV.

EXAMPLE 4

Use of the Complete E1 Protein as a Vaccine

Mammals are immunized with purified or partially purified E1 protein in an amount sufficient to stimulate the production of protective antibodies. The immunized mammals challenged with various genotypes of HCV are protected.

It is understood by one skilled in the art that the recombinant E1 protein used in the above vaccine can also be used in combination with other recombinant E1 proteins having an amino acid sequence shown in SEQ ID NOs:52–102.

EXAMPLE 5

Determination of the Genotype of an HCV Isolate Via Hybridization of Genotype-Specific Oligonucleotides to RT-PCR Amplification Products.

Viral RNA is isolated from serum obtained from a mammal and is subjected to RT-PCR as in Example 1. Following amplification, the amplified DNA is purified as described in Example 1 and aliquots of 100 mg of amplification product are applied to twelve dots on a nitrocellulose filter set in a dot blot apparatus. The twelve dots are then cut into separate dots and each dot is hybridized to a $^{32}$p-labelled oligonucleotide specific for a single genotype of HCV. The oligonucleotides to be used as hybridization probes are selected from SEQ ID NOs:109–135.

EXAMPLE 6

ELISA Based on Synthetic Peptides Derived From E1 cDNA Sequences

Synthetic peptides specific for genotype I/1a and having amino acid sequences according to SEQ ID NOs:136–148 are placed in 0.1% PBS buffer and 50 ul of 1 mg/ml of peptide is used to cover each well of the microtiter assay plate. Serum samples from two mammals infected with genotype I/1a HCV and from one mammal infected with genotype 5a HCV are diluted as in Example 3 and the ELISA is carried out as in Example 3. Both mammals infected with genotype I HCV react positively with peptides while the mammal infected with genotype 5a HCV exhibit no reactivity.

EXAMPLE 7

Use of the E1 Peptides as a Vaccine

Since the E1 genotype-specific peptides of the present invention are derived from two variable regions in the complete E1 protein, there exists support for the use of these peptides as a vaccine to protect against a variety of HCV genotypes. Mammals are immunized with peptide(s) selected from SEQ ID NOs: 136–159 in an amount sufficient to stimulate production of protective antibodies. The immunized mammals challenged with various genotypes of HCV are protected.

We claim:

1. A method for detecting the presence of hepatitis C virus comprising:
   (a) amplifying RNA via reverse transcription-polymerase chain reaction to produce amplification products;
   (b) contacting said products with a nucleotide sequence selected from the sequences shown in SEQ ID NO: 1–51; and
   (c) detecting complexes of said products and said nucleotide sequence.

2. A method for detecting the presence of hepatitis C virus comprising:
   (a) amplifying RNA via a reverse transcription-polymerase chain reaction process using primers selected from the group consisting of SEQ ID NO.: 103 through SEQ ID NO. 108; and
   (b) detecting said amplification product.

3. Isolated primers, wherein said primers have nucleic acid sequences selected from the group consisting of SEQ ID NO: 103 through SEQ ID NO: 108.

4. A diagnostic kit for use in detecting the presence of hepatitus C virus, said kit comprising: primers having nucleic acid sequences selected from the group consisting of SEQ ID NO:103 through SEQ ID NO:108.

5. A method for determining the genotype of a hepatitis C virus, said method comprising:
   (a) amplifying RNA via reverse transcription-polymerase chain reaction to produce amplification products;
   (b) contacting said products with at least one E1 region genotype-specific oligonucleotide; and
   (c) detecting complexes of said products and said oligonucleotide(s).

6. The method of claim 5, wherein said amplification of step (a) uses primers having sequences according to SEQ ID NO:103 through SEQ ID NO:108.

7. The method of claim 6, wherein said oligonucleotide of step (b) is a nucleic acid sequence selected from the group consisting of SEQ ID NO:109 through SEQ ID NO:135.

8. Isolated genotype-specific oligonucleotides having nucleic acid sequences deduced from genotype-specific nucleic acid domains located in SEQ ID Nos: 1 through 51 or in consensus sequences produced from at least two sequences shown in SEQ ID Nos: 1 through 51.

9. Isolated genotype-specific oligonucleotides having nucleic acid sequences selected from the group consisting of SEQ ID NO: 109 through SEQ ID NO: 135.

10. A diagnostic kit for determining the genotype of a hepatitis C virus, said kit comprising primers selected from the group consisting of SEQ ID NO:103 through SEQ ID NO:108 and hybridization probes selected from the group consisting of SEQ ID NO:109 through SEQ ID NO:135.

* * * * *